(12) United States Patent
Sommer et al.

(10) Patent No.: US 12,409,172 B2
(45) Date of Patent: Sep. 9, 2025

(54) DOSAGE REGIMEN

(71) Applicant: UNION therapeutics A/S, Hellerup (DK)

(72) Inventors: Morten Otto Alexander Sommer, Hellerup (DK); Jakob Felding, Hellerup (DK); Kim Domela Kjøller, Hellerup (DK); Mads Jellingsø, Hellerup (DK); Morten Lind Jensen, Hellerup (DK); Eckhard Niemeier, Hellerup (DK)

(73) Assignee: UNION therapeutics A/S, Hellerup (DK)

( * ) Notice: Subject to any disclaimer, the term of this patent is extended or adjusted under 35 U.S.C. 154(b) by 0 days.

(21) Appl. No.: 18/790,828

(22) Filed: Jul. 31, 2024

(65) Prior Publication Data

US 2025/0090512 A1   Mar. 20, 2025

Related U.S. Application Data

(63) Continuation of application No. PCT/EP2024/062355, filed on May 3, 2024.

(30) Foreign Application Priority Data

May 5, 2023   (GB) .................................... 2306662

(51) Int. Cl.
*A61K 31/4436* (2006.01)
*A61K 9/00* (2006.01)
*A61K 9/20* (2006.01)
*A61P 17/06* (2006.01)

(52) U.S. Cl.
CPC ........ *A61K 31/4436* (2013.01); *A61K 9/0053* (2013.01); *A61K 9/20* (2013.01); *A61P 17/06* (2018.01)

(58) Field of Classification Search
CPC ................................................ A61K 31/4436
See application file for complete search history.

(56) References Cited

U.S. PATENT DOCUMENTS

| | | | |
|---|---|---|---|
| 5,712,298 A | 1/1998 | Amschler | |
| 6,094,614 A | 7/2000 | Hiwatashi | |
| 6,549,840 B1 | 4/2003 | Mikami et al. | |
| 6,630,813 B2 | 10/2003 | Berels et al. | |
| 8,338,431 B2 | 12/2012 | Bollu et al. | |
| 8,940,761 B2 | 1/2015 | Nielsen et al. | |
| 8,952,162 B2 | 2/2015 | Nielsen et al. | |
| 8,980,905 B2 * | 3/2015 | Nielsen ................... | A61P 17/04 546/15 |
| 9,181,248 B2 | 11/2015 | Nielsen et al. | |
| 9,273,064 B2 | 3/2016 | Nielsen | |
| 9,637,499 B2 | 5/2017 | Nielsen | |
| 9,908,894 B2 | 3/2018 | Metzler et al. | |
| 10,793,580 B2 | 10/2020 | Liang et al. | |
| 10,906,915 B2 | 2/2021 | Liang et al. | |
| 11,065,257 B2 | 7/2021 | Liang et al. | |
| 11,220,514 B2 | 1/2022 | Dahl et al. | |
| 11,292,799 B2 | 4/2022 | Andrews et al. | |
| 11,299,497 B2 | 4/2022 | Larsen et al. | |
| 11,365,204 B2 | 6/2022 | Larsen | |
| 11,370,799 B2 | 6/2022 | Dahl et al. | |
| 11,384,096 B2 | 7/2022 | Andrews et al. | |
| 11,434,286 B2 | 9/2022 | Lin et al. | |
| 11,866,445 B2 | 1/2024 | Larsen | |
| 11,981,681 B2 | 5/2024 | Andrews et al. | |
| 2002/0128290 A1 | 9/2002 | Ohshima et al. | |
| 2005/0186276 A1 | 8/2005 | Berchielli et al. | |
| 2005/0192333 A1 | 9/2005 | Hinze et al. | |
| 2007/0104792 A1 | 5/2007 | Jenkins | |
| 2010/0099688 A1 | 4/2010 | Felding et al. | |
| 2012/0028974 A1 | 2/2012 | Nielsen et al. | |
| 2013/0123291 A1 | 5/2013 | Nielson | |
| 2013/0225609 A1 | 8/2013 | Nickolaus | |
| 2014/0329853 A1 | 11/2014 | Nielsen et al. | |
| 2015/0105420 A1 | 4/2015 | Nielsen et al. | |
| 2015/0111915 A1 | 4/2015 | Nielsen | |
| 2016/0022657 A1 | 1/2016 | Nielsen | |
| 2017/0137438 A1 | 5/2017 | Metzler et al. | |
| 2019/0330223 A1 | 10/2019 | Liang et al. | |
| 2020/0010477 A1 | 1/2020 | Liang et al. | |
| 2020/0239493 A1 | 7/2020 | Larsen | |
| 2020/0262842 A1 | 8/2020 | Dahl et al. | |

(Continued)

FOREIGN PATENT DOCUMENTS

| | | | |
|---|---|---|---|
| EP | 0943613 A1 | 9/1999 | |
| EP | 1029860 A1 | 8/2000 | |

(Continued)

OTHER PUBLICATIONS (2022) "Abrocitinib Prescribing Information", Administration FaD., https://www.accessdata.fda.gov/drugsatfda_docs/label/2022/213871s000lbl.pdf, 31 pages.
(2014) "Apremilast Prescribing Information", Administration FaD., Retrieved From https://www.accessdata.fda.gov/drugsatfda_docs/label/2021/205437s011lbl.pdf, 21 pages.
(1987) "Chemical Abstract Registry No. 109264-30-4", 1 page.
(2016) "Crisaborole Prescribing Information", Retrieved From https://www.accessdata.fda.gov/drugsatfda_docs/label/2020/207695s007s009s010lbl.pdf, 9 pages.
(2017) "Dupixent (dupilumab) Prescribing Information", Administration FaD., Retrieved From https://www.accessdata.fda.gov/drugsatfda_docs/label/2022/761055s046lbl.pdf, 79 pages.

(Continued)

*Primary Examiner* — Rei Tsang Shiao
(74) *Attorney, Agent, or Firm* — Mintz, Levin, Cohn, Ferris, Glovsky and Popeo, P.C.

(57) ABSTRACT

Provided herein is orismilast for use in the treatment a disease or disorder ameliorated by inhibiting PDE4 in a subject, wherein the orismilast is administered to the subject according to a specific dosage regimen. Also provided is orismilast for use the treatment of pruritus associated with atopic dermatitis.

23 Claims, 36 Drawing Sheets

(56) References Cited

U.S. PATENT DOCUMENTS

| | | |
|---|---|---|
| 2020/0323869 A1 | 10/2020 | Liang et al. |
| 2020/0385400 A1 | 12/2020 | Larsen et al. |
| 2021/0070769 A1 | 3/2021 | Andrews et al. |
| 2021/0079012 A1 | 3/2021 | Andrews et al. |
| 2021/0147440 A1 | 5/2021 | Dahl et al. |
| 2021/0386674 A1* | 12/2021 | Rasmussen .......... A61K 9/2013 |
| 2022/0162227 A1 | 5/2022 | Dahl et al. |
| 2022/0281889 A1 | 9/2022 | Larsen |
| 2022/0362259 A1 | 11/2022 | Liang et al. |
| 2022/0372131 A1 | 11/2022 | Lin et al. |
| 2023/0073362 A1 | 3/2023 | Dahl et al. |
| 2023/0087354 A1 | 3/2023 | Andrews et al. |
| 2024/0228606 A1 | 7/2024 | Lin et al. |

FOREIGN PATENT DOCUMENTS

| | | |
|---|---|---|
| EP | 2266541 | 12/2010 |
| EP | 3528838 B1 | 7/2023 |
| JP | H03148337 A | 6/1991 |
| JP | H08512041 A | 12/1996 |
| JP | 2010519332 A | 6/2010 |
| JP | 2012067143 A | 4/2012 |
| JP | 6850886 B2 | 3/2021 |
| JP | 6850887 B2 | 3/2021 |
| WO | 9501338 A1 | 1/1995 |
| WO | 9744337 A1 | 11/1997 |
| WO | 0050011 A1 | 8/2000 |
| WO | 2005066183 A1 | 7/2005 |
| WO | 2008104175 A2 | 9/2008 |
| WO | 2011160632 A1 | 12/2011 |
| WO | 2012016280 A1 | 2/2012 |
| WO | 2015197534 A2 | 12/2015 |
| WO | 2017103058 A1 | 6/2017 |
| WO | 2018057849 A1 | 3/2018 |
| WO | 2018234299 A1 | 12/2018 |
| WO | 2019057806 A1 | 3/2019 |
| WO | 2019115776 A1 | 6/2019 |
| WO | 2020148271 A1 | 7/2020 |
| WO | 2022200339 A1 | 9/2022 |
| WO | 2023203022 A1 | 10/2023 |

OTHER PUBLICATIONS (2020) "Efficacy and Safety Study of Apremilast in Subjects with Moderate to Severe Atopic Dermatitis", Retrieved From https://clinicaltrials.gov/study/NCT02087943?cond=Atopic%20Dermatitis&intr=Apremilast&viewType=Table&rank=1#study-plan., 14 pages.

International Search Report and Written Opinion received for PCT Patent International Application No. PCT/DK2008/000080, mailed on Dec. 5, 2008, 16 pages.

International Search Report and Written Opinion received for PCT Patent International Application No. PCT/DK2011/000069, mailed on Aug. 19, 2011, 8 pages.

International Search Report and Written Opinion received for PCT Patent International Application No. PCT/EP2020/050798, mailed on Mar. 17, 2020, 9 pages.

International Search Report and Written Opinion received for PCT Patent International Application No. PCT/EP2022/057472, mailed on Jul. 21, 2022, 11 pages.

Japanese Office Action issued in Japanese Application No. 2013-515698, mailed on Mar. 10, 2015, 2 pages.

(2014) "New Drug Application Otezla® 205437Orig1s000", Clinical Pharmacology and Biopharmaceutics review, 73 pages.

(Mar. 2023) "Orismilast", Retrieved From https://web.archive.org/web/20230324144811/https://uniontherapeutics.com/orismilast/, 4 pages.

Partial International Search Results and Provisional Opinion of PCT Application No. PCT/EP2024/062355, Mailed on Jul. 22, 2024, 15 pages.

Russian Office Action issued in Russian Application No. 2013103079/04, mailed on Dec. 21, 2015, 7 pages.

(2024) "Study to Assess the Efficacy and Safety of Orismilast in Psoriasis (IASOS)", NCT05190419 Clinical Trials, 15 pages.

(2019) "Upadacitinib Prescribing Information", Retrieved From https://www.accessdata.fda.gov/drugsatfda_docs/label/2022/211675s007lbl.pdf, 59 pages.

Aarts et al. (Jul. 2021) "Long-term Treatment with Apremilast in hidradenitis suppurativa: A 2-year Follow-up of Initial Responders", Journal of the American Academy of Dermatology, 85(1):258-260.

Abud-Mendoza et al. (2009) "Treating Severe Systemic Lupus Erythematosus With Rituximab. An Open Study", Reumatol Clinica, 5(4):147-152.

Ahlehoff et al. (Feb. 2013) "Cardiovascular Disease Event Rates in Patients with Severe Psoriasis Treated with Systemic Anti-Inflammatory Drugs: A Danish Real-World Cohort Study", Journal of internal medicine, 273(2):197-204.

Ahlehoff et al. (Aug. 2011) "Psoriasis is Associated with Clinically Significant Cardiovascular Risk: A Danish Nationwide Cohort Study", Journal of internal medicine, 270(2):147-157.

Ariga et al. (2004) "Nonredundant Function of Phosphodiesterases 4D and 4B in Neutrophil Recruitment to the Site of Inflammation", The Journal of Immunology, 173(12):7531-7538.

Banner et al. (2009) "Dual PDE3/4 Inhibitors as Therapeutic Agents for Chronic Obstructive Pulmonary Disease", British Journal of Pharmacology, 157(6):892-906.

Batycka-Baran et al. (2021) "Serum Concentration and Skin Expression of S100A7 (Psoriasin) in Patients Suffering from Hidradenitis Suppurativa", Dermatology, 237(5):1-7.

Baumer et al. (2006) "Highly Selective Phosphodiesterase 4 Inhibitors for the Treatment of Allergic Skin Diseases and Psoriasis", Inflammation & Allergy-Drug Targets, 6(1):17-26.

Bieber et al. (Sep. 2022) "Atopic Dermatitis: Pathomechanisms and Lessons Learned from Novel Systemic Therapeutic Options", Journal of the European Academy of Dermatology and Venereology, 36(9):1432-1449.

Bissonnette et al. (Jul. 1, 2016) "Apremilast, an Oral Phosphodiesterase-4 Inhibitor, in the Treatment of Palmoplantar Psoriasis: Results of a Pooled Analysis from Phase II PSOR-005 and Phase III Efficacy and Safety Trial Evaluating the Effects of Apremilast in Psoriasis (ESTEEM) Clinical Trials in Patients with Moderate to Severe Psoriasis ", Journal of the American Academy of Dermatology, 75(1):99-105.

Blauvelt et al. (Dec. 2023) "Next Generation PDE4 Inhibitors that Selectively Target PDE4B/D Subtypes: A Narrative Review", Dermatology and therapy, 13(12):3031-3042.

Blok et al. (Jun. 2016) "Gene Expression Profiling of Skin and Blood in Hidradenitis Suppurativa", The British Journal of Dermatology, 174(6):1392-1394.

Boswell-Smith et al. (2005) "Selective Phosphodiesterase 4 Inhibitors in the Treatment of Allergy and Inflammation", Current Opinion in Investigational Drugs, 6(11):1136-1141.

Bundschuh et al. (Jan. 1, 2001) "In Vivo Efficacy in Airway Disease Models of Roflumilast, a Novel Orally Active PDE4 Inhibitor", 297(1):280-290.

Butler et al. (May 1983) "Increased Leukocyte Histamine Release with Elevated Cyclic AMP-Phosphodiesterase Activity in Atopic Dermatitis", The Journal of Allergy and Clinical Immunology, 71(5):490-497.

Chauret et al. (Aug. 19, 2002) "Improving Metabolic Stability of Phosphodiesterase-4 Inhibitors Containing a Substituted Catechol: Prevention of Reactive Intermediate Formation and Covalent Binding", 12(16):2149-2152.

Contreras et al. (2017) "Selective Inhibition of Phosphodiesterases 4A, B, C and D Isoforms in Chronic Respiratory Diseases: Current and Future Evidences", Current Pharmaceutical Design, 23(14):2073-2083.

Cooper, Kevind. (Jan. 1994) "Atopic Dermatitis: Recent Trends in Pathogenesis and Therapy", Journal of Investigative Dermatology, 102(1):128-137.

Dastidar et al. (May 2007) "Therapeutic Benefit of PDE4 Inhibitors in Inflammatory Diseases", Current Opinion in Investigational Drugs, 8(5):364-372.

Daxhelet et al. (2020) "Proposed Definitions of Typical Lesions in Hidradenitis Suppurativa", Dermatology, 236(5):1-8.

Dermer, Gerald B. (Mar. 12, 1994) "Another Anniversary for the War on Cancer", Bio/Technology, 12:320 (4 pages).

(56) References Cited

OTHER PUBLICATIONS

Dietsch et al. (2006) "Characterization of the Inflammatory Response to a Highly Selective PDE4 Inhibitor in the Rat and the Identification of Biomarkers that Correlate with Toxicity", Toxicologic Pathology, 34(1):39-51.
Egeberg et al. (May 2017) "Prevalence and Risk of Inflammatory Bowel Disease in Patients with Hidradenitis Suppurativa", The Journal of Investigative Dermatology, 137(5):1060-1064.
Egeberg et al. (2016) "Risk of Major Adverse Cardiovascular Events and All-Cause Mortality in Patients with Hidradenitis Suppurativa", JAMA Dermatology, 152(4):429-434.
Eichenfield et al. (Feb. 2014) "Guidelines for the Management of Atopic Dermatitis", Journal of the American Academy of Dermatology, 70(2):338-351.
Finlay et al. (May 1994) "Dermatology Life Quality Index (DLQI)—A Simple Practical Measure for Routine Clinical Use", Clinical and Experimental Dermatology, 19(3):210-216.
Frederiksen et al. (May 2024) "Orismilast for the Treatment of Mild to Severe Hidradenitis Suppurativa: Week 16 Data from OSIRIS, A Phase 2a, Open-Label, Single-Centre, Single-Arm, Dose-Finding Clinical Trial", Journal of the European Academy of Dermatology and Venereology, 38(5):920-930.
Freshney, Ian R. (1983) "Culture of Animal Cells", A Manual of Basic Technique, Alan R. Liss, Inc., New York, 4 pages.
Frew et al. (2019) "Topical, Systemic and Biologic Therapies in Hidradenitis Suppurativa: Pathogenic Insights by Examining Therapeutic Mechanisms", Therapeutic Advances in Chronic Disease, 10:1-24.
Garcia-Osta et al. (2012) "Phophodieserases as Therapeutic Targets for Alzheimer's Disease", ACS Chemical Neuroscience, 3(11):832-844.
Garcovich et al. (2020) "Apremilast for the Treatment of Hidradenitis Suppurative Associate With Psoriatic Arthritis in Multimorbid Patients", Medicine (Baltimore), 99(5):e18991 (4 pages).
Giembycz, Mark A. (Jun. 2005) "Life After PDE4: Overcoming Adverse Events with Dual-Specificity Phosphodiesterase Inhibitors", Current Opinion in Pharmacology, 5(3):238-244.
Gooderham et al. (Oct. 2015) "Selective Phosphodiesterase Inhibitors for Psoriasis: Focus on Apremilast", BioDrugs, 29(5):327-339.
Guay et al. (Jun. 3, 2002) "Discovery of L-791,943: A Potent, Selective, Non Emetic and Orally Active Phosphodiesterase-4 Inhibitor", Bioorganic & Medicinal Chemistry Letters, 12(11):1457-1461.
Guttman-Yassky et al. (Jan. 2019) "The Role of Phosphodiesterase 4 in the Pathophysiology of Atopic Dermatitis and the Perspective for its Inhibition", Experimental dermatology, 28(1):3-10.
Hanifin et al. (Jul. 1, 1996) "Type 4 Phosphodiesterase Inhibitors have Clinical and in Vitro Anti-Inflammatory Effects in Atopic Dermatitis", Journal of Investigative Dermatology, 107(1):51-56.
Harada et al. (Sep. 2008) "Curative Effects of Phosphodiesterase 4 Inhibitors Cilomilast, Roflumilast, and Rolipram in Dermatitis Mouse Model", Journal of Dermatological Science, 51(3):215-219.
Herdman et al. (Dec. 2011) "Development and Preliminary Testing of the New Five-Level Version of EQ-5D (EQ-5D-5L)", Quality of Life Research, 20(10):1727-1736.
Holden et al. (Sep. 1986) "Monocyte Localization of Elevated cAMP Phosphodiesterase Activity in Atopic Dermatitis", J. Investigative Dermatology, 87(3):372-376.
Hotz et al. (Sep. 2016) "Intrinsic Defect in Keratinocyte Function Leads to Inflammation in Hidradenitis Suppurativa", Journal of Investigative Dermatology, 136(9):1768-1780.
Houslay et al. (Nov. 15, 2005) "Phosphodiesterase-4 as a Therapeutic Target", Drug Discovery Today, 10(22):1503-1519.
Hsiao et al. (Nov. 2010) "Hidradenitis Suppurativa and Concomitant Pyoderma Gangrenosum: A Case Series and Literature Review", Archives of Dermatology, 146(11):1265-1270.
Huang et al. (2006) "Phosphodiesterase 4 Inhibitors for the Treatment of Asthma and COPD", Current Medicinal Chemistry, 13(27):3253-3262.
Huanget al. (2001) "The Next Generation of PDE4 Inhibitors", Current Opinion in Chemical Biology, 5(4):432-438.

Jemec, Gregor B. E. (2012) "Hidradenitis Suppurativa", The New England Journal of Medicine, 366(2):158-164.
Jin et al. (May 28, 2002) "Induction of the Cyclic Nucleotide Phosphodiesterase PDE4B is Essential for LPS-Activated TNF-α Responses", PNAS, 99(11):7628-7633.
Jin et al. (2007) "Insights into the Physiological Functions of PDE4 from Knockout Mice", Cyclic Nucleotide Phosphodiesterases in Health and Disease, CRC Press, 323-346.
Jin et al. (2012) "Phosphodiesterase 4 and Its Inhibitors in Inflammatory Diseases", Chang Gung Med J, 35(3):197-210.
Jin et al. (2005) "Specific Role of Phosphodiesterase 4B in Lipopolysaccharide-Induced Signaling in Mouse Macrophages", Journal of Immunology, 175(3):1523-1531.
Kamata et al. (May 1, 2023) "Optimal Use of Jak Inhibitors and Biologics for Atopic Dermatitis on the Basis of the Current Evidence", JID Innovations, 3(3):100195 (13 pages).
Kerdel et al. (Feb. 1, 2019) "Apremilast for the Treatment of Mild-to-Moderate Hidradenitis Suppurativa in a Prospective, Open-Label, Phase 2 Study", Journal of Drugs in Dermatology, Strategic Communication in Dermatology, 18(2):170-176.
Kimball et al. (2012) "Adalimumab for the Treatment of Moderate to Severe Hidradenitis Suppurativa: A Parallel Randomized Trial", Annals of Internal Medicine, 157(12):846-855.
Kimball et al. (2014) "Assessing the Validity, Responsiveness and Meaningfulness of the Hidradenitis Suppurativa Clinical Response (HiSCR) as the Clinical Endpoint for Hidradenitis Suppurativa Treatment", British Journal of Dermatology, 171(6):1434-1442.
Kimball et al. (2016) "HiSCR (Hidradenitis Suppurativa Clinical Response): A Novel Clinical Endpoint to Evaluate Therapeutic Outcomes in Patients with Hidradenitis Suppurativa from the Placebo-Controlled Portion of a Phase 2 Adalimumab Study", Journal of the European Academy of Dermatology and Venereology, 30:989-994.
Kirby et al. (Aug. 2020) "The Hidradenitis Suppurativa Quality of Life (HiSQOL) Score: Development and Validation of a Measure for Clinical Trials", The British Journal of Dermatology, 183(2):340-348.
Kofoed et al. (2015) "New Drugs and Treatment Targets in Psoriasis", Acta Dermato-Venereologica, 95(2):133-139.
Kroegel et al. (2007) "Phosphodiesterase-4 Inhibitors as a Novel Approach for the Treatment of Respiratory Disease: Cilomilast", Expert Opinion on Investigational Drug, 16(1):109-124.
Lagente et al. (2005) "Selective PDE4 Inhibitors as Potent Anti-Inflammatory Drugs for the Treatment of Airway Diseases", Mem Inst Oswaldo Cruz, 100(Suppl 1):131-136.
Laughter et al. (Feb. 1, 2021) "The Global Burden of Atopic Dermatitis: Lessons from the Global Burden of Disease Study 1990-2017*", British Journal of Dermatology, 184(2):304-309.
Lebwohl, Mark. (Apr. 5, 2003) "Psoriasis", Lancet, 361(9364):1197-1204.
Lee et al. (2017) "What is Hidradenitis Suppurativa?", Can Fam Physician, 63(2):114-120.
Leroux et al. (Mar. 1, 2005) "Alpha-fluorinated Ethers, Thioethers, and Amines: Anomerically Biased Species", Chemical Reviews, 105(3):827-856.
Li et al. (Oct. 17, 2018) "Phosphodiesterase-4 Inhibitors for the Treatment of Inflammatory Diseases", Frontiers in pharmacology, 9:1048 (21 pages).
Lim et al. (2019) "Systematic Review of Immunomodulatory Therapies for Hidradenitis Suppurativa", Biologics: Targets and Therapy, 13:53-78.
Lipworth, Brian J. (Jan. 8, 2005) "Phosphodiesterase-4 Inhibitors for Asthma And Chronic Obstructive Pulmonary Disease", Lancet, 365(9454):167-175.
Lugnier et al. (Apr. 1, 2020) "Cyclic Nucleotide Phosphodiesterases: New Targets in the Metabolic Syndrome?", Pharmacology & therapeutics, 208:107475 (17 pages).
Manning et al. (1999) "Suppression of Human Inflammatory Cell Function by Subtype-Selective PDE4 Inhibitors Correlates with Inhibition of PDE4A and PDE4B", British Journal of Pharmacology, 128(7):1393-1398.
Martín-Santiago et al. (Jan. 1, 2022) "Safety Profile and Tolerability of Topical Phosphodiesterase 4 Inhibitors for the Treatment of

(56) References Cited

OTHER PUBLICATIONS

Atopic Dermatitis: A Systematic Review and Meta-Analysis", Current Therapeutic Research, 96:100679 (12 pages).
Marzano et al. (Dec. 2014) "Association of Pyoderma Gangrenosum, Acne, and Suppurative Hidradenitis (PASH) Shares Genetic and Cytokine Profiles with other Autoinflammatory Diseases", Medicine, 93(27):1-11.
McDonough et al. (2020) "Nonselective Inhibition of PDE4 Induces Gastroparesis in Mice", The FASEB Journal, 34(S1):1-1.
McDowell et al. (Aug. 2019) "Crisaborole: A Novel Nonsteroidal Topical Treatment for Atopic Dermatitis", Journal of Pharmacy Technology, 35(4):172-178.
Menter et al. (May 2008) "Guidelines of Care for the Management of Psoriasis and Psoriatic Arthritis: Section 1. Overview of Psoriasis and Guidelines of Care for the Treatment of Psoriasis with Biologics", Journal of the American Academy of Dermatology, 58(5):826-850.
Menter et al. (Sep. 2009) "Guidelines of Care for the Management of Psoriasis and Psoriatic Arthritis: Section 4. Guidelines of Care for the Management and Treatment of Psoriasis with Traditional Systemic Agents", Journal of the American Academy of Dermatology, 61(3):451-485.
Menter et al. (Jan. 2010) "Guidelines of Care for the Management of Psoriasis and Psoriatic Arthritis: Section 5. Guidelines of Care for the Treatment of Psoriasis with Phototherapy and Photochemotherapy", Journal of the American Academy of Dermatology, 62(1):114-135.
Mozeika et al. (May 2013) "Tumour Necrosis Factor-alpha and Matrix Metalloproteinase-2 are Expressed Strongly in Hidradenitis Suppurativa", Acta Derm Venereol, 93(3):301-304.
Müller et al. (Jan. 8, 2024) "Treatment of Atopic Dermatitis: Recently Approved Drugs and advanced Clinical Development Programs", Allergy, 79(6):1501-1515.
Muselík et al. (Oct. 15, 2021) "A Critical Overview of FDA and EMA Statistical Methods to Compare In Vitro Drug Dissolution Profiles of Pharmaceutical Products", Pharmaceutics, 13(10):1703 (12 pages).
Napolitano et al. (Apr. 2017) "Hidradenitis Suppurativa: from Pathogenesis to Diagnosis and Treatment", Clinical, Cosmetic and Investigational Dermatology, 10:105-115.
Napolitano et al. (Apr. 18, 2023) "The Hidden Sentinel of the Skin: An Overview on The Role of Interleukin-13 in Atopic Dermatitis", Frontiers in Medicine, 10:1165098 (7 pages).
Newton et al. (2019) "Exploring Content and Psychometric Validity of Newly Developed Assessment Tools for Itch and Skin Pain in Atopic Dermatitis", Journal of Patient-Reported Outcomes, 3(1):42 (12 pages).
Niv et al. (2017) "Pyoderma Gangrenosum, Acne, and Hidradenitis Suppurativa (PASH) Syndrome with Recurrent vVasculitis", JAAD Case Reports, 3(1):70-73.
Paes et al. (Jul. 1, 2021) "The Molecular Biology of Phosphodiesterase 4 Enzymes as Pharmacological Targets: An Interplay of Isoforms, Conformational States, and Inhibitors", Pharmacological Reviews, 73(3):1016-1049 (34 pages).
Park et al. (2001) "Metabolism of Fluorine-Containing Drugs", Annual Review of Pharmacology and Toxicology, 41:443-470.
Peter et al. (2007) "Differential expression and function of phosphodiesterase 4 (PDE4) subtypes in human primary CD4+ T cells: Predominant Role of PDE4D", 178(8):4820-4831.
Press et al. (2009) "PDE4 Inhibitors—A Review of the Current Field", Progress in Medicinal Chemistry, 47:37-74.
Quaglino et al. (2011) "Th1, Th2, Th17 and Regulatory T Cell Pattern in Psoriatic Patients: Modulation of Cytokines and Gene Targets Induced by Etanercept Treatment and Correlation with Clinical Response", Dermatology, 223(1):57-67.
Ravindran et al. (2008) "A Systemic Review and Meta-Analysis of Efficacy and Toxicity of Disease Modifying Anti-Rheumatic Drugs and Biological Agents for Psoriatic Arthritis", Annals of the Rheumatic Diseases, 67(6):855-859.

Reilly et al. (1993) "The Validity and Reproducibility of a Work Productivity and Activity Impairment Instrument", PharmacoEconomics, 4(5):353-365.
Richert et al. (2009) "Rolipram not Good for MS", Multiple Sclerosis Research, 15:1206-1214.
Richter et al. (Sep. 1, 2013) "PDE4 as a Target for Cognition Enhancement", Expert Opinion on Therapeutic Targets, 17(9):1011-1027.
Riis et al. (2018) "Investigational Drugs in Clinical Trials for Hidradenitis Suppurativa", Expert Opinion on Investigation Drugs, Informa Healthcare, 27(1):43-53.
Rondags et al. (2019) "Correlation of the Refined Hurley Classification for Hidradenitis Suppurativa with Patient-Reported Quality of Life and Objective Disease Severity Assessment", The British Journal of Dermatology, 180(5):1214-1220.
Roy et al. (Dec. 22, 2022) "Efficacy of Topical and Systemic Treatments for Atopic Dermatitis on Pruritus: A Systematic Literature Review and Meta-Analysis", Frontiers in Medicine, 9:1079323 (16 pages).
Sabat et al. (2020) "Hidradenitis Suppurativa", Nature Reviews Disease Primers, 6(1):18 (20 pages).
Samrao et al. (Aug. 2012) "A Pilot Study of an Oral Phosphodiesterase Inhibitor (Apremilast) for Atopic Dermatitis in Adults", Arch Dermatol, 148(8):890-897.
Samynathan et al. (2023) "Navigating the Atopic Dermatitis Toolbox: Challenging Scenarios and Shared Decision Making", Annals of Allergy, Asthma & Immunology, 132(3):337-343.
Saunte et al. (2015) "Diagnostic Delay in Hidradenitis Suppurativa is a Global Problem", British Journal of Dermatology, 173(6):1546-1549.
Schafer et al. (2014) "Apremilast is a Selective PDE4 Inhibitor with Regulatory Effects on Innate Immunity", Cellular Signaling, 26(9):2016-2029.
Schafer et al. (Feb. 2010) "Apremilast, a CAMP Phosphodiesterase-4 Inhibitor, Demonstrates Anti-Inflammatory Activity in Vitro and in a Model of Psoriasis", British Journal of Pharmacology, 159(4):842-855.
Schafer, Torsten (2006) "Epidemiology of Psoriasis: Review and the German Perspective", Dermatology, 212(4):327-337.
Schett et al. (2010) "Apremilast: A Novel PDE4 Inhibitor in the Treatment of Autoimmune and Inflammatory Diseases", Therapeutic Advances in Musculoskeletal Disease, 2(5):271-278.
Schlapbach et al. (Oct. 2011) "Expression of the IL-23/Th17 Pathway in Lesions of Hidradenitis Suppurativa", Journal of the American Academy of Dermatology, 65(4):790-798.
Schlapbach et al. (Jul. 2009) "Human β-Defensin-2 and Psoriasin are Overexpressed in Lesions of Acne Inversa", Journal of the American Academy of Dermatology, 61(1):58-65.
Sideris et al. (Aug. 24, 2022) "New and Upcoming Topical Treatments for Atopic Dermatitis: A Review of the Literature", Journal of Clinical Medicine, 11(17):4974 (20 pages).
Silverberg et al. (Nov. 1, 2018) "Association of Atopic Dermatitis with Allergic, Autoimmune, and Cardiovascular Comorbidities in US Adults", Annals of Allergy, Asthma & Immunology, 121(5):604-612 (26 pages).
Silverberg et al. (Mar. 1, 2023) "Burden of Disease and Unmet Needs in Atopic Dermatitis:Results from a Patient Survey", Dermatitis, 34(2):135-144.
Silverberg et al. (2022) "Expert Perspectives on Key Parameters that Impact Interpretation of Randomized Clinical Trials in Moderate-to-Severe Atopic Dermatitis", American Journal of Clinical Dermatology, 23(1):1-11.
Silverberg et al. (Apr. 2023) "Pharmacology of Orismilast, A Potent and Selective PDE4 Inhibitor", Journal of the European Academy of Dermatology and Venereology, 37(4):721-729.
Simone, Joseph V. (Feb. 3, 1997) "Oncology: Introduction 20th Edition", Cecil: Textbook of Medicine, 8 pages.
Simpson et al. (2018) "A phase 2 Randomized Trial of Apremilast in Patients with Atopic Dermatitis", The Journal of Investigative Dermatology, 139(5):1063-1072.
Smets et al. (1995) "The Multidimensional Fatigue Inventory (MFI) Psychometric Qualities of an Instrument to Assess Fatigue", Journal of Psychosomatic Research, 39(5):315-325.

(56) References Cited

OTHER PUBLICATIONS

Spina, D. (Oct. 2008) "PDE4 Inhibitors: Current Status", British Journal of Pharmacology, 155(3):308-315.

Tello et al. (2021) "Multidisciplinary Management of the Adverse Effects of Apremilast", Actas Dermo-Sifiliográficas, 112(2):134-141.

Thorlacius et al. (2019) "Development of HiSQOL: A Hidradenitis Suppurativa-Specific Quality of Life Instrument", Skin Appendage Disorders, 5(4):221-229.

Thorlacius et al. (2018) "Increased Suicide Risk in Patients with Hidradenitis Suppurativa", Journal of Investigative Dermatology, 138(1):52-57.

Torphy, Theodore J. (1998) "Phosphodiesterase Isozymes: Molecular Targets for Novel Antiasthma Agents", American Journal of Respiratory and Critical Care Medicine, 157(2):351-370.

Tsuji et al. (2023) "PDE4 Inhibition by Difamilast Regulates Filaggrin and Loricrin Expression Via Keratinocyte Proline-Rich Protein in Human Keratinocytes", Journal of Dermatological Science, 110(2):61-68.

Tzanetakou et al. (2016) "Safety and Efficacy of Anakinra in Severe Hidradenitis Suppurativa: A Randomized Clinical Trial", JAMA Dermatology, 152(1):52-59 (E1-E8).

Vignola, Antonio M. (Jun. 2004) "PDE4 Inhibitors in COPD—a More Selective Approach to Treatment", Respiratory Medicine, 98(6):495-503.

Vippagunta et al. (May 16, 2001) "Crystalline Solids", Advanced Drug Delivery Reviews, 48(1):3-26.

Voorhees et al. (Jul. 1, 2020) "Efficacy and Safety of Apremilast in Patients with Moderate to Severe Plaque Psoriasis of the Scalp: Results of a Phase 3b, Multicenter, Randomized, Placebo-Controlled, Double-Blind Study", Journal of the American Academy of Dermatology, 83(1):96-103.

Vossen et al. (2018) "Apremilast for Moderate Hidradenitis Suppurativa: Results of a Randomized Controlled Trial", Journal of the American Academy of Dermatology, 80(1):80-88.

Warren et al. (Mar. 17, 2023) "Efficacy and Safety of Orismilast in Patients with Moderate-to-Severe Psoriasis: Results from the Phase IIb IASOS Trial", Annual Meeting of the American Academy of Dermatology, 12 pages.

Warren et al. (Apr. 2023) "Oral Orismilast: Efficacy and Safety in Moderate-To-Severe Psoriasis and Development of Modified Release Tables", Journal of the European Academy of Dermatology and Venereology, 37(4):711-720.

Warren et al. (Mar. 1, 2024) "Orismilast in Moderate-To-Severe Psoriasis: Efficacy and Safety From a 16-Week, Randomized, Double-Blinded, Placebo-Controlled, Dose-Finding, and Phase 2b Trial (IASOS)", Journal of the American Academy of Dermatology, 90(3):494-503.

Weber et al. (Jun. 2017) "Apremilast in the Treatment of Moderate to Severe Hidradenitis Suppurativa: A Case Series of 9 Patients", Journal of the American Academy Dermatology, 76(6):1189-1191.

Weifeng et al. (2017) "Pharmaceutical Professional Knowledge", 11th Edition, China Medical Science and Technology Press, 6 pages.

Wolk et al. (Nov. 2017) "Lipocalin-2 is Expressed by Activated Granulocytes and Keratinocytes in Affected Skin and Reflects Disease Activity in Acne Inversa/Hidradenitis Suppurativa", British Journal of Dermatology, 177(5):1385-1393.

Wollenberg et al. (Dec. 2020) "ETFAD/EADV Eczema Task Force 2020 Position Paper on Diagnosis and Treatment of Atopic Dermatitis in Adults and Children", Journal of the European Academy of Dermatology and Venereology, 34(12):2717-2744.

Zigmond et al. (1983) "The Hospital Anxiety and Depression Scale", Acta Psychiatrica Scandinavica, 67(6):361-370.

Zouboulis et al. (2017) "Development and validation of the International Hidradenitis Suppurativa Severity Score System (IHS4), A Novel Dynamic Scoring System to Assess HS Severity", The British Journal of Dermatology, 177(5):1401-1409.

Chaumeil et al., "Micronization: a method of improving the bioavailability of poorly soluble drugs," Methods and Findings in Experimental and Clinical Pharmacology 1998, 20(3), 211-215.

Teckoe et al., "Process Optimization of a Novel Immediate Release Film Coating System using QbD Principles," AAPS PharmSciTech, 2013, 14, 531-540.

Dow (2007) *Using METHOCEL Cellulose Ethers for Controlled Release of Drugs in Hydrophilic Matrix Systems* [Brochure] n.p.

\* cited by examiner

| Parameter | Age Group | Dose | Mean (SD) | GM (CV%) | Min | Median (P5; P95) | Max |
|---|---|---|---|---|---|---|---|
| AUC$_{\tau=ss}$ (h·ng/mL) | 12 - 17 years | 10 mg | 242 (99.3) | 224 (70.5) | 69.2 | 229 (114; 409) | 781 |
| | | 20 mg | 478 (180) | 446 (67.1) | 153 | 450 (244; 827) | 1059 |
| | | 30 mg | 710 (269) | 663 (67.2) | 253 | 679 (355; 1257) | 1747 |
| | | 40 mg | 986 (395) | 913 (69.9) | 310 | 924 (454; 1764) | 2249 |
| | Adult | 10 mg | 172 (72.1) | 159 (68.5) | 60.5 | 160 (84.5; 303) | 502 |
| | | 20 mg | 341 (116) | 323 (62.2) | 119 | 311 (201; 571) | 751 |
| | | 30 mg | 506 (181) | 477 (64.2) | 185 | 485 (259; 845) | 1226 |
| | | 40 mg | 722 (282) | 672 (67.7) | 248 | 658 (368; 1243) | 2136 |

$\tau = 12h$

| Parameter | Age Group | Dose | N | Mean (SD) | GM (CV%) | Min | Median (P5; P95) | Max |
|---|---|---|---|---|---|---|---|---|
| AUC∞ (h·ng/mL) | Reference (< 100 kg) | 10 mg | 200 | 172 (72.1) | 159 (68.5) | 60.5 | 160 (84.5; 303) | 502 |
| | | 20 mg | 200 | 341 (116) | 323 (62.2) | 119 | 311 (201; 573) | 751 |
| | | 30 mg | 200 | 506 (181) | 477 (64.2) | 185 | 485 (259; 849) | 1226 |
| | | 40 mg | 200 | 722 (282) | 672 (67.7) | 248 | 658 (368; 1243) | 2136 |
| | Group 1 (100-109 kg) | 10 mg | 87 | 149 (52.7) | 141 (60.9) | 84.1 | 131 (95.1; 253) | 316 |
| | | 20 mg | 89 | 299 (106) | 280 (66.2) | 105 | 282 (155; 507) | 552 |
| | | 30 mg | 68 | 392 (133) | 373 (59.4) | 224 | 355 (235; 652) | 948 |
| | | 40 mg | 108 | 580 (183) | 551 (61.9) | 229 | 569 (293; 903) | 1202 |
| | Group 2 (110-119 kg) | 10 mg | 109 | 138 (50.0) | 130 (64.9) | 55.0 | 128 (75.6; 222) | 332 |
| | | 20 mg | 105 | 267 (98.3) | 252 (64.5) | 104 | 247 (151; 449) | 613 |
| | | 30 mg | 115 | 409 (123) | 392 (59.2) | 164 | 383 (239; 618) | 845 |
| | | 40 mg | 91 | 554 (185) | 525 (63.0) | 241 | 528 (285; 878) | 1093 |
| | Group 3 (120-129 kg) | 10 mg | 93 | 125 (37.2) | 119 (60.1) | 59.2 | 118 (68.1; 198) | 220 |
| | | 20 mg | 108 | 241 (67.7) | 231 (58.6) | 92.9 | 237 (142; 345) | 446 |
| | | 30 mg | 113 | 373 (105) | 358 (57.7) | 176 | 361 (220; 577) | 620 |
| | | 40 mg | 106 | 506 (153) | 485 (58.3) | 262 | 481 (286; 807) | 1070 |
| | Group 4 (130-139 kg) | 10 mg | 105 | 119 (39.1) | 113 (61.6) | 54.4 | 111 (67.9; 193) | 217 |
| | | 20 mg | 97 | 231 (67.0) | 221 (58.6) | 94.9 | 221 (131; 346) | 441 |
| | | 30 mg | 108 | 351 (121) | 331 (63.6) | 155 | 333 (168; 591) | 748 |
| | | 40 mg | 92 | 497 (157) | 474 (60.3) | 227 | 471 (288; 801) | 979 |
| | Group 5 (140-150 kg) | 10 mg | 108 | 109 (43.4) | 101 (66.8) | 44.9 | 99.8 (55.9; 183) | 308 |
| | | 20 mg | 101 | 237 (79.6) | 224 (63.7) | 102 | 223 (128; 366) | 460 |
| | | 30 mg | 96 | 353 (125) | 331 (66.8) | 117 | 333 (172; 588) | 704 |
| | | 40 mg | 103 | 462 (147) | 438 (61.4) | 191 | 436 (253; 746) | 846 |

| Parameter | Age Group | Dose | N | Mean (SD) | GM (CV%) | Min | Median (P5; P95) | Max |
|---|---|---|---|---|---|---|---|---|
| $C_{max,ss}$ (ng/mL) | Reference (< 100 kg) | 10 mg | 200 | 30.1 (10.8) | 28.4 (63.4) | 11.7 | 27.6 (17.6; 50.0) | 70.3 |
| | | 20 mg | 200 | 61.2 (17.6) | 58.7 (57.7) | 23.9 | 58.2 (36.0; 93.8) | 128 |
| | | 30 mg | 200 | 92.0 (27.9) | 87.9 (60.0) | 36.0 | 90.3 (51.6; 137) | 194 |
| | | 40 mg | 200 | 124 (37.2) | 119 (59.7) | 47.3 | 119 (72.0; 188) | 254 |
| | Group 1 (100-109 kg) | 10 mg | 87 | 25.2 (6.45) | 24.5 (52.0) | 15.6 | 24.1 (17.5; 39.6) | 45.2 |
| | | 20 mg | 89 | 50.8 (14.0) | 48.9 (57.5) | 19.1 | 50.5 (30.5; 76.0) | 84.8 |
| | | 30 mg | 68 | 69.9 (18.0) | 67.8 (52.8) | 41.6 | 65.5 (45.1; 102) | 136 |
| | | 40 mg | 108 | 100 (25.2) | 96.8 (54.9) | 45.3 | 98.0 (58.1; 144) | 194 |
| | Group 2 (110-119 kg) | 10 mg | 109 | 23.5 (6.54) | 22.6 (56.9) | 9.71 | 22.5 (14.4; 35.0) | 40.6 |
| | | 20 mg | 105 | 46.6 (13.1) | 44.8 (57.1) | 19.6 | 44.6 (28.9; 73.9) | 87.5 |
| | | 30 mg | 115 | 70.4 (16.4) | 68.4 (52.0) | 32.6 | 68.9 (44.8; 98.5) | 117 |
| | | 40 mg | 91 | 94.3 (25.9) | 90.9 (56.2) | 43.9 | 92.3 (56.1; 146) | 174 |
| | Group 3 (120-129 kg) | 10 mg | 93 | 21.5 (5.30) | 20.8 (54.2) | 10.7 | 20.9 (12.7; 30.7) | 34.7 |
| | | 20 mg | 108 | 40.9 (9.08) | 39.9 (51.4) | 16.2 | 41.2 (27.7; 53.8) | 75.0 |
| | | 30 mg | 113 | 63.9 (14.4) | 62.3 (50.4) | 33.0 | 62.4 (40.9; 89.0) | 108 |
| | | 40 mg | 106 | 86.6 (20.8) | 84.2 (51.5) | 46.0 | 83.4 (56.5; 123) | 155 |
| | Group 4 (130-139 kg) | 10 mg | 105 | 20.1 (4.98) | 19.5 (52.5) | 10.3 | 19.3 (13.1; 29.6) | 35.9 |
| | | 20 mg | 97 | 39.6 (9.21) | 38.6 (52.3) | 17.9 | 39.2 (24.1; 54.4) | 65.6 |
| | | 30 mg | 108 | 59.1 (14.7) | 57.2 (54.1) | 28.1 | 56.6 (33.0; 84.9) | 101 |
| | | 40 mg | 92 | 84.4 (21.0) | 81.9 (52.6) | 45.0 | 82.8 (53.6; 129) | 150 |
| | Group 5 (140-150 kg) | 10 mg | 106 | 18.4 (5.09) | 17.7 (56.6) | 8.94 | 18.1 (11.1; 27.1) | 36.1 |
| | | 20 mg | 101 | 38.8 (9.84) | 37.6 (54.0) | 19.9 | 36.8 (24.2; 56.9) | 65.8 |
| | | 30 mg | 98 | 58.7 (15.3) | 56.5 (57.4) | 22.5 | 58.7 (34.1; 89.8) | 97.0 |
| | | 40 mg | 103 | 76.5 (19.3) | 74.2 (53.0) | 38.1 | 73.2 (49.4; 115) | 127 |

FIG. 23B

| Parameter | Age Group | Dose | N | Mean (SD) | GM (CV%) | Min | Median (P5; P95) | Max |
|---|---|---|---|---|---|---|---|---|
| $C_{trough,ss}$ (ng/mL) | Reference (< 100 kg) | 10 mg | 200 | 30.1 (10.8) | 28.4 (63.4) | 11.7 | 27.6 (17.6; 50.0) | 70.3 |
| | | 20 mg | 200 | 61.2 (17.6) | 58.7 (57.7) | 23.9 | 58.2 (36.0; 93.8) | 128 |
| | | 30 mg | 200 | 92.0 (27.9) | 87.9 (60.0) | 36.0 | 90.3 (51.6; 137) | 194 |
| | | 40 mg | 200 | 124 (37.2) | 119 (59.7) | 47.3 | 119 (72.0; 188) | 254 |
| | Group 1 (100-109 kg) | 10 mg | 87 | 25.2 (6.45) | 24.5 (52.0) | 15.6 | 24.1 (17.5; 39.6) | 45.2 |
| | | 20 mg | 89 | 50.8 (14.0) | 48.9 (57.5) | 19.1 | 50.5 (30.5; 76.0) | 84.8 |
| | | 30 mg | 68 | 69.9 (18.0) | 67.8 (52.8) | 41.6 | 65.5 (45.1; 102) | 136 |
| | | 40 mg | 108 | 100 (25.2) | 96.8 (54.9) | 45.3 | 98.0 (58.1; 144) | 194 |
| | Group 2 (110-119 kg) | 10 mg | 109 | 23.5 (6.54) | 22.6 (56.9) | 9.71 | 22.5 (14.4; 35.0) | 40.6 |
| | | 20 mg | 105 | 46.6 (13.1) | 44.8 (57.1) | 19.6 | 44.6 (28.9; 73.9) | 87.5 |
| | | 30 mg | 115 | 70.4 (16.4) | 68.4 (52.0) | 32.6 | 68.9 (44.8; 98.5) | 117 |
| | | 40 mg | 91 | 94.3 (25.9) | 90.9 (56.2) | 43.9 | 92.3 (56.1; 146) | 174 |
| | Group 3 (120-129 kg) | 10 mg | 93 | 21.5 (5.30) | 20.8 (54.2) | 10.7 | 20.9 (12.7; 30.7) | 34.7 |
| | | 20 mg | 108 | 40.9 (9.08) | 39.9 (51.4) | 16.2 | 41.2 (27.7; 53.8) | 75.0 |
| | | 30 mg | 113 | 63.9 (14.4) | 62.3 (50.4) | 33.0 | 62.4 (40.9; 89.0) | 108 |
| | | 40 mg | 106 | 86.6 (20.8) | 84.2 (51.5) | 46.0 | 83.4 (56.5; 123) | 155 |
| | Group 4 (130-139 kg) | 10 mg | 105 | 20.1 (4.98) | 19.5 (52.5) | 10.3 | 19.3 (13.1; 29.6) | 35.9 |
| | | 20 mg | 97 | 39.6 (9.21) | 38.6 (52.3) | 17.9 | 39.2 (24.1; 54.4) | 65.6 |
| | | 30 mg | 108 | 59.1 (14.7) | 57.2 (54.1) | 28.1 | 56.6 (33.0; 84.9) | 101 |
| | | 40 mg | 92 | 84.4 (21.0) | 81.9 (52.6) | 45.0 | 82.8 (53.6; 129) | 150 |
| | Group 5 (140-150 kg) | 10 mg | 106 | 18.4 (5.09) | 17.7 (56.6) | 8.94 | 18.1 (11.1; 27.1) | 36.1 |
| | | 20 mg | 101 | 38.8 (9.84) | 37.6 (54.0) | 19.9 | 36.8 (24.2; 56.9) | 65.8 |
| | | 30 mg | 96 | 58.7 (15.3) | 56.5 (57.4) | 22.5 | 58.7 (34.1; 89.8) | 97.0 |
| | | 40 mg | 103 | 76.5 (19.3) | 74.2 (53.0) | 38.1 | 73.2 (49.4; 115) | 127 |

FIG. 24B

DOSAGE REGIMEN

This invention relates to orismilast for use in the treatment a disease or disorder ameliorated by inhibiting PDE4 in a subject, wherein the orismilast is administered to the subject according to a specific dosage regimen.

BACKGROUND

Phosphodiesterases (PDEs) constitute a superfamily of enzymes catalysing the hydrolysis of the intracellular secondary messengers cyclic adenosine monophosphate (cAMP) and cyclic guanosine monophosphate that play key roles in mediating biological responses generated by a variety of extracellular signals. Eleven families of PDE enzymes have been identified, with the PDE4 family constituting 4 subtypes (A-D) and more than 20 isoforms (Houslay M D, et al., "Keynote review: phosphodiesterase-4 as a therapeutic target", Drug Discov Today; 2005, 10(22): 1503-1519 2005). PDEs represent the only cellular pathway for the degradation of cyclic nucleotides, which emphasizes their critical role in the regulation of the intracellular levels of these secondary messengers and, consequently, various functional responses of cells (Dastidar S G et al., "Therapeutic benefit of PDE4 inhibitors in inflammatory diseases". Curr Opin Investig. Drugs. 2007; 8(5):364-372). PDE4 is a cAMP-specific PDE expressed by immune and inflammatory cells, including T-lymphocytes, neutrophils, eosinophils, monocytes, dendritic cells, and macrophages (Spina et al., "PDE4 inhibitors: current status"; Br. J. Pharmacol. 2008; 155(3):308-315). In these cells, PDE4 is the predominant PDE form, and PDE4 inhibitors increase cAMP levels. High intracellular cAMP levels down-regulate inflammatory activity and up-regulate anti-inflammatory activity resulting in, for example, decreased proliferation and cytokine production, whereas low cAMP concentrations have the opposite effect. Accordingly, inhibition of PDE4 up-regulates anti-inflammatory cytokines, for example IL-10, and down-regulates inflammatory cytokines, for example one or more of TNF-α, IFN-γ, IL-5, IL-8, IL-13, IL-17, IL-22 and/or IL-23 (Samrao A et al., Arch Dermatol 2012; 148(8):890-897; and Li H et al., "Phosphodiesterase-4 Inhibitors for the Treatment of Inflammatory Diseases, Front. Pharmacol 2018; 9:1048)

PDE4 inhibitors demonstrate potent effects in inflammatory diseases, neurological disorders (e.g. cognitive impairment, depression, psychosis, schizophrenia and Alzheimer's disease), cancer, metabolic disease, and dermatological conditions (Paes et al., "The Molecular Biology of Phosphodiesterase 4 Enzymes as Pharmacological Targets: An Interplay of Isoforms, Conformational States, and Inhibitors"; Pharmacol Rev. 2021; 73(3):1016-1049; Richter et al., "PDE4 as a target for cognition enhancement", Expert Opin Ther Targets. 2013 September; 17(9):1011-27; Li et al., supra; and Lugnier et al., "Cyclic nucleotide phosphodiesterases: New targets in the metabolic syndrome≥" Pharmacol Ther. 2020.

Inhibition of PDE4 has therapeutic potential in the treatment of psoriasis and other skin diseases with an immunoinflammatory component (Dastidar et al. supra). In allergic skin disease, PDE4 inhibitors inhibit the migration of skin dendritic cells, and this inhibition is accompanied by an inhibition of matrix metalloproteinase 9 activity in epidermis and dermis. Furthermore, cytokine secretion (tumour necrosis factor [TNF]-α, IL-1β and IL-12) of human dendritic cells is inhibited by PDE4 inhibitors and an inhibition of T cell activation is also demonstrated in vitro. Both T helper (Th)1 and Th2 cytokines are reduced by PDE4 inhibitors in vitro and in inflamed murine skin (Jin S L et al., Phosphodiesterase 4 and its inhibitors in inflammatory diseases. Chang Gung Med J. 2012; 35(3):197-210).

Increased cAMP-PDE activity has been reported in patients with atopic dermatitis. Using immunohistochemistry staining, PDE4 isoforms PDE4A, PDE4B, PDE4C and PDE4D have also been observed to be increased in dermal fibroblasts of skin samples of patients with atopic dermatitis. PDE4 inhibitors are therefore expected to be useful in the treatment of atopic dermatitis (Guttman-Yassky et al., The role of phosphodiesterase 4 in the pathophysiology of atopic dermatitis and the perspective for its inhibition, Experimental Dermatology, 2019; 28:3-10).

Several PDE4-specific inhibitors are in late stages of clinical development or have recently been marketed. For example, the oral PDE4 inhibitor roflumilast (Daxas®/Daliresp®) is approved in the United States and Europe to reduce the risk of exacerbation in patients with chronic obstructive pulmonary disease and chronic bronchitis (Roflumilast Summary of Product Characteristics). The oral PDE4 inhibitor apremilast (Otezla®) is approved in the United States and Europe for multiple indications including psoriatic arthritis and psoriasis (Apremilast Summary of Product Characteristics) and it has been studied for atopic dermatitis and other chronic inflammatory diseases (Samrao A et al., Arch Dermatol. 2012; 148(8):890-897).

One of the key challenges for an effective oral PDE4 therapy has been the narrow therapeutic window. Most of the programs investigating PDE4 inhibitors failed because of safety issues, and there are currently only two approved oral PDE4 inhibitors available, roflumilast and apremilast. However, both of these therapies have tolerability issues affecting, primarily but not exclusively, the gastrointestinal (GI) tract, characterized by nausea and diarrhoea. These undesired GI effects were consistently observed from the beginning of treatment, and this led to the titration of those drugs if an attempt to reduce or mitigate undesirable side effects. Apremilast is administered orally twice daily at a starting dose of 10 mg and the twice daily dose is increased to 30 mg over a week (Apremilast Summary of Product Characteristics). Roflumilast is administered orally at a starting dose of 250 μg once daily for 28 days followed by a maintenance dose of 500 μg once per day (Roflumilast Summary of Product Characteristics). However, despite dose titration, GI side effects are still experienced by some patients such as diarrhoea, nausea, abdominal pain.

Orismilast, 2-(3,5-dichloro-1-oxidopyridin-1-ium-4-yl)-1-[7-(difluoromethoxy)-1',1'-dioxospiro[1,3-benzodioxole-2,4'-thiane]-4-yl]ethanone, is a potent and selective PDE4 inhibitor of the formula:

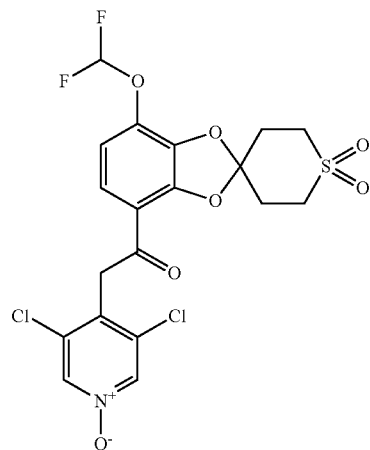 [SMILES: O=C(Cc1c(Cl)c[n+]([O-])cc1Cl)c1ccc(OC(F)F)c2c1OC1(CCS(=O)(=O)CC1)O2]

Orismilast is disclosed in WO 2011/160632 and is a selective PDE4 inhibitor and is a potent inhibitor of PDE4B and PDE4D subtype splice variants in vitro. When tested in vitro Orismilast inhibited human whole blood and human peripheral blood mononuclear cells PBMC production of tumour necrosis factor α (TNFα), and the secretion of T-helper (Th)1 (TNFα and IFNγ), Th17 (IL-22 and IL-23), and Th2 (IL-4, IL-5, and IL-13) related cytokines in PBMC. In vivo, 10 and 30 mg/kg doses of orismilast significantly reduced ear thickness and inflammation markers in a murine model of chronic oxazolone-induced ear skin inflammation (Silverberg J I et al., Pharmacology of orismilast, a potent and selective PDE4 inhibitor. J Eur Acad Dermatol Venereol. 2023; 37(4):721-729).

In a phase 2a prospective, randomized, double-blind, placebo-controlled clinical trial (NCT02888236), patients with moderate-to-severe psoriasis were randomized to receive 30 mg twice per day orally in the form of an immediate release (IR) formulation or placebo over 16 weeks. Treatment with orismilast IR significantly improved the mean Psoriasis Area Severity Index score at week 16 compared to placebo (Warren R B et al., Oral orismilast: Efficacy and safety in moderate-to-severe psoriasis and development of modified release tablets; J. Eur. Acad. Dermatol Venereol. 2023; 37(4):711-720).

WO2020/148271 discloses a modified release (MR) formulation comprising orismilast. The safety, tolerability, and PK of orismilast MR and IR formulations were tested in a phase 1 clinical trial (NCT03812198) on healthy volunteers. Participants were randomised (3:1) to received orismilast MR or placebo (n=12). Orismilast MR was administered twice-daily for a total of 17 days. Orismilast MR was initiated at 10 mg twice-daily on days 1-2, increased to 20 mg twice-daily on days 3-4, to 30 mg twice-daily on days 5-6, to 40 mg twice-daily on days 7-8, to 50 mg twice-daily on days 9-10, and finally to 60 mg twice-daily on days 11-17. The orismilast MR formulation achieved comparable PK properties to orismilast IR, however, fewer participants in the MR formulation group (16.7%) reported GI disorders compared to the IR formulation group (33.3%) (Warren et al., supra).

In a phase 2b study including 202 patients with moderate to severe plaque type psoriasis were randomized and treated for 16 weeks with a MR orismilast tablet formulation at orismilast doses of 20 mg twice-daily (BID), 30 mg BID, 40 mg BID. A statistically significant treatment effect was observed for all doses of orismilast versus placebo (Warren R et al., Efficacy and Safety of Orismilast in Patients with Moderate-to-Severe Psoriasis: Results from the Phase IIb IASOS Trial. Paper presented at: American Academy of Dermatology 2023 Annual Meeting; March 17-21. New Orleans, LA).

WO 2022/200339 discloses orismilast for the treatment of hidradenitis suppurativa (HS) and described a phase 2a clinical trial in which a modified release formulation of orismilast which includes a dose titration over an initial two week period with progressive increase in dose from 10 mg twice daily (BID) to 30 mg BID.

Despite the improvements in gastro-intestinal side effects obtained using the modified release formulation of orismilast, there remains a need for improved treatments that improve tolerability and/or efficacy of orismilast.

BRIEF SUMMARY OF THE DISCLOSURE

As described in more detail in the Examples herein, an analysis of phase 2b clinical trial data from a study on subjects with moderate to severe psoriasis treated orally with orismilast has revealed that the body mass of the subject has a significant impact on treatment efficacy. Subjects with a body mass greater than or equal to 100 kg treated with 30 mg orismilast twice daily resulted in more efficacious treatment compared to subjects with a body mass of less than 100 kg treated with the same dose. This was unexpected because analysis of PK data shows that subjects with a body mass of less than 100 kg had a higher systemic exposure to orismilast compared to subjects with a body mass of greater than or equal to 100 kg. The higher systemic exposure in the lighter subjects would have been expected to achieve better treatment efficacy than subjects weighing more than 100 kg, whereas the opposite was observed.

There is therefore a need for an orismilast dosage regimen which is correlated with the body mass of the subject to optimise treatment efficacy and/or tolerability.

According to a first aspect of the invention there is provided orismilast for use in a method of treating a disease or disorder ameliorated by inhibiting PDE4 in a subject, the method comprising administering the orismilast to the subject, wherein:
 (Ai) an initial orismilast dose is administered to the subject once per day for an initial time period followed by;
 (Aii) an interim orismilast dose administered to the subject twice per day for an interim time period followed by;
 (Aiii) a maintenance orismilast dose administered to the subject twice per day; wherein:
 (a) the initial orismilast dose and the interim orismilast dose are independently selected from 10 mg to 30 mg orismilast, provided that the interim orismilast dose is greater than or equal to the initial orismilast dose;
 (b) the initial time period is two to eight weeks;
 (c) the interim time period is one to eight weeks; and
 (d) the maintenance orismilast dose is greater than the interim orismilast dose when the subject has a body mass that is greater than or equal to a threshold body mass, wherein the threshold body mass is at least 90 kg.

In certain embodiments the initial time period in (Ai) is two weeks to six weeks. In certain embodiments the initial time period in (Ai) is two weeks to four weeks. In certain embodiments the initial time period in (Ai) is two weeks to up to four weeks. In certain embodiments the initial time period in (Ai) is two weeks, four weeks or six weeks. In certain embodiments the initial time period in (Ai) is three weeks. In certain embodiments the initial time period in (Ai) is four weeks. Preferably the initial time period in (Ai) is two weeks.

In certain embodiments the interim time period in (Ai) is up to eight weeks. In certain embodiments the interim time period in (Aii) is up to six weeks. In certain embodiments the interim time period in (Aii) is up to four weeks. In certain embodiments the interim time period in (Aii) is from one week to eight weeks. In certain embodiments the interim time period in (Aii) is from six weeks to eight weeks In certain embodiments the interim time period in (Ai) is from one week to six weeks. In certain embodiments the interim time period in (Aii) is from four weeks to six weeks In certain embodiments the interim time period in (Aii) is from one week to four weeks. In certain embodiments the interim time period in (Aii) is from one week to three weeks. In certain embodiments the interim time period in (Aii) is from one week to two weeks.

In certain embodiments the interim time period in (Aii) is two weeks, four weeks or six weeks. In certain embodiments the interim time period in (Aii) is one week. In certain embodiments the interim time period in (Aii) is two weeks.

In certain embodiments the interim time period in (Aii) is four weeks. In certain embodiments the interim time period in (Aii) is six weeks. In certain embodiments the interim time period in (Aii) is eight weeks.

In certain embodiments the initial time period in (Ai) is two weeks and the interim period in (Aii) is from four weeks to eight weeks. In certain embodiments the initial time period in (Ai) is two weeks and the interim period in (Aii) is up to eight weeks. In certain embodiments the initial time period in (Ai) is two weeks and the interim period in (Aii) is up to six weeks. In certain embodiments the initial time period in (Ai) is two weeks and the interim period in (Aii) is from four weeks to six weeks. In certain embodiments the initial time period in (Ai) is two weeks and the interim period in (Aii) is from six weeks to eight weeks. In certain embodiments the initial time period in (Ai) is two weeks and the interim period in (Aii) is from one week to four weeks. In certain embodiments the initial time period in (Ai) is two weeks and the interim period in (Aii) is two weeks. In preferred embodiment the initial time period in (Ai) is two weeks and the interim period in (Aii) is six weeks.

Analysis of clinical data has shown that most of the adverse events associated with orismilast treatment (e.g. diarrhoea, nausea, headache, dizziness or vomiting) had an onset during the initial four weeks of treatment and very few of these events had an onset after eight weeks of treatment. Accordingly, in certain embodiments the total duration of the initial time period and the interim time period is from four weeks to eight weeks. In certain embodiments the total duration of the initial time period and the interim time period is four weeks. In certain embodiments the total duration of the initial time period and the interim time period is five weeks. In certain embodiments the total duration of the initial time period and the interim time period is six weeks. In certain embodiments the total duration of the initial time period and the interim time period is seven weeks. In certain embodiments the total duration of the initial time period and the interim time period is eight weeks.

Analysis of a phase 2b clinical trial data across all subjects treated with orismilast without stratifying the patients based on body mass found that the efficacy of 20 mg orismilast administered twice a day was comparable to the efficacy of 30 mg orismilast administered twice per day in the first 8 weeks of treatment for the treatment of moderate to severe plaque psoriasis. Accordingly, the dose titration during the initial and interim time periods using low doses of orismilast (for example 10 mg or particularly 20 mg) of orismilast are expected to provide therapeutic effects whilst also minimising undesirable side effects during the initial period of treatment, particularly in the first 4 to 8 weeks or treatment.

In certain embodiments the maintenance orismilast dose in (Aiii) is the same as the interim orismilast dose when the subject has a body mass which is less than the threshold body mass.

In certain embodiments the maintenance orismilast dose in (Aiii) is up to 40 mg orismilast when the subject has a body mass which is greater than or equal to the threshold body mass, provided the maintenance orismilast dose is greater than the interim orismilast dose. For example, it may be that the maintenance orismilast does is 30 mg to 40 mg orismilast. Preferably, the maintenance orismilast does is 30 mg when the subject has a body mass which is greater than or equal to the threshold body mass.

In certain embodiments the maintenance orismilast dose in (Aiii) is 30 mg orismilast when the subject has a body mass which is greater than or equal to the threshold body mass and the interim orismilast dose is less than 30 mg. For example, the interim orismilast dose is 10 mg to 25 mg orismilast. In certain embodiments the maintenance orismilast dose is 30 mg orismilast and the interim orismilast dose is 10 mg orismilast. In certain embodiments when the subject has a body mass which is greater than or equal to the threshold body mass the maintenance orismilast dose is 30 mg orismilast and the interim orismilast dose is 20 mg orismilast.

As described in the Examples herein, analysis of phase 2b clinical data in subjects with moderate to severe psoriasis has revealed that subjects with a body mass that is less than the threshold body mass (e.g. less than 100 kg) treated with orismilast doses greater than 20 mg did not benefit from increased treatment efficacy despite the fact that the subjects had a higher systemic exposure to orismilast at the higher doses. Moreover, this data suggests that doses greater than 20 mg in subjects with a body mass below the threshold body mass may reduce treatment efficacy.

Accordingly, in certain embodiments the interim orismilast dose in (Aii) and the maintenance orismilast dose in (Aiii) are both 20 mg orismilast when the subject has a body mass which is less than the threshold body mass. In certain embodiments the initial orismilast dose in (Ai) is 10 mg or 20 mg; and the interim orismilast dose in (Aii) and the maintenance orismilast dose in (Aiii) are both 20 mg orismilast when the subject has a body mass which is less than the threshold body mass. In certain embodiments the initial orismilast dose in (Ai), the interim orismilast dose in (Aii) and the maintenance orismilast dose in (Aiii) are all 20 mg orismilast when the subject has a body mass which is less than the threshold body mass. In certain embodiments the initial orismilast dose in (Ai) is 10 mg, and the interim orismilast dose in (Aii) and the maintenance orismilast dose in (Aiii) are both 20 mg orismilast when the subject has a body mass which is less than the threshold body mass. In certain embodiments the initial orismilast dose in (Ai) is 10 mg, the interim orismilast dose in (Aii) is 10 mg and the maintenance orismilast dose in (Aiii) is 10 mg orismilast when the subject has a body mass which is less than the threshold body mass.

Through population PK modelling based on clinical data together with analysis of the efficacy and tolerability data, the inventors have identified that 10 mg orismilast administered twice per day is expected to be an optimal orismilast maintenance dose to maximise efficacy and tolerability in subjects with a body mass that is less than a lower limit body mass, wherein the lower limit body mass is from 50 kg to 75 kg. For example where the subject has a lower limit body mass of 60 kg.

Accordingly, in certain embodiments when the subject has a body mass that is less than a lower limit body mass the initial orismilast dose in (Ai), the interim orismilast dose in (Aii) and the maintenance orismilast dose in (Aiii) are all 10 mg orismilast, wherein the lower limit body mass is from 50 kg to 75 kg. For example where the subject has a lower limit body mass of 60 kg.

In some embodiments an optimum orismilast maintenance dose is 20 mg administered twice per day when the subject has a body mass that is in the range of from a lower limit body mass to less than the threshold body mass.

Accordingly, in certain embodiments when the subject has a body mass that is in the range of from a lower limit body mass to less than the threshold body mass, the initial orismilast dose in (Ai), the interim orismilast dose in (Aii) and the maintenance orismilast dose in (Aiii) are all 20 mg orismilast, wherein the lower limit body mass is from 50 kg to 75 kg. For example where the subject has a lower limit body mass of 60 kg.

In some embodiments of the first aspect of the invention:
(i) when the subject has a body mass that is less than a lower limit body mass, the initial orismilast dose in (Ai), the interim orismilast dose in (Aii) and the maintenance orismilast dose in (Aiii) are all 10 mg orismilast; or
(ii) when the subject has a body mass that is in the range of from the lower limit body mass to less than the threshold body mass, the initial orismilast dose in (Ai), the interim orismilast dose in (Aii) and the maintenance orismilast dose in (Aiii) are all 20 mg orismilast;
wherein the lower limit body mass is from 50 kg to 75 kg. For example where the subject has a lower limit body mass of 60 kg.

In some embodiments the lower limit body mass is 50 kg. In some embodiments the lower limit body mass is 55 kg. In some embodiments the lower limit body mass is 60 kg. In some embodiments the lower limit body mass is 65 kg. In some embodiments the lower limit body mass is 70 kg. In some embodiments the lower limit body mass is 75 kg.

In certain embodiments when the subject has a body mass that is less than 75 kg the initial orismilast dose in (Ai), the interim orismilast dose in (Aii) and the maintenance orismilast dose in (Aiii) are all 10 mg orismilast.

In certain embodiments when the subject has a body mass that is less than 60 kg the initial orismilast dose in (Ai), the interim orismilast dose in (Aii) and the maintenance orismilast dose in (Aiii) are all 10 mg orismilast.

In certain embodiments when the subject has a body mass that is less than 50 kg the initial orismilast dose in (Ai), the interim orismilast dose in (Aii) and the maintenance orismilast dose in (Aiii) are all 10 mg orismilast.

In certain embodiments when the subject has a body mass that is in the range of from 75 kg to less than the threshold body mass the initial orismilast dose in (Ai), the interim orismilast dose in (Aii) and the maintenance orismilast dose in (Aiii) are all 20 mg orismilast.

In certain embodiments when the subject has a body mass that is in the range of from 60 kg to less than the threshold body mass, the initial orismilast dose in (Ai), the interim orismilast dose in (Aii) and the maintenance orismilast dose in (Aiii) are all 20 mg orismilast.

In certain embodiments when the subject has a body mass that is in the range of from 50 kg to less than the threshold body mass, the initial orismilast dose in (Ai), the interim orismilast dose in (Aii) and the maintenance orismilast dose in (Aiii) are all 20 mg orismilast.

As set out in the Examples herein, analysis of clinical trial data has identified that administration of orismilast according to the dosage regimens described herein provide improved tolerability and/or treatment efficacy compared to administering orismilast in a twice daily fixed dose regimen. In particular, the inventors have identified that subjects which have a body mass greater than or equal to the threshold body mass show improved tolerability and/or treatment response to orismilast when the maintenance orismilast dose is higher than the interim orismilast dose when following the dosage regimen described herein. More particularly, it has been found that subjects which have a body mass greater than the threshold bodyweight were less likely to experience side-effects that led to discontinuation of treatment when receiving a higher maintenance dose compared to lighter subjects with a body weight less than the threshold body mass.

Accordingly, a second aspect of the invention provides orismilast for use in a method of treating a disease or disorder ameliorated by inhibiting PDE4 in a subject with a body mass that is greater than or equal to a threshold body mass, the method comprising administering the orismilast to the subject, wherein:
(Bi) an initial orismilast dose is administered to the subject once per day for a preliminary time period followed by;
(Bii) a interim orismilast dose administered to the subject twice per day for an interim time period followed by;
(Biii) a maintenance orismilast dose administered to the subject twice per day, wherein the maintenance orismilast dose is greater than the interim orismilast dose;
wherein:
(a) the initial orismilast dose and the interim orismilast doses are independently selected from 10 mg to 30 mg orismilast, provided that the interim orismilast dose is greater than or equal to the initial orismilast dose;
(b) the preliminary time period is up to eight weeks;
(c) the interim time period is one week to eight weeks; and
(d) the threshold body mass is at least 90 kg.

In certain embodiments the preliminary time period in (Bi) is one day to eight weeks. In certain embodiments preliminary time period in (Bi) is two days to eight weeks. In certain embodiments the preliminary time period in (Bi) is four days to eight weeks In certain embodiments the preliminary time period in (Bi) is five days to eight weeks. In certain embodiments the preliminary time period in (Bi) is six days to eight weeks, In certain embodiments the preliminary time period in (Bi) is one week to eight weeks. In certain embodiments the preliminary time period in (Bi) is one week to six weeks. In certain embodiments the preliminary time period in (Bi) is one week to four weeks. In certain embodiments the preliminary time period in (Bi) is one week to two weeks. In certain embodiments the preliminary time period in (Bi) is two days to eight weeks In certain embodiments the preliminary time period in (Bi) is one day. In certain embodiments the preliminary time period in (Bi) is two days. In certain embodiments the preliminary time period in (Bi) is three days. In certain embodiments the preliminary time period in (Bi) is four days. In certain embodiments the preliminary time period in (Bi) is five days. In certain embodiments the preliminary time period in (Bi) is six days. In certain embodiments the preliminary time period in (Bi) is one week, two weeks, three weeks or four weeks. In certain embodiments the preliminary time period in (Bi) is one week. In certain embodiments the preliminary time period in (Bi) is two weeks. In certain embodiments the preliminary time period in (Bi) is three weeks. In certain embodiments the preliminary time period in (Bi) is four weeks. In certain embodiments the preliminary time period in (Bi) is five weeks. In certain embodiments the preliminary time period in (Bi) is six weeks. In certain embodiments the preliminary time period in (Bi) is seven weeks. In certain embodiments the preliminary time period in (Bi) is eight weeks.

In certain embodiments the preliminary time period in (Bi) is two weeks to four weeks. In certain embodiments the preliminary time period in (Bi) is two weeks to up to four weeks. In certain embodiments the preliminary time period in (Bi) is two weeks, four weeks or six weeks. Preferably the preliminary time period in (Bi) is two weeks.

In certain embodiments the interim time period in (Bii) is one week. In certain embodiments the interim time period in (Bii) is two weeks, four weeks or six weeks. In certain embodiments the interim time period in (Bii) is two weeks.

In certain embodiments the interim time period in (Bii) is four weeks. In certain embodiments the interim time period in (Bii) is six weeks. In certain embodiments the interim time period in (Bii) is eight weeks.

In certain embodiments the interim time period in (Bii) is up to eight weeks. In certain embodiments the interim time period in (Bii) is up to six weeks. In certain embodiments the interim time period in (Bii) is up to four weeks. In certain embodiments the interim time period in (Bii) is from one week to eight weeks. In certain embodiments the interim time period in (Bii) is from six weeks to eight weeks In certain embodiments the interim time period in (Bii) is from one week to six weeks. In certain embodiments the interim time period in (Bii) is from four weeks to six weeks In certain embodiments the interim time period in (Bii) is from one week to four weeks. In certain embodiments the interim time period in (Bii) is from one week to three weeks. In certain embodiments the interim time period in (Bii) is from one week to two weeks.

In certain embodiments the preliminary time period in (Bi) is two weeks and the interim period in (Bii) is from four weeks to eight weeks. In certain embodiments the preliminary time period in (Bi) is two weeks and the interim period in (Bii) is up to eight weeks. In certain embodiments the preliminary time period in (Bi) is two weeks and the interim period in (Bii) is up to six weeks. In certain embodiments the preliminary time period in (Bi) is two weeks and the interim period in (Bii) is from four weeks to six weeks. In certain embodiments the initial time period in (Bi) is two weeks and the interim period in (Bii) is from six weeks to eight weeks. In certain embodiments the initial time period in (Bi) is two weeks and the interim period in (Bii) is from one week to four weeks. In certain embodiments the initial time period in (Bi) is two weeks and the interim period in (Bii) is two weeks. In preferred embodiment the initial time period in (Bi) is two weeks and the interim period in (Bii) is six weeks.

As discussed above, most of the adverse events associated with orismilast generally have an onset in the first four to eight weeks of orismilast administration. The frequency of adverse events was generally lower after the first eight weeks of treatment. In certain embodiments the total duration of the preliminary time period and the interim time period is from four weeks to eight weeks. In certain embodiments the total duration of the preliminary time period and the interim time period is four weeks. In certain embodiments the total duration of the preliminary time period and the interim time period is five weeks. In certain embodiments the total duration of the preliminary time period and the interim time period is six weeks. In certain embodiments the total duration of the preliminary time period and the interim time period is seven weeks. In certain embodiments the total duration of the preliminary time period and the interim time period is eight weeks.

In certain embodiments the maintenance orismilast dose in (Biii) is up to 40 mg orismilast, provided the maintenance orismilast dose is greater than the interim orismilast dose. For example it may be that the maintenance orismilast dose in (Biii) is 30 mg to 40 mg orismilast. In a preferred embodiment the maintenance orismilast dose in (Biii) is 30 mg orismilast.

In certain embodiments the maintenance orismilast dose in (Biii) is 30 mg orismilast and the interim orismilast dose in (Bii) is less than 30 mg. For example, the interim orismilast dose in (Bii) is 10 mg to 25 mg orismilast. In certain embodiments the maintenance orismilast dose in (Biii) is 30 mg orismilast and the interim orismilast dose in (Bii) is 10 mg orismilast. In certain embodiments the maintenance orismilast dose in (Biii) is 30 mg orismilast and the interim orismilast dose in (Bii) is 20 mg orismilast.

In certain embodiments of the second aspect of the invention the initial orismilast dose in (Bi) is 10 mg or 20 mg orismilast. In a preferred embodiment of the second aspect of the invention the initial orismilast dose in (Bi) is 20 mg orismilast.

In certain embodiments of the second aspect of the invention there is provided orismilast for use in a method of treating a disease or disorder ameliorated by inhibiting PDE4 in a subject with a body mass that is greater than or equal to a threshold body mass, the method comprising administering the orismilast to the subject, wherein:
  (Bi) an initial orismilast dose of 20 mg is administered to the subject once per day for two weeks followed by;
  (Bii) a interim orismilast dose of 20 mg administered to the subject twice per day for one week to eight weeks followed by;
  (Biii) a maintenance orismilast dose of 30 mg administered to the subject twice per day;
  wherein the threshold body mass is at least 90 kg.

In certain embodiments of the second aspect of the invention there is provided orismilast for use in a method of treating a disease or disorder ameliorated by inhibiting PDE4 in a subject with a body mass that is greater than or equal to a threshold body mass, the method comprising administering the orismilast to the subject,
  wherein:
  (Bi) an initial orismilast dose of 20 mg is administered to the subject once per day for two weeks followed by;
  (Bii) a interim orismilast dose of 20 mg administered to the subject twice per day for two weeks to eight weeks followed by;
  (Biii) a maintenance orismilast dose of 30 mg administered to the subject twice per day;
  wherein the threshold body mass is at least 90 kg.

In certain embodiments of the second aspect of the invention there is provided orismilast for use in a method of treating a disease or disorder ameliorated by inhibiting PDE4 in a subject with a body mass that is greater than or equal to a threshold body mass, the method comprising administering the orismilast to the subject,
  wherein:
  (Bi) an initial orismilast dose of 20 mg is administered to the subject once per day for two weeks followed by;
  (Bii) a interim orismilast dose of 20 mg administered to the subject twice per day for six weeks to eight weeks followed by;
  (Biii) a maintenance orismilast dose of 30 mg administered to the subject twice per day;
  wherein the threshold body mass is at least 90 kg.

In a preferred embodiment of the second aspect of the invention there is provided orismilast for use in a method of treating a disease or disorder ameliorated by inhibiting PDE4 in a subject with a body mass that is greater than or equal to a threshold body mass, the method comprising administering the orismilast to the subject,
  wherein:
  (Bi) an initial orismilast dose of 20 mg is administered to the subject once per day for two weeks followed by;
  (Bii) a interim orismilast dose of 20 mg administered to the subject twice per day for six weeks followed by;
  (Biii) a maintenance orismilast dose of 30 mg administered to the subject twice per day;
  wherein the threshold body mass is at least 90 kg.

In a third aspect of the invention there is provided orismilast for use in a method of treating a disease or disorder ameliorated by inhibiting PDE4 in a subject with a body mass that is greater than or equal to a threshold body mass, the method comprising administering the orismilast to the subject, wherein:
(Ci) an initial orismilast dose is administered to the subject once per day for a preliminary time period followed by;
(Cii) a maintenance orismilast dose administered to the subject twice per day, wherein the maintenance orismilast dose is greater than the initial orismilast dose;
wherein:
(a) the initial orismilast dose is from 10 mg to 20 mg orismilast;
(b) the preliminary time period is up to eight weeks; and
(c) the threshold body mass is at least 90 kg.

In a fourth aspect of the invention there is provided orismilast for use in a method of treating a disease or disorder ameliorated by inhibiting PDE4 in a subject, the method comprising administering the orismilast to the subject, wherein:
(Di) an initial orismilast dose is administered to the subject once per day for an initial time period followed by;
(Dii) a maintenance orismilast dose is administered to the subject twice per day;
wherein:
(a) the initial orismilast dose and the maintenance orismilast dose are both 20 mg orismilast;
(b) the initial time period is two to eight weeks; and
(c) the subject has a body mass that is from a lower limit body mass to less than a threshold body mass;
wherein the threshold body mass is at least 90 kg, and the lower limit body mass is from 50 kg to 75 kg.

In some embodiments of the fourth aspect of the invention the lower limit body mass is selected from 50 kg, 55 kg, 60 kg, 65 kg, 70 kg or 75 kg. Thus it may be that the lower limit body mass is 50 kg. It may be that the lower limit body mass is 60 kg. It may be that the lower limit body mass is 75 kg.

In some embodiments of the fourth aspect of the invention the threshold body mass is 90 kg. In some embodiments of the fourth aspect of the invention the threshold body mass is 95 kg. In some embodiments of the fourth aspect of the invention the threshold body mass is 105 kg. Preferably in the fourth aspect of the invention the threshold body mass is 100 kg. For example in the fourth aspect of the invention the threshold body mass is 100 kg and the lower limit body mass is 50 kg. Suitably in the fourth aspect of the invention the threshold body mass is 100 kg and the lower limit body mass is 60 kg.

As described in the Examples herein, a population PK model based on pooled orismilast clinical trial data has identified that treatment of subjects with a body mass less than threshold body mass (e.g. 50 kg) with 20 mg orismilast twice daily results in a higher systemic exposure to orismilast compared to heavier subjects. As discussed above analysis of the psoriasis phase 2b data has shown that increasing systemic exposure above that required for initial efficacy may not increase efficacy and could reduce efficacy. Accordingly, a specific dosing regimen may be required for lighter subjects, such as for adolescent subjects.

In a fifth aspect of the invention there is provided orismilast for use in a method of treating a disease or disorder ameliorated by inhibiting PDE4 in a subject with a body mass that is less than a lower limit body mass, the method comprising administering the orismilast to the subject, wherein:
(Ei) an initial orismilast dose of 10 mg is administered to the subject once per day for an initial time period followed by;
(Eii) a maintenance orismilast dose of 10 mg administered to the subject twice per day; wherein the initial time period is two to eight weeks;
wherein the lower limit body mass is from 50 kg to 75 kg.

In some embodiments of the fifth aspect of the invention the lower limit body mass is selected from 50 kg, 55 kg, 60 kg, 65 kg, 70 kg or 75 kg. Thus it may be that the lower limit body mass is 50 kg. It may be that the lower limit body mass is 60 kg. It may be that the lower limit body mass is 75 kg.

In certain embodiments in any of the dosage regimens disclosed herein the initial orismilast dose is administered to the subject in the evening. In certain embodiments in any of the dosage regimens disclosed herein the initial orismilast dose is administered to the subject in the morning.

In certain embodiments in any of the dosage regimens disclosed herein when the orismilast is administered twice per day (e.g. in the interim orismilast doses and the maintenance orismilast doses) the doses are suitably administered about 12 hours apart. Suitably one dose is administered in the morning and one dose is administered in the evening.

In certain embodiments the orismilast is administered to the subject without any restriction on the intake of food or drink by the subject. However, gastrointestinal side effects may be further minimised by avoiding large meals and/or fatty foods prior to administering the orismilast. Accordingly, in some embodiments in any of the dosage regimens disclosed herein the orismilast is administered to the subject is a fasted state. For example, the orismilast is administered at least 4 hours after a meal. Suitably administering in a fasted state also requires the subject to fast for two hours after administration of the orismilast. In certain embodiments in any of the dosage regimens disclosed herein orismilast is administered to the subject is a fed state. For example the orismilast is administered to the subject in a time period of 30 minutes prior to a meal and 1 hour after a meal. In certain embodiments the orismilast is administered to the subject in a time period of 30 minutes prior to a meal and 1 hour after a meal, wherein the meal is a low fat meal (less than 50% of the total calorific value of the meal is from fat). In certain embodiments the orismilast is administered to the subject in a time period of 30 minutes prior to a meal and 1 hour after a meal, wherein the meal is a low calorie meal (less than about 1000 calories). In certain embodiments the orismilast is administered to the subject in a time period of 30 minutes prior to a meal and 1 hour after a meal, wherein the meal is a low-fat, low calorie meal. In certain embodiments in any of the dosage regimens disclosed herein orismilast is administered to the subject without restriction of food or drink intake.

In certain embodiments in any of the dosage regimens disclosed herein the initial orismilast dose and the interim orismilast dose are the same. In certain embodiments the initial orismilast dose and the interim orismilast are both 20 mg orismilast.

In certain embodiments in any of the dosage regimens disclosed herein the interim orismilast dose is greater than the initial orismilast dose. In certain embodiments the interim orismilast dose is 20 mg orismilast and the interim orismilast dose is greater than the initial orismilast dose. For example, the initial orismilast dose is 10 mg and the interim orismilast dose is 20 mg.

In certain embodiments in any of the dosage regimens disclosed herein the threshold body mass is 90 kg In certain embodiments in any of the dosage regimens disclosed herein the threshold body mass is 95 kg.

In certain embodiments in any of the dosage regimens disclosed herein the threshold body mass is 105 kg.

In preferred embodiments in any of the dosage regimens disclosed herein the threshold body mass is 100 kg.

In certain embodiments in any of the dosage regimens disclosed herein the maintenance orismilast dose is administered to the subject twice per day for the remainder of the treatment period. Accordingly, in certain embodiments the maintenance orismilast dose is administered to the subject twice per day for at least one week, at least two weeks, at least three weeks, at least four weeks, at least one month, at least two months, at least three months, at least four months, at least six months, at least nine months, at least one year, at least 18 months, at least 2 years.

In certain embodiments the disease or disorder is selected from: an inflammatory disease, an autoimmune disease, a disease of the central nervous system, a cerebrovascular disease, diabetes, obesity, metabolic syndrome, a wound and a proliferative disease.

In certain embodiments the disease or disorder is an inflammatory disease, for example an inflammatory pulmonary, dermatological or neurological disease.

In certain embodiments the disease or disorder is psoriasis (e.g. psoriasis vulgaris and plaque psoriasis). In certain embodiments the disease or disorder is moderate to severe psoriasis.

In certain embodiments the disease or disorder is atopic dermatitis. In certain embodiments the disease or disorder is moderate to severe atopic dermatitis.

In certain embodiments the disease or disorder is ulcerative colitis.

In certain embodiments the disease or disorder is hidradenitis suppurativa.

As described in the Examples herein, an analysis of Phase 2b clinical trial data from a study on subjects with moderate to severe atopic dermatitis treated orally with orismilast has revealed that orismilast has a surprisingly strong and rapid effect on pruritus (itch) associated with the atopic dermatitis.

Accordingly, a sixth aspect of the invention s provided orismilast for use in a method of treating pruritus (itch) associated with atopic dermatitis in a subject, the method comprising administering a therapeutically effective amount of orismilast to the subject. The orismilast may be administered to the subject using any suitable route of administration. Suitably the orismilast is administered orally as a pharmaceutical composition, for example any of the orismilast pharmaceutical compositions described herein. In some embodiments the orismilast is orally administered as a modified release pharmaceutical compositions, for example any of the modified release pharmaceutical compositions described herein. The orismilast may be administered to the subject using any suitable dosage regimen, for example 10 mg, 20 mg or 30 mg one or twice per day. Thus the orismilast may be administered to the subject in a dose of 10 mg twice per day. It may be that the orismilast may be administered to the subject in a dose of 20 mg twice per day. It may be that the orismilast may be administered to the subject in a dose of 30 mg twice per day. Suitably however, the orismilast is administered to the subject according to a dosage regimen according to any one of the first to the fifth aspects of the invention.

In certain embodiments in any of the dosage regimens disclosed herein the orismilast is orally administered to the subject.

In certain embodiments in any of the dosage regimens or uses of orismilast disclosed herein the orismilast is administered to the subject in the form of a modified release formulation comprising orismilast. In certain embodiments the modified release formulation releases a mean amount of about 10% to about 70% of the orismilast after 45 minutes and more than about 70% after 180 minutes. In certain embodiments the modified release formulation releases a mean amount of from about 11% to about 65% of the orismilast after 45 minutes and more than 75% of the orismilast after 180 minutes. In certain embodiments the modified release formulation releases a mean amount of from about 35% to about 65% of the orismilast after 45 minutes and more than 70% of the orismilast after 180 minutes. In certain embodiments the modified release formulation releases a mean amount of from about 35% to about 55% of the orismilast after 45 minutes and more than about 80% of the orismilast after 180 minutes In each case above dissolution is determined using Ph. Eur. 2.9.3 Apparatus II, with a dissolution medium of 900 ml 0.5% sodium dodecyl sulfate in 0.1N HCl, a paddle speed of 75 rpm, and the dissolution medium at 37±0.5° C.

The subject may be a human or an animal. Preferably the subject is a human. In some embodiments the subject is a human male. In some embodiments the subject is a human female.

In certain embodiments the orismilast is administered to the subject simultaneously, separately or sequentially with one or more additional therapeutic agent.

BRIEF DESCRIPTION OF THE DRAWINGS

Embodiments of the invention are further described hereinafter with reference to the accompanying drawings, in which:

FIG. 1A shows the % of patients that achieved a 50% reduction in PASI score (PASI-50). FIG. 1B shows the % of patients that achieved a 75% reduction in PASI score (PASI-75). The y-axis shows the % of patients reaching the PASI-50 or PASI-75 scores at Week 0 (W0), Week 4 (W4), Week 8 (W8), Week 12 (W12) and week 16 (W16). "NRI" in this figure refers to non-responder imputation for missing data.

FIG. 5 shows results of the post-hoc analysis for the PASI-75, PASI-90 and PASI-100 responses.

FIG. 22B Table providing descriptive statistics of orismilast $AUC_{\tau\text{-}ss}$ at steady-state in overweight subjects after repeated administration of MR formulation with dose 10, 20, 30 and 40 mg b.i.d as described in the simulation in Example 6.

FIG. 23B Table providing descriptive statistics of $C_{max\text{-}ss}$ (ng/mL) at steady-state in obese subjects after repeated b.i.d administration of MR formulation with dose 10, 20, 30 and 40 mg b.i.d as described in the simulation in Example 6.

FIG. 24B Table providing descriptive statistics of $C_{trough\text{-}ss}$ (ng/mL) at steady-state in obese subjects after repeated b.i.d administration of MR formulation with dose 10, 20, 30 and 40 mg b.i.d as described in the simulation in Example 6.

FIG. 28A shows NRI data; and FIG. 28B shows observed data. "NRI" refers to non-responder imputation for missing data.

FIG. 29A shows NRI data; and FIG. 29B shows observed data. "NRI" refers to non-responder imputation for missing data.

FIG. 30A shows NRI data; and FIG. 30B shows observed data. "NRI" refers to non-responder imputation for missing data.

DETAILED DESCRIPTION

Figure 1A:
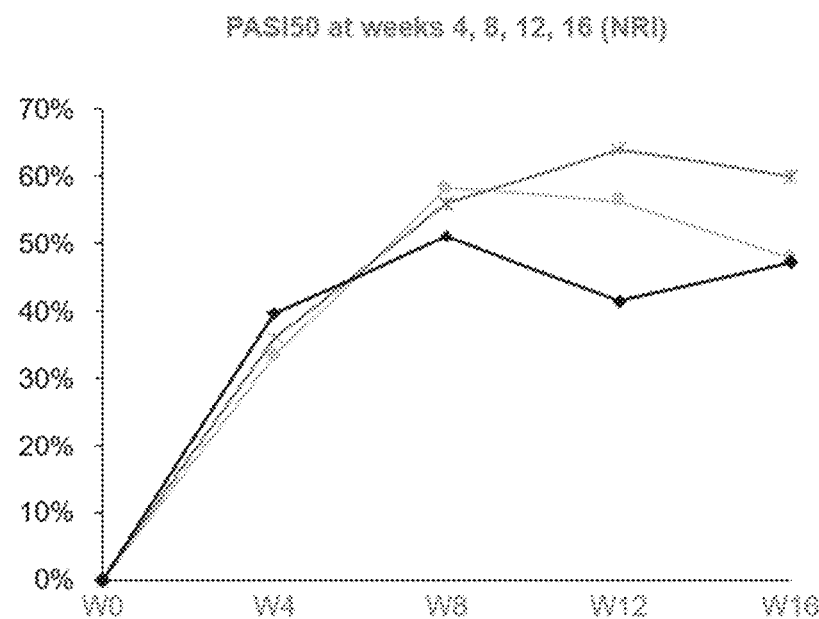
FIG. 1A and FIG. 1B show the % reduction in the Psoriasis Area and Severity Index (PASI) score relative to baseline following treatment with orismilast at doses of 20 mg BID, 30 mg BID and 40 mg BID in the phase 2b clinical trial described in Example 3.

Unless otherwise stated, the following terms used in the specification and claims have the following meanings set out below.

The terms "treating", "treatment" or "efficacy" refer to any indicia of success in the treatment or amelioration of a disease, pathology or condition, including any objective or subjective parameter such as abatement; remission; diminishing of symptoms or making the pathology or condition more tolerable to the subject; slowing in the rate of degeneration or decline; making the final point of degeneration less debilitating; or improving the physical or mental well-being of the subject.

Reference to treating a disease or disorder "ameliorated by inhibiting PDE4" refers to the inhibition of PDE4 providing a beneficial treatment effect on the disease of condition being treated using orismilast.

Reference herein to improving "tolerability" to orismilast includes reducing or eliminating undesirable side effects associated with the administration of orismilast to a subject. For example improving tolerability includes reducing or eliminating one or more of diarrhoea, nausea, headache, dizziness, vomiting or stomach pain associated with administration of orismilast to a subject. Improving tolerability include a reduction in the frequency and/or severity of a side-effect associated with administration of orismilast to a subject.

When a compound described in this specification is administered to treat a disorder, a "therapeutically effective amount" is an amount sufficient to reduce or completely alleviate symptoms or other detrimental effects of the disorder; cure the disorder; reverse, completely stop, or slow the progress of the disorder; or reduce the risk of the disorder getting worse.

Reference to a treatment period of "a week" refers to treatment for 7 days. Thus by way of an example, where the initial time period is two weeks followed by an interim period of six weeks, followed by the administration of a maintenance dose, this refers to treatment of the subject in the initial time period from day 1 to day 14, followed by treatment of the subject in the interim time period from day 15 to day 56, and administration of the maintenance dose starting on day 57 of the dosage regimen.

References to a treat period, for example "at week 2" or "at week 16" refers to the end of that treatment period. Thus "at week 2" refers to the end of week 2 of the treatment and "at week 16" refers to the end of week 16 of treatment.

The term "pharmaceutically acceptable salt" refers to salts that retain the biological effectiveness and properties of the compounds described herein, and which are not biologically or otherwise undesirable. Pharmaceutically acceptable salts are well known to skilled persons in the art. It is intended that the present invention encompasses any pharmaceutically acceptable salts of orismilast. The invention covers all crystalline modifications, polymorphic forms and mixtures thereof of the compounds described herein, for example orismilast. In some embodiments, the treatment comprises administration of the polymorphic form E of orismilast.

The term "solvate" is intended to indicate a species formed by interaction between a compound, e.g. orismilast and a solvent, e.g. alcohol, glycerol or water, wherein said species are in a solid form. When water is the solvent, said species is referred to as a "hydrate". It is intended that the invention encompasses all solvates (e.g. hydrates) of orismilast.

The phrase "phosphodiesterase" as used herein refers to one or more of the phosphodiesterases (PDEs), PDE4, PDE7 and PDE8 being selective for cAMP. PDE4 is the most important modulator of cAMP. PDE4 is cAMP-specific and the dominant PDE in inflammatory cells. PDE4 enzymes are encoded by four genes (PDE4A, PDE4B, PDE4C and PDE4D), each of which is capable of producing a number of isoforms through mRNA splicing and the use of different promoters. Each PDE4 isoform within a particular PDE4 sub-family comprises a common core region, consisting of the catalytic unit and the C-terminal portion, and is defined by its unique N-terminal region. The PDE4 isoforms are further classified as long, short or super-short, depending on the presence or absence (or truncation) of two highly conserved sequences: Upstream Conserved Region 1 (UCR1) and Upstream Conserved Region 2 (UCR2). "Long" isoforms comprise both UCR1 and UCR2; "short" isoforms lack UCR1 and "super-short" isoforms lack UCR1 and have a truncated UCR2.

The phrase "PDE4 inhibitor" as used herein refers to a substance which inhibits PDE4.

Reference herein to the "threshold body mass" or "lower limit body mass" means the body mass of the subject immediately prior to administering the first dose of orismilast to the subject (i.e. body mass at baseline).

Unless stated otherwise herein, reference to "moderate to severe atopic dermatitis" refers to a subject with atopic dermatitis that has affected an affected body surface area (BSA) of ≥10%, an IGA-AD grade of ≥3, and an Eczema Area and Severity Index (EASI) score of ≥16 at baseline.

Unless stated otherwise herein, reference to "moderate atopic dermatitis" refers to subject with atopic dermatitis with EASI score of ≥16 to ≤21 at baseline. Suitably subjects with moderate atopic dermatitis have a baseline BSA of ≥10% to ≤28%.

Unless stated otherwise herein, reference to "severe atopic dermatitis" refers to subject with atopic dermatitis with EASI score of >21 at baseline. Suitably subjects with severe atopic dermatitis have a baseline BSA of >28%.

Unless stated otherwise herein, reference to "moderate to severe psoriasis" refers to a subject with psoriasis with a Psoriasis Area and Severity Index (PASI)≥12, an affected Body Surface Area (BSA)≥10%, and Static Physician Global Assessment sPGA)≥3 at baseline.

The term "baseline" refers to a level or score (for example PASI or EASI) in a subject prior to treatment of the subject with orismilast.

Reference to the term "Investigator Global Assessment for AD" or "IGA-AD" herein is to be considered equivalent to, and interchangeable with the term "validated Investigator Global Assessment for AD" or "vIGA-AD". Thus a reference herein to an "IGA-AD" score encompasses and is equivalent to the corresponding "vIGA-AD score".

References to "Peak Pruritus Numerical Rating Scale", "Peak Pruritis (NRS)" or PPNRS" herein is to be considered to be equivalent to, and interchangeable with a reference to "Worst Pruritus NRS". Thus a reference herein to a "PPNRS score" also encompasses and is equivalent to the corresponding "Worst Pruritus NRS score".

The term "particle size distribution" of a powder refers to a value that defines the relative amounts of particles present, sorted according to size. The D(50) and D(90) values indicate that 50% and 90% of the particles measured are less than or equal to the size stated. For example a D(50)=6 μm means that 50% of the particles are less than or equal to 6 μm. A D(90) of <10 μm mean that 90% of the particles have a particle size of less than or equal to 10 μm. Particle size may be measured using conventional methods such as laser diffraction technique.

The term "immediate release" refers to a pharmaceutical composition or formulation which does not significantly delay release of the active ingredient following oral administration. Generally immediate release refers to compositions or formulations wherein ≥85% of the active ingredient is released within 30 minutes when placed in a aqueous dissolution medium.

The term "modified release" refers to a pharmaceutical formulation or composition where the rate and/or site of release of the active ingredient are different from that of an immediate release dosage form administered orally. The modified release composition may be a delayed release composition wherein release of the active is delayed for a period or time following oral administration.

Reference to a "subject" herein means a human or animal subject. Preferably the subject is warm-blooded mammal. More preferably the subject is a human. In some embodiments the subject is an adolescent or adult human, for example a human aged at least 12 years or over. In some embodiment the subject is an adult human aged 18 years or over. In some embodiments the subject is an adolescent human aged from 12 years to up to 18 years.

Reference to "about" in the context of a numerical is intended to encompass the value+/−10%. For example, about 20% includes the range of from 18% to 22%.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Orismilast

The present invention relates to dosage regimens for the administration of the compound orismilast, 2-(3,5-dichloro-1-oxidopyridin-1-ium-4-yl)-1-[7-(difluoromethoxy)-1',1'-dioxospiro[1,3-benzodioxole-2,4'-thiane]-4-yl]ethanone, is a potent and selective PDE4 inhibitor of the formula:

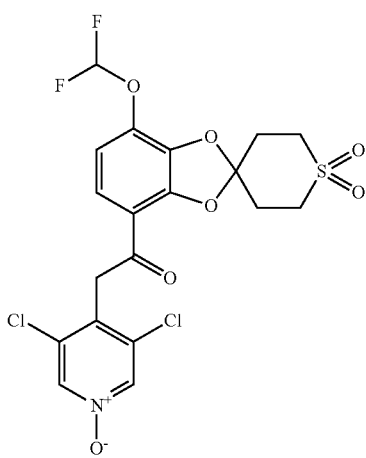 [SMILES: O=C(Cc1c(Cl)c[n+]([O-])cc1Cl)c1ccc(OC(F)F)c2c1OC1(CCS(=O)(=O)CC1)O2]

The Chem Abstracts name for orismilast is ethanone, 2-(3,5-dichloro-1-oxido-4-pyridinyl)-1-[7-(difluoromethoxy)-2',3',5',6'-tetrahydro-1',1'-dioxidospiro[1,3-benzodioxole-2,4'-[4H]thiopyran]-4-yl]; CAS Number 1353546-86-7.

Orismilast and methods for synthesizing the compound, are disclosed in WO 2011/160632, WO 2015/197534, WO 2017/103058, and WO 2018/234299.

In certain embodiments the orismilast may be administered to the subject as a solid, which may be amorphous, crystalline or semi-crystalline. In some embodiments the orismilast is crystalline. In preferred embodiments the orismilast is in the form of polymorphic Form E. Polymorphic Form E of orismilast ("Form E) is described in WO 2018/234299.

In some embodiments the orismilast is Form E characterised by a powder X-ray diffraction pattern with at least one 2θ peak selected from 8.0, 8.6, 11.8, 14.1, 15.0, 16.0, 16.8, 18.1, 18.5, 20.0, 21.4, 23.4, 25.6 and 29.7°±0.2°, when measured using a CuKα radiation (λ=1.5418 Å).

In some embodiments the orismilast is Form E characterised by a powder X-ray diffraction pattern with two 2θ peaks selected from 8.0, 8.6, 11.8, 14.1, 15.0, 16.0, 16.8, 18.1, 18.5, 20.0, 21.4, 23.4, 25.6 and 29.70±0.20, when measured using a CuKα radiation (λ=1.5418 Å).

In some embodiments the orismilast is Form E characterised by a powder X-ray diffraction pattern with five 2θ peaks selected from 8.0, 8.6, 11.8, 14.1, 15.0, 16.0, 16.8, 18.1, 18.5, 20.0, 21.4, 23.4, 25.6 and 29.7°±0.2°, when measured using a CuKα radiation (λ=1.5418 Å).

In some embodiments the orismilast is Form E characterised by a powder X-ray diffraction pattern with 2θ peaks at 15.0, 16.0, 18.1, 18.5, 21.4 and 23.40 0.20, when measured using a CuKα radiation (λ=1.5418 Å).

In some embodiments the orismilast is Form E characterised by a powder X-ray diffraction pattern with 2θ peaks at 8.0, 11.8, 15.0, 16.0, 16.8, 18.1, 18.5, 23.4, 25.6 and 29.70° 0.2°, when measured using a CuKα radiation (λ=1.5418 Å)

In some embodiments the orismilast is Form E characterised by a powder X-ray diffraction pattern with 2θ peaks at 8.0, 8.6, 11.8, 14.1, 15.0, 16.0, 16.8, 18.1, 18.5, 21.4, 23.4, 25.6 and 29.7°±0.2°, when measured using a CuKα radiation (λ=1.5418 Å).

In some embodiments the orismilast is Form E characterised by a powder X-ray diffraction pattern with at least 10 of the 2θ peaks shown in Table X, when measured using a CuKα radiation (λ=1.5418 Å).

In some embodiments the orismilast is Form E characterised by a powder X-ray diffraction pattern with the 2θ peaks shown in Table X, when measured using a CuKα radiation (λ=1.5418 Å).

TABLE X

| Peak Position (2θ ± 0.2°) |
| --- |
| 5.9 |
| 8.0 |
| 8.6 |
| 8.7 |
| 9.8 |
| 11.8 |
| 12.1 |
| 14.1 |
| 14.4 |
| 15.0 |
| 15.2 |
| 16.0 |
| 16.4 |
| 16.6 |
| 16.8 |
| 17.0 |
| 17.3 |
| 17.7 |
| 18.1 |
| 18.5 |

TABLE X-continued

| Peak Position (2θ ± 0.2°) |
|---|
| 19.3 |
| 19.7 |
| 19.9 |
| 20.0 |
| 20.2 |
| 20.3 |
| 21.4 |
| 21.5 |
| 21.6 |
| 21.9 |
| 22.0 |
| 22.3 |
| 22.9 |
| 23.1 |
| 23.4 |
| 23.6 |
| 23.9 |
| 24.1 |
| 24.4 |
| 24.7 |
| 25.6 |
| 25.8 |
| 26.2 |
| 26.3 |
| 26.6 |
| 27.3 |
| 27.8 |
| 28.1 |
| 28.3 |
| 28.6 |
| 29.2 |
| 29.5 |
| 29.7 |
| 30.0 |
| 30.5 |
| 31.5 |
| 31.7 |

Figure 9:
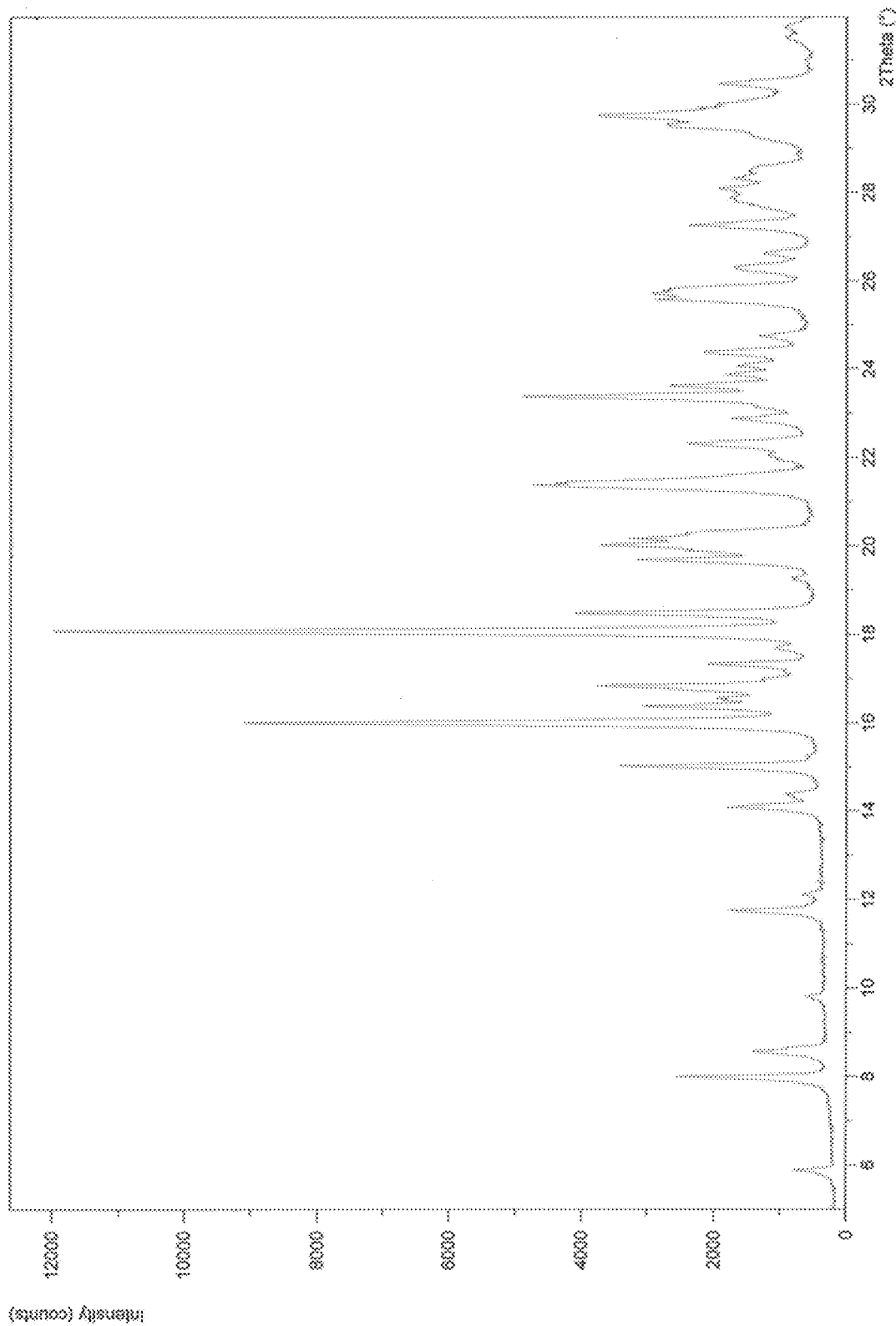
FIG. 9 (landscape) shows the X-ray powder diffraction pattern for orismilast crystalline Form E measured using CuKα radiation λ=1.5418 Å. The x-axis shows the 2θ values and the y-axis the intensity (counts).

In some embodiments the orismilast is Form E characterised by a powder X-ray diffraction pattern substantially as shown in FIG. 9, when measured using a CuKα radiation (λ=1.5418 Å).

Figure 10:
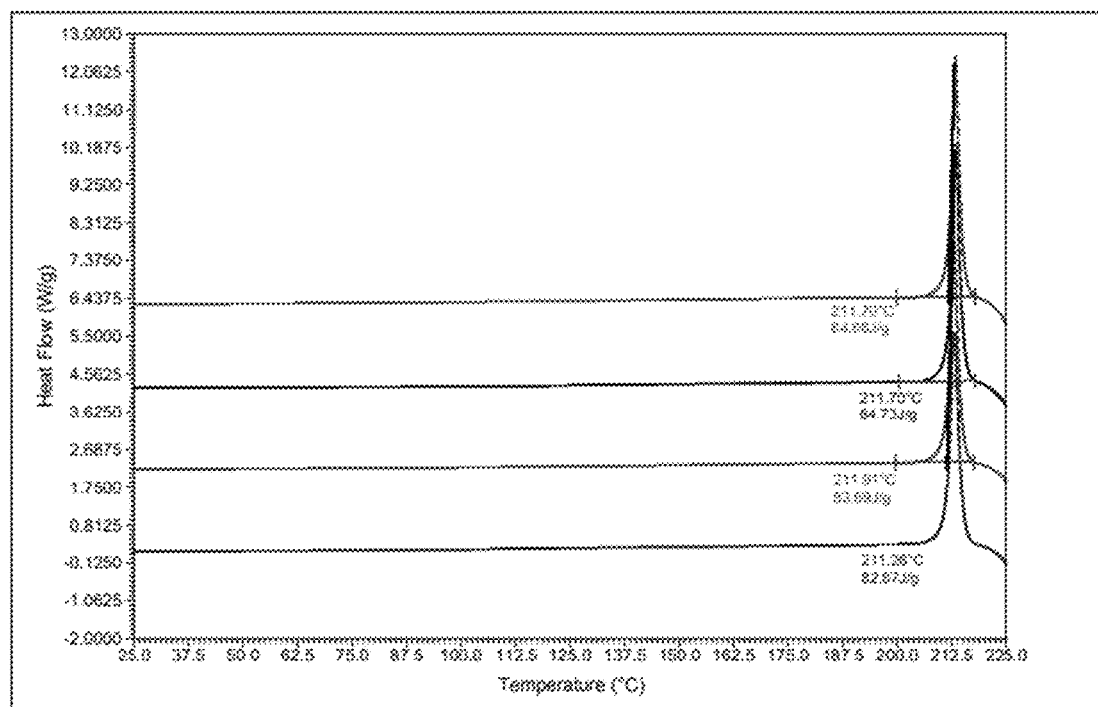
FIG. 10 shows a DSC trace for two different batches of orismilast crystalline Form E measured with a heating rate of 2 to 10° C./minute (two measurements per batch). The x-axis shows temperature and the y-axis heat flow (W/g). Each trace shows the melting onset temperature and the enthalpy change for each sample of the Form E.

In certain embodiments Form E is characterised as having a melting endotherm with an onset temperature of about 210° C. to about 213° C. (e.g. about 211.6° C.) when measured by Differential Scanning Calorimetry (DSC) with a heating rate of 2 to 10° C./minute in a sealed aluminium pan with a pierced lid under a nitrogen atmosphere. In certain embodiments the Form E has a melting enthalpy change of about 80 to 90 J/g when measured under the DSC conditions above. In certain embodiments the Form E has DSC curve substantially as shown in FIG. 10.

Form E may be obtained by crystallisation from a suitable solvent for example one or more solvents selected from ethanol, isopropanol, dimethylsulfoxide, acetonitrile and acetone. In some embodiments the solvent is acetone or ethanol. Crystallisation of Form E may be obtained by, for example dissolving orismilast in the hot solvent (e.g. at 50° C.) to form a solution and allowing the resulting solution to cool to room temperature.

Orismilast is a selective and efficient inhibitor of PDE4. It has been found that orismilast is a selective inhibitor of PDE4D and PDE4B. In some embodiments orismilast is a selective inhibitor of PDE4B. In some embodiments orismilast is a selective inhibitor of PDE4D. In some embodiments orismilast is a selective inhibitor of PDE4B1, PDE4B2, PDE4B3, PDE4D1, PDE4D2, PDE4D3, PDE4D4, PDE4D5 and/or PDE4D7. In some embodiments orismilast is a selective inhibitor of PDE4B2, PDE4B3, PDE4D2, PDE4D3, PDE4D4, PDE4D5 and/or PDE4D7. In some embodiments orismilast is a selective inhibitor of PDE4B2, PDE4B3, PDE4D5 and PDE4D7. In some embodiments orismilast is a selective inhibitor of PDE4B3, PDE4D5 and PDE4D7. In particular, it has been found that orismilast is a selective inhibitor of the PDE4 isoforms PDE4D3 and PDE4B2. In addition, orismilast has been found to potently inhibit the secretion of TNF-α and IL-13, two cytokines that are highly associated with inflammation. The compound also inhibits IFN-γ. IFN-γ is a T-cell derived Th1 cytokine that plays a role in Th1 immune responses. Significantly, orismilast has been shown to an average of 23 times more potent than apremilast on a molar basis, in both LPS and SEB-induced TNF-α secretion from human whole blood. The ability of orismilast to inhibit cytokines involved in inflammation supports the use of orismilast in the treatment of inflammatory conditions such as psoriasis, atopic dermatitis, ulcerative colitis, asthma, COPD and hidradenitis suppurativa (HS).

Dosage Regimens

The present invention related to dosage regimens using orismilast. Reference herein to a method of treating a disease or disorder ameliorated by inhibiting PDE4 are also intended to encompass: (i) orismilast for use in the treatment of the disease or disorder; and/or (ii) the use of orismilast for the manufacture of a medicament for treating the disease or condition according to the dosage regimens described herein.

Dosage Regimen A (first aspect of the invention)

Analysis of clinical trial data in a study of subjects with moderate to severe plaque type psoriasis has identified that when orismilast is administered to subjects using a twice daily dosage regimen of 20 mg, 30 mg or 40 mg orismilast some side effects were observed, for example diarrhoea, nausea, headache, dizziness, vomiting and stomach pain. The onset of most side-effects occurred during the first 4 weeks of treatment and very few side effects occurred after 8 week of treatment. Moreover, it has been found that subjects with a body mass which is greater than or equal to a threshold body mass that are treated with high doses of orismilast showed improved treatment efficacy, but without a significant increase in undesirable side effects leading to treatment discontinuation. Still further, treating subjects with a body mass that is less that the threshold body mass with high interim or maintenance doses may not improve efficacy and could result in increased side effects. Dosage Regimen A provides a reduction in side-effects in the initial stages of treatment and is also expected to provide improved efficacy and/or tolerability in heavier subjects treated with higher maintenance doses of orismilast and optimised efficacy and/or tolerability in subjects with a body mass below the threshold body mass.

Accordingly, there is provided orismilast for use in a method of treating a disease or disorder ameliorated by inhibiting PDE4 in a subject, the method comprising administering the orismilast to the subject, wherein:

(Ai) an initial orismilast dose is administered to the subject once per day for an initial time period followed by;

(Aii) an interim orismilast dose administered to the subject twice per day for an interim time period followed by;

(Aiii) a maintenance orismilast dose administered to the subject twice per day;

wherein:
(a) the initial orismilast dose and the interim orismilast dose are independently selected from 10 mg to 30 mg orismilast, provided that the interim orismilast dose is greater than or equal to the initial orismilast dose;
(b) the initial time period is two to eight weeks;
(c) the interim time period is one to eight weeks; and
(d) the maintenance orismilast dose is greater than the interim orismilast dose when the subject has a body mass that is greater than or equal to a threshold body mass,
wherein the threshold body mass is at least 90 kg.

Also provided is a method of treating a disease or disorder ameliorated by inhibiting PDE4 in a subject, the method comprising administering orismilast to the subject according to the dosage regimen (Ai), (Aii) and (Aiii) described above. Accordingly, there is provided a method of treating a disease or disorder ameliorated by inhibiting PDE4 in a subject, the method comprising administering orismilast to the subject, wherein:
(Ai) an initial orismilast dose is administered to the subject once per day for an initial time period followed by;
(Aii) an interim orismilast dose administered to the subject twice per day for an interim time period followed by;
(Aiii) a maintenance orismilast dose administered to the subject twice per day;
wherein:
(a) the initial orismilast dose and the interim orismilast dose are independently selected from 10 mg to 30 mg orismilast, provided that the interim orismilast dose is greater than or equal to the initial orismilast dose;
(b) the initial time period is two to eight weeks;
(c) the interim time period is one to eight weeks; and
(d) the maintenance orismilast dose is greater than the interim orismilast dose when the subject has a body mass that is greater than or equal to a threshold body mass, wherein the threshold body mass is at least 90 kg.

Also provided is the use of orismilast for the manufacture of a medicament for the treatment a disease or disorder ameliorated by inhibiting PDE4 in a subject, the method comprising administering the orismilast to the subject according to the dosage regimen (Ai), (Aii) and (Aiii) described above.

In certain embodiments of Dosage Regimen A the interim orismilast dose is 10 to 20 mg orismilast. In certain embodiments the interim orismilast dose is 10 mg orismilast. In certain embodiments the interim orismilast dose is 20 mg orismilast.

In certain embodiments of Dosage Regimen A the maintenance orismilast dose is the same as the interim orismilast dose when the subject has a body mass that is less than the threshold body mass. Accordingly, in some embodiments the interim orismilast dose is 20 mg BID and the maintenance dose is 20 mg BID when the subject has a body mass that is less than the threshold body mass. In some embodiments the interim orismilast dose is 10 mg BID and the maintenance dose is 10 mg BID when the subject has a body mass that is less than the threshold body mass.

In Dosage Regimen A the maintenance orismilast dose is greater than the interim orismilast dose when the subject has a body mass that is greater than or equal to the threshold body mass. Suitably the maintenance orismilast dose for subjects which have a body mass that is greater than or equal to the threshold body mass is up to 40 mg orismilast, for example the maintenance orismilast dose is up to 35 mg orismilast, or up to 30 mg orismilast, provided that the maintenance orismilast dose is greater than the interim orismilast dose. In some embodiments the maintenance orismilast dose is selected from 30, 31, 32, 33, 34, 35, 36, 37, 38, 39 or 40 mg orismilast, provided that the maintenance orismilast dose is greater than the interim orismilast dose. In a preferred embodiment the maintenance orismilast dose is 30 mg orismilast, provided that the maintenance orismilast dose is greater than the interim orismilast dose.

Embodiment A1

In certain embodiments of Dosage Regimen A, the dosage regimen comprises:
(Ai) the initial orismilast dose is 20 mg orismilast administered to the subject once per day for two weeks;
(Aii) the interim orismilast dose is 20 mg orismilast administered to the subject twice per day for one week to eight weeks; and
(Aiii) the maintenance orismilast dose is 20 mg orismilast administered to the subject twice per day if the subject has a body mass which is less than the threshold body mass; or
the maintenance orismilast dose is 30 mg orismilast administered to the subject twice per day if the subject has a body mass which is greater than or equal to the threshold body mass.

Embodiment A2

In certain embodiments of Dosage Regimen A, the dosage regimen comprises:
(Ai) the initial orismilast dose is 20 mg orismilast administered to the subject once per day for two weeks;
(Aii) the interim orismilast dose is 20 mg orismilast administered to the subject twice per day for two weeks; and
(Aiii) the maintenance orismilast dose is 20 mg orismilast administered to the subject twice per day if the subject has a body mass which is less than the threshold body mass; or
the maintenance orismilast dose is 30 mg orismilast administered to the subject twice per day if the subject has a body mass which is greater than or equal to the threshold body mass.

Embodiment A3

In certain embodiments of Dosage Regimen A, the dosage regimen comprises:
(Ai) the initial orismilast dose is 20 mg orismilast administered to the subject once per day for two weeks;
(Aii) the interim orismilast dose is 20 mg orismilast administered to the subject twice per day for two weeks; and
(Aiii) the maintenance orismilast dose is 20 mg orismilast administered to the subject twice per day if the subject has a body mass which is less than the threshold body mass; or
the maintenance orismilast dose is 30 mg orismilast administered to the subject twice per day if the subject has a body mass which is greater than or equal to the threshold body mass.

Embodiment A4

In certain embodiments of Dosage Regimen A, the dosage regimen comprises:

(Ai) the initial orismilast dose is 20 mg orismilast administered to the subject once per day for two weeks;
(Aii) the interim orismilast dose is 20 mg orismilast administered to the subject twice per day for four weeks; and
(Aiii) the maintenance orismilast dose is 20 mg orismilast administered to the subject twice per day if the subject has a body mass which is less than the threshold body mass; or
the maintenance orismilast dose is 30 mg orismilast administered to the subject twice per day if the subject has a body mass which is greater than or equal to the threshold body mass.

Embodiment A5

In certain embodiments of Dosage Regimen A, the dosage regimen comprises:
(Ai) the initial orismilast dose is 20 mg orismilast administered to the subject once per day for two weeks;
(Ai) the interim orismilast dose is 20 mg orismilast administered to the subject twice per day for six weeks;
(Aiii) the maintenance orismilast dose is 20 mg orismilast administered to the subject twice per day if the subject has a body mass which is less than the threshold body mass; or
the maintenance orismilast dose is 30 mg orismilast administered to the subject twice per day if the subject has a body mass which is greater than or equal to the threshold body mass.

Embodiment A6

In certain embodiments of Dosage Regimen A, the dosage regimen comprises:
(Ai) the initial orismilast dose is 20 mg orismilast administered to the subject once per day for two weeks;
(Aii) the interim orismilast dose is 20 mg orismilast administered to the subject twice per day for eight weeks;
(Aiii) the maintenance orismilast dose is 20 mg orismilast administered to the subject twice per day if the subject has a body mass which is less than the threshold body mass; or
the maintenance orismilast dose is 30 mg orismilast administered to the subject twice per day if the subject has a body mass which is greater than or equal to the threshold body mass.

Embodiment A7

In certain embodiments of Dosage Regimen A, the dosage regimen comprises:
(Ai) the initial orismilast dose is 10 mg orismilast administered to the subject once per day for two weeks;
(Aii) the interim orismilast dose is 10 mg orismilast administered to the subject twice per day for one week to eight weeks; and
(Aiii) the maintenance orismilast dose is 10 mg orismilast administered to the subject twice per day if the subject has a body mass which is less than the threshold body mass; or
the maintenance orismilast dose is 20 mg orismilast administered to the subject twice per day if the subject has a body mass which is greater than or equal to the threshold body mass.

Embodiment A8

In certain embodiments of Dosage Regimen A, the dosage regimen comprises:
(Ai) the initial orismilast dose is 10 mg orismilast administered to the subject once per day for two weeks;
(Aii) the interim orismilast dose is 10 mg orismilast administered to the subject twice per day for two weeks; and
(Aiii) the maintenance orismilast dose is 10 mg orismilast administered to the subject twice per day if the subject has a body mass which is less than the threshold body mass; or
the maintenance orismilast dose is 20 mg orismilast administered to the subject twice per day if the subject has a body mass which is greater than or equal to the threshold body mass.

Embodiment A9

In certain embodiments of Dosage Regimen A, the dosage regimen comprises:
(Ai) the initial orismilast dose is 10 mg orismilast administered to the subject once per day for two weeks;
(Aii) the interim orismilast dose is 10 mg orismilast administered to the subject twice per day for two weeks; and
(Aiii) the maintenance orismilast dose is 10 mg orismilast administered to the subject twice per day if the subject has a body mass which is less than the threshold body mass; or
the maintenance orismilast dose is 20 mg orismilast administered to the subject twice per day if the subject has a body mass which is greater than or equal to the threshold body mass.

Embodiment A10

In certain embodiments of Dosage Regimen A, the dosage regimen comprises:
(Ai) the initial orismilast dose is 10 mg orismilast administered to the subject once per day for two weeks;
(Aii) the interim orismilast dose is 10 mg orismilast administered to the subject twice per day for four weeks; and
(Aiii) the maintenance orismilast dose is 10 mg orismilast administered to the subject twice per day if the subject has a body mass which is less than the threshold body mass; or
the maintenance orismilast dose is 20 mg orismilast administered to the subject twice per day if the subject has a body mass which is greater than or equal to the threshold body mass.

Embodiment A11

In certain embodiments of Dosage Regimen A, the dosage regimen comprises:
(Ai) the initial orismilast dose is 10 mg orismilast administered to the subject once per day for two weeks;
(Aii) the interim orismilast dose is 10 mg orismilast administered to the subject twice per day for six weeks;
(Aiii) the maintenance orismilast dose is 10 mg orismilast administered to the subject twice per day if the subject has a body mass which is less than the threshold body mass; or the maintenance orismilast dose is 20 mg orismilast administered to the subject twice per day if the subject has a body mass which is greater than or equal to the threshold body mass.

Embodiment A12

In certain embodiments of Dosage Regimen A, the dosage regimen comprises:
(Ai) the initial orismilast dose is 10 mg orismilast administered to the subject once per day for two weeks;
(Aii) the interim orismilast dose is 10 mg orismilast administered to the subject twice per day for eight weeks;
(Aiii) the maintenance orismilast dose is 10 mg orismilast administered to the subject twice per day if the subject has a body mass which is less than the threshold body mass; or
the maintenance orismilast dose is 20 mg orismilast administered to the subject twice per day if the subject has a body mass which is greater than or equal to the threshold body mass.

Embodiment A13

In certain embodiments of Dosage Regimen A, the dosage regimen comprises:
(Ai) the initial orismilast dose is 10 mg orismilast administered to the subject once per day for two weeks to four weeks if the subject has a body mass of less than a lower limit body mass, or the initial orismilast dose is 20 mg orismilast administered to the subject once per day for two weeks to eight weeks if the subject has a body mass of from the lower limit body mass to less than the threshold body mass;
(Aii) the interim orismilast dose is 10 mg orismilast administered to the subject twice per day for one week to eight weeks if the subject has a body mass of less than the lower limit body mass; or
the interim orismilast dose is 20 mg orismilast administered to the subject twice per day for one week to eight weeks if the subject has a body mass of from the lower limit body mass to less than the threshold body mass; and
(Aiii) the maintenance orismilast dose is 10 mg orismilast administered to the subject twice per day if the subject has a body mass which is less than the lower limit body mass, or
the maintenance orismilast dose is 20 mg orismilast administered to the subject twice per day if the subject has a body mass of from the lower limit body mass to less than the threshold body mass, or
the maintenance orismilast dose is 30 mg orismilast administered to the subject twice per day if the subject has a body mass which is greater than or equal to the threshold body mass;
wherein the lower limit body mass is from 50 kg to 75 kg.

In some embodiments of Embodiment A13 the interim orismilast dose is administered to the subject twice per day for one week to four weeks. In some embodiments of Embodiment A13 the interim orismilast dose is administered to the subject twice per day for two weeks to eight weeks. In some embodiments of Embodiment A13 the interim orismilast dose is administered to the subject twice per day for four weeks to eight weeks. In some embodiments of Embodiment A13 the interim orismilast dose is administered to the subject twice per day for two weeks. In some embodiments of Embodiment A13 the interim orismilast dose is administered to the subject twice per day for four weeks. In some embodiments of Embodiment A13 the interim orismilast dose is administered to the subject twice per day for six weeks.

Embodiment A14

In certain embodiments of Dosage Regimen A, the dosage regimen comprises:
(Ai) the initial orismilast dose is 10 mg orismilast administered to the subject once per day for two weeks to four weeks if the subject has a body mass of less than a lower limit body mass, or
the initial orismilast dose is 20 mg orismilast administered to the subject once per day for two weeks to four weeks if the subject has a body mass of from the lower limit body mass to less than the threshold body mass;
(Aii) the interim orismilast dose is 10 mg orismilast administered to the subject twice per day for six weeks to eight weeks if the subject has a body mass of less than the lower limit body mass, or
the interim orismilast dose is 20 mg orismilast administered to the subject twice per day for six weeks to eight weeks if the subject has a body mass of from the lower limit body mass to less than the threshold body mass; and
(Aiii) the maintenance orismilast dose is 10 mg orismilast administered to the subject twice per day if the subject has a body mass which is less than the lower limit body mass; or
the maintenance orismilast dose is 20 mg orismilast administered to the subject twice per day if the subject has a body mass which is from the lower limit body mass to less than the threshold body mass; or
the maintenance orismilast dose is 30 mg orismilast administered to the subject twice per day if the subject has a body mass which is greater than or equal to the threshold body mass;
wherein the lower limit body mass is from 50 kg to 75 kg.

Embodiment A15

In certain embodiments of Dosage Regimen A, the dosage regimen comprises:
(Ai) the initial orismilast dose is 10 mg orismilast administered to the subject once per day for two weeks, if the subject has a body mass of less than a lower limit body mass, or
the initial orismilast dose is 20 mg orismilast administered to the subject once per day for two weeks if the subject has a body mass of from the lower limit body mass to less than the threshold body mass;
(Aii) the interim orismilast dose is 10 mg orismilast administered to the subject twice per day for two weeks if the subject has a body mass of less than the lower limit body mass, or
the interim orismilast dose is 20 mg orismilast administered to the subject twice per day for two weeks if the subject has a body mass of from the lower limit body mass to less than the threshold body mass; and
(Aiii) the maintenance orismilast dose is 10 mg orismilast administered to the subject twice per day if the subject has a body mass which is less than the lower limit body mass, or
the maintenance orismilast dose is 20 mg orismilast administered to the subject twice per day if the subject has a body mass which is from the lower limit body mass to less than the threshold body mass; or the maintenance orismilast dose is 30 mg orismilast administered to the subject twice per day if the subject has a body mass which is greater than or equal to the threshold body mass;

wherein the lower limit body mass is from 50 kg to 75 kg.

Embodiment A16

In certain embodiments of Dosage Regimen A, the dosage regimen comprises:
(Ai) the initial orismilast dose is 10 mg orismilast administered to the subject once per day for two weeks, if the subject has a body mass of less than a lower limit body mass, or
the initial orismilast dose is 20 mg orismilast administered to the subject once per day for two weeks if the subject has a body mass of from the lower limit body mass to less than the threshold body mass;
(Aii) the interim orismilast dose is 10 mg orismilast administered to the subject twice per day for four weeks if the subject has a body mass of less than the lower limit body mass, or
the interim orismilast dose is 20 mg orismilast administered to the subject twice per day for four weeks if the subject has a body mass of from the lower limit body mass to less than the threshold body mass; and
(Aiii) the maintenance orismilast dose is 10 mg orismilast administered to the subject twice per day if the subject has a body mass which is less than the lower limit body mass, or
the maintenance orismilast dose is 20 mg orismilast administered to the subject twice per day if the subject has a body mass which is of from the lower limit body mass to less than the threshold body mass; or
the maintenance orismilast dose is 30 mg orismilast administered to the subject twice per day if the subject has a body mass which is greater than or equal to the threshold body mass;
wherein the lower limit body mass is from 50 kg to 75 kg.

Embodiment A17

In certain embodiments of Dosage Regimen A, the dosage regimen comprises:
(Ai) the initial orismilast dose is 10 mg orismilast administered to the subject once per day for two weeks, if the subject has a body mass of less than a lower limit body mass, or
the initial orismilast dose is 20 mg orismilast administered to the subject once per day for two weeks if the subject has a body mass of from the lower limit body mass to less than the threshold body mass;
(Ai) the interim orismilast dose is 10 mg orismilast administered to the subject twice per day for six weeks if the subject has a body mass of less than the lower limit body mass, or
the interim orismilast dose is 20 mg orismilast administered to the subject twice per day for six weeks if the subject has a body mass of from the lower limit body mass to less than the threshold body mass; and
(Aiii) the maintenance orismilast dose is 10 mg orismilast administered to the subject twice per day if the subject has a body mass which is less than the lower limit body mass, or the maintenance orismilast dose is 20 mg orismilast administered to the subject twice per day if the subject has a body mass which is of from the lower limit body mass to less than the threshold body mass; or
the maintenance orismilast dose is 30 mg orismilast administered to the subject twice per day if the subject has a body mass which is greater than or equal to the threshold body mass;
wherein the lower limit body mass is from 50 kg to 75 kg.

Embodiment A18

In certain embodiments of Dosage Regimen A, the dosage regimen comprises:
(Ai) the initial orismilast dose is 10 mg orismilast administered to the subject once per day for two weeks, if the subject has a body mass of less than a lower limit body mass, or
the initial orismilast dose is 20 mg orismilast administered to the subject once per day for two weeks if the subject has a body mass of from the lower limit body mass to less than the threshold body mass;
(Aii) the interim orismilast dose is 10 mg orismilast administered to the subject twice per day for eight weeks if the subject has a body mass of less than the lower limit body mass, or
the interim orismilast dose is 20 mg orismilast administered to the subject twice per day for eight weeks if the subject has a body mass of from the lower limit body mass to less than the threshold body mass; and
(Aiii) the maintenance orismilast dose is 10 mg orismilast administered to the subject twice per day if the subject has a body mass which is less than the lower limit body mass, or
the maintenance orismilast dose is 20 mg orismilast administered to the subject twice per day if the subject has a body mass which is from the lower limit body mass to less than the threshold body mass; or
the maintenance orismilast dose is 30 mg orismilast administered to the subject twice per day if the subject has a body mass which is greater than or equal to the threshold body mass;
wherein the lower limit body mass is from 50 kg to 75 kg.

In any one of Embodiments A13 to A18 it may be that the lower limit body mass is selected from 50 kg, 55 kg, 60 kg, 65 kg, 70 kg and 75 kg. It may be that the lower limit body mass is 50 kg. It may be that the lower limit body mass is 60 kg. It may be that the lower limit body mass is 70 kg. It may be that the lower limit body mass is 75 kg.

The dosage regimen described in Dosage Regimen A (including any of Embodiments A1 to A18) are particularly suitable for the treatment of psoriasis, for example the treatment of moderate to severe psoriasis. The psoriasis may be plaque-type psoriasis. Preferably the dosage regimen is for the treatment of moderate to severe plaque-type psoriasis.

In some embodiments the dosage regimen described in Dosage Regimen A (including any of Embodiments A1 to A18) are for the treatment of atopic dermatitis. In some embodiments the dosage regimen is for the treatment of moderate to severe atopic dermatitis. In some embodiments the dosage regimen is for the treatment of severe atopic dermatitis. In some embodiments the dosage regimen is for the treatment of moderate atopic dermatitis.

In some embodiments the dosage regimen described in Dosage Regimen A (including any of Embodiments A1 to A18) are for the treatment of hidradenitis suppurativa (HS).

In some embodiments the dosage regimen is for the treatment of mild to severe HS In some embodiments the dosage regimen is for the treatment of moderate to severe HS. In some embodiments the dosage regimen is for the treatment of severe HS. In some embodiments the dosage regimen is for the treatment of moderate HS.

Dosage Regimen B (Second Aspect of the Invention)

As discussed above in relation to Dosage Regimen A, subjects which have a body mass which is greater than or equal to the threshold body mass are expected to show improved efficacy and/or tolerability when treated with higher orismilast maintenance doses. Dosage Regimen B described herein is for the treatment of subjects with a body mass that is greater than or equal to a threshold body mass.

Accordingly also provided is orismilast for use in a method of treating a disease or disorder ameliorated by inhibiting PDE4 in a subject with a body mass that is greater than or equal to a threshold body mass, the method comprising administering the orismilast to the subject,
wherein:
(Bi) an initial orismilast dose is administered to the subject once per day for a preliminary time period followed by;
(Bii) a interim orismilast dose administered to the subject twice per day for an interim time period followed by;
(Biii) a maintenance orismilast dose administered to the subject twice per day, wherein the maintenance orismilast dose is greater than the interim orismilast dose;
wherein:
(a) the initial orismilast dose and the interim orismilast doses are independently selected from 10 mg to 30 mg orismilast, provided that the interim orismilast dose is greater than or equal to the initial orismilast dose;
(b) the preliminary time period is up to eight weeks;
(c) the interim time period is one week to eight weeks; and
(d) the threshold body mass is at least 90 kg.

Also provided is a method of treating a disease or disorder ameliorated by inhibiting PDE4 in a subject with a body mass that is greater than or equal to a threshold body mass, the method comprising administering the orismilast to the subject according to the dosage regimen (Bi), (Bii) and (Biii) described above.

Also provided is the use of orismilast for the manufacture of a medicament for the treatment a disease or disorder ameliorated by inhibiting PDE4 in a subject with a body mass that is greater than or equal to a threshold body mass, the method comprising administering the orismilast to the subject according to the dosage regimen (Bi), (Bii) and (Biii) described above.

In certain embodiments of Dosage Regimen B the interim orismilast dose is 10 to 20 mg orismilast. In certain embodiments the interim orismilast dose is 10 mg orismilast. In certain embodiments the interim orismilast dose is 20 mg orismilast.

The administration of the initial and interim orismilast doses in (Bi) and (Bii) are expected to improve the subject tolerability to orismilast by reducing the number and or severity of side effects, for example diarrhoea, nausea, headache, dizziness or vomiting.

In Dosage Regimen B the maintenance orismilast dose is greater than the interim orismilast dose when the subject has a body mass that is greater than or equal to a threshold body mass. Suitably the maintenance orismilast dose for subjects which have a body mass that is greater than or equal to the threshold body mass is up to 40 mg orismilast, for example the maintenance orismilast dose is up to 35 mg orismilast, or up to 30 mg orismilast, provided that the maintenance orismilast dose is greater than the interim orismilast dose. In some embodiments the maintenance orismilast dose is selected from 30, 31, 32, 33, 34, 35, 36, 37, 38, 39 or 40 mg orismilast, provided that the maintenance orismilast dose is greater than the interim orismilast dose.

In certain embodiments of Dosage Regimen B, the dosage regimen comprises:
(Bi) the initial orismilast dose is 20 mg orismilast administered to the subject once per day for one week;
(Bii) the interim orismilast dose is 20 mg orismilast administered to the subject twice per day for one week to eight weeks;
(Biii) the maintenance orismilast dose is 30 mg orismilast administered to the subject twice per day.

Thus it may be that the interim orismilast dose is administered to the subject twice per day for two weeks to eight weeks. It may be that the interim orismilast dose is administered to the subject twice per day for one week to four weeks. It may be that the interim orismilast dose is administered to the subject twice per day for four weeks to eight weeks. It may be that the interim orismilast dose is administered to the subject twice per day for six weeks to eight weeks.

Embodiment B1

In certain embodiments of Dosage Regimen B, the dosage regimen comprises:
(Bi) the initial orismilast dose is 20 mg orismilast administered to the subject once per day for one week;
(Bii) the interim orismilast dose is 20 mg orismilast administered to the subject twice per day for two weeks;
(Biii) the maintenance orismilast dose is 30 mg orismilast administered to the subject twice per day.

Embodiment B2

In certain embodiments of Dosage Regimen B, the dosage regimen comprises:
(Bi) the initial orismilast dose is 20 mg orismilast administered to the subject once per day for one week;
(Bii) the interim orismilast dose is 20 mg orismilast administered to the subject twice per day for four weeks;
(Biii) the maintenance orismilast dose is 30 mg orismilast administered to the subject twice per day.

Embodiment B3

In certain embodiments of Dosage Regimen B, the dosage regimen comprises:
(Bi) the initial orismilast dose is 20 mg orismilast administered to the subject once per day for one week;
(Bii) the interim orismilast dose is 20 mg orismilast administered to the subject twice per day for six weeks;
(Biii) the maintenance orismilast dose is 30 mg orismilast administered to the subject twice per day.

Embodiment B4

In certain embodiments of Dosage Regimen B, the dosage regimen comprises:
(Bi) the initial orismilast dose is 20 mg orismilast administered to the subject once per day for one week;

(Bii) the interim orismilast dose is 20 mg orismilast administered to the subject twice per day for eight weeks;
(Biii) the maintenance orismilast dose is 30 mg orismilast administered to the subject twice per day.

Embodiment B5

In certain embodiments of Dosage Regimen B, the dosage regimen comprises:
(Bi) the initial orismilast dose is 20 mg orismilast administered to the subject once per day for two weeks;
(Bii) the interim orismilast dose is 20 mg orismilast administered to the subject twice per day for one week to eight weeks;
(Biii) the maintenance orismilast dose is 30 mg orismilast administered to the subject twice per day.

Thus it may be that the interim orismilast dose is administered to the subject twice per day for two weeks to eight weeks. It may be that the interim orismilast dose is administered to the subject twice per day for one week to four weeks. It may be that the interim orismilast dose is administered to the subject twice per day for four weeks to eight weeks. It may be that the interim orismilast dose is administered to the subject twice per day for six weeks to eight weeks.

Embodiment B6

In certain embodiments of Dosage Regimen B, the dosage regimen comprises:
(Bi) the initial orismilast dose is 20 mg orismilast administered to the subject once per day for two weeks;
(Bii) the interim orismilast dose is 20 mg orismilast administered to the subject twice per day for two weeks;
(Biii) the maintenance orismilast dose is 30 mg orismilast administered to the subject twice per day.

Embodiment B7

In certain embodiments of Dosage Regimen B, the dosage regimen comprises:
(Bi) the initial orismilast dose is 20 mg orismilast administered to the subject once per day for two weeks;
(Bii) the interim orismilast dose is 20 mg orismilast administered to the subject twice per day for four weeks;
(Biii) the maintenance orismilast dose is 30 mg orismilast administered to the subject twice per day.

Embodiment B8

In certain embodiments of Dosage Regimen B, the dosage regimen comprises:
(Bi) the initial orismilast dose is 20 mg orismilast administered to the subject once per day for two weeks;
(Bii) the interim orismilast dose is 20 mg orismilast administered to the subject twice per day for six weeks;
(Biii) the maintenance orismilast dose is 30 mg orismilast administered to the subject twice per day.

Embodiment B9

In certain embodiments of Dosage Regimen B, the dosage regimen comprises:
(Bi) the initial orismilast dose is 20 mg orismilast administered to the subject once per day for two weeks;
(Bii) the interim orismilast dose is 20 mg orismilast administered to the subject twice per day for eight weeks;
(Biii) the maintenance orismilast dose is 30 mg orismilast administered to the subject twice per day.

The dosage regimens described in Dosage Regimen B (including any of Embodiments B1 to B9) are particularly suitable for the treatment of psoriasis, for example the treatment of moderate to severe psoriasis. The psoriasis may be plaque-type psoriasis. Preferably the dosage regimen is for the treatment of moderate to severe plaque-type psoriasis.

In some embodiments the dosage regimens described in described in Dosage Regimen B (including any of Embodiments B1 to B9) are for the treatment of atopic dermatitis. It may be that the dosage regimen is for the treatment of moderate to severe atopic dermatitis. It may be that the dosage regimen is for the treatment of moderate atopic dermatitis. It may be that the dosage regimen is for the treatment of severe atopic dermatitis.

In certain embodiments in Dosage Regimen A and Dosage Regimen B the threshold body mass is 90 kg. In certain embodiments in Dosage Regimen A and Dosage Regimen B the threshold body mass is 95 kg. In certain embodiments in Dosage Regimen A and Dosage Regimen B the threshold body mass is 105 kg. In preferred embodiments in Dosage Regimen A and Dosage Regimen B the threshold body mass is 100 kg.

The improved tolerability and/or efficacy provided by the dosage regimens described herein may also provide improved patient compliance with the treatment thereby enhancing the effectiveness of the orismilast treatment.

In certain embodiments the initial time period/preliminary time period, the initial orismilast dose, the interim time period and the interim orismilast dose used in Dosage Regimen A or Dosage Regimen B is any one of the dosage regimens in Table 1. In Table 1 the initial time period used in Dosage Regimen A are any of the regimens in Table 1 where the initial time period is between 2 and 8 weeks in accordance with Dosage Regimen A.

TABLE 1

| Dosage Regimen # | Initial time period/preliminary time period (weeks) | Initial orismilast dose (mg) | Interim time period (weeks) | Interim orismilast dose (mg) |
|---|---|---|---|---|
| 1 | 1-8 | 10-30 | 1-8 | 10-30 |
| 2 | 2-8 | 10-30 | 1-8 | 10-30 |
| 3 | 2-7 | 10-30 | 1-8 | 10-30 |
| 4 | 2-6 | 10-30 | 1-8 | 10-30 |
| 5 | 2-5 | 10-30 | 1-8 | 10-30 |
| 6 | 2-4 | 10-30 | 1-8 | 10-30 |
| 7 | 2-3 | 10-30 | 1-8 | 10-30 |
| 8 | 1-2 | 10-30 | 1-8 | 10-30 |
| 9 | 1-3 | 10-30 | 1-8 | 10-30 |
| 10 | 1-4 | 10-30 | 1-8 | 10-30 |
| 11 | 1 | 10-30 | 1-8 | 10-30 |
| 12 | 2 | 10-30 | 1-8 | 10-30 |
| 13 | 3 | 10-30 | 1-8 | 10-30 |
| 14 | 4 | 10-30 | 1-8 | 10-30 |
| 15 | 5 | 10-30 | 1-8 | 10-30 |
| 16 | 6 | 10-30 | 1-8 | 10-30 |
| 17 | 7 | 10-30 | 1-8 | 10-30 |
| 18 | 8 | 10-30 | 1-8 | 10-30 |
| 19 | 1-8 | 10 | 1-8 | 10-30 |
| 20 | 2-8 | 10 | 1-8 | 10-30 |
| 21 | 2-7 | 10 | 1-8 | 10-30 |

TABLE 1-continued

| Dosage Regimen # | Initial time period/preliminary time period (weeks) | Initial orismilast dose (mg) | Interim time period (weeks) | Interim orismilast dose (mg) |
|---|---|---|---|---|
| 22 | 2-6 | 10 | 1-8 | 10-30 |
| 23 | 2-5 | 10 | 1-8 | 10-30 |
| 24 | 2-4 | 10 | 1-8 | 10-30 |
| 25 | 2-3 | 10 | 1-8 | 10-30 |
| 26 | 1-2 | 10 | 1-8 | 10-30 |
| 27 | 1-3 | 10 | 1-8 | 10-30 |
| 28 | 1-4 | 10 | 1-8 | 10-30 |
| 29 | 1 | 10 | 1-8 | 10-30 |
| 30 | 2 | 10 | 1-8 | 10-30 |
| 31 | 3 | 10 | 1-8 | 10-30 |
| 32 | 4 | 10 | 1-8 | 10-30 |
| 33 | 5 | 10 | 1-8 | 10-30 |
| 34 | 6 | 10 | 1-8 | 10-30 |
| 35 | 7 | 10 | 1-8 | 10-30 |
| 36 | 8 | 10 | 1-8 | 10-30 |
| 37 | 1-8 | 20 | 1-8 | 20-30 |
| 38 | 2-8 | 20 | 1-8 | 20-30 |
| 39 | 2-7 | 20 | 1-8 | 20-30 |
| 40 | 2-6 | 20 | 1-8 | 20-30 |
| 41 | 2-5 | 20 | 1-8 | 20-30 |
| 42 | 2-4 | 20 | 1-8 | 20-30 |
| 43 | 2-3 | 20 | 1-8 | 20-30 |
| 44 | 1-2 | 20 | 1-8 | 20-30 |
| 45 | 1-3 | 20 | 1-8 | 20-30 |
| 46 | 1-4 | 20 | 1-8 | 20-30 |
| 47 | 1 | 20 | 1-8 | 20-30 |
| 48 | 2 | 20 | 1-8 | 20-30 |
| 49 | 3 | 20 | 1-8 | 20-30 |
| 50 | 4 | 20 | 1-8 | 20-30 |
| 51 | 5 | 20 | 1-8 | 20-30 |
| 52 | 6 | 20 | 1-8 | 20-30 |
| 53 | 7 | 20 | 1-8 | 20-30 |
| 54 | 8 | 20 | 1-8 | 20-30 |
| 55 | 1-8 | 30 | 1-8 | 30 |
| 56 | 2-8 | 30 | 1-8 | 30 |
| 57 | 2-7 | 30 | 1-8 | 30 |
| 58 | 2-6 | 30 | 1-8 | 30 |
| 59 | 2-5 | 30 | 1-8 | 30 |
| 60 | 2-4 | 30 | 1-8 | 30 |
| 61 | 2-3 | 30 | 1-8 | 30 |
| 62 | 1-2 | 30 | 1-8 | 30 |
| 63 | 1-3 | 30 | 1-8 | 30 |
| 64 | 1-4 | 30 | 1-8 | 30 |
| 65 | 1 | 30 | 1-8 | 30 |
| 66 | 2 | 30 | 1-8 | 30 |
| 67 | 3 | 30 | 1-8 | 30 |
| 68 | 4 | 30 | 1-8 | 30 |
| 69 | 5 | 30 | 1-8 | 30 |
| 70 | 6 | 30 | 1-8 | 30 |
| 71 | 7 | 30 | 1-8 | 30 |
| 72 | 8 | 30 | 1-8 | 30 |
| 73 | 1-8 | 10-30 | 1-6 | 10-30 |
| 74 | 2-8 | 10-30 | 1-6 | 10-30 |
| 75 | 2-7 | 10-30 | 1-6 | 10-30 |
| 76 | 2-6 | 10-30 | 1-6 | 10-30 |
| 77 | 2-5 | 10-30 | 1-6 | 10-30 |
| 78 | 2-4 | 10-30 | 1-6 | 10-30 |
| 79 | 2-3 | 10-30 | 1-6 | 10-30 |
| 80 | 1-2 | 10-30 | 1-6 | 10-30 |
| 81 | 1-3 | 10-30 | 1-6 | 10-30 |
| 82 | 1-4 | 10-30 | 1-6 | 10-30 |
| 83 | 1 | 10-30 | 1-6 | 10-30 |
| 84 | 2 | 10-30 | 1-6 | 10-30 |
| 85 | 3 | 10-30 | 1-6 | 10-30 |
| 86 | 4 | 10-30 | 1-6 | 10-30 |
| 87 | 5 | 10-30 | 1-6 | 10-30 |
| 88 | 6 | 10-30 | 1-6 | 10-30 |
| 89 | 7 | 10-30 | 1-6 | 10-30 |
| 90 | 8 | 10-30 | 1-6 | 10-30 |
| 91 | 1-8 | 10 | 1-6 | 10-30 |
| 92 | 2-8 | 10 | 1-6 | 10-30 |
| 93 | 2-7 | 10 | 1-6 | 10-30 |
| 94 | 2-6 | 10 | 1-6 | 10-30 |
| 95 | 2-5 | 10 | 1-6 | 10-30 |
| 96 | 2-4 | 10 | 1-6 | 10-30 |
| 97 | 2-3 | 10 | 1-6 | 10-30 |
| 98 | 1-2 | 10 | 1-6 | 10-30 |
| 99 | 1-3 | 10 | 1-6 | 10-30 |
| 100 | 1-4 | 10 | 1-6 | 10-30 |
| 101 | 1 | 10 | 1-6 | 10-30 |
| 102 | 2 | 10 | 1-6 | 10-30 |
| 103 | 3 | 10 | 1-6 | 10-30 |
| 104 | 4 | 10 | 1-6 | 10-30 |
| 105 | 5 | 10 | 1-6 | 10-30 |
| 106 | 6 | 10 | 1-6 | 10-30 |
| 107 | 7 | 10 | 1-6 | 10-30 |
| 108 | 8 | 10 | 1-6 | 10-30 |
| 109 | 1-8 | 20 | 1-6 | 20-30 |
| 110 | 2-8 | 20 | 1-6 | 20-30 |
| 111 | 2-7 | 20 | 1-6 | 20-30 |
| 112 | 2-6 | 20 | 1-6 | 20-30 |
| 113 | 2-5 | 20 | 1-6 | 20-30 |
| 114 | 2-4 | 20 | 1-6 | 20-30 |
| 115 | 2-3 | 20 | 1-6 | 20-30 |
| 116 | 1-2 | 20 | 1-6 | 20-30 |
| 117 | 1-3 | 20 | 1-6 | 20-30 |
| 118 | 1-4 | 20 | 1-6 | 20-30 |
| 119 | 1 | 20 | 1-6 | 20-30 |
| 120 | 2 | 20 | 1-6 | 20-30 |
| 121 | 3 | 20 | 1-6 | 20-30 |
| 122 | 4 | 20 | 1-6 | 20-30 |
| 123 | 5 | 20 | 1-6 | 20-30 |
| 124 | 6 | 20 | 1-6 | 20-30 |
| 125 | 7 | 20 | 1-6 | 20-30 |
| 126 | 8 | 20 | 1-6 | 20-30 |
| 127 | 1-8 | 30 | 1-6 | 30 |
| 128 | 2-8 | 30 | 1-6 | 30 |
| 129 | 2-7 | 30 | 1-6 | 30 |
| 130 | 2-6 | 30 | 1-6 | 30 |
| 131 | 2-5 | 30 | 1-6 | 30 |
| 132 | 2-4 | 30 | 1-6 | 30 |
| 133 | 2-3 | 30 | 1-6 | 30 |
| 134 | 1-2 | 30 | 1-6 | 30 |
| 135 | 1-3 | 30 | 1-6 | 30 |
| 136 | 1-4 | 30 | 1-6 | 30 |
| 137 | 1 | 30 | 1-6 | 30 |
| 138 | 2 | 30 | 1-6 | 30 |
| 139 | 3 | 30 | 1-6 | 30 |
| 140 | 4 | 30 | 1-6 | 30 |
| 141 | 5 | 30 | 1-6 | 30 |
| 142 | 6 | 30 | 1-6 | 30 |
| 143 | 7 | 30 | 1-6 | 30 |
| 144 | 8 | 30 | 1-6 | 30 |
| 145 | 1-8 | 10-30 | 1-4 | 10-30 |
| 146 | 2-8 | 10-30 | 1-4 | 10-30 |
| 147 | 2-7 | 10-30 | 1-4 | 10-30 |
| 148 | 2-6 | 10-30 | 1-4 | 10-30 |
| 149 | 2-5 | 10-30 | 1-4 | 10-30 |
| 150 | 2-4 | 10-30 | 1-4 | 10-30 |
| 151 | 2-3 | 10-30 | 1-4 | 10-30 |
| 152 | 1-2 | 10-30 | 1-4 | 10-30 |
| 153 | 1-3 | 10-30 | 1-4 | 10-30 |
| 154 | 1-4 | 10-30 | 1-4 | 10-30 |
| 155 | 1 | 10-30 | 1-4 | 10-30 |
| 156 | 2 | 10-30 | 1-4 | 10-30 |
| 157 | 3 | 10-30 | 1-4 | 10-30 |
| 158 | 4 | 10-30 | 1-4 | 10-30 |
| 159 | 5 | 10-30 | 1-4 | 10-30 |
| 160 | 6 | 10-30 | 1-4 | 10-30 |
| 161 | 7 | 10-30 | 1-4 | 10-30 |
| 162 | 8 | 10-30 | 1-4 | 10-30 |
| 163 | 1-8 | 10 | 1-4 | 10-30 |
| 164 | 2-8 | 10 | 1-4 | 10-30 |
| 165 | 2-7 | 10 | 1-4 | 10-30 |
| 166 | 2-6 | 10 | 1-4 | 10-30 |
| 167 | 2-5 | 10 | 1-4 | 10-30 |
| 168 | 2-4 | 10 | 1-4 | 10-30 |
| 169 | 2-3 | 10 | 1-4 | 10-30 |
| 170 | 1-2 | 10 | 1-4 | 10-30 |
| 171 | 1-3 | 10 | 1-4 | 10-30 |

TABLE 1-continued

| Dosage Regimen # | Initial time period/preliminary time period (weeks) | Initial orismilast dose (mg) | Interim time period (weeks) | Interim orismilast dose (mg) |
|---|---|---|---|---|
| 172 | 1-4 | 10 | 1-4 | 10-30 |
| 173 | 1 | 10 | 1-4 | 10-30 |
| 174 | 2 | 10 | 1-4 | 10-30 |
| 175 | 3 | 10 | 1-4 | 10-30 |
| 176 | 4 | 10 | 1-4 | 10-30 |
| 177 | 5 | 10 | 1-4 | 10-30 |
| 178 | 6 | 10 | 1-4 | 10-30 |
| 179 | 7 | 10 | 1-4 | 10-30 |
| 180 | 8 | 10 | 1-4 | 10-30 |
| 181 | 1-8 | 20 | 1-4 | 20-30 |
| 182 | 2-8 | 20 | 1-4 | 20-30 |
| 183 | 2-7 | 20 | 1-4 | 20-30 |
| 184 | 2-6 | 20 | 1-4 | 20-30 |
| 185 | 2-5 | 20 | 1-4 | 20-30 |
| 186 | 2-4 | 20 | 1-4 | 20-30 |
| 187 | 2-3 | 20 | 1-4 | 20-30 |
| 188 | 1-2 | 20 | 1-4 | 20-30 |
| 189 | 1-3 | 20 | 1-4 | 20-30 |
| 190 | 1-4 | 20 | 1-4 | 20-30 |
| 191 | 1 | 20 | 1-4 | 20-30 |
| 192 | 2 | 20 | 1-4 | 20-30 |
| 193 | 3 | 20 | 1-4 | 20-30 |
| 194 | 4 | 20 | 1-4 | 20-30 |
| 195 | 5 | 20 | 1-4 | 20-30 |
| 196 | 6 | 20 | 1-4 | 20-30 |
| 197 | 7 | 20 | 1-4 | 20-30 |
| 198 | 8 | 20 | 1-4 | 20-30 |
| 199 | 1-8 | 30 | 1-4 | 30 |
| 200 | 2-8 | 30 | 1-4 | 30 |
| 201 | 2-7 | 30 | 1-4 | 30 |
| 202 | 2-6 | 30 | 1-4 | 30 |
| 203 | 2-5 | 30 | 1-4 | 30 |
| 204 | 2-4 | 30 | 1-4 | 30 |
| 205 | 2-3 | 30 | 1-4 | 30 |
| 206 | 1-2 | 30 | 1-4 | 30 |
| 207 | 1-3 | 30 | 1-4 | 30 |
| 208 | 1-4 | 30 | 1-4 | 30 |
| 209 | 1 | 30 | 1-4 | 30 |
| 210 | 2 | 30 | 1-4 | 30 |
| 211 | 3 | 30 | 1-4 | 30 |
| 212 | 4 | 30 | 1-4 | 30 |
| 213 | 5 | 30 | 1-4 | 30 |
| 214 | 6 | 30 | 1-4 | 30 |
| 215 | 7 | 30 | 1-4 | 30 |
| 216 | 8 | 30 | 1-4 | 30 |
| 217 | 1-8 | 10-30 | 1-3 | 10-30 |
| 218 | 2-8 | 10-30 | 1-3 | 10-30 |
| 219 | 2-7 | 10-30 | 1-3 | 10-30 |
| 220 | 2-6 | 10-30 | 1-3 | 10-30 |
| 221 | 2-5 | 10-30 | 1-3 | 10-30 |
| 222 | 2-4 | 10-30 | 1-3 | 10-30 |
| 223 | 2-3 | 10-30 | 1-3 | 10-30 |
| 224 | 1-2 | 10-30 | 1-3 | 10-30 |
| 225 | 1-3 | 10-30 | 1-3 | 10-30 |
| 226 | 1-4 | 10-30 | 1-3 | 10-30 |
| 227 | 1 | 10-30 | 1-3 | 10-30 |
| 228 | 2 | 10-30 | 1-3 | 10-30 |
| 229 | 3 | 10-30 | 1-3 | 10-30 |
| 230 | 4 | 10-30 | 1-3 | 10-30 |
| 231 | 5 | 10-30 | 1-3 | 10-30 |
| 232 | 6 | 10-30 | 1-3 | 10-30 |
| 233 | 7 | 10-30 | 1-3 | 10-30 |
| 234 | 8 | 10-30 | 1-3 | 10-30 |
| 235 | 1-8 | 10 | 1-3 | 10-30 |
| 236 | 2-8 | 10 | 1-3 | 10-30 |
| 237 | 2-7 | 10 | 1-3 | 10-30 |
| 238 | 2-6 | 10 | 1-3 | 10-30 |
| 239 | 2-5 | 10 | 1-3 | 10-30 |
| 240 | 2-4 | 10 | 1-3 | 10-30 |
| 241 | 2-3 | 10 | 1-3 | 10-30 |
| 242 | 1-2 | 10 | 1-3 | 10-30 |
| 243 | 1-3 | 10 | 1-3 | 10-30 |
| 244 | 1-4 | 10 | 1-3 | 10-30 |
| 245 | 1 | 10 | 1-3 | 10-30 |
| 246 | 2 | 10 | 1-3 | 10-30 |
| 247 | 3 | 10 | 1-3 | 10-30 |
| 248 | 4 | 10 | 1-3 | 10-30 |
| 249 | 5 | 10 | 1-3 | 10-30 |
| 250 | 6 | 10 | 1-3 | 10-30 |
| 251 | 7 | 10 | 1-3 | 10-30 |
| 252 | 8 | 10 | 1-3 | 10-30 |
| 253 | 1-8 | 20 | 1-3 | 20-30 |
| 254 | 2-8 | 20 | 1-3 | 20-30 |
| 255 | 2-7 | 20 | 1-3 | 20-30 |
| 256 | 2-6 | 20 | 1-3 | 20-30 |
| 257 | 2-5 | 20 | 1-3 | 20-30 |
| 258 | 2-4 | 20 | 1-3 | 20-30 |
| 259 | 2-3 | 20 | 1-3 | 20-30 |
| 260 | 1-2 | 20 | 1-3 | 20-30 |
| 261 | 1-3 | 20 | 1-3 | 20-30 |
| 262 | 1-4 | 20 | 1-3 | 20-30 |
| 263 | 1 | 20 | 1-3 | 20-30 |
| 264 | 2 | 20 | 1-3 | 20-30 |
| 265 | 3 | 20 | 1-3 | 20-30 |
| 266 | 4 | 20 | 1-3 | 20-30 |
| 267 | 5 | 20 | 1-3 | 20-30 |
| 268 | 6 | 20 | 1-3 | 20-30 |
| 269 | 7 | 20 | 1-3 | 20-30 |
| 270 | 8 | 20 | 1-3 | 20-30 |
| 271 | 1-8 | 30 | 1-3 | 30 |
| 272 | 2-8 | 30 | 1-3 | 30 |
| 273 | 2-7 | 30 | 1-3 | 30 |
| 274 | 2-6 | 30 | 1-3 | 30 |
| 275 | 2-5 | 30 | 1-3 | 30 |
| 276 | 2-4 | 30 | 1-3 | 30 |
| 277 | 2-3 | 30 | 1-3 | 30 |
| 278 | 1-2 | 30 | 1-3 | 30 |
| 279 | 1-3 | 30 | 1-3 | 30 |
| 280 | 1-4 | 30 | 1-3 | 30 |
| 281 | 1 | 30 | 1-3 | 30 |
| 282 | 2 | 30 | 1-3 | 30 |
| 283 | 3 | 30 | 1-3 | 30 |
| 284 | 4 | 30 | 1-3 | 30 |
| 285 | 5 | 30 | 1-3 | 30 |
| 286 | 6 | 30 | 1-3 | 30 |
| 287 | 7 | 30 | 1-3 | 30 |
| 288 | 8 | 30 | 1-3 | 30 |
| 289 | 1-8 | 10-30 | 1-2 | 10-30 |
| 290 | 2-8 | 10-30 | 1-2 | 10-30 |
| 291 | 2-7 | 10-30 | 1-2 | 10-30 |
| 292 | 2-6 | 10-30 | 1-2 | 10-30 |
| 293 | 2-5 | 10-30 | 1-2 | 10-30 |
| 294 | 2-4 | 10-30 | 1-2 | 10-30 |
| 295 | 2-3 | 10-30 | 1-2 | 10-30 |
| 296 | 1-2 | 10-30 | 1-2 | 10-30 |
| 297 | 1-3 | 10-30 | 1-2 | 10-30 |
| 298 | 1-4 | 10-30 | 1-2 | 10-30 |
| 299 | 1 | 10-30 | 1-2 | 10-30 |
| 300 | 2 | 10-30 | 1-2 | 10-30 |
| 301 | 3 | 10-30 | 1-2 | 10-30 |
| 302 | 4 | 10-30 | 1-2 | 10-30 |
| 303 | 5 | 10-30 | 1-2 | 10-30 |
| 304 | 6 | 10-30 | 1-2 | 10-30 |
| 305 | 7 | 10-30 | 1-2 | 10-30 |
| 306 | 8 | 10-30 | 1-2 | 10-30 |
| 307 | 1-8 | 10 | 1-2 | 10-30 |
| 308 | 2-8 | 10 | 1-2 | 10-30 |
| 309 | 2-7 | 10 | 1-2 | 10-30 |
| 310 | 2-6 | 10 | 1-2 | 10-30 |
| 311 | 2-5 | 10 | 1-2 | 10-30 |
| 312 | 2-4 | 10 | 1-2 | 10-30 |
| 313 | 2-3 | 10 | 1-2 | 10-30 |
| 314 | 1-2 | 10 | 1-2 | 10-30 |
| 315 | 1-3 | 10 | 1-2 | 10-30 |
| 316 | 1-4 | 10 | 1-2 | 10-30 |
| 317 | 1 | 10 | 1-2 | 10-30 |
| 318 | 2 | 10 | 1-2 | 10-30 |
| 319 | 3 | 10 | 1-2 | 10-30 |
| 320 | 4 | 10 | 1-2 | 10-30 |
| 321 | 5 | 10 | 1-2 | 10-30 |

TABLE 1-continued

| Dosage Regimen # | Initial time period/preliminary time period (weeks) | Initial orismilast dose (mg) | Interim time period (weeks) | Interim orismilast dose (mg) |
|---|---|---|---|---|
| 322 | 6 | 10 | 1-2 | 10-30 |
| 323 | 7 | 10 | 1-2 | 10-30 |
| 324 | 8 | 10 | 1-2 | 10-30 |
| 325 | 1-8 | 20 | 1-2 | 20-30 |
| 326 | 2-8 | 20 | 1-2 | 20-30 |
| 327 | 2-7 | 20 | 1-2 | 20-30 |
| 328 | 2-6 | 20 | 1-2 | 20-30 |
| 329 | 2-5 | 20 | 1-2 | 20-30 |
| 330 | 2-4 | 20 | 1-2 | 20-30 |
| 331 | 2-3 | 20 | 1-2 | 20-30 |
| 332 | 1-2 | 20 | 1-2 | 20-30 |
| 333 | 1-3 | 20 | 1-2 | 20-30 |
| 334 | 1-4 | 20 | 1-2 | 20-30 |
| 335 | 1 | 20 | 1-2 | 20-30 |
| 336 | 2 | 20 | 1-2 | 20-30 |
| 337 | 3 | 20 | 1-2 | 20-30 |
| 338 | 4 | 20 | 1-2 | 20-30 |
| 339 | 5 | 20 | 1-2 | 20-30 |
| 340 | 6 | 20 | 1-2 | 20-30 |
| 341 | 7 | 20 | 1-2 | 20-30 |
| 342 | 8 | 20 | 1-2 | 20-30 |
| 343 | 1-8 | 30 | 1-2 | 30 |
| 344 | 2-8 | 30 | 1-2 | 30 |
| 345 | 2-7 | 30 | 1-2 | 30 |
| 346 | 2-6 | 30 | 1-2 | 30 |
| 347 | 2-5 | 30 | 1-2 | 30 |
| 348 | 2-4 | 30 | 1-2 | 30 |
| 349 | 2-3 | 30 | 1-2 | 30 |
| 350 | 1-2 | 30 | 1-2 | 30 |
| 351 | 1-3 | 30 | 1-2 | 30 |
| 352 | 1-4 | 30 | 1-2 | 30 |
| 353 | 1 | 30 | 1-2 | 30 |
| 354 | 2 | 30 | 1-2 | 30 |
| 355 | 3 | 30 | 1-2 | 30 |
| 356 | 4 | 30 | 1-2 | 30 |
| 357 | 5 | 30 | 1-2 | 30 |
| 358 | 6 | 30 | 1-2 | 30 |
| 359 | 7 | 30 | 1-2 | 30 |
| 360 | 8 | 30 | 1-2 | 30 |
| 361 | 1-8 | 10-30 | 1 | 10-30 |
| 362 | 2-8 | 10-30 | 1 | 10-30 |
| 363 | 2-7 | 10-30 | 1 | 10-30 |
| 364 | 2-6 | 10-30 | 1 | 10-30 |
| 365 | 2-5 | 10-30 | 1 | 10-30 |
| 366 | 2-4 | 10-30 | 1 | 10-30 |
| 367 | 2-3 | 10-30 | 1 | 10-30 |
| 368 | 1-2 | 10-30 | 1 | 10-30 |
| 369 | 1-3 | 10-30 | 1 | 10-30 |
| 370 | 1-4 | 10-30 | 1 | 10-30 |
| 371 | 1 | 10-30 | 1 | 10-30 |
| 372 | 2 | 10-30 | 1 | 10-30 |
| 373 | 3 | 10-30 | 1 | 10-30 |
| 374 | 4 | 10-30 | 1 | 10-30 |
| 375 | 5 | 10-30 | 1 | 10-30 |
| 376 | 6 | 10-30 | 1 | 10-30 |
| 377 | 7 | 10-30 | 1 | 10-30 |
| 378 | 8 | 10-30 | 1 | 10-30 |
| 379 | 1-8 | 10 | 1 | 10-30 |
| 380 | 2-8 | 10 | 1 | 10-30 |
| 381 | 2-7 | 10 | 1 | 10-30 |
| 382 | 2-6 | 10 | 1 | 10-30 |
| 383 | 2-5 | 10 | 1 | 10-30 |
| 384 | 2-4 | 10 | 1 | 10-30 |
| 385 | 2-3 | 10 | 1 | 10-30 |
| 386 | 1-2 | 10 | 1 | 10-30 |
| 387 | 1-3 | 10 | 1 | 10-30 |
| 388 | 1-4 | 10 | 1 | 10-30 |
| 389 | 1 | 10 | 1 | 10-30 |
| 390 | 2 | 10 | 1 | 10-30 |
| 391 | 3 | 10 | 1 | 10-30 |
| 392 | 4 | 10 | 1 | 10-30 |
| 393 | 5 | 10 | 1 | 10-30 |
| 394 | 6 | 10 | 1 | 10-30 |
| 395 | 7 | 10 | 1 | 10-30 |
| 396 | 8 | 10 | 1 | 10-30 |
| 397 | 1-8 | 20 | 1 | 20-30 |
| 398 | 2-8 | 20 | 1 | 20-30 |
| 399 | 2-7 | 20 | 1 | 20-30 |
| 400 | 2-6 | 20 | 1 | 20-30 |
| 401 | 2-5 | 20 | 1 | 20-30 |
| 402 | 2-4 | 20 | 1 | 20-30 |
| 403 | 2-3 | 20 | 1 | 20-30 |
| 404 | 1-2 | 20 | 1 | 20-30 |
| 405 | 1-3 | 20 | 1 | 20-30 |
| 406 | 1-4 | 20 | 1 | 20-30 |
| 407 | 1 | 20 | 1 | 20-30 |
| 408 | 2 | 20 | 1 | 20-30 |
| 409 | 3 | 20 | 1 | 20-30 |
| 410 | 4 | 20 | 1 | 20-30 |
| 411 | 5 | 20 | 1 | 20-30 |
| 412 | 6 | 20 | 1 | 20-30 |
| 413 | 7 | 20 | 1 | 20-30 |
| 414 | 8 | 20 | 1 | 20-30 |
| 415 | 1-8 | 30 | 1 | 30 |
| 416 | 2-8 | 30 | 1 | 30 |
| 417 | 2-7 | 30 | 1 | 30 |
| 418 | 2-6 | 30 | 1 | 30 |
| 419 | 2-5 | 30 | 1 | 30 |
| 420 | 2-4 | 30 | 1 | 30 |
| 421 | 2-3 | 30 | 1 | 30 |
| 422 | 1-2 | 30 | 1 | 30 |
| 423 | 1-3 | 30 | 1 | 30 |
| 424 | 1-4 | 30 | 1 | 30 |
| 425 | 1 | 30 | 1 | 30 |
| 426 | 2 | 30 | 1 | 30 |
| 427 | 3 | 30 | 1 | 30 |
| 428 | 4 | 30 | 1 | 30 |
| 429 | 5 | 30 | 1 | 30 |
| 430 | 6 | 30 | 1 | 30 |
| 431 | 7 | 30 | 1 | 30 |
| 432 | 8 | 30 | 1 | 30 |
| 433 | 1-8 | 10-30 | 2 | 10-30 |
| 434 | 2-8 | 10-30 | 2 | 10-30 |
| 435 | 2-7 | 10-30 | 2 | 10-30 |
| 436 | 2-6 | 10-30 | 2 | 10-30 |
| 437 | 2-5 | 10-30 | 2 | 10-30 |
| 438 | 2-4 | 10-30 | 2 | 10-30 |
| 439 | 2-3 | 10-30 | 2 | 10-30 |
| 440 | 1-2 | 10-30 | 2 | 10-30 |
| 441 | 1-3 | 10-30 | 2 | 10-30 |
| 442 | 1-4 | 10-30 | 2 | 10-30 |
| 443 | 1 | 10-30 | 2 | 10-30 |
| 444 | 2 | 10-30 | 2 | 10-30 |
| 445 | 3 | 10-30 | 2 | 10-30 |
| 446 | 4 | 10-30 | 2 | 10-30 |
| 447 | 5 | 10-30 | 2 | 10-30 |
| 448 | 6 | 10-30 | 2 | 10-30 |
| 449 | 7 | 10-30 | 2 | 10-30 |
| 450 | 8 | 10-30 | 2 | 10-30 |
| 451 | 1-8 | 10 | 2 | 10-30 |
| 452 | 2-8 | 10 | 2 | 10-30 |
| 453 | 2-7 | 10 | 2 | 10-30 |
| 454 | 2-6 | 10 | 2 | 10-30 |
| 455 | 2-5 | 10 | 2 | 10-30 |
| 456 | 2-4 | 10 | 2 | 10-30 |
| 457 | 2-3 | 10 | 2 | 10-30 |
| 458 | 1-2 | 10 | 2 | 10-30 |
| 459 | 1-3 | 10 | 2 | 10-30 |
| 460 | 1-4 | 10 | 2 | 10-30 |
| 461 | 1 | 10 | 2 | 10-30 |
| 462 | 2 | 10 | 2 | 10-30 |
| 463 | 3 | 10 | 2 | 10-30 |
| 464 | 4 | 10 | 2 | 10-30 |
| 465 | 5 | 10 | 2 | 10-30 |
| 466 | 6 | 10 | 2 | 10-30 |
| 467 | 7 | 10 | 2 | 10-30 |
| 468 | 8 | 10 | 2 | 10-30 |
| 469 | 1-8 | 20 | 2 | 20-30 |
| 470 | 2-8 | 20 | 2 | 20-30 |
| 471 | 2-7 | 20 | 2 | 20-30 |

TABLE 1-continued

| Dosage Regimen # | Initial time period/preliminary time period (weeks) | Initial orismilast dose (mg) | Interim time period (weeks) | Interim orismilast dose (mg) |
|---|---|---|---|---|
| 472 | 2-6 | 20 | 2 | 20-30 |
| 473 | 2-5 | 20 | 2 | 20-30 |
| 474 | 2-4 | 20 | 2 | 20-30 |
| 475 | 2-3 | 20 | 2 | 20-30 |
| 476 | 1-2 | 20 | 2 | 20-30 |
| 477 | 1-3 | 20 | 2 | 20-30 |
| 478 | 1-4 | 20 | 2 | 20-30 |
| 479 | 1 | 20 | 2 | 20-30 |
| 480 | 2 | 20 | 2 | 20-30 |
| 481 | 3 | 20 | 2 | 20-30 |
| 482 | 4 | 20 | 2 | 20-30 |
| 483 | 5 | 20 | 2 | 20-30 |
| 484 | 6 | 20 | 2 | 20-30 |
| 485 | 7 | 20 | 2 | 20-30 |
| 486 | 8 | 20 | 2 | 20-30 |
| 487 | 1-8 | 30 | 2 | 30 |
| 488 | 2-8 | 30 | 2 | 30 |
| 489 | 2-7 | 30 | 2 | 30 |
| 490 | 2-6 | 30 | 2 | 30 |
| 491 | 2-5 | 30 | 2 | 30 |
| 492 | 2-4 | 30 | 2 | 30 |
| 493 | 2-3 | 30 | 2 | 30 |
| 494 | 1-2 | 30 | 2 | 30 |
| 495 | 1-3 | 30 | 2 | 30 |
| 496 | 1-4 | 30 | 2 | 30 |
| 497 | 1 | 30 | 2 | 30 |
| 498 | 2 | 30 | 2 | 30 |
| 499 | 3 | 30 | 2 | 30 |
| 500 | 4 | 30 | 2 | 30 |
| 501 | 5 | 30 | 2 | 30 |
| 502 | 6 | 30 | 2 | 30 |
| 503 | 7 | 30 | 2 | 30 |
| 504 | 8 | 30 | 2 | 30 |
| 505 | 1-8 | 10-30 | 3 | 10-30 |
| 506 | 2-8 | 10-30 | 3 | 10-30 |
| 507 | 2-7 | 10-30 | 3 | 10-30 |
| 508 | 2-6 | 10-30 | 3 | 10-30 |
| 509 | 2-5 | 10-30 | 3 | 10-30 |
| 510 | 2-4 | 10-30 | 3 | 10-30 |
| 511 | 2-3 | 10-30 | 3 | 10-30 |
| 512 | 1-2 | 10-30 | 3 | 10-30 |
| 513 | 1-3 | 10-30 | 3 | 10-30 |
| 514 | 1-4 | 10-30 | 3 | 10-30 |
| 515 | 1 | 10-30 | 3 | 10-30 |
| 516 | 2 | 10-30 | 3 | 10-30 |
| 517 | 3 | 10-30 | 3 | 10-30 |
| 518 | 4 | 10-30 | 3 | 10-30 |
| 519 | 5 | 10-30 | 3 | 10-30 |
| 520 | 6 | 10-30 | 3 | 10-30 |
| 521 | 7 | 10-30 | 3 | 10-30 |
| 522 | 8 | 10-30 | 3 | 10-30 |
| 523 | 1-8 | 10 | 3 | 10-30 |
| 524 | 2-8 | 10 | 3 | 10-30 |
| 525 | 2-7 | 10 | 3 | 10-30 |
| 526 | 2-6 | 10 | 3 | 10-30 |
| 527 | 2-5 | 10 | 3 | 10-30 |
| 528 | 2-4 | 10 | 3 | 10-30 |
| 529 | 2-3 | 10 | 3 | 10-30 |
| 530 | 1-2 | 10 | 3 | 10-30 |
| 531 | 1-3 | 10 | 3 | 10-30 |
| 532 | 1-4 | 10 | 3 | 10-30 |
| 533 | 1 | 10 | 3 | 10-30 |
| 534 | 2 | 10 | 3 | 10-30 |
| 535 | 3 | 10 | 3 | 10-30 |
| 536 | 4 | 10 | 3 | 10-30 |
| 537 | 5 | 10 | 3 | 10-30 |
| 538 | 6 | 10 | 3 | 10-30 |
| 539 | 7 | 10 | 3 | 10-30 |
| 540 | 8 | 10 | 3 | 10-30 |
| 541 | 1-8 | 20 | 3 | 20-30 |
| 542 | 2-8 | 20 | 3 | 20-30 |
| 543 | 2-7 | 20 | 3 | 20-30 |
| 544 | 2-6 | 20 | 3 | 20-30 |
| 545 | 2-5 | 20 | 3 | 20-30 |
| 546 | 2-4 | 20 | 3 | 20-30 |
| 547 | 2-3 | 20 | 3 | 20-30 |
| 548 | 1-2 | 20 | 3 | 20-30 |
| 549 | 1-3 | 20 | 3 | 20-30 |
| 550 | 1-4 | 20 | 3 | 20-30 |
| 551 | 1 | 20 | 3 | 20-30 |
| 552 | 2 | 20 | 3 | 20-30 |
| 553 | 3 | 20 | 3 | 20-30 |
| 554 | 4 | 20 | 3 | 20-30 |
| 555 | 5 | 20 | 3 | 20-30 |
| 556 | 6 | 20 | 3 | 20-30 |
| 557 | 7 | 20 | 3 | 20-30 |
| 558 | 8 | 20 | 3 | 30 |
| 559 | 1-8 | 30 | 3 | 30 |
| 560 | 2-8 | 30 | 3 | 30 |
| 561 | 2-7 | 30 | 3 | 30 |
| 562 | 2-6 | 30 | 3 | 30 |
| 563 | 2-5 | 30 | 3 | 30 |
| 564 | 2-4 | 30 | 3 | 30 |
| 565 | 2-3 | 30 | 3 | 30 |
| 566 | 1-2 | 30 | 3 | 30 |
| 567 | 1-3 | 30 | 3 | 30 |
| 568 | 1-4 | 30 | 3 | 30 |
| 569 | 1 | 30 | 3 | 30 |
| 570 | 2 | 30 | 3 | 30 |
| 571 | 3 | 30 | 3 | 30 |
| 572 | 4 | 30 | 3 | 30 |
| 573 | 5 | 30 | 3 | 30 |
| 574 | 6 | 30 | 3 | 30 |
| 575 | 7 | 30 | 3 | 30 |
| 576 | 8 | 30 | 3 | 30 |
| 577 | 1-8 | 10-30 | 4 | 10-30 |
| 578 | 2-8 | 10-30 | 4 | 10-30 |
| 579 | 2-7 | 10-30 | 4 | 10-30 |
| 580 | 2-6 | 10-30 | 4 | 10-30 |
| 581 | 2-5 | 10-30 | 4 | 10-30 |
| 582 | 2-4 | 10-30 | 4 | 10-30 |
| 583 | 2-3 | 10-30 | 4 | 10-30 |
| 584 | 1-2 | 10-30 | 4 | 10-30 |
| 585 | 1-3 | 10-30 | 4 | 10-30 |
| 586 | 1-4 | 10-30 | 4 | 10-30 |
| 587 | 1 | 10-30 | 4 | 10-30 |
| 588 | 2 | 10-30 | 4 | 10-30 |
| 589 | 3 | 10-30 | 4 | 10-30 |
| 590 | 4 | 10-30 | 4 | 10-30 |
| 591 | 5 | 10-30 | 4 | 10-30 |
| 592 | 6 | 10-30 | 4 | 10-30 |
| 593 | 7 | 10-30 | 4 | 10-30 |
| 594 | 8 | 10-30 | 4 | 10-30 |
| 595 | 1-8 | 10 | 4 | 10-30 |
| 596 | 2-8 | 10 | 4 | 10-30 |
| 597 | 2-7 | 10 | 4 | 10-30 |
| 598 | 2-6 | 10 | 4 | 10-30 |
| 599 | 2-5 | 10 | 4 | 10-30 |
| 600 | 2-4 | 10 | 4 | 10-30 |
| 601 | 2-3 | 10 | 4 | 10-30 |
| 602 | 1-2 | 10 | 4 | 10-30 |
| 603 | 1-3 | 10 | 4 | 10-30 |
| 604 | 1-4 | 10 | 4 | 10-30 |
| 605 | 1 | 10 | 4 | 10-30 |
| 606 | 2 | 10 | 4 | 10-30 |
| 607 | 3 | 10 | 4 | 10-30 |
| 608 | 4 | 10 | 4 | 10-30 |
| 609 | 5 | 10 | 4 | 10-30 |
| 610 | 6 | 10 | 4 | 10-30 |
| 611 | 7 | 10 | 4 | 10-30 |
| 612 | 8 | 10 | 4 | 10-30 |
| 613 | 1-8 | 20 | 4 | 20-30 |
| 614 | 2-8 | 20 | 4 | 20-30 |
| 615 | 2-7 | 20 | 4 | 20-30 |
| 616 | 2-6 | 20 | 4 | 20-30 |
| 617 | 2-5 | 20 | 4 | 20-30 |
| 618 | 2-4 | 20 | 4 | 20-30 |
| 619 | 2-3 | 20 | 4 | 20-30 |
| 620 | 1-2 | 20 | 4 | 20-30 |
| 621 | 1-3 | 20 | 4 | 20-30 |

TABLE 1-continued

| Dosage Regimen # | Initial time period/preliminary time period (weeks) | Initial orismilast dose (mg) | Interim time period (weeks) | Interim orismilast dose (mg) |
|---|---|---|---|---|
| 622 | 1-4 | 20 | 4 | 20-30 |
| 623 | 1 | 20 | 4 | 20-30 |
| 624 | 2 | 20 | 4 | 20-30 |
| 625 | 3 | 20 | 4 | 20-30 |
| 626 | 4 | 20 | 4 | 20-30 |
| 627 | 5 | 20 | 4 | 20-30 |
| 628 | 6 | 20 | 4 | 20-30 |
| 629 | 7 | 20 | 4 | 20-30 |
| 630 | 8 | 20 | 4 | 20-30 |
| 631 | 1-8 | 30 | 4 | 30 |
| 632 | 2-8 | 30 | 4 | 30 |
| 633 | 2-7 | 30 | 4 | 30 |
| 634 | 2-6 | 30 | 4 | 30 |
| 635 | 2-5 | 30 | 4 | 30 |
| 636 | 2-4 | 30 | 4 | 30 |
| 637 | 2-3 | 30 | 4 | 30 |
| 638 | 1-2 | 30 | 4 | 30 |
| 639 | 1-3 | 30 | 4 | 30 |
| 640 | 1-4 | 30 | 4 | 30 |
| 641 | 1 | 30 | 4 | 30 |
| 642 | 2 | 30 | 4 | 30 |
| 643 | 3 | 30 | 4 | 30 |
| 644 | 4 | 30 | 4 | 30 |
| 645 | 5 | 30 | 4 | 30 |
| 646 | 6 | 30 | 4 | 30 |
| 647 | 7 | 30 | 4 | 30 |
| 648 | 8 | 30 | 4 | 30 |
| 649 | 1-8 | 10-30 | 5 | 10-30 |
| 650 | 2-8 | 10-30 | 5 | 10-30 |
| 651 | 2-7 | 10-30 | 5 | 10-30 |
| 652 | 2-6 | 10-30 | 5 | 10-30 |
| 653 | 2-5 | 10-30 | 5 | 10-30 |
| 654 | 2-4 | 10-30 | 5 | 10-30 |
| 655 | 2-3 | 10-30 | 5 | 10-30 |
| 656 | 1-2 | 10-30 | 5 | 10-30 |
| 657 | 1-3 | 10-30 | 5 | 10-30 |
| 658 | 1-4 | 10-30 | 5 | 10-30 |
| 659 | 1 | 10-30 | 5 | 10-30 |
| 660 | 2 | 10-30 | 5 | 10-30 |
| 661 | 3 | 10-30 | 5 | 10-30 |
| 662 | 4 | 10-30 | 5 | 10-30 |
| 663 | 5 | 10-30 | 5 | 10-30 |
| 664 | 6 | 10-30 | 5 | 10-30 |
| 665 | 7 | 10-30 | 5 | 10-30 |
| 666 | 8 | 10-30 | 5 | 10-30 |
| 667 | 1-8 | 10 | 5 | 10-30 |
| 668 | 2-8 | 10 | 5 | 10-30 |
| 669 | 2-7 | 10 | 5 | 10-30 |
| 670 | 2-6 | 10 | 5 | 10-30 |
| 671 | 2-5 | 10 | 5 | 10-30 |
| 672 | 2-4 | 10 | 5 | 10-30 |
| 673 | 2-3 | 10 | 5 | 10-30 |
| 674 | 1-2 | 10 | 5 | 10-30 |
| 675 | 1-3 | 10 | 5 | 10-30 |
| 676 | 1-4 | 10 | 5 | 10-30 |
| 677 | 1 | 10 | 5 | 10-30 |
| 678 | 2 | 10 | 5 | 10-30 |
| 679 | 3 | 10 | 5 | 10-30 |
| 680 | 4 | 10 | 5 | 10-30 |
| 681 | 5 | 10 | 5 | 10-30 |
| 682 | 6 | 10 | 5 | 10-30 |
| 683 | 7 | 10 | 5 | 10-30 |
| 684 | 8 | 10 | 5 | 10-30 |
| 685 | 1-8 | 20 | 5 | 20-30 |
| 686 | 2-8 | 20 | 5 | 20-30 |
| 687 | 2-7 | 20 | 5 | 20-30 |
| 688 | 2-6 | 20 | 5 | 20-30 |
| 689 | 2-5 | 20 | 5 | 20-30 |
| 690 | 2-4 | 20 | 5 | 20-30 |
| 691 | 2-3 | 20 | 5 | 20-30 |
| 692 | 1-2 | 20 | 5 | 20-30 |
| 693 | 1-3 | 20 | 5 | 20-30 |
| 694 | 1-4 | 20 | 5 | 20-30 |
| 695 | 1 | 20 | 5 | 20-30 |
| 696 | 2 | 20 | 5 | 20-30 |
| 697 | 3 | 20 | 5 | 20-30 |
| 698 | 4 | 20 | 5 | 20-30 |
| 699 | 5 | 20 | 5 | 20-30 |
| 700 | 6 | 20 | 5 | 20-30 |
| 701 | 7 | 20 | 5 | 20-30 |
| 702 | 8 | 20 | 5 | 20-30 |
| 703 | 1-8 | 30 | 5 | 30 |
| 704 | 2-8 | 30 | 5 | 30 |
| 705 | 2-7 | 30 | 5 | 30 |
| 706 | 2-6 | 30 | 5 | 30 |
| 707 | 2-5 | 30 | 5 | 30 |
| 708 | 2-4 | 30 | 5 | 30 |
| 709 | 2-3 | 30 | 5 | 30 |
| 710 | 1-2 | 30 | 5 | 30 |
| 711 | 1-3 | 30 | 5 | 30 |
| 712 | 1-4 | 30 | 5 | 30 |
| 713 | 1 | 30 | 5 | 30 |
| 714 | 2 | 30 | 5 | 30 |
| 715 | 3 | 30 | 5 | 30 |
| 716 | 4 | 30 | 5 | 30 |
| 717 | 5 | 30 | 5 | 30 |
| 718 | 6 | 30 | 5 | 30 |
| 719 | 7 | 30 | 5 | 30 |
| 720 | 8 | 30 | 5 | 30 |
| 721 | 1-8 | 10-30 | 6 | 10-30 |
| 722 | 2-8 | 10-30 | 6 | 10-30 |
| 723 | 2-7 | 10-30 | 6 | 10-30 |
| 724 | 2-6 | 10-30 | 6 | 10-30 |
| 725 | 2-5 | 10-30 | 6 | 10-30 |
| 726 | 2-4 | 10-30 | 6 | 10-30 |
| 727 | 2-3 | 10-30 | 6 | 10-30 |
| 728 | 1-2 | 10-30 | 6 | 10-30 |
| 729 | 1-3 | 10-30 | 6 | 10-30 |
| 730 | 1-4 | 10-30 | 6 | 10-30 |
| 731 | 1 | 10-30 | 6 | 10-30 |
| 732 | 2 | 10-30 | 6 | 10-30 |
| 733 | 3 | 10-30 | 6 | 10-30 |
| 734 | 4 | 10-30 | 6 | 10-30 |
| 735 | 5 | 10-30 | 6 | 10-30 |
| 736 | 6 | 10-30 | 6 | 10-30 |
| 737 | 7 | 10-30 | 6 | 10-30 |
| 738 | 8 | 10-30 | 6 | 10-30 |
| 739 | 1-8 | 10 | 6 | 10-30 |
| 740 | 2-8 | 10 | 6 | 10-30 |
| 741 | 2-7 | 10 | 6 | 10-30 |
| 742 | 2-6 | 10 | 6 | 10-30 |
| 743 | 2-5 | 10 | 6 | 10-30 |
| 744 | 2-4 | 10 | 6 | 10-30 |
| 745 | 2-3 | 10 | 6 | 10-30 |
| 746 | 1-2 | 10 | 6 | 10-30 |
| 747 | 1-3 | 10 | 6 | 10-30 |
| 748 | 1-4 | 10 | 6 | 10-30 |
| 749 | 1 | 10 | 6 | 10-30 |
| 750 | 2 | 10 | 6 | 10-30 |
| 751 | 3 | 10 | 6 | 10-30 |
| 752 | 4 | 10 | 6 | 10-30 |
| 753 | 5 | 10 | 6 | 10-30 |
| 754 | 6 | 10 | 6 | 10-30 |
| 755 | 7 | 10 | 6 | 10-30 |
| 756 | 8 | 10 | 6 | 10-30 |
| 757 | 1-8 | 20 | 6 | 20-30 |
| 758 | 2-8 | 20 | 6 | 20-30 |
| 759 | 2-7 | 20 | 6 | 20-30 |
| 760 | 2-6 | 20 | 6 | 20-30 |
| 761 | 2-5 | 20 | 6 | 20-30 |
| 762 | 2-4 | 20 | 6 | 20-30 |
| 763 | 2-3 | 20 | 6 | 20-30 |
| 764 | 1-2 | 20 | 6 | 20-30 |
| 765 | 1-3 | 20 | 6 | 20-30 |
| 766 | 1-4 | 20 | 6 | 20-30 |
| 767 | 1 | 20 | 6 | 20-30 |
| 768 | 2 | 20 | 6 | 20-30 |
| 769 | 3 | 20 | 6 | 20-30 |
| 770 | 4 | 20 | 6 | 20-30 |
| 771 | 5 | 20 | 6 | 20-30 |

TABLE 1-continued

| Dosage Regimen # | Initial time period/preliminary time period (weeks) | Initial orismilast dose (mg) | Interim time period (weeks) | Interim orismilast dose (mg) |
|---|---|---|---|---|
| 772 | 6 | 20 | 6 | 20-30 |
| 773 | 7 | 20 | 6 | 20-30 |
| 774 | 8 | 20 | 6 | 20-30 |
| 775 | 1-8 | 30 | 6 | 30 |
| 776 | 2-8 | 30 | 6 | 30 |
| 777 | 2-7 | 30 | 6 | 30 |
| 778 | 2-6 | 30 | 6 | 30 |
| 779 | 2-5 | 30 | 6 | 30 |
| 780 | 2-4 | 30 | 6 | 30 |
| 781 | 2-3 | 30 | 6 | 30 |
| 782 | 1-2 | 30 | 6 | 30 |
| 783 | 1-3 | 30 | 6 | 30 |
| 784 | 1-4 | 30 | 6 | 30 |
| 785 | 1 | 30 | 6 | 30 |
| 786 | 2 | 30 | 6 | 30 |
| 787 | 3 | 30 | 6 | 30 |
| 788 | 4 | 30 | 6 | 30 |
| 789 | 5 | 30 | 6 | 30 |
| 790 | 6 | 30 | 6 | 30 |
| 791 | 7 | 30 | 6 | 30 |
| 792 | 8 | 30 | 6 | 30 |
| 793 | 1-8 | 10-30 | 7 | 10-30 |
| 794 | 2-8 | 10-30 | 7 | 10-30 |
| 795 | 2-7 | 10-30 | 7 | 10-30 |
| 796 | 2-6 | 10-30 | 7 | 10-30 |
| 797 | 2-5 | 10-30 | 7 | 10-30 |
| 798 | 2-4 | 10-30 | 7 | 10-30 |
| 799 | 2-3 | 10-30 | 7 | 10-30 |
| 800 | 1-2 | 10-30 | 7 | 10-30 |
| 801 | 1-3 | 10-30 | 7 | 10-30 |
| 802 | 1-4 | 10-30 | 7 | 10-30 |
| 803 | 1 | 10-30 | 7 | 10-30 |
| 804 | 2 | 10-30 | 7 | 10-30 |
| 805 | 3 | 10-30 | 7 | 10-30 |
| 806 | 4 | 10-30 | 7 | 10-30 |
| 807 | 5 | 10-30 | 7 | 10-30 |
| 808 | 6 | 10-30 | 7 | 10-30 |
| 809 | 7 | 10-30 | 7 | 10-30 |
| 810 | 8 | 10-30 | 7 | 10-30 |
| 811 | 1-8 | 10 | 7 | 10-30 |
| 812 | 2-8 | 10 | 7 | 10-30 |
| 813 | 2-7 | 10 | 7 | 10-30 |
| 814 | 2-6 | 10 | 7 | 10-30 |
| 815 | 2-5 | 10 | 7 | 10-30 |
| 816 | 2-4 | 10 | 7 | 10-30 |
| 817 | 2-3 | 10 | 7 | 10-30 |
| 818 | 1-2 | 10 | 7 | 10-30 |
| 819 | 1-3 | 10 | 7 | 10-30 |
| 820 | 1-4 | 10 | 7 | 10-30 |
| 821 | 1 | 10 | 7 | 10-30 |
| 822 | 2 | 10 | 7 | 10-30 |
| 823 | 3 | 10 | 7 | 10-30 |
| 824 | 4 | 10 | 7 | 10-30 |
| 825 | 5 | 10 | 7 | 10-30 |
| 826 | 6 | 10 | 7 | 10-30 |
| 827 | 7 | 10 | 7 | 10-30 |
| 828 | 8 | 10 | 7 | 10-30 |
| 829 | 1-8 | 20 | 7 | 20-30 |
| 830 | 2-8 | 20 | 7 | 20-30 |
| 831 | 2-7 | 20 | 7 | 20-30 |
| 832 | 2-6 | 20 | 7 | 20-30 |
| 833 | 2-5 | 20 | 7 | 20-30 |
| 834 | 2-4 | 20 | 7 | 20-30 |
| 835 | 2-3 | 20 | 7 | 20-30 |
| 836 | 1-2 | 20 | 7 | 20-30 |
| 837 | 1-3 | 20 | 7 | 20-30 |
| 838 | 1-4 | 20 | 7 | 20-30 |
| 839 | 1 | 20 | 7 | 20-30 |
| 840 | 2 | 20 | 7 | 20-30 |
| 841 | 3 | 20 | 7 | 20-30 |
| 842 | 4 | 20 | 7 | 20-30 |
| 843 | 5 | 20 | 7 | 20-30 |
| 844 | 6 | 20 | 7 | 20-30 |
| 845 | 7 | 20 | 7 | 20-30 |
| 846 | 8 | 20 | 7 | 20-30 |
| 847 | 1-8 | 30 | 7 | 30 |
| 848 | 2-8 | 30 | 7 | 30 |
| 849 | 2-7 | 30 | 7 | 30 |
| 850 | 2-6 | 30 | 7 | 30 |
| 851 | 2-5 | 30 | 7 | 30 |
| 852 | 2-4 | 30 | 7 | 30 |
| 853 | 2-3 | 30 | 7 | 30 |
| 854 | 1-2 | 30 | 7 | 30 |
| 855 | 1-3 | 30 | 7 | 30 |
| 856 | 1-4 | 30 | 7 | 30 |
| 857 | 1 | 30 | 7 | 30 |
| 858 | 2 | 30 | 7 | 30 |
| 859 | 3 | 30 | 7 | 30 |
| 860 | 4 | 30 | 7 | 30 |
| 861 | 5 | 30 | 7 | 30 |
| 862 | 6 | 30 | 7 | 30 |
| 863 | 7 | 30 | 7 | 30 |
| 864 | 8 | 30 | 7 | 30 |
| 865 | 1-8 | 10-30 | 8 | 10-30 |
| 866 | 2-8 | 10-30 | 8 | 10-30 |
| 867 | 2-7 | 10-30 | 8 | 10-30 |
| 868 | 2-6 | 10-30 | 8 | 10-30 |
| 869 | 2-5 | 10-30 | 8 | 10-30 |
| 870 | 2-4 | 10-30 | 8 | 10-30 |
| 871 | 2-3 | 10-30 | 8 | 10-30 |
| 872 | 1-2 | 10-30 | 8 | 10-30 |
| 873 | 1-3 | 10-30 | 8 | 10-30 |
| 874 | 1-4 | 10-30 | 8 | 10-30 |
| 875 | 1 | 10-30 | 8 | 10-30 |
| 876 | 2 | 10-30 | 8 | 10-30 |
| 877 | 3 | 10-30 | 8 | 10-30 |
| 878 | 4 | 10-30 | 8 | 10-30 |
| 879 | 5 | 10-30 | 8 | 10-30 |
| 880 | 6 | 10-30 | 8 | 10-30 |
| 881 | 7 | 10-30 | 8 | 10-30 |
| 882 | 8 | 10-30 | 8 | 10-30 |
| 883 | 1-8 | 10 | 8 | 10-30 |
| 884 | 2-8 | 10 | 8 | 10-30 |
| 885 | 2-7 | 10 | 8 | 10-30 |
| 886 | 2-6 | 10 | 8 | 10-30 |
| 887 | 2-5 | 10 | 8 | 10-30 |
| 888 | 2-4 | 10 | 8 | 10-30 |
| 889 | 2-3 | 10 | 8 | 10-30 |
| 890 | 1-2 | 10 | 8 | 10-30 |
| 891 | 1-3 | 10 | 8 | 10-30 |
| 892 | 1-4 | 10 | 8 | 10-30 |
| 893 | 1 | 10 | 8 | 10-30 |
| 894 | 2 | 10 | 8 | 10-30 |
| 895 | 3 | 10 | 8 | 10-30 |
| 896 | 4 | 10 | 8 | 10-30 |
| 897 | 5 | 10 | 8 | 10-30 |
| 898 | 6 | 10 | 8 | 10-30 |
| 899 | 7 | 10 | 8 | 10-30 |
| 900 | 8 | 10 | 8 | 10-30 |
| 901 | 1-8 | 20 | 8 | 20-30 |
| 902 | 2-8 | 20 | 8 | 20-30 |
| 903 | 2-7 | 20 | 8 | 20-30 |
| 904 | 2-6 | 20 | 8 | 20-30 |
| 905 | 2-5 | 20 | 8 | 20-30 |
| 906 | 2-4 | 20 | 8 | 20-30 |
| 907 | 2-3 | 20 | 8 | 20-30 |
| 908 | 1-2 | 20 | 8 | 20-30 |
| 909 | 1-3 | 20 | 8 | 20-30 |
| 910 | 1-4 | 20 | 8 | 20-30 |
| 911 | 1 | 20 | 8 | 20-30 |
| 912 | 2 | 20 | 8 | 20-30 |
| 913 | 3 | 20 | 8 | 20-30 |
| 914 | 4 | 20 | 8 | 20-30 |
| 915 | 5 | 20 | 8 | 20-30 |
| 916 | 6 | 20 | 8 | 20-30 |
| 917 | 7 | 20 | 8 | 20-30 |
| 918 | 8 | 20 | 8 | 20-30 |
| 919 | 1-8 | 30 | 8 | 30 |
| 920 | 2-8 | 30 | 8 | 30 |
| 921 | 2-7 | 30 | 8 | 30 |

TABLE 1-continued

| Dosage Regimen # | Initial time period/preliminary time period (weeks) | Initial orismilast dose (mg) | Interim time period (weeks) | Interim orismilast dose (mg) |
|---|---|---|---|---|
| 922 | 2-6 | 30 | 8 | 30 |
| 923 | 2-5 | 30 | 8 | 30 |
| 924 | 2-4 | 30 | 8 | 30 |
| 925 | 2-3 | 30 | 8 | 30 |
| 926 | 1-2 | 30 | 8 | 30 |
| 927 | 1-3 | 30 | 8 | 30 |
| 928 | 1-4 | 30 | 8 | 30 |
| 929 | 1 | 30 | 8 | 30 |
| 930 | 2 | 30 | 8 | 30 |
| 931 | 3 | 30 | 8 | 30 |
| 932 | 4 | 30 | 8 | 30 |
| 933 | 5 | 30 | 8 | 30 |
| 934 | 6 | 30 | 8 | 30 |
| 935 | 7 | 30 | 8 | 30 |
| 936 | 8 | 30 | 8 | 30 |
| 937 | 1-8 | 10 | 1-8 | 20 |
| 938 | 2-8 | 10 | 1-8 | 20 |
| 939 | 2-7 | 10 | 1-8 | 20 |
| 940 | 2-6 | 10 | 1-8 | 20 |
| 941 | 2-5 | 10 | 1-8 | 20 |
| 942 | 2-4 | 10 | 1-8 | 20 |
| 943 | 2-3 | 10 | 1-8 | 20 |
| 944 | 1-2 | 10 | 1-8 | 20 |
| 945 | 1-3 | 10 | 1-8 | 20 |
| 946 | 1-4 | 10 | 1-8 | 20 |
| 947 | 1 | 10 | 1-8 | 20 |
| 948 | 2 | 10 | 1-8 | 20 |
| 949 | 3 | 10 | 1-8 | 20 |
| 950 | 4 | 10 | 1-8 | 20 |
| 951 | 5 | 10 | 1-8 | 20 |
| 952 | 6 | 10 | 1-8 | 20 |
| 953 | 7 | 10 | 1-8 | 20 |
| 954 | 8 | 10 | 1-8 | 20 |
| 955 | 1-8 | 20 | 1-8 | 20 |
| 956 | 2-8 | 20 | 1-8 | 20 |
| 957 | 2-7 | 20 | 1-8 | 20 |
| 958 | 2-6 | 20 | 1-8 | 20 |
| 959 | 2-5 | 20 | 1-8 | 20 |
| 960 | 2-4 | 20 | 1-8 | 20 |
| 961 | 2-3 | 20 | 1-8 | 20 |
| 962 | 1-2 | 20 | 1-8 | 20 |
| 963 | 1-3 | 20 | 1-8 | 20 |
| 964 | 1-4 | 20 | 1-8 | 20 |
| 965 | 1 | 20 | 1-8 | 20 |
| 966 | 2 | 20 | 1-8 | 20 |
| 967 | 3 | 20 | 1-8 | 20 |
| 968 | 4 | 20 | 1-8 | 20 |
| 969 | 5 | 20 | 1-8 | 20 |
| 970 | 6 | 20 | 1-8 | 20 |
| 971 | 7 | 20 | 1-8 | 20 |
| 972 | 8 | 20 | 1-8 | 20 |
| 973 | 1-8 | 20 | 1-6 | 20 |
| 974 | 2-8 | 20 | 1-6 | 20 |
| 975 | 2-7 | 20 | 1-6 | 20 |
| 976 | 2-6 | 20 | 1-6 | 20 |
| 977 | 2-5 | 20 | 1-6 | 20 |
| 978 | 2-4 | 20 | 1-6 | 20 |
| 979 | 2-3 | 20 | 1-6 | 20 |
| 980 | 1-2 | 20 | 1-6 | 20 |
| 981 | 1-3 | 20 | 1-6 | 20 |
| 982 | 1-4 | 20 | 1-6 | 20 |
| 983 | 1 | 20 | 1-6 | 20 |
| 984 | 2 | 20 | 1-6 | 20 |
| 985 | 3 | 20 | 1-6 | 20 |
| 986 | 4 | 20 | 1-6 | 20 |
| 987 | 5 | 20 | 1-6 | 20 |
| 988 | 6 | 20 | 1-6 | 20 |
| 989 | 7 | 20 | 1-6 | 20 |
| 990 | 8 | 20 | 1-6 | 20 |
| 991 | 1-8 | 20 | 1-4 | 20 |
| 992 | 2-8 | 20 | 1-4 | 20 |
| 993 | 2-7 | 20 | 1-4 | 20 |
| 994 | 2-6 | 20 | 1-4 | 20 |
| 995 | 2-5 | 20 | 1-4 | 20 |
| 996 | 2-4 | 20 | 1-4 | 20 |
| 997 | 2-3 | 20 | 1-4 | 20 |
| 998 | 1-2 | 20 | 1-4 | 20 |
| 999 | 1-3 | 20 | 1-4 | 20 |
| 1000 | 1-4 | 20 | 1-4 | 20 |
| 1001 | 1 | 20 | 1-4 | 20 |
| 1002 | 2 | 20 | 1-4 | 20 |
| 1003 | 3 | 20 | 1-4 | 20 |
| 1004 | 4 | 20 | 1-4 | 20 |
| 1005 | 5 | 20 | 1-4 | 20 |
| 1006 | 6 | 20 | 1-4 | 20 |
| 1007 | 7 | 20 | 1-4 | 20 |
| 1008 | 8 | 20 | 1-4 | 20 |
| 1009 | 1-8 | 20 | 1-3 | 20 |
| 1010 | 2-8 | 20 | 1-3 | 20 |
| 1011 | 2-7 | 20 | 1-3 | 20 |
| 1012 | 2-6 | 20 | 1-3 | 20 |
| 1013 | 2-5 | 20 | 1-3 | 20 |
| 1014 | 2-4 | 20 | 1-3 | 20 |
| 1015 | 2-3 | 20 | 1-3 | 20 |
| 1016 | 1-2 | 20 | 1-3 | 20 |
| 1017 | 1-3 | 20 | 1-3 | 20 |
| 1018 | 1-4 | 20 | 1-3 | 20 |
| 1019 | 1 | 20 | 1-3 | 20 |
| 1020 | 2 | 20 | 1-3 | 20 |
| 1021 | 3 | 20 | 1-3 | 20 |
| 1022 | 4 | 20 | 1-3 | 20 |
| 1023 | 5 | 20 | 1-3 | 20 |
| 1024 | 6 | 20 | 1-3 | 20 |
| 1025 | 7 | 20 | 1-3 | 20 |
| 1026 | 8 | 20 | 1-3 | 20 |
| 1027 | 1-8 | 20 | 1-2 | 20 |
| 1028 | 2-8 | 20 | 1-2 | 20 |
| 1029 | 2-7 | 20 | 1-2 | 20 |
| 1030 | 2-6 | 20 | 1-2 | 20 |
| 1031 | 2-5 | 20 | 1-2 | 20 |
| 1032 | 2-4 | 20 | 1-2 | 20 |
| 1033 | 2-3 | 20 | 1-2 | 20 |
| 1034 | 1-2 | 20 | 1-2 | 20 |
| 1035 | 1-3 | 20 | 1-2 | 20 |
| 1036 | 1-4 | 20 | 1-2 | 20 |
| 1037 | 1 | 20 | 1-2 | 20 |
| 1038 | 2 | 20 | 1-2 | 20 |
| 1039 | 3 | 20 | 1-2 | 20 |
| 1040 | 4 | 20 | 1-2 | 20 |
| 1041 | 5 | 20 | 1-2 | 20 |
| 1042 | 6 | 20 | 1-2 | 20 |
| 1043 | 7 | 20 | 1-2 | 20 |
| 1044 | 8 | 20 | 1-2 | 20 |
| 1045 | 1-8 | 20 | 1 | 20 |
| 1046 | 2-8 | 20 | 1 | 20 |
| 1047 | 2-7 | 20 | 1 | 20 |
| 1048 | 2-6 | 20 | 1 | 20 |
| 1049 | 2-5 | 20 | 1 | 20 |
| 1050 | 2-4 | 20 | 1 | 20 |
| 1051 | 2-3 | 20 | 1 | 20 |
| 1052 | 1-2 | 20 | 1 | 20 |
| 1053 | 1-3 | 20 | 1 | 20 |
| 1054 | 1-4 | 20 | 1 | 20 |
| 1055 | 1 | 20 | 1 | 20 |
| 1056 | 2 | 20 | 1 | 20 |
| 1057 | 3 | 20 | 1 | 20 |
| 1058 | 4 | 20 | 1 | 20 |
| 1059 | 5 | 20 | 1 | 20 |
| 1060 | 6 | 20 | 1 | 20 |
| 1061 | 7 | 20 | 1 | 20 |
| 1062 | 8 | 20 | 1 | 20 |
| 1063 | 1-8 | 10 | 2 | 20 |
| 1064 | 2-8 | 10 | 2 | 20 |
| 1065 | 2-7 | 10 | 2 | 20 |
| 1066 | 2-6 | 10 | 2 | 20 |
| 1067 | 2-5 | 10 | 2 | 20 |
| 1068 | 2-4 | 10 | 2 | 20 |
| 1069 | 2-3 | 10 | 2 | 20 |
| 1070 | 1-2 | 10 | 2 | 20 |
| 1071 | 1-3 | 10 | 2 | 20 |

TABLE 1-continued

| Dosage Regimen # | Initial time period/preliminary time period (weeks) | Initial orismilast dose (mg) | Interim time period (weeks) | Interim orismilast dose (mg) |
|---|---|---|---|---|
| 1072 | 1-4 | 10 | 2 | 20 |
| 1073 | 1 | 10 | 2 | 20 |
| 1074 | 2 | 10 | 2 | 20 |
| 1075 | 3 | 10 | 2 | 20 |
| 1076 | 4 | 10 | 2 | 20 |
| 1077 | 5 | 10 | 2 | 20 |
| 1078 | 6 | 10 | 2 | 20 |
| 1079 | 7 | 10 | 2 | 20 |
| 1080 | 8 | 10 | 2 | 20 |
| 1081 | 1-8 | 20 | 2 | 20 |
| 1082 | 2-8 | 20 | 2 | 20 |
| 1083 | 2-7 | 20 | 2 | 20 |
| 1084 | 2-6 | 20 | 2 | 20 |
| 1085 | 2-5 | 20 | 2 | 20 |
| 1086 | 2-4 | 20 | 2 | 20 |
| 1087 | 2-3 | 20 | 2 | 20 |
| 1088 | 1-2 | 20 | 2 | 20 |
| 1089 | 1-3 | 20 | 2 | 20 |
| 1090 | 1-4 | 20 | 2 | 20 |
| 1091 | 1 | 20 | 2 | 20 |
| 1092 | 2 | 20 | 2 | 20 |
| 1093 | 3 | 20 | 2 | 20 |
| 1094 | 4 | 20 | 2 | 20 |
| 1095 | 5 | 20 | 2 | 20 |
| 1096 | 6 | 20 | 2 | 20 |
| 1097 | 7 | 20 | 2 | 20 |
| 1098 | 8 | 20 | 2 | 20 |
| 1099 | 1-8 | 10 | 3 | 20 |
| 1100 | 2-8 | 10 | 3 | 20 |
| 1101 | 2-7 | 10 | 3 | 20 |
| 1102 | 2-6 | 10 | 3 | 20 |
| 1103 | 2-5 | 10 | 3 | 20 |
| 1104 | 2-4 | 10 | 3 | 20 |
| 1105 | 2-3 | 10 | 3 | 20 |
| 1106 | 1-2 | 10 | 3 | 20 |
| 1107 | 1-3 | 10 | 3 | 20 |
| 1108 | 1-4 | 10 | 3 | 20 |
| 1109 | 1 | 10 | 3 | 20 |
| 1110 | 2 | 10 | 3 | 20 |
| 1111 | 3 | 10 | 3 | 20 |
| 1112 | 4 | 10 | 3 | 20 |
| 1113 | 5 | 10 | 3 | 20 |
| 1114 | 6 | 10 | 3 | 20 |
| 1115 | 7 | 10 | 3 | 20 |
| 1116 | 8 | 10 | 3 | 20 |
| 1117 | 1-8 | 20 | 3 | 20 |
| 1118 | 2-8 | 20 | 3 | 20 |
| 1119 | 2-7 | 20 | 3 | 20 |
| 1120 | 2-6 | 20 | 3 | 20 |
| 1121 | 2-5 | 20 | 3 | 20 |
| 1122 | 2-4 | 20 | 3 | 20 |
| 1123 | 2-3 | 20 | 3 | 20 |
| 1124 | 1-2 | 20 | 3 | 20 |
| 1125 | 1-3 | 20 | 3 | 20 |
| 1126 | 1-4 | 20 | 3 | 20 |
| 1127 | 1 | 20 | 3 | 20 |
| 1128 | 2 | 20 | 3 | 20 |
| 1129 | 3 | 20 | 3 | 20 |
| 1130 | 4 | 20 | 3 | 20 |
| 1131 | 5 | 20 | 3 | 20 |
| 1132 | 6 | 20 | 3 | 20 |
| 1133 | 7 | 20 | 3 | 20 |
| 1134 | 8 | 20 | 3 | 20 |
| 1135 | 1-8 | 10 | 4 | 20 |
| 1136 | 2-8 | 10 | 4 | 20 |
| 1137 | 2-7 | 10 | 4 | 20 |
| 1138 | 2-6 | 10 | 4 | 20 |
| 1139 | 2-5 | 10 | 4 | 20 |
| 1140 | 2-4 | 10 | 4 | 20 |
| 1141 | 2-3 | 10 | 4 | 20 |
| 1142 | 1-2 | 10 | 4 | 20 |
| 1143 | 1-3 | 10 | 4 | 20 |
| 1144 | 1-4 | 10 | 4 | 20 |
| 1145 | 1 | 10 | 4 | 20 |
| 1146 | 2 | 10 | 4 | 20 |
| 1147 | 3 | 10 | 4 | 20 |
| 1148 | 4 | 10 | 4 | 20 |
| 1149 | 5 | 10 | 4 | 20 |
| 1150 | 6 | 10 | 4 | 20 |
| 1151 | 7 | 10 | 4 | 20 |
| 1152 | 8 | 10 | 4 | 20 |
| 1153 | 1-8 | 20 | 4 | 20 |
| 1154 | 2-8 | 20 | 4 | 20 |
| 1155 | 2-7 | 20 | 4 | 20 |
| 1156 | 2-6 | 20 | 4 | 20 |
| 1157 | 2-5 | 20 | 4 | 20 |
| 1158 | 2-4 | 20 | 4 | 20 |
| 1159 | 2-3 | 20 | 4 | 20 |
| 1160 | 1-2 | 20 | 4 | 20 |
| 1161 | 1-3 | 20 | 4 | 20 |
| 1162 | 1-4 | 20 | 4 | 20 |
| 1163 | 1 | 20 | 4 | 20 |
| 1164 | 2 | 20 | 4 | 20 |
| 1165 | 3 | 20 | 4 | 20 |
| 1166 | 4 | 20 | 4 | 20 |
| 1167 | 5 | 20 | 4 | 20 |
| 1168 | 6 | 20 | 4 | 20 |
| 1169 | 7 | 20 | 4 | 20 |
| 1170 | 8 | 20 | 4 | 20 |
| 1171 | 1-8 | 10 | 5 | 20 |
| 1172 | 2-8 | 10 | 5 | 20 |
| 1173 | 2-7 | 10 | 5 | 20 |
| 1174 | 2-6 | 10 | 5 | 20 |
| 1175 | 2-5 | 10 | 5 | 20 |
| 1176 | 2-4 | 10 | 5 | 20 |
| 1177 | 2-3 | 10 | 5 | 20 |
| 1178 | 1-2 | 10 | 5 | 20 |
| 1179 | 1-3 | 10 | 5 | 20 |
| 1180 | 1-4 | 10 | 5 | 20 |
| 1181 | 1 | 10 | 5 | 20 |
| 1182 | 2 | 10 | 5 | 20 |
| 1183 | 3 | 10 | 5 | 20 |
| 1184 | 4 | 10 | 5 | 20 |
| 1185 | 5 | 10 | 5 | 20 |
| 1186 | 6 | 10 | 5 | 20 |
| 1187 | 7 | 10 | 5 | 20 |
| 1188 | 8 | 10 | 5 | 20 |
| 1189 | 1-8 | 20 | 5 | 20 |
| 1190 | 2-8 | 20 | 5 | 20 |
| 1191 | 2-7 | 20 | 5 | 20 |
| 1192 | 2-6 | 20 | 5 | 20 |
| 1193 | 2-5 | 20 | 5 | 20 |
| 1194 | 2-4 | 20 | 5 | 20 |
| 1195 | 2-3 | 20 | 5 | 20 |
| 1196 | 1-2 | 20 | 5 | 20 |
| 1197 | 1-3 | 20 | 5 | 20 |
| 1198 | 1-4 | 20 | 5 | 20 |
| 1199 | 1 | 20 | 5 | 20 |
| 1200 | 2 | 20 | 5 | 20 |
| 1201 | 3 | 20 | 5 | 20 |
| 1202 | 4 | 20 | 5 | 20 |
| 1203 | 5 | 20 | 5 | 20 |
| 1204 | 6 | 20 | 5 | 20 |
| 1205 | 7 | 20 | 5 | 20 |
| 1206 | 8 | 20 | 5 | 20 |
| 1207 | 1-8 | 10 | 6 | 20 |
| 1208 | 2-8 | 10 | 6 | 20 |
| 1209 | 2-7 | 10 | 6 | 20 |
| 1210 | 2-6 | 10 | 6 | 20 |
| 1211 | 2-5 | 10 | 6 | 20 |
| 1212 | 2-4 | 10 | 6 | 20 |
| 1213 | 2-3 | 10 | 6 | 20 |
| 1214 | 1-2 | 10 | 6 | 20 |
| 1215 | 1-3 | 10 | 6 | 20 |
| 1216 | 1-4 | 10 | 6 | 20 |
| 1217 | 1 | 10 | 6 | 20 |
| 1218 | 2 | 10 | 6 | 20 |
| 1219 | 3 | 10 | 6 | 20 |
| 1220 | 4 | 10 | 6 | 20 |
| 1221 | 5 | 10 | 6 | 20 |

TABLE 1-continued

| Dosage Regimen # | Initial time period/preliminary time period (weeks) | Initial orismilast dose (mg) | Interim time period (weeks) | Interim orismilast dose (mg) |
|---|---|---|---|---|
| 1222 | 6 | 10 | 6 | 20 |
| 1223 | 7 | 10 | 6 | 20 |
| 1224 | 8 | 10 | 6 | 20 |
| 1225 | 1-8 | 20 | 6 | 20 |
| 1226 | 2-8 | 20 | 6 | 20 |
| 1227 | 2-7 | 20 | 6 | 20 |
| 1228 | 2-6 | 20 | 6 | 20 |
| 1229 | 2-5 | 20 | 6 | 20 |
| 1230 | 2-4 | 20 | 6 | 20 |
| 1231 | 2-3 | 20 | 6 | 20 |
| 1232 | 1-2 | 20 | 6 | 20 |
| 1233 | 1-3 | 20 | 6 | 20 |
| 1234 | 1-4 | 20 | 6 | 20 |
| 1235 | 1 | 20 | 6 | 20 |
| 1236 | 2 | 20 | 6 | 20 |
| 1237 | 3 | 20 | 6 | 20 |
| 1238 | 4 | 20 | 6 | 20 |
| 1239 | 5 | 20 | 6 | 20 |
| 1240 | 6 | 20 | 6 | 20 |
| 1241 | 7 | 20 | 6 | 20 |
| 1242 | 8 | 20 | 6 | 20 |
| 1243 | 1-8 | 10 | 7 | 20 |
| 1244 | 2-8 | 10 | 7 | 20 |
| 1245 | 2-7 | 10 | 7 | 20 |
| 1246 | 2-6 | 10 | 7 | 20 |
| 1247 | 2-5 | 10 | 7 | 20 |
| 1248 | 2-4 | 10 | 7 | 20 |
| 1249 | 2-3 | 10 | 7 | 20 |
| 1250 | 1-2 | 10 | 7 | 20 |
| 1251 | 1-3 | 10 | 7 | 20 |
| 1252 | 1-4 | 10 | 7 | 20 |
| 1253 | 1 | 10 | 7 | 20 |
| 1254 | 2 | 10 | 7 | 20 |
| 1255 | 3 | 10 | 7 | 20 |
| 1256 | 4 | 10 | 7 | 20 |
| 1257 | 5 | 10 | 7 | 20 |
| 1258 | 6 | 10 | 7 | 20 |
| 1259 | 7 | 10 | 7 | 20 |
| 1260 | 8 | 10 | 7 | 20 |
| 1261 | 1-8 | 20 | 7 | 20 |
| 1262 | 2-8 | 20 | 7 | 20 |
| 1263 | 2-7 | 20 | 7 | 20 |
| 1264 | 2-6 | 20 | 7 | 20 |
| 1265 | 2-5 | 20 | 7 | 20 |
| 1266 | 2-4 | 20 | 7 | 20 |
| 1267 | 2-3 | 20 | 7 | 20 |
| 1268 | 1-2 | 20 | 7 | 20 |
| 1269 | 1-3 | 20 | 7 | 20 |
| 1270 | 1-4 | 20 | 7 | 20 |
| 1271 | 1 | 20 | 7 | 20 |
| 1272 | 2 | 20 | 7 | 20 |
| 1273 | 3 | 20 | 7 | 20 |
| 1274 | 4 | 20 | 7 | 20 |
| 1275 | 5 | 20 | 7 | 20 |
| 1276 | 6 | 20 | 7 | 20 |
| 1277 | 7 | 20 | 7 | 20 |
| 1278 | 8 | 20 | 7 | 20 |
| 1279 | 1-8 | 10 | 8 | 20 |
| 1280 | 2-8 | 10 | 8 | 20 |
| 1281 | 2-7 | 10 | 8 | 20 |
| 1282 | 2-6 | 10 | 8 | 20 |
| 1283 | 2-5 | 10 | 8 | 20 |
| 1284 | 2-4 | 10 | 8 | 20 |
| 1285 | 2-3 | 10 | 8 | 20 |
| 1286 | 1-2 | 10 | 8 | 20 |
| 1287 | 1-3 | 10 | 8 | 20 |
| 1288 | 1-4 | 10 | 8 | 20 |
| 1289 | 1 | 10 | 8 | 20 |
| 1290 | 2 | 10 | 8 | 20 |
| 1291 | 3 | 10 | 8 | 20 |
| 1292 | 4 | 10 | 8 | 20 |
| 1293 | 5 | 10 | 8 | 20 |
| 1294 | 6 | 10 | 8 | 20 |
| 1295 | 7 | 10 | 8 | 20 |
| 1296 | 8 | 10 | 8 | 20 |
| 1297 | 1-8 | 20 | 8 | 20 |
| 1298 | 2-8 | 20 | 8 | 20 |
| 1299 | 2-7 | 20 | 8 | 20 |
| 1300 | 2-6 | 20 | 8 | 20 |
| 1301 | 2-5 | 20 | 8 | 20 |
| 1302 | 2-4 | 20 | 8 | 20 |
| 1303 | 2-3 | 20 | 8 | 20 |
| 1304 | 1-2 | 20 | 8 | 20 |
| 1305 | 1-3 | 20 | 8 | 20 |
| 1306 | 1-4 | 20 | 8 | 20 |
| 1307 | 1 | 20 | 8 | 20 |
| 1308 | 2 | 20 | 8 | 20 |
| 1309 | 3 | 20 | 8 | 20 |
| 1310 | 4 | 20 | 8 | 20 |
| 1311 | 5 | 20 | 8 | 20 |
| 1312 | 6 | 20 | 8 | 20 |
| 1313 | 7 | 20 | 8 | 20 |
| 1314 | 8 | 20 | 8 | 20 |

It is to be understood that when Table 1 shows an interim orismilast dose as a range, the interim dose is selected to be greater than or equal to the initial or preliminary orismilast dose in accordance with Dosage Regimen A and Dosage Regimen B.

The maintenance orismilast dose administered to the subject after the interim time period in each of the dosage regimens shown in Table 1 may be any of the maintenance orismilast doses described herein.

Accordingly, for the dosage regimens according to Dosage Regimen A and Dosage Regimen B in Table 1 the maintenance orismilast dose is greater than the interim orismilast dose when the subject has a body mass that is greater than or equal to the threshold body mass. In a preferred embodiment the maintenance orismilast dose is from to 40 mg orismilast when the subject has a body mass that is greater than or equal to the threshold body mass, and wherein the maintenance dose is higher than the interim dose. More preferably the maintenance orismilast dose is 30 mg orismilast when the subject has a body mass that is greater than or equal to the threshold body mass, and wherein the maintenance dose is higher than the interim dose. Particular embodiments of Dosage Regimen A and Dosage Regimen B when the subject has a body mass that is greater than or equal to the threshold body mass are the dosage regimens in Table 1 wherein the interim orismilast dose is 10 or 20 mg orismilast (e.g. 20 mg orismilast) and the maintenance orismilast dose is 30 mg.

Suitably, in the dosage regimens according to Dosage Regimen A in Table 1 when the subject has a body mass that is below the threshold body mass the maintenance orismilast dose is the same as the interim orismilast dose. For example, in preferred dosage regimens according to Dosage Regimen A in Table 1 the interim orismilast dose and the maintenance orismilast dose are the same and are in the range of 10 to 20 mg in subjects that have a body mass that below the threshold body mass. Particular embodiments of Dosage Regimen A in Table 1 are those wherein the interim orismilast dose and the maintenance orismilast dose are the same and are in the range of 10 to 20 mg in subjects that have a body mass that is below the threshold body mass. In preferred embodiments of Dosage Regimen A in Table 1 the interim orismilast dose and the maintenance orismilast dose are both 20 mg in subjects that have a body mass that is below the threshold body mass.

Preferred embodiments in Table 1 are the dosage regimens wherein the total duration of the initial/preliminary time period and the interim time period is from 4 to 8 weeks. Thus it may be that the dosage regimen is a dosage regimen in Table 1 wherein the total duration of the initial/preliminary time period and the interim time period is 4 weeks. It may be that the dosage regimen is a dosage regimen in Table 1 wherein the total duration of the initial/preliminary time period and the interim time period is 6 weeks. It may be that the dosage regimen is a dosage regimen in Table 1 wherein the total duration of the initial/preliminary time period and the interim time period is 8 weeks.

Suitably in any of the embodiments described in Table 1 the threshold body mass is 90 kg. Suitably in any of the embodiments described in Table 1 the threshold body mass is 95 kg. Suitably in any of the embodiments described in Table 1 the threshold body mass is 105 kg. Preferably in any of the embodiments described in Table 1 the threshold body mass is 100 kg.

Dosage Regimen C (Third Aspect of the Invention)

Also contemplated is a dosage regimen wherein a subject with a body mass greater than or equal to the threshold body mass is transitioned to a maintenance dose immediately after completing an initial dose titration.

Accordingly in some embodiments there is provided orismilast for use in a method of treating a disease or disorder ameliorated by inhibiting PDE4 in a subject with a body mass that is greater than or equal to a threshold body mass, the method comprising administering the orismilast to the subject,
wherein:
(Ci) an initial orismilast dose is administered to the subject once per day for a preliminary time period followed by;
(Cii) a maintenance orismilast dose administered to the subject twice per day, wherein the maintenance orismilast dose is greater than the initial orismilast dose;
wherein:
(a) the initial orismilast dose is from 10 mg to 20 mg orismilast;
(b) the preliminary time period is up to eight weeks; and
(c) the threshold body mass is at least 90 kg.

Also provided is a method of treating a disease or disorder ameliorated by inhibiting PDE4 in a subject with a body mass that is greater than or equal to a threshold body mass, the method comprising administering the orismilast to the subject according to the dosage regimen (Ci) and (Cii) described above, wherein the threshold body mass is at least 90 kg.

Also provided is the use of orismilast for the manufacture of a medicament for the treatment a disease or disorder ameliorated by inhibiting PDE4 in a subject with a body mass that is greater than or equal to a threshold body mass, the method comprising administering the orismilast to the subject according to the dosage regimen (Ci) and (Cii) described above, wherein the threshold body mass is at least 90 kg.

In certain embodiments the preliminary time period in (Ci) is one week to four weeks. In certain embodiments the preliminary time period in (Ci) is one week to three weeks. In certain embodiments the preliminary time period in (Ci) is one week to two weeks. In certain embodiments the preliminary time period in (Ci) is two weeks to four weeks. In certain embodiments the preliminary time period in (Ci) is two weeks to up to four weeks. In certain embodiments the preliminary time period in (Ci) is one week. In certain embodiments the preliminary time period in (Ci) is three weeks. In certain embodiments the preliminary time period in (Ci) is four weeks. Preferably the preliminary time period in (Ci) is two weeks.

In a preferred embodiment the initial orismilast dose in (Ci) is 20 mg orismilast.

In certain embodiments the maintenance orismilast dose in (Ciii) is up to 40 mg orismilast, provided the maintenance orismilast dose is greater than the initial orismilast dose. For example, it may be that the maintenance orismilast dose is 30 mg to 40 mg orismilast. In a preferred embodiment the maintenance orismilast dose in (Ciii) is 30 mg orismilast.

In a preferred embodiment the initial orismilast dose in (Ci) is 20 mg orismilast and the maintenance orismilast dose in (Ciii) is 30 mg orismilast.

In another embodiment the initial orismilast dose in (Ci) is 20 mg orismilast, the preliminary time period in (Ci) is two weeks to four weeks, and the maintenance orismilast dose in (Ciii) is 30 mg orismilast.

In another embodiment the initial orismilast dose in (Ci) is 20 mg orismilast, the preliminary time period in (Ci) is two weeks, and the maintenance orismilast dose in (Ciii) is 30 mg orismilast.

In certain embodiments of Dosage Regimen C the threshold body mass is 90 kg. In certain embodiments of Dosage Regimen C the threshold body mass is 95 kg. In certain embodiments of Dosage Regimen C the threshold body mass is 105 kg. Preferably in Dosage Regimen C the threshold body mass is 100 kg.

Variants of Dosage Regimens A, B and C

It is possible that a sub-set of subjects with a body mass that is greater than or equal to the threshold body mass will show a satisfactory clinical response during the interim period ("heavier responding subjects"). Such heavier responding subjects may not require a maintenance orismilast dose that is higher than the interim orismilast dose, and can instead be administered a maintenance orismilast dose which is the same as the interim orismilast dose. This stratified dosing of heavier patients may maximise the therapeutic response to orismilast whilst further minimising the frequency an/or severity of undesirable side-effects.

Accordingly, also contemplated are variants of any one of Dosage Regimens A, B and C described herein wherein:
(i) if a subject that has a body mass greater than or equal to the threshold body mass and the subject shows a satisfactory therapeutic response during the interim time period, then the subject is administered a maintenance orismilast dose that is the same as the interim orismilast dose; and
(ii) if a subject that has a body mass greater than or equal to the threshold body mass and the subject does not show a satisfactory therapeutic response during the interim time period, then the subject is administered a maintenance orismilast dose that is greater than the interim orismilast dose.

Thus in some embodiments there is provided orismilast for use in a method of treating a disease or disorder ameliorated by inhibiting PDE4 in a subject, the method comprising administering the orismilast to the subject, wherein:
(Ai) an initial orismilast dose of 20 mg is administered to the subject once per day for an initial time period of two weeks followed by;
(Aii) an interim orismilast dose of 20 mg administered to the subject twice per day for an interim time period of one week to eight weeks (e.g. one week to four weeks, two weeks to eight weeks, or six weeks to eight weeks) followed by;

(Aiii-a) a maintenance orismilast dose of 20 mg administered to the subject twice per day if the subject has a body mass less than a threshold body mass; or (Aiii-b) a maintenance orismilast dose of 20 mg administered to the subject twice per day if the subject has a body mass that is greater than or equal to the threshold body mass and the subject shows a satisfactory clinical response during the interim time period; or (Aiii-c) a maintenance orismilast dose of 30 mg administered to the subject twice per day if the subject has a body mass that is greater than or equal to the threshold body mass and the subject does not show a satisfactory clinical response during the interim time period; and wherein the threshold body mass is at least 90 kg.

Preferably the threshold body mass is 100 kg.

In some embodiments there is provided orismilast for use in a method of treating a disease or disorder ameliorated by inhibiting PDE4 in a subject, the method comprising administering the orismilast to the subject, wherein:

(Ai) an initial orismilast dose of 20 mg is administered to the subject once per day for an initial time period of two weeks followed by;

(Aii) an interim orismilast dose of 20 mg administered to the subject twice per day for an interim time period of six weeks followed by;

(Aiii-a) a maintenance orismilast dose of 20 mg administered to the subject twice per day if the subject has a body mass less than a threshold body mass; or (Aiii-b) a maintenance orismilast dose of 20 mg administered to the subject twice per day if the subject has a body mass that is greater than or equal to the threshold body mass and the subject shows a satisfactory clinical response during the interim time period; or (Aiii-c) a maintenance orismilast dose of 30 mg administered to the subject twice per day if the subject has a body mass that is greater than or equal to the threshold body mass and the subject does not show a satisfactory clinical response during the interim time period;

and wherein the threshold body mass is at least 90 kg.

Preferably the threshold body mass is 100 kg.

In some embodiments there is provided orismilast for use in a method of treating a disease or disorder ameliorated by inhibiting PDE4 in a subject, the method comprising administering the orismilast to the subject, wherein:

(Ai) an initial orismilast dose of 20 mg is administered to the subject once per day for an initial time period of two weeks followed by;

(Aii) an interim orismilast dose of 20 mg administered to the subject twice per day for an interim time period of four weeks followed by;

(Aiii-a) a maintenance orismilast dose of 20 mg administered to the subject twice per day if the subject has a body mass less than a threshold body mass; or (Aiii-b) a maintenance orismilast dose of 20 mg administered to the subject twice per day if the subject has a body mass that is greater than or equal to the threshold body mass and the subject shows a satisfactory clinical response during the interim time period; or (Aiii-c) a maintenance orismilast dose of 30 mg administered to the subject twice per day if the subject has a body mass that is greater than or equal to the threshold body mass and the subject does not show a satisfactory clinical response during the interim time period;

and wherein the threshold body mass is at least 90 kg.

Preferably the threshold body mass is 100 kg.

In some embodiments there is provided orismilast for use in a method of treating a disease or disorder ameliorated by inhibiting PDE4 in a subject, the method comprising administering the orismilast to the subject, wherein:

(Ai) an initial orismilast dose of 20 mg is administered to the subject once per day for an initial time period of two weeks followed by;

(Aii) an interim orismilast dose of 20 mg administered to the subject twice per day for an interim time period of two weeks followed by;

(Aiii-a) a maintenance orismilast dose of 20 mg administered to the subject twice per day if the subject has a body mass less than a threshold body mass; or (Aiii-b) a maintenance orismilast dose of 20 mg administered to the subject twice per day if the subject has a body mass that is greater than or equal to the threshold body mass and the subject shows a satisfactory clinical response during the interim time period; or (Aiii-c) a maintenance orismilast dose of 30 mg administered to the subject twice per day if the subject has a body mass that is greater than or equal to the threshold body mass and the subject does not show a satisfactory clinical response during the interim time period;

and wherein the threshold body mass is at least 90 kg.

Preferably the threshold body mass is 100 kg.

In some embodiments there is provided orismilast for use in a method of treating a disease or disorder ameliorated by inhibiting PDE4 in a subject with a body mass that is greater than or equal to a threshold body mass, the method comprising administering the orismilast to the subject, wherein:

(Bi) an initial orismilast dose of 20 mg is administered to the subject once per day for a preliminary time period of two weeks followed by;

(Bii) a interim orismilast dose of 20 mg administered to the subject twice per day for an interim time period of one week to eight weeks followed by;

(Biii-a) a maintenance orismilast dose of 20 mg administered to the subject twice per day if the subject shows a satisfactory clinical response during the interim time period; or (Biii-b) a maintenance orismilast dose of 30 mg administered to the subject twice per day if the subject does not show a satisfactory clinical response during the interim time period;

and wherein the threshold body mass is at least 90 kg.

Preferably the threshold body mass is 100 kg.

In some embodiments there is provided orismilast for use in a method of treating a disease or disorder ameliorated by inhibiting PDE4 in a subject with a body mass that is greater than or equal to a threshold body mass, the method comprising administering the orismilast to the subject, wherein:

(Bi) an initial orismilast dose of 20 mg is administered to the subject once per day for a preliminary time period of two weeks followed by;

(Bii) a interim orismilast dose of 20 mg administered to the subject twice per day for an interim time period of six weeks followed by;

(Biii-a) a maintenance orismilast dose of 20 mg administered to the subject twice per day if the subject shows a satisfactory clinical response during the interim time period; or (Biii-b) a maintenance orismilast dose of 30 mg administered to the subject twice per day if the subject does not show a satisfactory clinical response during the interim time period; and wherein the threshold body mass is at least 90 kg.

Preferably the threshold body mass is 100 kg.

Thus also provided in some embodiments is orismilast for use in a method of treating a disease or disorder ameliorated by inhibiting PDE4 in a subject with a body mass that is greater than or equal to a threshold body mass, the method comprising administering the orismilast to the subject, wherein:
(Ci) an initial orismilast dose of 20 mg is administered to the subject once per day for a preliminary time period followed by;
(Ci-a) a maintenance orismilast dose of 20 mg administered to the subject twice per day if the subject shows a satisfactory clinical response during the preliminary time period; or
(Cli-b) a maintenance orismilast dose of 30 mg administered to the subject twice per day if the subject does not show a satisfactory clinical response during the preliminary time period;
wherein the threshold body mass is at least 90 kg; and the preliminary period is one week to four weeks.

Preferably the threshold body mass is 100 kg. Preferably the preliminary period is two weeks.

A "satisfactory clinical response" referred to in the variants of Dosage Regimens A, B and C above will depend upon the disease or disorder being treated and may be one or more of a reduction in one or more signs and symptoms of the disease and will be readily determined by a physician.

In some embodiments where the disease or disorder is psoriasis, a satisfactory clinical response during the interim time period may be one or more of: a reduction from baseline in the Psoriasis Area and Severity Index (PASI) score (e.g. a reduction of 50% (PASI50) or more, a reduction of 75% (PASI75) or more, a reduction of 90% (PASI90) or more, or a reduction of 100% (PASI100) or more;
a reduction from baseline of the Investigator Global Assessment (IGA) score (e.g. subjects achieving a score of Clear (0) or Almost Clear (1) and an at least a 2-point improvement in IGA);
achieving an IGA score of 0;
a reduction from baseline of the Static Physician Global Assessment (sPGA) score;
a reduction from baseline of the total Psoriasis Symptoms Scale (PSS) score;
a reduction from baseline of the affected body surface area (BSA);
a reduction from baseline of the Dermatology Life Quality Index (DLQI) score;
a reduction from baseline of the Scalp-specific Investigator Global Assessment (ss-IGA) score;
a reduction from baseline of the Scalp Specific Physician Global Assessment (ScPGA) score;
a reduction from baseline of the Static Physician Global Assessment of Genitalia (sPGA-GTM) score;
a reduction in baseline of the Palmoplantar Psoriasis Physician Global Assessment (PPPGA);
a reduction from baseline of the Physician's Global Assessment of Fingernail Psoriasis (PGA-F) score;
a reduction from baseline of the whole body itch numeric rating scale (NRS);
a reduction from baseline of the pain NRS;
a reduction from baseline of the Scalp Itch Numeric Rating Scale (NRS) score; and/or an increase from baseline of the EuroQol Quality of Life 5-Dimension-5 five-level (EQ-5D-5L™) score.

In some embodiments where the disease is psoriasis (e.g. moderate to severe psoriasis) a satisfactory clinical response during the interim time period may be at least a 75% reduction in PASI score from baseline (PASI75) or an sPGA of 0 or 1.

In some embodiments where the disease is psoriasis (e.g. moderate to severe psoriasis) a satisfactory clinical response during the interim time period may be and of the primary secondary or tertiary endpoints in the psoriasis clinical trials disclosed in Examples 3, 4 and 5 herein.

In some embodiments where the disease is atopic dermatitis (e.g. moderate to severe atopic dermatitis) a satisfactory clinical response during the interim time period may be one or more of:
a reduction from baseline of Eczema Area and Severity Index (EASI) score (e.g. a reduction of 50% (EASI50) or more, a reduction of 75% (EASI75) or more, a reduction of 90% (EASI90) or more, or a reduction of 100% (EASI100) or more);
a reduction from baseline of Investigator Global Assessment for AD (IGA-AD) score (e.g. subjects achieving a score of clear (0) or almost clear (1) and at least a 2-point improvement in IGA-AD);
achieving an IGA-AD of 0;
a reduction from baseline of the validated Investigator Global Assessment for AD (vIGA-AD) score (e.g. subjects achieving a score of clear (0) or almost clear (1) and at least a 2-point improvement in vIGA-AD);
achieving an vIGA-AD of 0;
a reduction from baseline of the Peak Pruritus Numerical Rating Scale (NRS);
a reduction from baseline of the Worst Pruritus Numerical Rating Scale (NRS);
a reduction from baseline affected body surface area (BSA);
a reduction from baseline in the Dermatology Life Quality Index score;
a reduction from baseline in the Patient Oriented Eczema Measure score;
a reduction from baseline in the Patient Global Impression of Severity;
an Patient Global Impression of Change score of 1 or 2;
a reduction from baseline in the sleep disturbance NRS score;
a reduction from baseline in the skin pain NRS score; or
a change from baseline in skin biomarkers, for example a reduction in TARC (thymus and activation-regulated chemokine, also known as CCL17) or C6A6.

In some embodiments where the disease is atopic dermatitis (e.g. moderate to severe atopic dermatitis) a satisfactory clinical response during the interim time period may be and of the primary secondary or tertiary endpoints in the atopic dermatitis clinical trials disclosed in Examples 8 and 13 herein.

In some embodiments where the disease is hidradenitis suppurativa (HS) a satisfactory clinical response during the interim time period may be one or more of: a reduction from baseline in the number of abscesses and nodules (AN count) a reduction from baseline of the International Hidradenitis Suppurativa Severity Score System (IHS4) score;
a reduction from baseline in the Hidradenitis Suppurativa Clinical Response (HiSCR) score;
a reduction from baseline in the Hidradenitis Suppurativa Quality of Life (HiSQoL) score;
a reduction from baseline in the Physician's Global Assessment of disease severity (HS-PGA);
a reduction from baseline in the Dermatology Life Quality Index (DLQI) score;

a reduction from baseline in the Patient's Global Assessment of Skin Pain NRS score;
a reduction from baseline in the amount of C-Reactive Protein Dosage Regimen D (Fourth Aspect of the Invention)

The fourth aspect of the invention provides a dosage regimen optimised for subjects with a body mass that is from a lower limit body mass to less than the threshold body mass, wherein the lower limit body mass is from 50 kg to 75 kg.

Accordingly there is provided orismilast for use in a method of treating a disease or disorder ameliorated by inhibiting PDE4 in a subject, the method comprising administering the orismilast to the subject, wherein:
(Di) an initial orismilast dose is administered to the subject once per day for an initial time period followed by;
(Dii) a maintenance orismilast dose is administered to the subject twice per day;
wherein:
(a) the initial orismilast dose and the maintenance orismilast dose are both 20 mg orismilast;
(b) the initial time period is two to eight weeks;
(c) the subject has a body mass that is from a lower limit body mass to less than a threshold body mass, wherein the threshold body mass is at least 90 kg and the lower limit body mass is from 50 kg to 75 kg.

Also provided is a method of treating a disease or disorder ameliorated by inhibiting PDE4 in a subject with a body mass that is from a lower limit body mass to less than a threshold body mass, the method comprising administering the orismilast to the subject according to the dosage regimen (Di) and (Dii) described above, wherein the threshold body mass is at least 90 kg and the lower limit body mass is from 50 kg to 75 kg.

Also provided is the use of orismilast for the manufacture of a medicament for the treatment a disease or disorder ameliorated by inhibiting PDE4 in a subject with a body mass that is from a lower limit body mass to less than a threshold body mass, the method comprising administering the orismilast to the subject according to the dosage regimen (Di) and (Dii) described above, wherein the threshold body mass is at least 90 kg and the lower limit body mass is from 50 kg to 75 kg.

In certain embodiments the initial time period in (Di) is two weeks to six weeks. In certain embodiments the initial time period in (Di) is two weeks to four weeks. In certain embodiments the initial time period in (Di) is two weeks to up to four weeks. In certain embodiments the initial time period in (Di) is three weeks. In certain embodiments the initial time period in (Di) is four weeks. Preferably the initial time period in (Di) is two weeks.

In certain embodiments of the fourth aspect the threshold body mass is 90 kg. In certain embodiments of the fourth aspect the threshold body mass is 90 kg. In certain embodiments of the fourth aspect the threshold body mass is 95 kg. In preferred embodiments of the fourth aspect the threshold body mass is 100 kg.

In certain embodiments of the fourth aspect the lower limit body mass is selected from 50 kg, 55 kg, 60 kg, 65 kg, 70 kg and 75 kg. In certain embodiments of the fourth aspect the lower limit body mass is 50 kg. In certain embodiments of the fourth aspect the lower limit body mass is 60 kg. In certain embodiments of the fourth aspect the lower limit body mass is 70 kg. In certain embodiments of the fourth aspect the lower limit body mass is 75 kg.

Thus it may be that the subject has a body mass of from 50 kg to less than 100 kg. In some embodiments the subject has a body mass of from 60 kg to less than 100 kg. the subject has a body mass of from 70 kg to less than 100 kg.

In one embodiment of the fourth aspect there is provided orismilast for use in a method of treating a disease or disorder ameliorated by inhibiting PDE4 in a subject, the method comprising administering the orismilast to the subject, wherein:
(Di) an initial orismilast dose of 20 mg orismilast is administered to the subject once per day for two weeks followed by;
(Dii) a maintenance orismilast dose of 20 mg orismilast administered to the subject twice per day;
wherein the subject has a body mass of from 75 kg to less than 100 kg.

In an embodiment of the fourth aspect there is provided orismilast for use in a method of treating a disease or disorder ameliorated by inhibiting PDE4 in a subject, the method comprising administering the orismilast to the subject, wherein:
(Di) an initial orismilast dose of 20 mg orismilast is administered to the subject once per day for two weeks followed by;
(Dii) a maintenance orismilast dose of 20 mg orismilast administered to the subject twice per day;
wherein the subject has a body mass of from 60 kg to less than 100 kg.

In another embodiment of the fourth aspect there is provided orismilast for use in a method of treating a disease or disorder ameliorated by inhibiting PDE4 in a subject, the method comprising administering the orismilast to the subject, wherein:
(Di) an initial orismilast dose of 20 mg orismilast is administered to the subject once per day for two weeks followed by;
(Dii) a maintenance orismilast dose of 20 mg orismilast administered to the subject twice per day;
wherein the subject has a body mass of from 50 kg to less than 100 kg.

Dosage Regimen E (Fifth Aspect of the Invention)

As described in the Examples herein, a population PK model based on pooled orismilast clinical trial data has identified that treatment of subjects with a low body mass, for example less than 50 kg (e.g. adolescent patients) with 20 mg orismilast twice daily results in a higher systemic exposure to orismilast compared to heavier subjects. As discussed above analysis of the psoriasis phase 2b data has shown that increasing systemic exposure beyond that required for initial efficacy may not increase efficacy and could even reduce efficacy. Accordingly, a specific dosing regimen may be required for lighter subjects.

In a fifth aspect of the invention there is provided orismilast for use in a method of treating a disease or disorder ameliorated by inhibiting PDE4 in a subject with a body mass that is less than a lower limit body mass, the method comprising administering the orismilast to the subject, wherein:
(Ei) an initial orismilast dose of 10 mg is administered to the subject once per day for an initial time period followed by;
(Eii) a maintenance orismilast dose of 10 mg administered to the subject twice per day; wherein the initial time period is two to eight weeks and the lower limit body mass is from 50 kg to 75 kg.

Also provided is a method of treating a disease or disorder ameliorated by inhibiting PDE4 in a subject with a body mass that is less than a lower limit body mass, the method comprising administering the orismilast to the subject according to the dosage regimen (Ei) and (Eii) described above, wherein the lower limit body mass is from 50 kg to 75 kg.

Also provided is the use of orismilast for the manufacture of a medicament for the treatment a disease or disorder ameliorated by inhibiting PDE4 in a subject with a body mass that is less than a lower limit body mass, the method comprising administering the orismilast to the subject according to the dosage regimen (Ei) and (Eii) described above, wherein the lower limit body mass is from 50 kg to 75 kg.

In certain embodiments the initial time period in (Ei) is two weeks to six weeks. In certain embodiments the initial time period in (Ei) is two weeks to four weeks. In certain embodiments the initial time period in (Ei) is two weeks to up to four weeks. In certain embodiments the initial time period in (Ei) is three weeks. In certain embodiments the initial time period in (Ei) is four weeks. Preferably the initial time period in (Ei) is two weeks.

In some embodiments of the fifth aspect of the invention there is provided orismilast for use in a method of treating a disease or disorder ameliorated by inhibiting PDE4 in a subject with a body mass that is less than a lower limit body mass, the method comprising administering the orismilast to the subject, wherein:
(Ei) an initial orismilast dose of 10 mg is administered to the subject once per day for two weeks followed by;
(Eii) a maintenance orismilast dose of 10 mg administered to the subject twice per day; wherein the lower limit body mass is from 50 kg to 75 kg.

twice daily administration of the interim or maintenance orismilast doses. Also provided are variations of dosage regimens A, B, C, D, or E, wherein in (Ai), (Bi), (Ci), (Di) or (Ei) an initial orismilast dose of 10 mg is administered to the subject once or twice per day during an initial or preliminary time period of one or two weeks prior to twice daily administration of the interim or maintenance orismilast doses. Also provided are variations of dosage regimens A, B, C, D, or E, wherein in (Ai), (Bi), (Ci), (Di) or (Ei) an initial orismilast dose of 10 mg is administered to the subject twice per day during an initial or preliminary time period of one or two weeks prior to twice daily administration of the interim or maintenance orismilast doses. Also provided are variations of dosage regimens A, B, C, D, or E, wherein in (Ai), (Bi), (Ci), (Di) or (Ei) an initial orismilast dose of 20 mg is administered to the subject once or twice per day during an initial or preliminary time period of one or two weeks prior to twice daily administration of the interim or maintenance orismilast doses. Also provided are variations of dosage regimens A, B, C, D, or E, wherein in (Ai), (Bi), (Ci), (Di) or (Ei) an initial orismilast dose of 20 mg is administered to the subject twice per day during an initial or preliminary time period of one or two weeks prior to twice daily administration of the interim or maintenance orismilast doses.

In some embodiments of the alternative initial dose titration, in any of Dosage Regimens A, B, C, D or E described herein steps (Ai), (Bi), (Ci), (Di) or (Ei) respectively are replaced by any one of the Variants 1, 2 or 3 shown in the table below for the first 14 days of treatment:

| Varaint # | Day 1 (mg) AM | Day 2 (mg) AM | Day 2 (mg) PM | Day 3 (mg) AM | Day 3 (mg) PM | Day 4 (mg) AM | Day 4 (mg) PM | Day 5 (mg) AM | Day 5 (mg) PM | Day 6 (mg) AM | Day 6 (mg) PM | Day 7 (mg) AM | Day 7 (mg) PM | Day 8 (mg) AM | Day 8 (mg) PM |
|---|---|---|---|---|---|---|---|---|---|---|---|---|---|---|---|
| 1 | 10 | 10 | 10 | 10 | 10 | 10 | 10 | 10 | 20 | 10 | 20 | 10 | 20 | 20 | 20 |
| 2 | 10 | 10 | 10 | 10 | 20 | 20 | 20 | 20 | 20 | 20 | 30 | 20 | 30 | 20 | 30 |
| 3 | 10 | 10 | 10 | 10 | 20 | 20 | 20 | 20 | 20 | 20 | 30 | 20 | 30 | 20 | 30 |

| Varaint # | Day 9 (mg) AM | Day 9 (mg) PM | Day 10 (mg) AM | Day 10 (mg) PM | Day 11 (mg) AM | Day 11 (mg) PM | Day 12 (mg) AM | Day 12 (mg) PM | Day 13 (mg) AM | Day 13 (mg) PM | Day 14 (mg) AM | Day 14 (mg) PM |
|---|---|---|---|---|---|---|---|---|---|---|---|---|
| 1 | 20 | 20 | 20 | 20 | 20 | 20 | 20 | 20 | 20 | 20 | 20 | 20 |
| 2 | 30 | 30 | 30 | 30 | 30 | 30 | 30 | 30 | 30 | 30 | 30 | 30 |
| 3 | 30 | 30 | 30 | 30 | 30 | 30 | 30 | 40 | 30 | 40 | 30 | 40 |

In some embodiments of the fifth aspect of the invention the lower limit body mass is selected from 50 kg, 55 kg, 60 kg, 65 kg, 70 kg and 75 kg. In certain embodiments of the fifth aspect the lower limit body mass is 50 kg. In certain embodiments of the fifth aspect the lower limit body mass is 60 kg. In certain embodiments of the fifth aspect the lower limit body mass is 70 kg. In certain embodiments of the fifth aspect the lower limit body mass is 75 kg.

Alternative Initial Dose Titrations

Also contemplated are variations of any of Dosage Regimens A, B, C, D or E described herein, wherein the initial orismilast dose, the frequency of dosing and/or the initial or preliminary time periods are varied from the once daily dosing described for Dosage Regimens A, B, C, D or E.

Thus also provided are variations of dosage regimens A, B, C, D, or E, wherein in (Ai), (Bi), (Ci), (Di) or (Ei) an initial orismilast dose (for example 10 mg or 20 mg) is administered to the subject once or twice per day during an initial or preliminary time period (e.g. two weeks) prior to Following completion of the initial 14 days of treatment the subject is then treated with the interim orismilast dose starting on day 15 of the treatment as described in any one of Dosage Regimens A or B, or with the maintenance orismilast dose as described in any one of Dosage Regimens C, D or E.

In some embodiments of the alternative initial dose titration, in any of Dosage Regimens A, B, C, D or E described herein steps (Ai), (Bi), (Ci), (Di) or (Ei) respectively are replaced by the initial dose titration shown in Table 5 in Example 3. Following completion of the initial 14 days of treatment the subject is then treated with the interim orismilast dose starting on day 15 of the treatment as described in any one of Dosage Regimens A or B, or with the maintenance orismilast dose as described in any one of Dosage Regimens C, D or E.

Pharmaceutical Compositions

The orismilast may be comprised within a pharmaceutical composition. Thus, the present invention also encompasses a pharmaceutical composition, comprising orismilast, for use any of the dosage regimens described herein.

Pharmaceutical compositions comprising orismilast may optionally further comprise one or more viscosity modifying agents, carriers (e.g. mannitol, lactose, microcrystalline cellulose or trehalose), emulsifiers, surfactants, humectants, oils, waxes, polymers, preservatives, pH modifying agents (for example a suitable acid or base, for example an organic acid or organic amine base), buffers, stabilizers, electrolytes antioxidants (for example, butylated hydroxyanisol or butylated hydroxytoluene), crystallisation inhibitors (for example a cellulose derivative such as hydroxypropylmethyl cellulose or polyvinylpyrrolidone), colorants, fragrances and taste-masking agents. Such excipients are well-known, for example as listed in the Handbook of Pharmaceutical Excipients, 10$^{th}$ Edition, Sheskey et al.

In some embodiments the orismilast is present in the pharmaceutical composition in an amount of from about 0.01 to 50% by weight of the composition. Thus it may be that the orismilast, is present in the solid composition in an amount of about 0.05 to 40%, from 0.1 to 30%, from 0.2 to 20%, from 0.3 to 15%, from 0.4 to 12%, from 0.5 to 11%, from 1 to 10%, from 1.5 to 9.5%, from 2 to 9%, from 2.5 to 8.5%, from 3 to 8%, from 3.5 to 7.5%, from 4 to 7%, from 4.5 to 6.5%, or from about 5 to 6%, e.g. about 5.5%, wherein the % are by weight based on the weight of the composition.

Pharmaceutical Compositions for Oral Administration

In some embodiments the pharmaceutical composition comprising orismilast is suitable for oral administration. Suitably the pharmaceutical composition is a solid pharmaceutical composition, preferably a solid pharmaceutical composition suitably for oral administration. The pharmaceutical composition comprising orismilast may be in the form of discrete units such as capsules, sachets, tablets, lozenges or granules, each containing a predetermined amount of orismilast. The discrete units may contain the composition in the form of a powder or granules, a solution or a suspension in aqueous or non-aqueous liquid, such as ethanol or glycerol, or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropyl methylcellulose, hydroxypropylcellulose, carbomers and polyvinylpyrrolidone. The formulation may also be administered in the form of a bolus, electuary or paste.

Powders may be prepared using well-known methods, for example by milling, blending, micro-precipitation, lyophilisation or spray drying, or spray-freeze drying a solution comprising orismilast.

The amount of orismilast, in each oral dosage form (e.g. tablet, capsule, sachet or lozenge) may range from about 1 mg to about 40 mg. The amount of orismilast may for example range from 5 mg to 40 mg, from 10 mg to 40 mg, from 15 mg to 35 mg, from 20 to 30 mg, from 25 mg to 30 mg, form 5 mg to 30 mg or from 10 mg to 30 mg. In some embodiments, the amount of orismilast, in each oral dosage form (e.g. tablet, capsule, sachet or lozenge) is 1 mg, 2 mg, 5 mg, 10 mg, 15 mg, 20 mg, 25 mg, 30 mg, 35 mg or 40 mg.

In certain embodiments particles comprising orismilast, may be prepared by precipitation, lyophilisation or spray drying, or spray-freeze drying a solution comprising the orismilast and a suitable carrier to provide powder particles comprising the orismilast and the carrier as composite particles. Suitable carriers include inert carriers such as starch, sugars (e.g. mannitol, lactose, microcrystalline cellulose or trehalose).

In some embodiments the orismilast is present in the composition as a micronised powder, for example a micronised crystalline powder (e.g. micronised crystalline form E of orismilast). Thus it may be that the particle size distribution of the orismilast in the composition has a D(50)≤25 μm, for example D(50)≤20 μm, D(50) 10 μm, D(50)≤5 μm, or D(50)≤3 μm. In some embodiments the particle size distribution of the orismilast in the composition has a D(90)≤10 μm. In some embodiments the particle size distribution of the orismilast in the composition has a D(50) of about 1 μm to about 6 μm.

Powders comprising orismilast, as described herein, may be dissolved or suspended in a suitable solvent (preferably water) prior to administration, e.g. application of a spray or gel. Alternatively, a powder or granule comprising orismilast may be sprinkled onto food or into a liquid prior to administration.

A tablet may be made by compressing or moulding the composition, optionally with one or more accessory ingredients. Compressed tablets may be prepared by compressing, in a suitable tabletting machine, the formulation in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropyl methylcellulose, polyethylene glycol, waxes or the like; a lubricant such as sodium oleate, sodium stearate, magnesium stearate, sodium benzoate, sodium acetate, sodium chloride or the like; a disintegrating agent such as starch, methylcellulose, agar, bentonite, croscarmellose sodium, sodium starch glycollate, crospovidone or the like or a dispersing agent, such as polysorbate 80.

Moulded tablets may be made by moulding. Suitable techniques for moulding tablets are well-known in the art. For example, in a suitable machine, a mixture of the powdered active ingredient and suitable carrier may be moistened with an inert liquid diluent. In some embodiments, moulded tablets may be made by dispersing a water-soluble excipient with the powdered orismilast in a suitable solvent such as water, alcohol or organic solvents (e.g. acetone, hydrocarbons). Alternatively, moulded tablets may be made using thermoplastic polymers (e.g. polyethyleneoxide or polyvinyl caprolactam-polyvinylacetate-polyethylene glycol copolymers), without an inert liquid diluent.

Representative examples of oral pharmaceutical compositions comprising orismilast are shown in Table 2

TABLE 2

|  | 1: hard capsule | 2: modified release tablet | 3: soft capsule | 4: blend, hard capsule | 5: gastro-resistant capsule |
| --- | --- | --- | --- | --- | --- |
| core ingredients | orismilast | orismilast Lactose | orismilast Triglyceride, | orismilast Microcrystalline | orismilast Microcrystalline |

TABLE 2-continued

| | 1: hard capsule | 2: modified release tablet | 3: soft capsule | 4: blend, hard capsule | 5: gastro-resistant capsule |
|---|---|---|---|---|---|
| | | monohydrate | medium chain | cellulose | cellulose |
| | | Hypromellose | Lecithin | Lactose monohydrate | Lactose monohydrate |
| | | Silica, colloidal anhydrous | Hard fat | Hypromellose | Coscarmellose sodium |
| | | Magnesium stearate | Silica, colloidal anhydrous | Silica, colloidal anhydrous | Silica, colloidal anhydrous |
| | | | | Magnesium stearate | Magnesium stearate |
| shell/coating | Gelatin | Macrogol | Gelatin | Gelatin | Hypromellose |
| | Ferric oxide red | PVA | Glycerol | Ferric oxide red | Hypromellose acetate succinate |
| | Titanium dioxide | Titanium dioxide | Ferric oxide red | Titanium dioxide | Titanium dioxide |
| | | Talc | Water, purified | | |
| | | Ferric oxide yellow | | | |

Modified Release Compositions

In some embodiments, the orismilast is comprised within a modified release composition formulation, for example a modified release composition for oral administration. Thus it may be that the orismilast may be comprised within a modified release tablet composition for oral administration. The use of modified release compositions may control the release of the therapeutic agent and thus control absorption of orismilast from gastrointestinal tract. It has previously been described by the Applicant (in a PCT application published as WO2020/148271) that beneficial effects with respect to improved tolerability towards gastrointestinal adverse events and maintained systemic exposure can be achieved by formulating orismilast in a modified release tablet formulation, wherein the in-vitro release is fast in comparison to convention delayed or extended release oral release profiles but not yet as fast as for an immediate release tablet where major tolerability issues were seen.

It will be appreciated that the rate of dissolution of a modified release composition will be determined by several factors e.g. the composition excipients and nature of the composition, the particle sizes of the components used in the composition, particularly the particle size of the orismilast, and the use of coatings or capsules to modulate release of orismilast from the composition. The dissolution target area in FIG. 1 of WO2020/0148271 illustrates suitable dissolution profiles for modified release compositions comprising orismilast are suitably determined in-vitro using Ph. Eur. 2.9.3 Apparatus II, with a dissolution medium of 900 ml 0.5% sodium dodecyl sulfate in 0.1N HCl, a paddle speed of 75 rpm, and the dissolution medium at 37±0.5° C., referred herein as "the Standard Dissolution Assay".

In some embodiments the orismilast is formulated as a modified release formulation described in WO2020/0148271, which is incorporated herein by reference thereto.

Other modified release compositions comprising orismilast are also contemplated. For example the orismilast may be dispersed, dissolved or conjugated (e.g. complexed) with a polymer matrix. The polymer matrix may be hydrophobic or hydrophilic, but is preferably hydrophilic. In some embodiments the composition comprises orismilast and a polymeric matrix, wherein the polymer is one or more polymers selected from hydroxypropyl methylcellulose, methyl cellulose, hydroxypropyl cellulose, hydroxyethyl cellulose, sodium carboxymethyl cellulose a polyethylene oxide, polyethylene glycols; polyethyleneoxide and polypropyleneoxide block-co-polymers (e.g. poloxamers), cellulose acetate phthalate, hydroxypropylmethyl cellulose phthalate, polyvinylpyrrolidone (PVP), copolymers of PVP and vinyl acetate, a poly (ethylene-vinyl acetate), polyvinyl alcohol, sugar alcohols (e.g. xylitol or sorbitol) and a biodegradable polymer (e.g. a poly(lactide-co-glycolide)).

Orismilast may also be dissolved, dispersed or conjugated with one or more protein-based polymers, such as collagen, albumin, gelatin, and polysaccharides, such as agarose, alginate, carrageenan, hyaluronic acid (HA), dextran, chitosan, galactomannan, guar gum; carob gum; gum arabic; sterculia gum, agar or a cyclodextrin.

In some embodiments the polymer matrix is present in the composition in an amount of from 10 to 40% by weight of the composition, for example from 15 to 30% by weight of the composition. The modified release composition comprising orismilast may further comprise one or more fillers, binders, or glidants. Such additional excipients are well known to the skilled person.

In some embodiments the orismilast is dissolved or dispersed within the polymer matrix by melt extrusion. Alternatively the orismilast may be dispersed or dissolved in the polymer matrix by blending the excipients followed by wet or dry granulation and/or pressing composition into a suitable dosage form such as a tablet. The orismilast may also be dispersed or dissolved in a gel matrix, for example a hydrogel system comprising a gel-forming polymer.

The modified release composition comprising orismilast may also be prepared as a nanoparticulate composition. For example nanoparticles comprising orismilast and a biodegradable polymer such as a poly(lactide-co-glycolide) or orismilast conjugated with a suitable polymer carrier.

In some embodiments the composition comprising orismilast is a solid dispersion wherein the orismilast is present in a matrix (typically a polymer matrix) in an amorphous form. Examples of amorphous solid dispersions are disclosed in Jain S et al. Solubility and dissolution enhancement strategies: Current understanding and recent trends.

Drug Dev. Ind. Pharm. 2015; 41:875-887. Solid dispersions may be prepared using known methods, for example hot melt extrusion.

Modified release of orismilast may also be achieved through the use of coatings on a core composition (e.g. a tablet core) comprising the orismilast, or wherein orismilast is present in a coating applied to a suitable substrate (e.g. and inert core such as a sugar or polymeric core) to provide layer containing orismilast on the core. Suitable coatings which could provide modified release of orismilast include, for example, modified celluloses, polymethacrylates, polyvinylpyrrolidone, polyvinyl acetate phthalate, zein and/or shellac or natural gum, such as, for example, carrageenan. For example, a coating comprising a water-soluble polymers, such as, for example, low-viscosity hydroxypropylmethyl cellulose, hydroxypropyl cellulose or a PVA polymer.

Also contemplated are coatings applied to a core composition comprising orismilast, for example a core comprising orismilast and a polymer matrix as described herein. The coating may be any of the coatings described herein and acts to further modulate release of the orismilast from the composition. In certain embodiments the composition comprises a core comprising orismilast wherein the core is coated with a coating comprising orismilast. In this embodiment orismilast is released from both the coating and the core.

Modified release compositions comprising orismilast may also be formulated as a lipid-based composition, for example as a liposome, emulsion or micro emulsion, a self-emulsifying drug delivery system, a nano-emulsion, a lipid-drug conjugate, solid-lipid nanoparticles or solid lipid microparticles. Accordingly the composition may, for example, be a self-emulsifying drug delivery (SEDD) composition, a self-microemulsifying drug delivery (SMEDD) composition or a self-nanoemulsifying drug delivery (SNEDD) composition. The lipid may be, for example, mono-, di- or triglycerides (e.g. a medium chain triglyceride) a lipid emulsifiers, for example, phosphatidylcholine, 1,2-dipalmitoyl-sn-glycero-3-phosphocholine (DPPC), 1,2-distearoyl-sn-glycero-3-phosphocholine (DSPC), hydrogenated soy phosphatidylcholine (HSPC), 1-myristoyl-2-stearoyl-sn-glycero-3-phosphocholine (MSPC), 1-hexadecenyl-2-oleoyl-sn-glycero-3-phosphocholine (HOPC), 1,2-dipalmitoyl-sn-glycero-3-phosphatidylglycerol (DPPG), 1,2-distearoyl-sn-glycero-3-phosphatidylglycerol (DSPG), represents 1,2-dimyristoyl-sn-glycero-3-phosphatidylglycerol (DMPG), 1,2-distearoyl-sn-glycero-3-phosphoethanolamine-N-[amino (polyethylene glycol)-2000](DSPE-PEG2000), 1,2-dimyristoyl-sn-glycero-3-phosphoethanolamine (DMPE), 1,2-dioleoyl-sn-glycero-3-phosphoethanolamine (DOPE), unsaturated polyglycolized glycerides (e.g. oleoyl macrogolglycerides or linoleoyl macrogolglycerides), sorbitan esters (e.g. sorbitan monooleate, sorbitan monostearate, sorbitan monolaurate or sorbitan monopalmitate), polyoxyethylene sorbitan esters (e.g. Polysorbate 20, polysorbate 40, polysorbate 60, and polysorbate 80), polyoxyl castor oil derivatives (e.g. polyoxyl 35 castor oil or polyoxyl 40 hydrogenated castor oil), polyoxyethylene polyoxypropylene block copolymers (e.g. poloxamer 188 or poloxamer 407), saturated polyglycolized glycerides (e.g. lauroyl macrogolglycerides or stearoyl macrogolglycerides), PEGylated caprylic/capric glycerides (e.g. caprylocaproyl macrogolglycerides) or vitamin E derivatives (e.g. D-tocopheryl polyethylene glycol succinate). The lipid formulations may further comprise one or more surfactant and/or co-solvent. Lipid drug delivery systems are described in Examples, of emulsifiers in Rahim M A et al, Recent Advancements in Stimuli Responsive Drug Delivery Platforms for Active and Passive Cancer Targeting. Cancers (Basel). 2021 Feb. 7; 13(4):670; and Yingchoncharoen et al., Lipid-Based Drug Delivery Systems in Cancer Therapy: What Is Available and What Is Yet to Come. Pharmacol Rev. 2016 July; 68(3):701-87.

Also contemplated are osmotic-release drug delivery systems comprising a composition comprising orismilast and an osmotic agent surrounded by a semipermeable membrane capsule containing a small orifice. In use water is drawn is drawn through the semipermeable membrane by the osmotic agent, and the osmotic agent becomes hydrated and swells, forcing the drug out through the orifice in the capsule.

In some embodiments the modified release formulation releases less than 40% of the orismilast after 12 minutes. In some embodiments the modified release formulation releases less than 20% of the orismilast after 12 minutes. In some embodiments the modified release composition releases less than 40% of the orismilast after 30 minutes. In some embodiments the modified release composition releases less than 35% of the orismilast after 30 minutes. In some embodiments the modified release composition releases from about 20% to about 40% of the orismilast after 30 minutes. In some embodiments the modified release composition releases from about 25% to about 35% of the orismilast after 30 minutes. In some embodiments the modified release composition releases from about 25% to about 50% of the orismilast after 30 minutes. In some embodiments the modified release composition releases from about 25% to about 45% of the orismilast after 30 minutes. In some embodiments the modified release composition releases from about 24% to about 36% of the orismilast after 30 minutes. In some embodiments the modified release composition releases from about 11% to about 65% of the orismilast after 45 minutes. In some embodiments the modified release composition releases from about 25% to about 60% of the orismilast after 45 minutes. In some embodiments the modified release composition releases from about 35% to about 55% of the orismilast after 45 minutes. In some embodiments the modified release composition releases from about 30% to about 45% of the orismilast after 45 minutes. In some embodiments the modified release composition releases from about 30% to about 46% of the orismilast after 45 minutes. In some embodiments the modified release composition releases from about 40% to about 65% of the orismilast after 60 minutes. In some embodiments the modified release composition releases from about 40% to about 55% of the orismilast after 60 minutes. In some embodiments the modified release composition releases more than about 60% of the orismilast after 60 minutes. In some embodiments the modified release composition releases more than about 40% of the orismilast after 60 minutes. In some embodiments the modified release composition releases more than about 60% of the orismilast after 60 minutes. In some embodiments the modified release composition releases from about 35% to about 65% of the orismilast after 60 minutes. In some embodiments the modified release composition releases from about 35% to about 50% of the orismilast after 60 minutes. In some embodiments the modified release composition releases from about 40% to about 50% of the orismilast after 60 minutes. In some embodiments the modified release composition releases from about 35% to about 53% of the orismilast after 60 minutes. In some embodiments the modified release composition releases from about 50% to about 75% of the orismilast after 90 minutes. In some embodiments the modified release composition releases from about 50% to about 60% of the orismilast after 90 minutes. In some embodiments the modified release composition releases from about 44% to about 66% of the orismilast after 90 minutes. In some embodiments the modified release composition releases from about 60% to about 80% of the orismilast after 120 minutes. In some embodiments the modified release composition releases from about 65% to about 80% of the orismilast after 120 minutes. In some embodiments the modified release composition releases from about 60% to about 70% of the orismilast after 120 minutes. In some embodiments the modified release composition releases from about 52% to about 78% of the orismilast after 120 minutes. In some embodiments the modified release composition releases more than about 70% of the orismilast after 180 minutes. In some embodiments the modified release composition releases more than about 80% of the orismilast after 180 minutes. In some embodiments the modified release composition releases from about 66% to about 100% of the orismilast after 180 minutes. In some embodiments the modified release composition releases from about 70% to about 100% of the orismilast after 180 minutes. In some embodiments the modified release composition releases from about 80% to about 100% of the orismilast after 180 minutes. In some embodiments the modified release composition releases from about 85% to about 100% of the orismilast after 180 minutes. In some embodiments the modified release composition releases from about 90% to about 100% of the orismilast after 180 minutes. In some embodiments the modified release composition releases from about 95% to about 100% of the orismilast after 180 minutes.

In certain embodiments the modified release composition releases from about 11% to about 65% of the orismilast after 45 minutes and more than 80% of the orismilast after 180 minutes. In certain embodiments the modified release composition releases from about 25% to about 65% of the orismilast after 45 minutes and at least 75% of the orismilast after 180 minutes. In certain embodiments the modified release composition releases from about 30% to about 50% of the orismilast after 45 minutes and at least 75% of the orismilast after 180 minutes. In some embodiments the modified release composition releases from about 30% to about 55% of the orismilast after 45 minutes and at least 80% of the orismilast after 180 minutes.

In some embodiments the modified release composition releases from about 30% to about 46% of the orismilast after 45 minutes and at least 80% of the orismilast after 180 minutes. In certain embodiments the modified release composition releases from about 30% to about 50% of the orismilast after 45 minutes and about 80% to about 100% of the orismilast after 180 minutes. In some embodiments the modified release composition releases from about 30% to about 55% of the orismilast after 45 minutes, from about 44% to about 66% after 90 minutes and at least 80% of the orismilast after 180 minutes.

In some embodiments the modified release composition releases about 50% of the orismilast between about 60 and 100 minutes. In some embodiments the modified release composition releases about 80% of the orismilast between about 120 and 180 minutes. In some embodiments the modified release composition releases less than 40% of the orismilast after 30 minutes; 50% of the orismilast is released between 60 and 100 minutes; and 80% of the orismilast is released between 115 and 180 minutes. In some embodiments the modified release composition releases from about 30% to about 46% of the orismilast after 45 minutes; about 52% to about 78% of the orismilast after 120 minutes and at least about 80% of the orismilast after 180 minutes.

In any of the embodiments in the four paragraphs above the modified release composition releases, for example, less than 40% of the orismilast after 30 minutes, for example, less than about 30% after 30 minutes. In any of the embodiments in the four paragraphs above the modified release composition releases, for example, less than 20% of the orismilast after 12 minutes.

In each case in the paragraphs above and as described elsewhere, the release of orismilast refers to the release in-vitro sis measured using the "Standard Dissolution Assay" defined herein.

In the paragraph above reference to "release of the orismilast" from a composition refers to the % by weight of the compound of orismilast initially present in the modified release composition that is released into a dissolution medium at the specified time point as measured using the Standard Dissolution Assay. The amount of the orismilast present in the dissolution medium may be determined by reversed phase, isocratic HPLC using a C18 column and UV detection at 272 nm. Suitably the % release values of the compound of orismilast is a mean value obtained by measuring the release profile of more than one sample of the modified release composition, thereby reducing the effects of inter- or intra-batch variability. The mean release % may be obtained by measuring the release from, for example 6, 12 or 24 samples of the modified-release composition.

The modified release composition may, for example, be any of the modified release compositions described herein which provides a release profile described herein.

Figure 11:
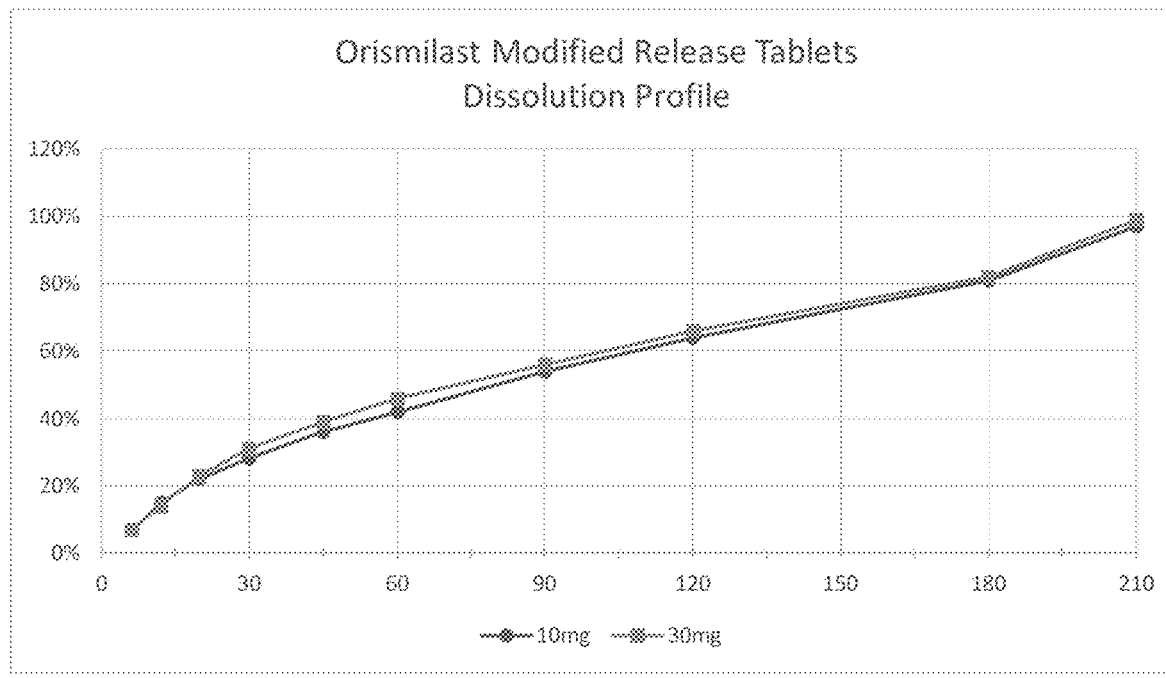
FIG. 11 shows the in-vitro dissolution profile for 10 mg and 30 mg orismilast modified release tablets measured using the Standard Dissolution Assay defined in the description herein. The x-axis shows time and the y-axis the % orismilast released into the dissolution medium.

In some embodiments the composition comprising orismilast has an in-vitro release profile which is similar to the release profile shown in FIG. 11 measured using the Standard Dissolution Assay. Reference to a "similar" release profile means a release profile that would be considered to be similar from a regulatory perspective, for example as set out in FDA Dissolution Testing of Immediate Release Solid Oral Dosage Forms. Guidance for Industry August 1997, available online:
https://www.fda.qov/downloads/druqs/quidances/ ucm070237.pdf; or EMA Guideline on the Investigation of Bioequivalence 2010, available online:
https://www.ema.europa.eu/en/documents/scientific- quideline/quideline-investiqation-bioequivalence- rev1_en.pdf.

Accordingly in some embodiments the composition comprising orismilast has an in-vitro release profile that has a similarity factor $f_2$ of between 50 and 100 compared to the release profile in FIG. 11, wherein:

$$f_2 = 50 \cdot \log \left\{ 100 \cdot \left[ 1 + \frac{1}{n}\sum_{t=1}^{n}(R_t - T_t)^2 \right]^{-0.5} \right\}$$

wherein R is the one of the reference compositions comprising orismilast in FIG. 11, T is the similar composition, n is a number of time points and $R_t$ and $T_t$ are the mean percentages of the released drug from the (R) and (T) products, respectively, at the t time point, $1 \leq t \leq n$, and the log is $\log_{10}$.

Suitably the following conditions are applied to the $f_2$ value in accordance with the FDA guidelines above:
(1) the dissolution measurements are made under the same conditions for both products;
(2) a minimum of three-time points (time zero excluded) is considered for both products;

(3) the time points at which the dissolutions are measured are the same for both products;
(4) at least 12 individual dosage units are used for both products;
(5) not more than one mean percentage value is higher than 85% for any of the products;
(6) the coefficient of variation (CV) of either product should be less than 20% at the first (non-zero) time point and less than 10% at the following time points.

In some embodiments the composition comprising orismilast has an in-vitro release profile that has a difference factor $f_1$ of between 0 and 15 compared to the release profile in FIG. 11, wherein $$f_1 = \left\{\left[\sum_{t=1}^{n} |R_t - T_t|\right] / \left[\sum_{t=1}^{n} R_t\right]\right\} \cdot 100$$

The difference factor is a sum of the absolute values for the differences between the (T) product and (R) products relative to the sum of the mean percentage of the released drug from the (R) product.

In some embodiments the composition comprising orismilast has an in-vitro release profile corresponding to the release profile shown in Table C in Example 1, wherein the % orismilast released at each time point corresponds to ±20% of the value shown in Table C for the 30 mg composition measured using the Standard Dissolution Assay. By way of illustration, at 45 minutes the 30 mg tablet had released 39% of the orismilast at 45 minutes. Accordingly, in this embodiment the composition comprising orismilast releases ±20% of that value at 45 minutes, i.e. from 31.2% to 46.8% of the orismilast is released at 45 minutes. The same ±20% values apply to the other time points shown in Table C.

In some embodiments the modified release composition comprises orismilast and a pharmaceutically acceptable hydrophilic matrix former (e.g. HPMC). In some embodiments the modified release composition comprises orismilast; a pharmaceutically acceptable hydrophilic matrix former (e.g. HPMC); and a filler (e.g. lactose monohydrate). In some embodiments the modified release composition comprises orismilast; and 15% w/w to 30% w/w of a pharmaceutically acceptable hydrophilic matrix former (e.g. HPMC). In some embodiments the modified release composition comprises a compound of the orismilast; and 15% w/w to 25% w/w of HPMC.

In some embodiments the modified release composition comprises orismilast; and 15% w/w to 20% w/w of HPMC.

In some embodiments, the modified release composition comprises a core comprising
(i) orismilast;
(ii) one or more of a pharmaceutically acceptable hydrophilic matrix former;
(iii) optionally, one or more pharmaceutically acceptable excipients selected from the group consisting of fillers, glidants and lubricants; and
(iv) optionally a pharmaceutically acceptable coating system on the core.

In some embodiments the hydrophilic matrix former in the modified release composition comprises hydroxypropyl methylcellulose or hydroxypropylcellulose, or mixtures thereof.

In some embodiments the one or more pharmaceutically acceptable excipients present in the modified release composition comprises a filler, selected from lactose monohydrate and microcrystalline cellulose, and mixtures thereof. In some embodiments the fillers are present in a concentration from about 30% to about 78% w/w of lactose monohydrate and from 0% to about 40% w/w of microcrystalline cellulose, based on the weight of the core. In some embodiments the filler is lactose monohydrate. In some embodiments the filler is lactose monohydrate and is present in a concentration from about 30% to about 78% w/w based on the weight of the core. Thus it may be that the lactose monohydrate is present in a concentration of about 71% w/w based on the weight of the core. Reference herein to a "% w/w based on the weight of the core" refers to the % by weight of a component of the core prior to the application of a coating system.

In some embodiments the modified release composition comprises a coating on the core. For example a PVA-based coating system.

In some embodiments the modified release composition comprises a core comprising
(i) orismilast;
(ii) a hydrophilic matrix former, wherein the hydrophilic matrix former is present in a concentration of from about 15% w/w to about 25% w/w hydroxypropyl methylcellulose based on the weight of the core;
(iii) from about 30% w/w to about 78% w/w lactose monohydrate based on the weight of the core; and
(iv) optionally one or more pharmaceutically acceptable excipients selected from the group consisting of glidants and lubricants;
optionally wherein the composition further comprises a pharmaceutically acceptable coating system on the core.

In some embodiments the modified release composition comprises a core comprising orismilast, about 0.5% w/w colloidal silicon dioxide, about 1.0% w/w magnesium stearate based on the weight of the core; and optionally a PVA-based coating system on the core.

In some embodiments the modified release composition comprises a core comprising orismilast, about 17.5% w/w HPMC, about 71.0% w/w lactose monohydrate, about 0.5% w/w colloidal silicon dioxide, and about 1.0% w/w magnesium stearate based on the weight of the core; and optionally a PVA-based coating system on the core.

In some embodiments the orismilast is present in the modified release composition in an amount of from about 1% w/w to about 40% w/w. In some embodiments the orismilast is present in the modified release composition in an amount of about 1% w/w to about 30% w/w. In some embodiments the orismilast is present in the modified release composition in an amount of from about 1% w/w to about 20% w/w. In some embodiments the orismilast is present in the modified release composition in an amount of from about 2% w/w to about 15% w/w. In some embodiments the orismilast is present in the modified release composition in an amount of from about 2% w/w to about 5% w/w. In some embodiments the orismilast is present in the modified release composition in an amount of from about 8% w/w to about 12% w/w.

In some embodiments the orismilast is present in the modified release composition in an amount of from about 5 mg to about 60 mg; about 10 mg to about 50 mg. For example about 10 mg, or about 30 mg.

In some embodiments, the orismilast is evenly distributed in the pharmaceutical composition. In some embodiments the orismilast in the pharmaceutical composition is micronized. In some embodiments, the orismilast in the pharmaceutical composition is crystalline. In some embodiments, the orismilast present in the pharmaceutical composition is crystalline and micronized.

In some embodiments the pharmaceutical composition comprises polymorphic form E of orismilast. In some embodiments, the polymorphic form E of orismilast is micronized. In some embodiments, the polymorphic form E of the orismilast is crystalline and micronized.

The hydrophilic matrix former may be hydroxypropyl methylcellulose (HPMC), hydroxypropylcellulose (HPC), or mixtures thereof. For example, the hydrophilic matrix former could be hydroxypropyl methylcellulose, and mixtures thereof. The hydrophilic matrix former may be present at various concentrations and combinations from about 10% w/w to about 30% w/w HPMC. In some embodiments the hydrophilic matrix former is present in an amount of from about 15% w/w to about 25% w/w HPMC. In some embodiments the hydrophilic matrix former is present in an amount of from about 15% w/w to about 20% w/w HPMC. In some embodiments the hydrophilic matrix former is present in an amount of 17.5% w/w HMPC.

In some embodiments the hydrophilic matrix former in the modified release composition comprises hydroxypropyl methylcellulose (HPMC). In some embodiments the hydrophilic matrix former in the modified release composition consists of HPMC. In some embodiments the HPMC has a viscosity of from 30 to 150 mPa·s. In some embodiments the HPMC has a viscosity of from 35 to 130 mPa·s. In some embodiments the HPMC has a viscosity of from 40 to 60 mPa·s. In some embodiments the HPMC has a viscosity of from 80 to 120 mPa·s. Reference herein to the viscosity of HPMC refers to the viscosity of a 2% (w/w) solution of the HPMC in water at 20° C. in accordance with United States Pharmacopoeia (USP XXIII).

In some embodiments the hydrophilic matrix former in the modified release composition comprises HPMC with a methoxyl substitution of from about 5% to about 35% In some embodiments the HPMC has a methoxyl substitution of from about 15% to about 30%. In some embodiments the HPMC has a methoxyl substitution of from about 19% to about 24%. In some embodiments the HPMC has a methoxyl substitution of from about 25% to about 35%. In some embodiments the HPMC has a methoxyl substitution of from about 28% to about 30%. In some embodiments the HPMC has a methoxyl substitution of from about 22% to about 24%.

In some embodiments the hydrophilic matrix former in the modified release composition comprises HPMC with a hydroxypropyl substitution of from about 4% to about 15%. In some embodiments the hydrophilic matrix former in the modified release composition comprises HPMC with a hydroxypropyl substitution of from about 4% to about 12%. In some embodiments the hydrophilic matrix former in the modified release composition comprises HPMC with a hydroxypropyl substitution of from about 7% to about 12%. In some embodiments the hydrophilic matrix former in the modified release composition comprises HPMC with a hydroxypropyl substitution of from about 7.5% to about 9.5%.

In some embodiments the hydrophilic matrix former in the modified release composition comprises HPMC with a methoxyl substitution of from about 19% to about 24%; and a hydroxypropyl substitution of from about 4% to about 12%.

In some embodiments the hydrophilic matrix former in the modified release composition comprises HPMC with a methoxyl substitution of from about 19% to about 24%; and a hydroxypropyl substitution of from about 7% to about 12%.

In some embodiments the hydrophilic matrix former in the modified release composition comprises HPMC with a methoxyl substitution of from about 28% to about 30%; and a hydroxypropyl substitution of from about 7% to about 12%.

In some embodiments the hydrophilic matrix former in the modified release composition comprises HPMC with a methoxyl substitution of from about 22% to about 24%; and a hydroxypropyl substitution of from about 7.5% to about 9.5%.

Suitably in any of the six paragraphs above the HPMC has a viscosity of from 80 to 120 mPa·s. Reference herein to the viscosity of HPMC refers to the viscosity of a 2% (w/w) solution of the HPMC in water at 20° C. in accordance with United States Pharmacopoeia (USP XXIII).

In some embodiments the hydroxypropyl methylcellulose is Hypromellose 2910, Hypromellose 2208, Methocel K100 or mixtures thereof.

Suitably the hydrophilic matrix former is present in a concentration from about 10% w/w to about 30% w/w hydroxypropyl methylcellulose based on the weight of the core. Thus it may be that the hydrophilic matrix former is present in a concentration from about 15% w/w to about 25% w/w hydroxypropyl methylcellulose based on the weight of the core. For example, wherein the hydrophilic matrix former is present in a concentration of 17.5% w/w hydroxypropyl methylcellulose based on the weight of the core. The hydroxypropyl methylcellulose may be, for example, any of the grades of hydroxypropyl methylcellulose disclosed herein (e.g. Hypromellose 2910, Hypromellose 2208, Methocel K100 or mixtures thereof).

In some embodiments the modified release composition comprises one or more fillers and/or binders. The term "filler" as used herein may also function as a binder. The filler or binder may be selected from lactose monohydrate, lactose hydrous or anhydrous, microcrystalline cellulose, mannitol, isomalt, and mixtures thereof. For example, the filler could be lactose monohydrate. The filler may be present at various concentrations from about 30% w/w to about 78% w/w. For example, the filler may comprise about from about 30% w/w to about 78% w/w of lactose monohydrate and from about 0 to about 40% w/w of microcrystalline cellulose. For example, the filler could be lactose monohydrate in an amount of about 71% w/w.

In some embodiment the modified release composition (e.g. modified release tablet composition) comprises one or more glidants. The term "glidant" as used herein includes colloidal silicon dioxide, talc, etc. For example, the glidant could be colloidal silicon dioxide. The glidant may be present at various concentrations from about 0.1% w/w to about 2% w/w, for example from about 0.2% w/w to about 1% w/w, e.g. about 0.5% w/w.

In some embodiment the modified release composition (e.g. modified release tablet composition) further comprises one or more lubricants. The term "lubricant" as used herein includes magnesium stearate, sodium stearyl fumarate, talc, etc. For example, the lubricant may be magnesium stearate. The lubricant may be present at various concentrations from about 0.1% w/w to about 2% w/w, for example from about 0.5% w/w to about 1.5% w/w, e.g. about 1.0% w/w.

The % w/w of the components comprising the modified release compositions (e.g. modified release tablet compositions, (e.g. those comprising the orismilast, the hydrophilic matrix former, the filler, glidant and/or lubricant)) refer to the % w/w prior to adding the optional coating to the composition (e.g. onto the core comprising orismilast and the other excipients). Thus as will be realised by the skilled person, in those embodiments where the modified release compositions (e.g. tablets) are coated, the % w/w of each component in the coated composition based on the total weight of the coated composition will be lower than the % w/w based on the uncoated composition due to the additional weight of the coating.

In some embodiments the modified release composition comprises a film coating on the cores. A suitable coating may be a PVA-based coating system. The term "coating system", as used herein includes HPMC-based coating systems, PVA-based coating systems (polyvinyl alcohol), PVA-PEG based coating systems (polyethylene glycol) or ethylcellulose based functional barrier membrane coating systems. For example, the coating system could be the PVA-based coating system. For example, the coating system could be Opadry® II. For example the coating system could be present in an amount from about 3% to about 5% weight gain of the core composition, for example a 4% weight gain of the core.

In some embodiments the composition comprising orismilast is a core composition comprising Core 1, Core 2 or Core 3 selected from Table A or Core 4, Core 5 or Core 6 selected from Table B:

TABLE A

| | % w/w of the core | | |
|---|---|---|---|
| Component | Core 1 | Core 2 | Core 3 |
| orismilast | 2.5-4.5% | 5.5-7.7% | 9-11% |
| Lactose monohydrate | 70-85% | 69-80% | 66-76% |
| HPMC | 12-23% | 12-23% | 12-23% |
| Anhydrous colloidal silica | 0.01-1.5% | 0.01-1.5% | 0.01-1.5% |
| Magnesium stearate | 0.01-2.0% | 0.01-2.0% | 0.01-2.0% | wherein the core is coated with a water-soluble film coating in an amount to provide about 3% to 5% weight gain of the core.

TABLE B

| | Amount | | |
|---|---|---|---|
| Component | Core 4 | Core 5 | Core 6 |
| orismilast | 10 mg | 20 mg | 30 mg |
| Lactose monohydrate | 233 mg | 223 mg | 213 mg |
| HPMC | 52.5 mg | 52.5 mg | 52.5 mg |
| Anhydrous colloidal silica | 1.5 mg | 1.5 mg | 1.5 mg |
| Magnesium stearate | 3.0 mg | 3.0 mg | 3.0 mg |
| Core weight | 300 mg | 300 mg | 300 mg |
| Water-soluble film coating | 12 mg | 12 mg | 12 mg |
| Coated core weight | 312 mg | 312 mg | 312 mg |

Suitably the film coating on the cores in Table A and Table B is a PVA-based coating. Preferably the film coating comprises polyvinyl alcohol (Ph. Eur. 1961), macrogol (Ph. Eur. 1444), titanium dioxide (Ph. Eur. 0150), talc (Ph. Eur. 0438) and optionally a colorant. For example the film coating may be Opadry® II.

Suitably the lactose monohydrate in the compositions described herein, including those in Tables A and B complies with European Pharmacopeia (Ph. Eur.) 0187. Suitably the anhydrous colloidal silica in the compositions described herein, including those in Tables A and B complies with Ph. Eur. 0434. Suitably the magnesium stearate in the compositions described herein, including those in Tables A and B complies with Ph. Eur.0229. Suitably the hydroxymethyl cellulose (HPMC, Hypromellose) in the compositions described herein, including those in Tables A and B complies with Ph. Eur. 0348.

Suitably the HPMC in Tables A and B comprises HPMC with a methoxyl substitution of from about 22% to about 24%; and a hydroxypropyl substitution of from about 7.5% to about 9.5%. Suitably the HPMC has a viscosity of from 80 to 120 mPa·s. Reference herein to the viscosity of HPMC refers to the viscosity of a 2% (w/w) solution of the HPMC in water at 20° C. in accordance with United States Pharmacopoeia (USP XXIII). For example the HPMC is Methocel™ K100 or mixtures thereof The modified release compositions comprising a hydrophilic matrix such as HPMC described herein, including the compositions in Table A and Table B may be prepared may be prepared using well-known methods. For example by blending and sieving steps of the orismilast and excipients followed by direct compression, or roller compaction followed by compression. The water-soluble coating is then applied to the cores using, for example, a spray coater.

In preferred embodiments the modified release composition comprising orismilast described herein is a modified release tablet comprising orismilast. In some embodiments the modified release composition comprising orismilast is a modified release tablet comprising orismilast described in the Examples herein.

In some embodiments, the particle size distribution of the orismilast present in the pharmaceutical composition (e.g. tablet composition) may be $D(50) \leq 25$ μm, for example $D(50) \leq 20$ μm, $D(50) \leq 10$ μm, $D(50) \leq 5$ μm, $D(50) \leq 3$ μm and/or $D(90) \leq 10$ μm. For example in the compositions in Table A and Table B the orismilast particle size distribution may be $D(90) \leq 10$ μm and a $D(50) < 1$ to 6 μm.

In some embodiments the pharmaceutical composition comprising orismilast is formulated as a unit dosage form, for example a tablet or capsule. The amount of orismilast in each unit dosage (e.g. tablet) may range from about 1 mg to about 40 mg, from about 5 mg to about 35 mg, from 5 mg to 30 mg, from 10 mg to 30 mg, or from 10 to 20 mg. In some embodiments, the amount of orismilast in each unit dosage form (e.g. tablet) may be from about 10 to about 30 mg. In some embodiments, the amount of orismilast in each unit dosage form (e.g. tablet) is 1 mg, 2 mg, 5 mg, 10 mg, 15 mg, 20 mg, 25 mg, 30 mg, 35 mg or 40 mg. In some embodiments, the amount of orismilast in each unit dosage form (e.g. tablet) is 10 mg. In some embodiments, the amount of orismilast in each unit dosage form (e.g. tablet) is 20 mg. In some embodiments, the amount of orismilast in each unit dosage form (e.g. tablet) is 30 mg. In some embodiments, the amount of orismilast in each unit dosage form (e.g. tablet) is 40 mg.

In some embodiments, orismilast is comprised within a granulated blend composition. A granulated blend composition may comprise:
  orismilast; and
  one or more of a pharmaceutically acceptable hydrophilic matrix former;
  one or more pharmaceutically acceptable excipients selected from the group consisting of fillers, binders, glidants and lubricants; and
  a hard capsule shell material.

The hydrophilic matrix former could be hydroxypropyl methylcellulose (HPMC), hydroxypropylcellulose (HPC), or mixtures thereof. The hydrophilic matrix former could be present at various concentrations and combinations from about 10% w/w to about 20% w/w HPMC.

The fillers/binders could be selected from lactose monohydrate, lactose hydrous or microcrystalline cellulose, and mixtures thereof. The fillers/binders could be present at various concentrations from about 20% w/w to about 75% w/w of lactose monohydrate and from 0 to about 50% w/w of microcrystalline cellulose. The glidant could be colloidal silicon dioxide, which could be present at various concentrations from about 0.1% w/w to about 2% w/w.

The lubricant could be magnesium stearate, which could be present at various concentrations from about 0.1% w/w to about 2% w/w.

In some embodiments the orismilast is present in the granulated blend composition in an amount of from about 1% w/w to about 40% w/w, for example about 1% w/w to about 30% w/w, from about 1% w/w to about 20% w/w, or from about 2% w/w to about 15% w/w.

The blend composition could be dispensed in a hard capsule. Capsule shell material for hard capsules could be made of several materials such as gelatin (pig, bovine, fish etc), hydroxypropyl methylcellulose (HPMC), polyvinyl alcohol, starch and pullulan could be applied.

In some embodiments the granulated blend composition is formulated as a unit dosage form (e.g. a capsule composition). The amount of orismilast in each unit dose form may range from about 1 mg to about 40 mg, or from about 5 mg to about 30 mg. The amount of the compound may for example range from 10 mg to 30 mg. In some embodiments, the amount of the compound in unit dosage form comprising the granulated blend composition may be from about 10 mg to about 30 mg. In some embodiments, the amount of orismilast in each unit dosage form is 1 mg, 2 mg, 5 mg, 10 mg, 15 mg, 20 mg, 25 mg, 30 mg, 35 mg or 40 mg.

The granulated blend composition can be prepared by, for example, consist of blending and sieving steps of the drug substance and excipients followed by granulation, e.g. roller compaction, and encapsulation.

Diseases and Disorders

Administration of the orismilast in accordance with the dosage regimens described herein may be used to treat or prevent diseases or disorders ameliorated by inhibiting PDE4.

In certain embodiments the disease or disorder treated with orismilast according to the dosage regimen is selected from: an inflammatory disease, an autoimmune disease, a disease of the central nervous system, a cerebrovascular disease, diabetes, obesity, metabolic syndrome, a wound and a proliferative disease.

Inhibition of PDE4 is expected to be beneficial in a wide range of diseases with an inflammatory component. accordingly in a preferred embodiment the disease or disorder treated with orismilast is an inflammatory disease.

In certain embodiments the disease or disorder treated with orismilast according to the dosage regimen is an inflammatory disease, for example an inflammatory airway disease (e.g. asthma or COPD), allergic rhinitis, acute lung injury, acute respiratory distress syndrome, an allergic disease, nephritis, rheumatoid arthritis, psoriatic arthritis, ankylosing spondylitis, Crohn's disease, inflammatory bowel disease, colitis (e.g. ulcerative colitis), lupus (e.g. systemic lupus erythematosus or discoid lupus erythematosus), depression, amnesia, cognitive dysfunction, dementia, Alzheimer's disease, Parkinson's disease, schizophrenia, multiple sclerosis, diabetes (e.g. insulin-resistant diabetes) an acute or chronic wound disorder (e.g. wound healing), vulvodynia, a cancer, an inflammatory or proliferative skin disorder (e.g. psoriasis (including psoriasis vulgaris and plaque psoriasis), epidermal inflammation, acne, dermatitis, atopic dermatitis, seborrheic dermatitis, contact dermatitis, urticaria, pruritus, eczema, a neutrophilic dermatoses (e.g. pyoderma gangrenosum, prurigo nodularis), alopecia, skin atrophy, steroid induced skin atrophy, skin ageing, photo skin ageing, vitiligo, lichen planus, organopathy associated with ischemic reflux (e.g. caused by cardiac failure, shock, and cerebrovascular diseases, and the like), uveitis and Behget disease (e.g. oral ulcers associated with Behget disease).

In certain embodiments the disease or disorder treated with orismilast according to the dosage regimen is selected from: dermatitis, atopic dermatitis, seborrheic dermatitis, contact dermatitis, including irritative contact dermatitis and allergic contact dermatitis, hand dermatitis, psoriasis, psoriasis vulgaris, plaque psoriasis, inverse psoriasis, nail psoriasis, psoriatic arthritis, spondyloarthritis, epidermal inflammation, alopecia, alopecia areata, rosacea, skin atrophy, steroid induced skin atrophy, photo skin ageing, SAPHO syndrome, (synovitis, acne, pustulosis, hyperostosis and osteitis), acne vulgaris, hidradenitis suppurativa (HS), urticaria, pruritus, eczema, and a neutrophilic dermatoses (e.g. pyoderma gangrenosum (PG), pustular PG, atypical/bullous PG, vegetative PG, pathergic PG, necrotizing-fasciitis-like PG, peristomal PG, and post-operative PG), Sweet's syndrome (SS, also known as acute febrile neutrophilic dermatosis, including bullous SS, pustular SS, giant cellulitis-like SS, necrotizing fasciitis-like SS, drug-induced SS and subcutaneous SS), Sneddon-Wilkinson disease (also known as subcorneal pustular dermatosis), Behget disease, neutrophilic panniculitis, neutrophilic eccrine hidradenitis, erythema elevatum diutinum, neutrophilic urticaria, Group of IgA neutrophilic dermatosis, amicrobial pustulosis of the folds, Hallopeau's continuous acrodermatitis, acute generalised exanthematous pustulosis, infantile acropustulosis, aseptic abscesses, PASH syndrome (pyoderma gangrenosum, acne and HS), PAPA syndrome (pyoderma gangrenosum, acne and pyogenic arthritis), PASS syndrome (PG, acne conglobate, HS, seropositive spondyloarthropathies), PAPASH syndrome (PG, pyogenic arthritis, acne, HS), PsAPASH (psoriatic arthritis, PG, acne, HS) histiocytoid neutrophilic dermatitis, neutrophilic dermatitis of the dorsal hands, bowel bypass syndrome (bowel-associated dermatitis-arthritis syndrome), palisading neutrophilic granulomatous dermatitis and VEXAS syndrome.

Psoriasis

In certain embodiments the disease or disorder treated with orismilast according to the dosage regimen is psoriasis. In some embodiments the psoriasis is psoriasis vulgaris or plaque psoriasis. The psoriasis may be mild, moderate or severe psoriasis. The severity of psoriasis in a subject may be assessed using known methods for example:

The Static Physician Global Assessment (sPGA) which determines psoriasis severity at a single point in time on a 5-point scale as clear (0), almost clear (1), mild (2), moderate (3), or severe (4);

Body Surface Area (BSA) estimates the extent of disease or skin involvement with respect to psoriasis and is expressed as a percentage of total body surface. Mild psoriasis is considered to by <3%, moderate is 3-10% and severe >10% of the body is affected by lesions.

Psoriasis Area and Severity Index (PASI) scores range from 0 to 72, with higher scores reflecting greater disease severity (Fredriksson et al., Dermatologica. 1978; 157(4):238-244). Erythema, induration/thickness, and scaling are scored on a scale of 0 (none) to 4 (very severe) on 4 anatomic regions of the body: head, trunk, upper limbs, and lower limbs. Degree of involvement on each of the 4 anatomic regions is scored on a scale of 0 (no involvement) to 6 (90% to 100% involvement). The total qualitative score (sum of erythema, thickness, and scaling scores) is multiplied by the degree of involvement for each anatomic region and then multiplied by a constant. The scores for each anatomic region are combined to yield the final PASI.

Investigator Global Assessment (IGA) for psoriasis: The IGA is a measure used by physicians to determine the patient's overall severity of disease. The static version (Langley et al., J Dermatolog Treat. 2015, February; 26(1):23-31) is used in this trial for measurement at a single point in time as indicated in the schedule of assessments. The Investigator will rate the severity of patient's psoriasis on a 5-point scale ranging from 0 (clear) to 4 (severe)

Details of the sPGA, BSA, PASI and IGA for psoriasis are provided in the Examples.

The severity of disease is the severity at baseline (i.e. before treatment with orismilast)

In some embodiments the psoriasis may be moderate or severe psoriasis wherein the subject has a PASI≥12, BSA≥10%, and sPGA≥3 prior to treatment with orismilast.

In some embodiments the psoriasis is moderate psoriasis, for example where a subject has an IGA for psoriasis of 3 prior to treatment with orismilast.

In some embodiments the psoriasis is severe psoriasis, for example where a subject has an IGA for psoriasis of 4 prior to treatment with orismilast.

In some embodiments treatment with orismilast according to the dosage regimen reduces the Psoriasis Area and Severity Index (PASI) score from baseline. In some embodiments the PASI score is reduced by 50% (PASI50) or more at week 4, 8, 12, 16 or of treatment. Preferably a PASI50 or more at week 16 of treatment. In some embodiments the PASI score is reduced by 75% (PASI75) or more at week 4, 8, 12, 16 or of treatment. Preferably a PASI75 or more at week 16 of treatment. In some embodiments the PASI score is reduced by 90% (PASI90) or more at week 4, 8, 12, 16 or of treatment. Preferably a PASI90 ore more at week 16 of treatment. In some embodiments the PASI score is reduced by 100% (PASI100) at week 4, 8, 12, 16 or 20 of treatment. Preferably a PASI100 at week 16 of treatment. Details of the PASI assessment are provided in Example 4 herein.

In some embodiments treatment with orismilast according to the dosage regimen provides a score of Clear (0) or Almost Clear (1) and an at least 2-point improvement in Investigator Global Assessment (IGA). In some embodiments treatment with orismilast according to the dosage regimen provides a score of Clear (0) or Almost Clear (1) and an at least 2-point improvement in IGA at week 4, 8, 12, 16 or 20 of treatment. In some embodiments treatment with orismilast according to the dosage regimen provides a score of Clear (0) and an at least 2-point improvement in IGA at week 4, 8, 12, 16 or 20 of treatment. Preferably the dosage regimen provides an IGA of 0 or 1 at week 16 of treatment. Details of the IGA are provided in Example 3.

In some embodiments treatment with orismilast according to the dosage regimen reduces the total Psoriasis Symptoms Scale (PSS) score from baseline. In some embodiments treatment with orismilast according to the dosage regimen reduces the total PSS score from baseline at week 4, 8, 12, 16 or 20 of treatment. For example the treatment may reduce the total PSS by 1, 2 or 3 points. Details of the PSS are provided in Example 3.

In some embodiments treatment with orismilast according to the dosage regimen provides a Static Physician Global Assessment (sPGA) 0 (clear) or 1 (almost clear). In some embodiments treatment with orismilast according to the dosage regimen provides a sPGA of 0 or 1 at week 4, 8, 12, 16 or 20 of treatment. Preferably the dosage regimen provides an sPGA of 0 or 1 at week 16 of treatment. Details of the sPGA are provided in Example 4.

In some embodiments treatment with orismilast according to the dosage regimen reduces the affected body surface area (BSA) relative to baseline. In some embodiments the dosage regimen reduces BSA by 10%, 20%, 30%, 40%, 50%, 60%, 70%, 80% or 90% relative to baseline. In some embodiments the dosage regimen reduces BSA by 10%, 20%, 30%, 40%, 50%, 60%, 70%, 80% or 90% relative to baseline at week 4, 8, 12, 16 or of treatment. Preferably the dosage regimen reduces BSA by 30%, 40%, 50%, 60%, 70%, 80% or 90% relative to baseline at week 16 of treatment. Details of the BSA are provided in Example 3.

In some embodiments treatment with orismilast according to the dosage regimen provides a reduction from baseline in the Dermatology Life Quality Index (DLQI) score. In certain embodiments the dosage regimen provides a reduction in the DLQI score of ≥4 points at week 4, 8, 12, 16 or 20 of treatment relative to baseline. Preferably the dosage regimen provides a reduction in the DLQI score of 24 points at week 16 of treatment relative to baseline. In certain embodiments the dosage regimen provides a DLQI score of 0 or 1 at week 4, 8, 12, 16 or 20 of treatment. Preferably the dosage regimen provides a DLQI score of 0 or 1 at week 16 of treatment. Details of the DLQI are provided in Example 4.

In some embodiments treatment with orismilast according to the dosage regimen provides a Scalp Specific Physician Global Assessment (ScPGA) of 0 (clear) or 1 (almost clear). In some embodiments treatment with orismilast according to the dosage regimen provides a ScPGA of 0 or 1 at week 4, 8, 12, 16 or 20 of treatment. Preferably the dosage regimen provides a ScPGA of 0 or 1 at week 16 of treatment. Details of the ScPGA are provided in Example 4.

In some embodiments treatment with orismilast according to the dosage regimen provides a Scalp Specific Investigator Global Assessment (ss-IGA) of 0 (clear) or 1 (almost clear). In some embodiments treatment with orismilast according to the dosage regimen provides a ss-IGA of 0 or 1 at week 4, 8, 12, 16 or 20 of treatment. Preferably the dosage regimen provides a ss-IGA of 0 or 1 at week 16 of treatment. Details of the ss-IGA are provided in Example 3.

In some embodiments treatment with orismilast according to the dosage regimen provides a Static Physician Global Assessment of Genitalia (sPGA-G) of 0 (clear) or 1 (minimal). In some embodiments treatment with orismilast according to the dosage regimen provides a sPGA-G of 0 or 1 at week 4, 8, 12, 16 or 20 of treatment, preferably at week 16 of treatment. Details of the sPGA-G are provided in Example 4.

In some embodiments treatment with orismilast according to the dosage regimen provides a Palmoplantar Psoriasis Physician Global Assessment (PPPGA) of 0 (clear) or 1 (almost clear). In some embodiments treatment with orismilast according to the dosage regimen provides a PPPGA of 0 or 1 at week 4, 8, 12, 16 or 20 of treatment, preferably at week 16 of treatment. Details of the PPPGA are provided in Example 4.

In some embodiments treatment with orismilast according to the dosage regimen provides a Physician's Global Assessment of Fingernail Psoriasis (PGA-F) score of 0 or 1, preferably at week 16 of treatment. Details of the PGA-F are provided in Example 3.

In some embodiments treatment with orismilast according to the dosage regimen provides a reduction in the whole body itch numeric rating scale (NRS) from baseline. For example the dosage regimen provides a reduction of a ≥4 points in the whole body itch NRS from baseline. In some embodiments the dosage regimen provides a reduction of a ≥4 points in the whole body itch NRS at week 2, 8, 12, or 16 of treatment from baseline. Details of the whole body itch NRS are provided in Example 4.

In some embodiments treatment with orismilast according to the dosage regimen provides a reduction in the pain numeric rating scale (NRS) from baseline. For example the dosage regimen provides a reduction of a ≥4 points in the pain NRS from baseline. In some embodiments the dosage regimen provides a reduction of a ≥4 points in the pain NRS at week 2, 8, 12, or 16 of treatment from baseline. Details of the pain NRS are provided in Example 4.

In some embodiments treatment with orismilast according to the dosage regimen provides a reduction in the scalp itch numeric rating scale (NRS) from baseline. For example the dosage regimen provides a reduction of a ≥4 points in the scalp itch NRS from baseline. In some embodiments the dosage regimen provides a reduction of a 4 points in the scalp itch NRS at week 2, 8, 12, or 16 of treatment from baseline. Details of the scalp itch NRS are provided in Example 4.

In some embodiments treatment with orismilast according to the dosage regimen provides an increase from baseline of the EuroQol Quality of Life 5-Dimension-5 five-level (EQ-5D-5L™) score. Suitably the EQ-5D-5L™score is increased by at least 50%, such as at least 75% or such as at least 90%. In some embodiments the dosage regimen provides an increase from baseline of the EQ-5D-5L™score of least 50%, at least 75% or at least 90% at week 2, 8, 12 or 16 of treatment. Details of the EQ-5D-5L™are provided in Example 4.

In some embodiments treatment with orismilast according to the dosage regimen provides an increase from baseline of the 5-item World Health Organization Well-Being Index (WHO-5) score. Suitably the WHO-5 score is increased by at least 50%, such as at least 75% or such as at least 90%. In some embodiments the dosage regimen provides an increase from baseline of the WHO-5 score of least 50%, at least 75% or at least 90% at week 2, 8, 12 or 16 of treatment.

In some embodiments treatment with orismilast according to the dosage regimen provides a reduction in the body mass of the subject from baseline. In some embodiments the dosage regimen provides a reduction of body mass of the subject from baseline of 5%, 10% or 15%. In some embodiments the dosage regimen provides a reduction of body mass of the subject from baseline of 5%, 10% or 15% at week 16 of treatment. In some embodiments the dosage regimen provides a reduction of body mass of the subject from baseline of ≥5%, wherein the subject has a baseline BMI of ≥30. In some embodiments the dosage regimen provides a reduction of body mass of the subject from baseline of 5% at week 16 of treatment, wherein the subject has a baseline BMI of 30.

In some embodiments treatment with orismilast according to the dosage regimen reduces or eliminates one of more of the symptoms of psoriasis, for example one or more of erythema, induration (plaque elevation), scaling, psoriasis-related pain or pruritus (itching), the size (area) of lesions.

In some embodiments the subject with psoriasis suffers from a comorbidity, for example a comorbidity selected from the subject is suffering from a comorbidity selected from obesity, metabolic syndrome, diabetes, inflammatory bowel disease, spondyloarthropathy, or any combination thereof. In a particular embodiment the subject with psoriasis is obese.

In some embodiments treatment with orismilast according to the dosage regimen is for use in reducing inflammation caused by or associated with psoriasis. In some embodiments the orismilast is for use in reducing inflammation caused by or associated with psoriasis, wherein the treatment with orismilast reduces one or more inflammatory biomarkers associated with psoriasis in the subject, for example any of the inflammatory biomarkers associated with psoriasis described in the Examples. Thus it may be that the dosage regimen reduces C-Reactive Protein from baseline. In some embodiments the dosage regimen reduces an inflammatory biomarker associated with psoriasis by at least 30%, at least 40%, at least 50% at least 60%, at least 70% at least 80%, or at least 90% relative to baseline.

In some embodiments treatment with orismilast according to the dosage regimen meets any one of the primary secondary or tertiary endpoints described in the psoriasis clinical trials disclosed in Examples 3, 4 and 5 herein.

Atopic Dermatitis

In certain embodiments the disease or disorder treated with orismilast according to the dosage regimen is atopic dermatitis. In some embodiments the atopic dermatitis is mild, moderate, severe or very severe atopic dermatitis. The severity of atopic dermatitis may be assessed using well-established methods, for example the Eczema Area and Severity Index (EASI) score. The EASI assessment integrates body surface and the intensity of lesional skin into one composite score. The final EASI score is the summation of the 4 regional scores, ranging from 0 to 72. A score of 0 indicates clear or no eczema, 0.1 to 1.0 indicates almost clear, 1.1 to 7 indicates mild disease, 7.1 to 21 indicates moderate disease, 21.1 to 50 indicates severe disease, and greater than 51 indicates very severe disease (Leshem Y A et al., What the Eczema Area and Severity Index score tells us about the severity of atopic dermatitis: an interpretability study. Br J Dermatol 2015; 172(5):1353-1357).

In certain embodiments the atopic dermatitis is moderate to severe atopic dermatitis. Thus it may be that the subject has moderate to severe atopic dermatitis with a baseline EASI score of ≥16. Suitably subjects with moderate to severe atopic dermatitis have a baseline BSA of an affected body surface area (BSA) of ≥10%. Suitably subjects with moderate to severe atopic dermatitis have a baseline IGD-AD of 2 3. Suitably subjects with moderate to severe atopic dermatitis have a baseline peak pruritus NRS of ≥4. Suitably subjects with moderate to severe atopic dermatitis have a baseline weekly average peak pruritus NRS of ≥4.

In certain embodiments the atopic dermatitis is moderate atopic dermatitis. Thus it may be that the subject has moderate atopic dermatitis with a baseline EASI score of ≥16 to ≤21. Suitably subjects with moderate atopic dermatitis have a baseline BSA of ≥10% to: 28%. Suitably subjects with severe atopic dermatitis have a baseline peak pruritus NRS of ≥4 to ≤7. Suitably subjects with moderate to severe atopic dermatitis have a baseline weekly average peak pruritus peak pruritus NRS of ≥4 to <7.

In certain embodiments the atopic dermatitis is severe atopic dermatitis. Thus it may be that the subject has severe atopic dermatitis with a baseline EASI score of >21. Suitably subjects with severe atopic dermatitis have a baseline BSA of >28%. Suitably subjects with severe atopic dermatitis have a baseline peak pruritus NRS of >7. Suitably subjects with moderate to severe atopic dermatitis have a baseline weekly average peak pruritus NRS of >7. In some embodiments treatment with orismilast according to the dosage regimen reduces or eliminates one of more of the symptoms of atopic dermatitis, for example one or more of erythema, edema, papulation, excoriation, pruritus, lichenification size (area of lesions).

In some embodiments, treatment with orismilast according to the dosage regimen is for use in reducing inflammation caused by or associated with atopic dermatitis. In some embodiments the orismilast is for use in reducing inflammation caused by or associated with atopic dermatitis, wherein the treatment with orismilast reduces one or more inflammatory biomarkers associated with atopic dermatitis in the subject. For example the orismilast may reduce C-Reactive Protein. In some embodiments the dosage regimen reduces TARC (thymus and activation-regulated chemokine, also known as CCL17) relative to baseline. In some embodiments the dosage regimen reduces C6A6 relative to baseline. In some embodiments the dosage regimen reduces an inflammatory biomarker associated with atopic dermatitis by at least 30%, at least 40%, at least 50% at least 60%, at least 70% at least 80%, or at least 90% relative to baseline. In some embodiments the dosage regimen increases anti-inflammatory biomarkers in the skin relative to baseline. In some embodiments the dosage regimen increases anti-inflammatory biomarkers in blood (e.g. plasma or serum) relative to baseline. In some embodiments the dosage regimen reduces an anti-inflammatory biomarker associated with atopic dermatitis by at least 30%, at least 40%, at least 50% at least 60%, at least 70% at least 80%, or at least 90% relative to baseline In some embodiments the dosage regimen results in a change in the biomarker at week 1, 2, 4, 8, 12, 16 or 20. The skin biomarkers may be collected using tape stripping and analysed using well-known proteomics methods.

In some embodiments treatment with orismilast according to the dosage regimen reduces the Eczema Area and Severity Index (EASI) score from baseline. In some embodiments the EASI score is reduced by 50% (EASI50) at week 2, 4, 8, 12, 16 or 20 of treatment. Preferably a EASI at week 16 of treatment. In some embodiments the EASI score is reduced by 75% (EASI75) at week 2, 4, 8, 12, 16 or 20 of treatment. Preferably a EASI75 at week 16 of treatment. In some embodiments the EASI score is reduced by 90% (EASI90) at week 4, 8, 12, 16 or 20 of treatment. Preferably a EASI90 at week 16 of treatment. In some embodiments the EASI score is reduced by 100% (EASI100) at week 4, 8, 12, 16 or 20 of treatment. Preferably a EASI100 at week 16 of treatment. Details of the PASI assessment are provided in Example 8 herein.

In some embodiments treatment with orismilast according to the dosage regimen reduces the Investigator Global Assessment for Atopic Dermatitis (IGA-AD) from baseline. In some embodiments treatment with orismilast according to the dosage regimen provides IGA-AD score of Clear (0) or Almost Clear (1) and an at least 2-point improvement in from baseline. In some embodiments treatment with orismilast according to the dosage regimen provides a score of Clear (0) or Almost Clear (1) and an at least 2-point improvement in the IGA-AD at week 2, 4, 8, 12, 16 or 20 of treatment. In some embodiments treatment with orismilast according to the dosage regimen provides an IGA-AD score of Clear (0) or Almost Clear (1) at week 2, 4, 8, 12, 16 or 20 of treatment. In some embodiments treatment with orismilast according to the dosage regimen provides an IGA-AD score of Clear (0) at week 2, 4, 8, 12, 16 or 20 of treatment. Preferably the dosage regimen provides an IGA-AD of 0 or 1 at week 16 of treatment. Details of the IGA-AD are provided in Example 8.

In some embodiments treatment with orismilast according to the dosage regimen reduces the peak pruritus numerical rating scale (PPNRS) score from baseline in subjects with atopic dermatitis. In some embodiments treatment with orismilast according to the dosage regimen reduces the PPNRS by ≥4 points from baseline. In some embodiments treatment with orismilast according to the dosage regimen reduces the PPNRS by ≥4 points from baseline at week 1, 2, 4, 8, 12, 16 or 20 of treatment. Suitably treatment with orismilast according to the dosage regimen reduces the PPNRS by 4 points from baseline at week 1 of treatment. Preferably treatment with orismilast according to the dosage regimen reduces the PPNRS by ≥4 points from baseline at week 2 of treatment. In some embodiments treatment with orismilast according to the dosage regimen reduces the PPNRS score from baseline by ≥4 points and reduces reduce one or more of: EASI, IGA-AD, BSA, DLQI, POEM, PGIS, PGIC, sleep disturbance NRS and skin pain NRS relative to baseline as described herein. In some embodiments treatment with orismilast according to the dosage regimen reduces the PPNRS score from baseline by ≥4 points and reduces the EASI score by 50% (EASI50) or more at week 1, 2, 4, 8, 12, 16 or 20 of treatment. In some embodiments treatment with orismilast according to the dosage regimen reduces the PPNRS score from baseline by ≥4 points and reduces the EASI score by 75% (EASI75) or more at week 1, 2, 4, 8, 12, 16 or 20 of treatment. In some embodiments treatment with orismilast according to the dosage regimen reduces the PPNRS score from baseline by ≥4 points and reduces the EASI score by 90% (EAS190) or more at week 1, 2, 4, 8, 12, 16 or 20 of treatment. In some embodiments treatment with orismilast according to the dosage regimen reduces the PPNRS from baseline by 4 points and reduces the EASI score by 100% (EASI100) at week 1, 2, 4, 8, 12, 16 or 20 of treatment. In some embodiments treatment with orismilast according to the dosage regimen reduces the PPNRS score from baseline by 4 points and the subject achieves a IGA-AD score of Clear (0) or Almost Clear (1) at week 1, 2, 4, 8, 12, 16 or 20 of treatment. In some embodiments treatment with orismilast according to the dosage regimen reduces the PPNRS score from baseline by ≥4 points and the subject achieves a IGA-AD score of Clear (0) at week 1, 2, 4, 8, 12, 16 or 20 of treatment. In any of the embodiments above the treatment with orismilast may reduce the PPNRS score from baseline by, for example, 4, 5, 6, 7 or 8 points from baseline. For example, the treatment with orismilast may reduce the PPNRS to 4 or less, such as 53, 52 or <1. For example treatment with orismilast may reduce the PPNRS to 3, 2, 1 or 0.

In any of the embodiments in the above paragraph the baseline PPNRS may be ≥4. In some embodiments the subject has a PPNRS at baseline which is at least 4, 5, 6, 7, or 8. In some embodiments the subject may have a PPNRS at baseline which is 4, 5, 6, 7, or 8 Analysis of phase 2b clinical data in atopic dermatitis suggests that subjects with more severe baseline PPNRS may respond particularly well to treatment with orismilast and show a rapid reduction in the PPNRS score (see Example 9). Accordingly, in any of the embodiments in the above paragraph the subject may have a PPNRS at baseline of ≥7.

Details of the peak pruritus NRS are provided in Examples 8 and 9, where the subject records the peak pruritis NRS for previous day (i.e. previous 24 hour period). Alternatively, the peak pruritus NRS is the weekly average peak pruritus NRS. The "weekly average peak pruritus NRS" refers to a PPNRS score where subjects record their peak pruritus score for the previous day every day for a week, and then the weekly average of the PPNRS score for each subject is calculated.

In some embodiments treatment with orismilast according to the dosage regimen reduces the affected body surface area (BSA) relative to baseline. In some embodiments the dosage regimen reduces BSA by 10%, 20%, 30%, 40%, 50%, 60%, 70%, 75%, 80%, 85%, 90% or 95% relative to baseline. In some embodiments the dosage regimen reduces BSA by 10%, 20%, 30%, 40%, 50%, 60%, 70%, 75%, 80%, 85%, 90% or 95% relative to baseline at week 4, 8, 12, 16 or 20 of treatment. Preferably the dosage regimen reduces BSA by 30%, 40%, 50%, 60%, 70%, 75%, 80%, 85%, 90% or 95% relative to baseline at week 16 of treatment. Details of the BSA are provided in Example 8.

In some embodiments treatment with orismilast according to the dosage regimen reduces the Dermatology Life Quality Index (DLQI) relative to baseline. In certain embodiments the dosage regimen provides a reduction in the DLQI score of ≥4 points at week 8, 16 or 20 of treatment relative to baseline. Preferably the dosage regimen provides a reduction in the DLQI score of ≥4 points at week 16 of treatment relative to baseline. In certain embodiments the dosage regimen provides a DLQI score of 0 or 1 at week 8, 16 or 20 of treatment. Preferably the dosage regimen provides a DLQI score of 0 or 1 at week 16 of treatment. Details of the DLQI are provided in Example 8.

In some embodiments treatment with orismilast according to the dosage regimen reduces the Patient Oriented Eczema Measure (POEM) score relative to baseline. In certain embodiments the dosage regimen provides a reduction in the POEM score of 4 points at week 2, 4, 8, 12, 16, or 20 of treatment relative to baseline. Preferably the dosage regimen provides a reduction in the POEM score of 4 points at week 16 of treatment relative to baseline. In certain embodiments the dosage regimen provides a POEM score of 0 or 1 at week 2, 4, 8, 12, 16, or 20 of treatment. Preferably the dosage regimen provides a POEM score of 0 or 1 at week 16 of treatment. Details of the POEM are provided in Example 8.

In some embodiments treatment with orismilast according to the dosage regimen reduces the Patient Global Impression of Severity (PGIS) score relative to baseline. In certain embodiments the dosage regimen provides a PGIS score of 0 or 1 at week 2, 4, 8, 12, 16, or 20 of treatment. Preferably the dosage regimen provides a PGIS score of 0 or 1 at week 16 of treatment. Details of the PGIS are provided in Example 8.

In some embodiments treatment with orismilast according to the dosage regimen reduces the Patient Global Impression of Change (PGIC) score relative of 1 or 2. In certain embodiments the dosage regimen provides a PGIC score of 1 or 2 at week 2, 4, 8, 12, 16, or 20 of treatment. Preferably the dosage regimen provides a PGIC score of 1 or 2 at week 16 of treatment. Details of the PGIC are provided in Example 8.

In some embodiments treatment with orismilast according to the dosage regimen reduces the sleep disturbance NRS score relative to baseline. In certain embodiments the dosage regimen provides a reduction in the sleep disturbance NRS score of ≥4 points at week 1, 2, 4, 8, 12, 16, or 20 of treatment relative to baseline. Preferably the dosage regimen provides a reduction in the sleep disturbance NRS score of 4 points at week 16 of treatment relative to baseline. In certain embodiments the dosage regimen provides a sleep disturbance NRS score of 0 or 1 at week 1, 2, 4, 8, 12, 16, or 20 of treatment. Preferably the dosage regimen provides a sleep disturbance NRS score of 0 or 1 at week 16 of treatment. Details of the sleep disturbance NRS score are provided in Example 8.

In some embodiments treatment with orismilast according to the dosage regimen reduces the skin pain NRS score relative to baseline. In certain embodiments the dosage regimen provides a reduction in the skin pain NRS score of 24 points at week 1, 2, 4, 8, 12, 16, or 20 of treatment relative to baseline. Preferably the dosage regimen provides a reduction in the skin pain NRS score of ≥4 points at week 16 of treatment relative to baseline. In certain embodiments the dosage regimen provides a skin pain NRS score of 0 or 1 at week 1, 2, 4, 8, 12, 16, or 20 of treatment. Preferably the dosage regimen provides a skin pain NRS score of 0 or 1 at week 16 of treatment. Details of the skin pain NRS score are provided in Example 8.

In any of the clinical scoring or effect measures described above or herein in relation to atopic dermatitis a reference to an "IGA-AD" score is equivalent to the "vIGA-AD" score descried in Example 13. Thus a reference to an IGA-AD score of 0 or 1 is equivalent to a vIGA-AD of 0 or 1. Accordingly the terms "IGA-AD" and "vIGA-AD" herein are equivalent and interchangeable. Similarly reference to a "peak pruritus NRS" score is equivalent to and interchangeable with a "Worst Pruritus NRS", wherein the Worst Pruritus NRS is described in Example 13.

In some embodiments treatment with orismilast according to the dosage regimen meets any one of the primary secondary or tertiary endpoints described in the atopic dermatitis clinical trials disclosed in Examples 8 and 13 herein.

Hidradenitis Suppurativa

In certain embodiments the disease or disorder treated with orismilast according to the dosage regimen is hidradenitis suppurativa (HS).

The subject may have mild, moderate or severe HS. In some embodiments, the subject has mild HS. In some embodiments, the subject has moderate HS. In some embodiments, the subject has severe HS.

The severity of HS may assessed using known scoring methods, for example the severity (also referred to as the disease state or progression) may be defined according to the International Hidradenitis Suppurativa Severity Score System (IHS4), which is a validated international clinimetric scale (Zouboulis et al., Br J Dermatol. 2017; 177(5):1401-1409). The score is based on a count of inflamed lesions. The resulting IHS4 score is arrived at by the number of nodules (multiplied by 1) plus the number of abscesses (multiplied by 2) plus the number of draining tunnels (multiplied by 4). A total score of 4 or less signifies mild, 4-10 signifies moderate and 11 or higher signifies severe disease. In some embodiments, the subject with HS suffers from a comorbidity selected from obesity, metabolic syndrome, inflammatory bowel disease, spondyloarthropathy, or any combination thereof.

In some embodiments, the subject has not been previously treated with an antibody or other biological therapy for HS. In some embodiments, the subject has not been previously treated with a TNF-α inhibitor (e.g. adalimumab).

In other embodiments, the subject has been previously treated with an antibody or other biological therapy for HS. In some embodiments the subject has previously been treated with an anti-inflammatory antibody. In some embodiments, the subject has previously been treated with a TNF-α inhibitor (e.g. adalimumab). It may be that the subject is non-responsive or refractory to prior treatment of the HS with an antibody therapy, for example where the subject is non-responsive or refractory to treatment with a TNF-α inhibitor (e.g. adalimumab). Reference herein to a "biological therapy for HS" includes anti-TNF-α biologics (e.g. adalimumab, certolizumab infliximab, etanercept, or golimumab); anti-IL-17 biologics (e.g. bimekizumab, brodalumab, CJM112, ixekizumab or secukinumab); anti-IL-12/23 biologics (e.g. ustekinumab), anti-IL-23 biologics (e.g. guselkumab, risankizumab, or tildrakizumab); an anti-IL-1 biologic (e.g. anakinra, bermkimab or canakinumab); an anti CD (e.g. iscalimab); or an anti-IL-36 biologic (e.g. spesolimab or ismidolimab); anti CXCR1/CXCR2 biologics (e.g. LY 3041658), or a Complement C5a inhibitor, or any combination thereof. In some embodiments the biological therapy for HS is an anti-TNF-α biologic (e.g. adalimumab or infliximab). In some embodiments the biological therapy for HS is adalimumab.

In some embodiments, treatment with orismilast according to the dosage regimen treats a symptom of HS. For example, the compound may be for use in eliminating, or reducing the number, severity and/or spread of inflammatory nodules, abscesses, comedones and/or sinus tracts. In some embodiments the compound of the invention is for use in eliminating or reducing abscesses, nodules and/or draining fistulas caused by or associated with HS. In some embodiments the compound of the invention is for use in eliminating or reducing abscesses and/or nodules caused by or associated with HS.

In some embodiments, treatment with orismilast according to the dosage regimen reduces inflammation caused by or associated with HS. In some embodiments the orismilast is for use in reducing inflammation caused by or associated with HS, wherein the compound reduces one or more inflammatory biomarkers associated with HS in the subject. For example the orismilast may reduce one or more of: C-Reactive Protein (e.g. High-Sensitivity C-Reactive Protein (hs-CRP)); erythrocyte sedimentation rate; leukocyte count; or thrombocyte count relative to the baseline levels prior to treatment with the orismilast.

In some embodiments, treatment with the orismilast according to dosage regimen reduces the total number of number of abscesses and nodules (AN count) prior to treatment with the orismilast. For example the AN count is reduced by 10% 20%, 30%, 40%, 50%, 60%, 70%, 80%, or 90% relative to baseline. In some embodiments the AN count is reduced by 10% 20%, 30%, 40%, 50%, 60%, 70%, 80%, or 90% relative to baseline at week 2, 4, 8, 12, 16 or 20 of treatment. In some embodiments the AN count is reduced by 10% 20%, 30%, 40%, 50%, 60%, 70%, 80%, or 90% relative to baseline at week 16 of treatment.

In some embodiments, treatment with the orismilast according to dosage regimen eliminates or reduces pruritus caused by or associated with HS.

In some embodiments, the orismilast treatment according to the dosage regimen is for use in eliminating or reducing swelling caused by or associated with HS. For example, the orismilast may reduce swelling of HS lesions.

In some embodiments, the orismilast treatment according to the dosage regimen is for use in eliminating or reducing scarring caused by or associated with HS.

In some embodiments the orismilast treatment according to the dosage regimen is for use in reducing the size of lesions associated with HS. For example, it may be that the compound is for use in reducing or eliminating lesions associated with HS.

In some embodiments, the orismilast treatment according to the dosage regimen is for use in reducing pain caused by or associated with HS.

Pain may be assessed according to the Patient's Global Assessment of Skin Pain (0=no pain, 10=worst imaginable pain) 0-10 numerical rating scale (NRS) (Newton et al., J Patient Rep Outcomes. 2019; 3(1):42.). Suitably, NRS is reduced by at least 30%, compared to baseline. Other well-known pain scoring systems can be used to assess the reduction in pain associated with the HS. For example the reduction of pain could also be assessed using the Visual analog scale of pain (VAS pain), which also assesses pain on a visual scale of 0 (no pain) to 10 (worst imaginable pain).

Pain may also be assessed according to the McGill Pain questionnaire. The McGill Pain questionnaire can be used to evaluate the sensation, strength and change over time of experienced pain. It can monitor pain over time or determine the effectiveness of intervention (Melzack, Pain: September 1975, Volume 1, Issue 3, p277-299).

In some embodiments the pain associated with HS is reduced by at least about 10%, 20%, 30%, 40%, 50%, 60%, 70%, 80% or 90% using a suitable pain scoring method (e.g. one of the scoring methods described herein) relative to the baseline pain level prior to treating the HS with the orismilast. In some embodiments the pain associated with HS is reduced by at least about 10%, 20%, 30%, 40%, 50%, 60%, 70%, 80% or 90% relative to the baseline at week 2, 4, 8, 12, 16 or 20 of treatment. In some embodiments the pain associated with HS is reduced by at least about 10%, 20%, 30%, 40%, 50%, 60%, 70%, 80% or 90% relative to the baseline at week 16 of treatment.

In some embodiments, the Hidradenitis Suppurativa Quality of Life (HisQoL) total score of the patient treated with the compound is reduced during the treatment period. In some embodiments the HisQoL of the subject is reduced by at least about 10%, 20%, 30%, 40%, 50%, 60%, 70%, 80% or 90% relative to the baseline level prior to treating the HS with the orismilast. Suitably, the HisQoL of the patient is reduced by at least 50%, such as at least 75% or such as at least 90%. In some embodiments the HisQoL of the patient is reduced by at least 50%, such as at least 75% or such as at least 90% at week 2, 4, 8, 12, 16 or 20 of treatment, preferably at week 16 of treatment.

The HiSQOL is based on the work of the Hidradenitis SuppuraTiva cORe outcomes set International Collaboration (HISTORIC). HiSQOL has been developed and validated systematically and is a 17-item questionnaire that contains HS specific items such as drainage and odor in addition to more general skin specific items. HiSQOL is a HS-specific questionnaire designed to evaluate HRQOL in clinical trials (Thorlacius et al., Skin Appendage Disord. 2019 June; 5(4):221-229; Kirby et al., Br_J Dermatol. 2020 August; 183(2):340-348). It has a recall-period of 7 days and consists of 17 items divided into three domains: Four symptom questions, five psychosocial questions, and eight activities adaptation questions. For each item a score between 0 and 4 is given, with a higher score representing a greater adverse impact on HRQOL. In some embodiments the HRQOL of the subject is reduced by at least about 10%, 20%, 30%, 40%, 50%, 60%, 70%, 80% or 90% relative to the baseline level prior to treating the HS with the orismilast. In some embodiments the HRQOL of the subject is reduced by at least about 10%, 20%, 30%, 40%, 50%, 60%, 70%, 80% or 90% relative to the baseline at week 2, 4, 8, 12, 16 or 20 of treatment, preferably at week 16 of treatment.

In some embodiments, the Hidradenitis Suppurativa Clinical Response (HiSCR) of the patient treated with the compound is reduced during the treatment period. In some embodiments the HiSCR of the subject is reduced by at least about 10%, 20%, 30%, 40%, 50%, 60%, 70%, 80% or 90% relative to the baseline level prior to treating the HS with the orismilast. In some embodiments the HiSCR of the patient is reduced by at least 50%, such as at least 75% or such as at least 90% relative to baseline. In some embodiments the HiSCR of the patient is reduced by at least 50%, such as at least 75% or such as at least 90% relative to baseline at week 2, 4, 8, 12, 16 or 20 of treatment, preferably at week 16 of treatment.

HiSCR is a treatment target based on correlation between the changes in lesion counts and PROM (pain and HRQoL). Hidradenitis Suppurativa Clinical Response (HiSCR; a ≥50% reduction from baseline in abscess and inflammatory nodule count and no increase in abscess or draining fistula counts) (Kimball et al., Ann Intern Med. 2012 Dec. 18; 157(12):846-55; Kimball et al., J Eur Acad Dermatol Venereol. 2016 June; 30(6):989-94). Subsequently modified for further differentiation: HiSCR75; a ≥75% reduction from baseline in abscess and inflammatory nodule count and no increase in abscess or draining fistula counts) and HiSCR-90; a ≥90% reduction from baseline in abscess and inflammatory nodule count and no increase in abscess or draining fistula counts).

In some embodiments, the Physician's Global Assessment of disease severity (HS-PGA) of the patient treated with orismilast is reduced during the treatment period. Suitably, the HS-PGA of the patient during or after treatment is reduced to a score of 0 or 1. In some embodiments the dosage regimen provides a HS-PGA of 0 or 1 at week 2, 4, 8, 12, 16 or 20 of treatment, preferably at week 16 of treatment.

HS-PGA ranges from clear to very severe (Kimball et al., Ann Intern Med. 2012 Dec. 18; 157(12):846-55). It is used in clinical trials to measure clinical improvement in inflammatory nodules, abscesses, and draining fistulae. The six stages are;

Clear: No inflammatory or non-inflammatory nodules.
Minimal: Only the presence of non-inflammatory nodules.
Mild: Less than 5 inflammatory nodules or 1 abscess or draining fistula and no inflammatory nodules.
Moderate: Less than 5 inflammatory nodules, or 1 abscess or draining fistula and 1 or more inflammatory nodules, or 2-5 abscesses or draining fistulas and less than inflammatory nodules.
Severe: 2-5 abscesses or draining fistulas and 10 or more inflammatory nodules.
Very severe: More than 5 abscesses or draining.

In some embodiments the dosage regimen reduces the severity of the HS in the subject. For example it may be that the dosage regimen reduces the severity by one or more (e.g. 1, 2 or 3) HS-PGA levels. Thus it may be that the dosage regiment reduces the severity of the HS from very severe to severe, moderate or mild HS. In some embodiments the dosage regimen reduces the severity of the HS from very severe to severe, moderate or mild HS at week 16 of treatment.

In some embodiments, the compound reduces the amount of C-Reactive Protein (e.g. High-Sensitivity C-Reactive Protein (hs-CRP)) in the patient treated with the compound. Suitably, the amount of C-Reactive Protein (e.g. hs-CRP) in the patient is reduced by at least about 10%, 20%, 30%, 40%, 50%, 60%, 70%, 80%, 90% or 100% relative to the baseline level prior to treating the HS with the compound. For example the amount of C-Reactive Protein (e.g. hs-CRP) is reduced by at least 50%, such as at least 75% or such as at least 90%. In some embodiments the dosage regimen reduces the C-reactive protein by at least 50%, such as at least 75% or such as at least 90% at week 2, 4, 8, 12, 16 or 20 of treatment, preferably at week 16 of treatment.

In some embodiments, the Dermatology Life Quality Index (DLQI) of the subject treated with the compound is reduced during the treatment period. In some embodiments the DLQI of the subject is reduced by at least about 10%, 20%, 30%, 40%, 50%, 60%, 70%, 80% or 90% relative to the baseline level prior to treating the HS with the compound. In some embodiments, the DLQI of the subject is reduced by at least 50%, such as at least 75% or such as at least 90%. In some embodiments the dosage regimen reduces the DLQI by at least 50%, such as at least 75% or such as at least 90% at week 2, 4, 8, 12, 16 or 20 of treatment, preferably at week 16 of treatment.

DLQI is a questionnaire of 10 questions concerning the patients' perception of the impact of skin diseases on different aspects of their health-related quality of life over the last week. Each question is scored on a four-point scale (0-3) resulting in a range of 0-30 points (0=Disease has no impact on quality of life, 30=Disease has maximum impact on quality of life). A validated scale first introduced by Finlay and Khan, Clin. Exp. Dermatol., 19 (1994), pp. 210-216).

In some embodiments, the Work Productivity and Activity Questionnaire (WPAI) impairment percentage of the patient treated with the compound is reduced during the treatment period. Suitably, the impairment score of the patient is reduced by at least 50%, such as at least 75% or such as at least 90%. In some embodiments the impairment score of the patient is reduced by at least 50%, such as at least 75% or such as at least 90% at week 2, 4, 8, 12, 16 or 20 of treatment, preferably at week 16 of treatment.

WAPI is a questionnaire describing work impairment due to a specific disease. Outcomes are expressed as impairment percentages, with higher numbers indicating greater impairment and less productivity (Reilly et al., Pharmacoeconomics. 1993 November; 4(5):353-65).

In some embodiments, the Anxiety and Depression (HADS) score of the subject treated with the dosage regimen is reduced relative to baseline. Suitably, the HADS score of the patient is reduced by at least 50%, such as at least 75% or such as at least 90%. In some embodiments the dosage regimen reduces the HADS score by at least 50%, such as at least 75% or such as at least 90% at week 2, 4, 8, 12, 16 or 20 of treatment, preferably at week 16 of treatment.

HADS is a questionnaire comprising seven questions for anxiety and seven questions for depression. Each question is connected to four answers retrieving 0-3 points. For each condition, 0-7 points corresponds to normal case; 8-10 to borderline abnormal; and 11-21 to abnormal case (Zigmond and Snaith, Acta Psychiatrica Scandinavica (1983), 67(6): 361-370).

In some embodiments, the European quality of life—5 Dimensions (EQ-5D) score of the subject treated with the dosage regimen is increased during the treatment relative to baseline. Suitably, the EQ-5D score of the patient is increased by at least 50%, such as at least 75% or such as at least 90%. In some embodiments the dosage regimen increases the EQ-5D score by at least 50%, such as at least 75% or such as at least 90% relative to baseline at week 2, 4, 8, 12, 16 or 20 of treatment, preferably at week 16 of treatment.

EQ-5D is a standardized instrument for measuring generic health status in terms of five dimensions: mobility, self-care, usual activities, pain/discomfort, and anxiety/depression. Each dimension receives a value of 1-5 leaving 55 55) different health states. The score is combined with an overall patient rating of health from 0-100 where 0 is worst imaginable health and 100 is best imaginable health. The scale was further developed from the original EQ-5D by Herdman et al., Qual Life Res. 2011 December; 20(10):1727-36.

In some embodiments, the Multidimensional Fatigue Inventory 20 (MFI-20) response of the patient treated with the dosage regimen is improved relative to baseline. MFI-20 was invented by Smets et al., J Psychosom Res 1995; 39:315-25. It consists of items describing five subscales of fatigue: General Fatigue (GF), Physical Fatigue (PF), Reduced Motivation (RM), Reduced Activity (RA), and Mental Fatigue (MF). For each of the items the respondent must specify the extent to which the particular statements relate to him/her on a five-point scale, ranging from Yes, that is true to No, that is not true.

In some embodiments the orismilast treatment according to the dosage regimen is for use in preventing or reducing HS flares in the subject. In some embodiments the orismilast is for use in reducing the severity of HS flares in the subject. In some embodiments the orismilast treatment according to the dosage regimen is for use in reducing the frequency of HS flares in the subject. In some embodiments the orismilast treatment according to the dosage regimen is for use in reducing the frequency and severity of HS flares in the subject.

Colitis

In certain embodiments the disease or disorder treated with orismilast according to the dosage regimen is colitis, for example ulcerative colitis.

Pruritus Associated with Atopic Dermatitis (Sixth Aspect of the Invention)

As described in the Examples herein, an analysis of Phase 2b clinical trial data from a study on subjects with moderate to severe atopic dermatitis treated orally with orismilast has revealed that orismilast has a surprisingly strong and rapid effect on pruritus (itch). All active arms in the study demonstrated a significant ≥4-point reduction in peak pruritus NRS (PPNRS) from baseline at week 2 of treatment with orismilast (MI p<0.05 compared to placebo). In subjects with PPNRS >7 at baseline, all active arms in the clinical trial demonstrated a statistically significant 24 point reduction in PPNRS improvement from baseline at week 16 (Observed p<0.05 or p<0.1 compared to placebo).

Pruritis is a particularly significant symptom in subjects suffering with atopic dermatitis. Interestingly, the efficacy against pruritus of known treatments for atopic dermatitis is not always correlated with the efficacy against atopic dermatitis (Rodriguez-Le Roy Y et al., Efficacy of topical and systemic treatments for atopic dermatitis on pruritus: A systematic literature review and meta-analysis. Front Med (Lausanne). 2022 Dec. 22; 9:1079323. doi: 10.3389/fmed.2022.1079323. PMID: 36619624; PMCID: PMC9814490). There is therefore a need for new treatments of pruritis associated with atopic dermatitis.

Accordingly, a sixth aspect, the invention provides orismilast for use in a method of treating pruritus (itch) associated with atopic dermatitis in a subject, the method comprising administering a therapeutically effective amount of orismilast to the subject.

Also provided is a method of treating pruritus associated with atopic dermatitis in a subject, the method comprising administering a therapeutically effective amount of orismilast to the subject.

Also provided is the use of orismilast for the manufacture of a medicament for the treatment of pruritus associated with atopic dermatitis in a subject, wherein treatment comprises administering a therapeutically effective amount of orismilast to the subject.

In some embodiments of the sixth aspect of the invention the atopic dermatitis is mild, moderate, severe or very severe atopic dermatitis as described herein. In some embodiments the subject has moderate-to-severe atopic dermatitis. In some embodiments the subject has severe atopic dermatitis as described herein. For example, a subject may have an affected body surface area (BSA) of at least 10%, an IGA-AD grade of at least 3, and an Eczema Area and Severity Index (EASI) score of ≥16 at baseline. In some embodiments the subject has a baseline EASI score of >21.

In some embodiments of the sixth aspect of the invention the subject has a PPNRS at baseline which is at least 4. For example, the subject may have a PPNRS at baseline of at least 4, 5, 6, 7, or 8. In some embodiments the subject may have a PPNRS at baseline which is 4, 5, 6, 7, or 8. In some embodiments the subject has a baseline PPNRS which is >7. In some embodiments the subject has a severe itch at baseline, for example a baseline PPNRS of >7.

Details of PPNRS are provided in Example 8. As described, the severity of itch (pruritus) can be assessed using a horizontal 11-point NRS. Subjects may be asked to assess their "worst itching due to AD over the past 24 hours" on an NRS anchored by the terms "no itching" (0) and "worst possible itching" (10). In some embodiments the PPNRS is the average PPNRS for the previous day at the measurement timepoint. In some embodiments the PPNRS is a weekly average of daily PPNRS scores determined in this way.

Typically, treatment with orismilast produces a reduction in PPNRS in the subject. For example, treatment may reduce the PPNRS by at least 4 points from baseline, such as by at least 5 or 6 points from baseline. In some embodiments treatment with orismilast produces a reduction in PPNRS of 4, 5 or 6 points from baseline. In some embodiments treatment with orismilast may reduce absolute PPNRS to 4 or less, such as 53, 52 or <1. For example treatment with orismilast may reduce the absolute PPNRS to 3, 2, 1 or 0.

Treatment with orismilast may reduce the PPNRS at week 1, 2, 4, 8, 12, 16 or 20 of treatment, for example at week 1, 2, 8 or 16 of treatment. As illustrated in Example 9, treatment with orismilast results in rapid reduction of the PPNRS. Accordingly in some embodiments of the sixth aspect of the invention the treatment with orismilast reduces the PPNRS at week 2 of treatment. In some embodiments the treatment with orismilast reduces the PPNRS at week 1 of treatment.

In some embodiments of the sixth aspect of the invention treatment with orismilast reduces the PPNRS by ≥4 points from baseline at week 1, 2, 4, 8, 12, 16 or 20 of treatment. Suitably treatment with orismilast reduces the PPNRS by ≥4 points from baseline at week 2 or week 16 of treatment. In some embodiments orismilast reduces the PPNRS by ≥4 points from baseline at week 1 of treatment. Preferably orismilast reduces the PPNRS by ≥4 points from baseline at week 2 of treatment.

In some embodiments of the sixth aspect of the invention treatment with orismilast also results in an improvement in one of more additional efficacy measurements for atopic dermatitis treatment. For example, treatment may also reduce one or more of the additional atopic dermatitis measures described herein relative to baseline. In some embodiments, treatment with orismilast may reduce one or more of: EASI, IGA-AD, BSA, DLQI, POEM, PGIS, PGIC, sleep disturbance NRS and skin pain NRS relative to baseline as described herein. In some embodiments, treatment with orismilast reduces PPNRS relative to baseline (for example a reduction ≥4 points in PPNRS at week 2 or at week 16 of treatment) and also reduces one of more of EASI and IGA-D relative to baseline as described herein. In some embodiments, treatment reduces PPNRS relative to baseline (for example a reduction ≥4 points in PPNRS at week 2 or at week 16 of treatment) and also provides an IGA-AD of 0 or 1 at week 16 of treatment. Treatment with orismilast may cause changes in one or more biomarkers in skin as described herein, for example a reduction in TARC relative to baseline. In some embodiments treatment with orismilast reduction in TARC relative to baseline of at least 30%, at least 40%, at least 50%, at least 60%, at least 70%, at least 80% or at least 90% at week 1, 2, 4, 8, 12, 16 or 20 of treatment (for example at week 16 of treatment).

In some embodiments of the sixth aspect of the invention treatment with orismilast reduces the PPNRS score from baseline by ≥4 points and reduces the EASI score by 50% (EASI50) or more at week 1, 2, 4, 8, 12, 16 or 20 of treatment (for example at week 16 of treatment). In some embodiments treatment with orismilast reduces the PPNRS score from baseline by ≥4 points and reduces the EASI score by 75% (EASI75) or more at week 1, 2, 4, 8, 12, 16 or 20 of treatment (for example at week 16 of treatment). In some embodiments treatment with orismilast reduces the PPNRS score from baseline by ≥4 points and reduces the EASI score by 90% (EASI90) or more at week 1, 2, 4, 8, 12, 16 or 20 of treatment (for example at week 16 of treatment). In some embodiments treatment with orismilast reduces the PPNRS from baseline by ≥4 points and reduces the EASI score by 100% (EASI100) at week 1, 2, 4, 8, 12, 16 or 20 of treatment (for example at week 16 of treatment). In some embodiments treatment with orismilast reduces the PPNRS score from baseline by 4 points and the subject achieves a IGA-AD score of Clear (0) or Almost Clear (1) at week 1, 2, 4, 8, 12, 16 or 20 of treatment (for example at week 16 of treatment). In some embodiments treatment with orismilast reduces the PPNRS score from baseline by ≥4 points and the subject achieves a IGA-AD score of Clear (0) at week 1, 2, 4, 8, 12, 16 or 20 of treatment (for example at week 16 of treatment). In any of the embodiments above the treatment with orismilast may reduce the PPNRS score from baseline by, for example, 4, 5, 6, 7 or 8 points from baseline.

In any of the embodiments of the sixth aspect of the invention the baseline PPNRS may be ≥4. In some embodiments the subject has a PPNRS at baseline which is at least 4, 5, 6, 7, or 8. In some embodiments the subject may have a PPNRS at baseline which is 4, 5, 6, 7, or 8.

Analysis of phase 2b clinical data in atopic dermatitis suggests that subjects with more severe baseline PPNRS may respond particularly well to treatment with orismilast and show a rapid reduction in the PPNRS score (see Example 9). Accordingly, in any of the embodiments of the sixth aspect of the invention the baseline PPNRS may be ≥7.

In some embodiments of the sixth aspect of the invention the subject is treated with orismilast according to any of the dosage regimens and variations thereof described herein according to the first to fifth aspects of the invention.

In some embodiments of the sixth aspect of the invention the subject is treated as described herein for other aspects of the invention, for example, relating to any of the orismilast, pharmaceutical compositions, and combination therapies.

In the sixth aspect of the invention a reference to an "IGA-AD" score is equivalent to the "vIGA-AD" score descried in Example 13. Thus a reference to an IGA-AD score of 0 or 1 is equivalent to a vIGA-AD of 0 or 1. Accordingly the terms "IGA-AD" and "vIGA-AD" herein are equivalent and interchangeable. Similarly reference to a "peak pruritus NRS" score is equivalent to and interchangeable with a "Worst Pruritus NRS", wherein the Worst Pruritus NRS is described in Example 13.

Combination Therapies

The orismilast, or a formulation or composition comprising the compound, may be used alone to provide a therapeutic effect. The orismilast, or a formulation or composition comprising the compound, may also be used in combination with a further therapy.

In some embodiments the further therapy is selected from an anti-androgenic agent, a hormone, an antibiotic (e.g. dapsone, doxycycline, clindamycin, rifampin or a carbapenem (e.g. ertapenem)), a retinoid, vitamin D analogues, an anti-inflammatory agent (including steroids (e.g. budesonide, prednisolone)), non-steroidal anti-inflammatory agents, colchicine, mycophenolate, thioguanine, hydroxyurea, sulfasalazine, azathioprine, or fumaric acid esters, a PDE4 inhibitor other than orismilast, an analgesic, an immunosuppressive agent (e.g. tacrolimus, pimecrolimus, sirolimus or cyclosporine), methotrexate, anthralin/dithranol, metformin, a nutritional supplement (e.g. zinc gluconate), a TNF-α inhibitor (e.g. adalimumab, etanercept, infliximab or certolizumab pegol), and IL-1 inhibitor (e.g. anakinra), an anti-IL-17 (including and IL-17A, IL-17F and IL17AF) drug (e.g. secukinumab, bimekizumab, brodalumab or ixekizumab), and anti-IL-23 drug (e.g. risankizumab, tildrakizumab or guselkumab), anti-IL-12/23 drug (e.g. ustekinumab), an anti-IL-12 drugs, an anti-IL-23 drug (e.g. or guselkumab, a Janus Kinase (JAK) inhibitor (e.g. baricitinib, abrocitinib, tofacitinib, povorcitinib (also known as INCB054707), or upadacitinib), an anti-IL-4/13 drug (e.g. dupilumab), a tyrosine kinase 2 (TYK2) inhibitor (e.g. deucravacitinib), a TYK2/JAK1 inhibitor (e.g. PF-06700841), a complement C5a inhibitor (e.g. avacopan), a leukotriene A4 hydrolase inhibitor (e.g. LYS 006), a leukotriene A4 hydrolase inhibitor (e.g. LYS 006), an IRAK4 degrader (e.g.KT-474), a IRAK4 inhibitor (e.g. PF-06650833), phototherapy (e.g. ultraviolet B [UVB], psoralen and ultraviolet A [PUVA] radiation) and surgery, or any combination thereof.

In some embodiments the further therapy is a topical steroid, for example a topical steroid selected from amcinonide, clobetasol (e.g. clobetasol propionate or clobetasone butyrate), betamethasone (e.g. betamethasone dipropionate or betamethasone valerate), desonide, desoximetasone, diflorasone diacetate, diflucortolone (e.g. diflucortolone valerate), fluocinolone acetonide, fluocinonide, flurandrenolide, fluticasone (e.g. fluticasone propionate), halcinonide, halobetasol propionate, halometasone, a hydrocortisone (e.g. hydrocortisone, hydrocortisone butyrate, hydrocortisone acetate or hydrocortisone valerate), mometasone (e.g. mometasone furoate), methylprednisolone (e.g. methylprednisolone aceponate) and triamcinolone (e.g. triamcinolone acetonide), or a combination of two or more thereof.

Such combination treatment may be achieved by way of the simultaneous, sequential or separate dosing of the individual components of the treatment. Such combination products employ the orismilast dosage regimen of this invention and the other pharmaceutically-active agent within its approved dosage range.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

Embodiments

The following numbered embodiments further illustrate the invention.

A1. A method of treating a disease or disorder ameliorated by inhibiting PDE4 in a subject, the method comprising administering orismilast to the subject,
wherein:
(Ai) an initial orismilast dose is administered to the subject once per day for an initial time period followed by;
(Ai) an interim orismilast dose administered to the subject twice per day for an interim time period followed by;
(Aiii) a maintenance orismilast dose administered to the subject twice per day;
wherein:
(a) the initial orismilast dose and the interim orismilast dose are independently selected from 10 mg to 30 mg orismilast, provided that the interim orismilast dose is greater than or equal to the initial orismilast dose;
(b) the initial time period is two to eight weeks;
(c) the interim time period is one to eight weeks; and
(d) the maintenance orismilast dose is greater than the interim orismilast dose when the subject has a body mass that is greater than or equal to a threshold body mass, wherein the threshold body mass is at least 90 kg.

A2. The method according to embodiment A1, wherein the initial orismilast dose and the interim orismilast dose are the same;
optionally wherein the initial orismilast dose and the interim orismilast are both 20 mg orismilast.

A3. The method according to embodiment A1 or embodiment A2, wherein the maintenance orismilast dose is the same as the interim orismilast dose when the subject has a body mass which is less than the threshold body mass.

A4. The method according to any one of embodiments A1 to A3, wherein the maintenance orismilast dose is up to 40 mg orismilast when the subject has a body mass which is greater than or equal to the threshold body mass, provided the maintenance orismilast dose is greater than the interim orismilast dose.

A5. The method according to any one of embodiments A1 to A4, wherein the maintenance orismilast dose is 30 mg orismilast when the subject has a body mass which is greater than or equal to the threshold body mass.

A6. The method according to any one of embodiments A1 to A5, wherein the initial period is two weeks to six weeks;
optionally wherein the initial time period is two weeks, four weeks or six weeks.

A7. The method according to any one of embodiments A1 to A5, wherein the initial time period is two weeks.

A8. The method according to any one of embodiments A1 to A7, wherein the interim time period is one week to six weeks;
optionally wherein the interim time period is two weeks, four weeks or six weeks;
further optionally wherein the interim time period is two weeks.

A9. The method according to any one of embodiments A1 to A7, wherein the total duration of the initial time period and the interim time period is four to eight weeks; optionally wherein the total duration of the initial time period and the interim time period is eight weeks.

A10. The method according to any one of embodiments A1 to A12, wherein:
(i) when the subject has a body mass that is less than a lower limit body mass the initial orismilast dose in (Ai), the interim orismilast dose in (Aii) and the maintenance orismilast dose in (Aiii) are all 10 mg orismilast; or
(ii) when the subject has a body mass that is in the range of from the lower limit body mass to less than the threshold body mass, the initial orismilast dose in (Ai), the interim orismilast dose in (Aii) and the maintenance orismilast dose in (Aiii) are all 20 mg orismilast;
wherein the lower limit body mass is from 50 kg to 75 kg.

A11. The method according to any one of embodiments A1 to A12, wherein when the subject has a body mass that is less than a lower limit body mass, the initial orismilast dose, the interim orismilast dose and the maintenance orismilast dose are all 10 mg orismilast;
wherein the lower limit body mass is from 50 kg to 75 kg;
optionally, wherein when the subject has a body mass that is less than 60 kg the initial orismilast dose, the interim orismilast dose and the maintenance orismilast dose are all 10 mg orismilast.

A12. The method according to embodiment 1, wherein when the subject has a body mass that is in the range of from a lower limit body mass to less than the threshold body mass, the initial orismilast dose, the interim orismilast dose and the maintenance orismilast dose are all 20 mg orismilast;
wherein the lower limit body mass is from 50 kg to 75 kg;
optionally wherein when the subject has a body mass that is in the range of from 60 kg to less than the threshold body mass, the initial orismilast dose, the interim orismilast dose and the maintenance orismilast dose are all 20 mg orismilast.

A13. The method according to embodiment A1, wherein:
(Ai) the initial orismilast dose is 20 mg orismilast administered to the subject once per day for two weeks;
(Aii) the interim orismilast dose is 20 mg orismilast administered to the subject twice per day for two weeks; and
(Aiii) the maintenance orismilast dose is 20 mg orismilast administered to the subject twice per day if the subject has a body mass which is less than the threshold body mass; or
the maintenance orismilast dose is 30 mg orismilast administered to the subject twice per day if the subject has a body mass which is greater than or equal to the threshold body mass.

A14. The method according to embodiment A1, wherein:
(Ai) the initial orismilast dose is 20 mg orismilast administered to the subject once per day for two weeks;
(Aii) the interim orismilast dose is 20 mg orismilast administered to the subject twice per day for four weeks; and
(Aiii) the maintenance orismilast dose is 20 mg orismilast administered to the subject twice per day if the subject has a body mass which is less than the threshold body mass; or
    the maintenance orismilast dose is 30 mg orismilast administered to the subject twice per day if the subject has a body mass which is greater than or equal to the threshold body mass.
A15. The method according to embodiment A1, wherein:
(Ai) the initial orismilast dose is 20 mg orismilast administered to the subject once per day for two weeks;
(Aii) the interim orismilast dose is 20 mg orismilast administered to the subject twice per day for six weeks;
(Aiii) the maintenance orismilast dose is 20 mg orismilast administered to the subject twice per day if the subject has a body mass which is less than the threshold body mass; or
    the maintenance orismilast dose is 30 mg orismilast administered to the subject twice per day if the subject has a body mass which is greater than or equal to the threshold body mass.
A16. The method according to embodiment 1, wherein
(Ai) the initial orismilast dose is 10 mg orismilast administered to the subject once per day for two weeks to four weeks if the subject has a body mass of less than a lower limit body mass, or
    the initial orismilast dose is 20 mg orismilast administered to the subject once per day for two weeks to four weeks if the subject has a body mass of from the lower limit body mass to less than the threshold body mass;
(Aii) the interim orismilast dose is 10 mg orismilast administered to the subject twice per day for one week to eight weeks if the subject has a body mass of less than the lower limit body mass; or
    the interim orismilast dose is 20 mg orismilast administered to the subject twice per day for one week to eight weeks if the subject has a body mass of from the lower limit body mass to less than the threshold body mass; and
(Aiii) the maintenance orismilast dose is 10 mg orismilast administered to the subject twice per day if the subject has a body mass which is less than the lower limit body mass; or
    the maintenance orismilast dose is 20 mg orismilast administered to the subject twice per day if the subject has a body mass which is of from the lower limit body mass to less than the threshold body mass; or
    the maintenance orismilast dose is 30 mg orismilast administered to the subject twice per day if the subject has a body mass which is greater than or equal to the threshold body mass;
    wherein the lower limit body mass is from 50 kg to 75 kg.
A17. The method according to embodiment A16, wherein the lower limit body mass is selected from 50 kg, 55 kg, 60 kg, 65 kg, 70 kg and 75 kg;
optionally wherein lower limit body mass is 50 kg;
optionally wherein lower limit body mass is 60 kg.

A18. The method according to any one of embodiments A1 to A17, wherein the threshold body mass is 90 kg.
A19. The method according to any one of embodiments A1 to A17, wherein the threshold body mass is 95 kg.
A20. The method according to any one of embodiments A1 to A17, wherein the threshold body mass is 100 kg.
A21. The method according to any one of embodiments A1 to A17, wherein the threshold body mass is 105 kg.
A22. The method according to any one of embodiments A1 to A21, wherein the initial orismilast dose is administered to the subject in the evening.
A22. The method according to any one of embodiments A1 to A21, wherein the initial orismilast dose is administered to the subject in the morning.
A23. The method according to any one of embodiments A1 to A22, wherein the maintenance orismilast dose is administered twice per day to the subject for at least 1 week, for example for at least one month, at least six months or at least one year.
A24. A method of treating a disease or disorder ameliorated by inhibiting PDE4 in a subject with a body mass that is greater than or equal to a threshold body mass, the method comprising administering orismilast to the subject,
wherein:
(Bi) an initial orismilast dose is administered to the subject once per day for a preliminary time period followed by;
(Bii) a interim orismilast dose administered to the subject twice per day for an interim time period followed by;
(Biii) a maintenance orismilast dose administered to the subject twice per day, wherein the maintenance orismilast dose is greater than the interim orismilast dose;
wherein:
(a) the initial orismilast dose and the interim orismilast doses are independently selected from 10 mg to 30 mg orismilast, provided that the interim orismilast dose is greater than or equal to the initial orismilast dose;
(b) the preliminary time period is one week to eight weeks;
(c) the interim time period is up to eight weeks; and
(d) the threshold body mass is at least 90 kg.
A25. The method according to embodiment A24, wherein the initial orismilast dose and the interim orismilast dose are the same:
optionally wherein the initial orismilast dose and the interim orismilast dose are both 20 mg orismilast.
A26. The method according to embodiment A24 or embodiment A25, wherein the maintenance orismilast dose is up to 40 mg orismilast, provided the maintenance orismilast dose is greater than the interim orismilast dose.
A27. The method according to any one of embodiments A24 to A26, wherein the maintenance orismilast dose is 30 mg.
A28. The method according to any one of embodiments A24 to A27, wherein the preliminary period is 1 day to eight weeks;
optionally wherein the preliminary period is:
(i) 2 days to eight weeks
(ii) one week to eight weeks;
(iii) one week to six weeks;
(iv) two weeks to four weeks;
(v) one week;
(vi) two weeks;
(vii) four weeks; or
(viii) six weeks.

A29. The method according to any one of embodiments A24 to A28, wherein the preliminary time period is two weeks.

A30. The method according to any one of embodiments A24 to A29, wherein the interim time period is one week to eight weeks;
optionally wherein the interim time period is one week to six weeks;
optionally wherein the interim time period is one week to two weeks
optionally wherein the interim time period is two weeks to four weeks;
optionally wherein the interim time period is two weeks, four weeks or six weeks.

A31. The method according to any one of embodiments A24 to A30, wherein the total duration of the preliminary time period and the interim time period is four to eight weeks;
optionally wherein the total duration of the preliminary time period and the interim time period is eight weeks.

A32. The method according to embodiment A24, wherein:
(Bi) the initial orismilast dose is 20 mg orismilast administered to the subject once per day for two weeks;
(Bii) the interim orismilast dose is 20 mg orismilast administered to the subject twice per day for one week to eight weeks; and
(Biii) the maintenance orismilast dose is 30 mg orismilast administered to the subject twice per day.

A33. The method according to embodiment A24, wherein:
(Bi) the initial orismilast dose is 20 mg orismilast administered to the subject once per day for one week;
(Bii) the interim orismilast dose is 20 mg orismilast administered to the subject twice per day for two weeks;
(Biii) the maintenance orismilast dose is 30 mg orismilast administered to the subject twice per day.

A34. The method according to embodiment A24, wherein:
(Bi) the initial orismilast dose is 20 mg orismilast administered to the subject once per day for two weeks;
(Bii) the interim orismilast dose is 20 mg orismilast administered to the subject twice per day for two weeks;
(Biii) the maintenance orismilast dose is 30 mg orismilast administered to the subject twice per day.

A35. The method according to embodiment A24, wherein:
(Bi) the initial orismilast dose is 20 mg, orismilast administered to the subject once per day for two weeks;
(Bii) the interim orismilast dose is 20 mg orismilast administered to the subject twice per day for four weeks;
(Biii) the maintenance orismilast dose is 30 mg orismilast administered to the subject twice per day.

A36. The method according to embodiment A24, wherein:
(Bi) the initial orismilast dose is 20 mg orismilast administered to the subject once per day for two weeks;
(Bii) the interim orismilast dose is 20 mg orismilast administered to the subject twice per day for six weeks;
(Biii) the maintenance orismilast dose is 30 mg orismilast administered to the subject twice per day.

A37. The method according to any one of embodiments A24 to A36, wherein the threshold body mass is 90 kg.

A38. The method according to any one of embodiments A24 to A36, wherein the threshold body mass is 95 kg.

A39. The method according to any one of embodiments A24 to A36, wherein the threshold body mass is 100 kg.

A40. The method according to any one of embodiments A24 to A36, wherein the threshold body mass is 105 kg.

A41. The method according to any one of embodiments A24 to A40, wherein the initial orismilast dose is administered to the subject in the evening.

A42. The method according to any one of embodiments A24 to A40, wherein the initial orismilast dose is administered to the subject in the morning.

A43. The method according to any one of embodiments A24 to A42, wherein the maintenance orismilast dose is administered to the subject twice per day for at least one week, for example for at least one month, at least six months or at least one year.

A44. A method of treating a disease or disorder ameliorated by inhibiting PDE4 in a subject with a body mass that is greater than or equal to a threshold body mass, the method comprising administering the orismilast to the subject,
wherein:
(Ci) an initial orismilast dose is administered to the subject once per day for a preliminary time period followed by;
(Cii) a maintenance orismilast dose administered to the subject twice per day, wherein the maintenance orismilast dose is greater than the initial orismilast dose;
wherein:
(a) the initial orismilast dose is from 10 mg to 20 mg orismilast;
(b) the preliminary time period is up to eight weeks; and
(c) the threshold body mass is at least 90 kg (for example wherein the threshold body mass is 100 kg).

A45. A method of treating a disease or disorder ameliorated by inhibiting PDE4 in a subject with a body mass that is less than a lower limit body mass, the method comprising administering the orismilast to the subject,
wherein:
(Ei) an initial orismilast dose of 10 mg is administered to the subject once per day for an initial time period followed by;
(Eii) a maintenance orismilast dose of 10 mg administered to the subject twice per day;
wherein:
the initial time period is two to eight weeks, and
the lower limit body mass is from 50 kg to 75 kg;
optionally wherein the lower limit body mass is 50 kg;
optionally wherein the lower limit body mass is 60 kg.

A46. A method of treating pruritus associated with atopic dermatitis in a subject, the method comprising administering a therapeutically effective amount of orismilast to the subject.

A47. The method according to embodiment A46, wherein the subject has a baseline PPNRS of ≥4.

A48. The method according to embodiment A46, wherein the subject has a baseline PPNRS of >7.

A49. The method according to any one of embodiments A46 to A48, wherein the method reduces the baseline peak pruritus NRS (PPNRS) by 4-points.

A50. The method according to any one of embodiments A46 to A49, wherein the method reduces the baseline peak pruritus NRS (PPNRS) by 4-points after two weeks of treatment.

A51. The method according to any one of embodiments A46 to A50, wherein the subject has moderate to severe atopic dermatitis.

A52. The method according to any one of embodiments A1 to A51, wherein the orismilast is orally administered to the subject.

A53. The method according to any one of embodiments A1 to A51, wherein the orismilast is orally administered to the subject in the form of a modified release formulation comprising the orismilast.

A55. The method according to embodiment A53, wherein the modified release formulation releases a mean amount of about 10% to about 70% of the orismilast after 45 minutes and more than about 70% after 180 minutes, when measured in-vitro using the Standard Dissolution Assay described in the description.

A56. The method according to any one of embodiments A1 to A55, wherein the orismilast is administered to the subject simultaneously, separately or sequentially with a therapeutically effective amount of one or more additional therapeutic agent.

EXAMPLES

The invention is further illustrated by the following examples.

Example 1: Oral Modified Release Tablet Formulations 10 mg and 30 mg orismilast and placebo oral modified release tablets according to Table 3 were prepared:

TABLE 3

|  | Quantity per tablet | | | | Reference to |
| --- | --- | --- | --- | --- | --- |
| Name of Components | 10 mg | 30 mg | Placebo | Function | Quality Standard(s) |
| Drug Substance | | | | | |
| Orismilast [note 1] | 10 mg | 30 mg | — | Drug substance | |
| Excipients | | | | | |
| Lactose monohydrate | 233 mg | 213 mg | 243 mg | Filler | Ph. Eur. |
| Hypromellose [note 3] | 52.5 mg | 52.5 mg | 52.5 mg | Matrix former | Ph. Eur. |
| Silica, colloidal anhydrous | 1.5 mg | 1.5 mg | 1.5 mg | Glidant | Ph. Eur. |
| Magnesium stearate | 3.0 mg | 3.0 mg | 3.0 mg | Lubricant | Ph. Eur. |
| Tablet core weight | 300 mg | 300 mg | 300 mg | — | — |
| Film coating | | | | | |
| Opadry ® II [note 3] | 12 mg | 12 mg | 12 mg | Film coating system | |
| Coated tablet weight | 312 mg | 312 mg | 312 mg | — | — |

[note 1] The orismilast was used as milled crystalline Form E with a D50 particle size distribution of 1 to 6 μm.
[note 2] The Hypromellose was Methocel ™ K100 Premium LV DC2; 2% viscosity in water at 20° C. 80-120 mPa · s; methoxyl content 22-24%, and hydroxpropxyl content 7.5 to 9.5%
[note 3] Contain polyvinyl alcohol (Ph. Eur. 1961), macrogol (Ph. Eur. 1444), titanium dioxide (Ph. Eur. 0150), talc(Ph. Eur. 0438) and ferric oxide, yellow (NF).

The tablets were prepared by blending together the excipients and the orismilast and compressing into tablets using a rotary press to provide tablet cores. The tablet cores were then coated with the PVA based coating (Opadry II).

The mean dissolution profile for the 10 mg and 30 mg modified release tablets was measured using the Standard Dissolution Assay described in the description and gave the results shown in Table C, wherein the % values refer to the % of orismilast in the dissolution medium at each time point:

TABLE C

| in-vitro dissolution profile | | | | | | | | | | |
| --- | --- | --- | --- | --- | --- | --- | --- | --- | --- | --- |
| Time (min) | 6 | 12 | 20 | 30 | 45 | 60 | 90 | 120 | 180 | 210 |
| 10 mg | 7% | 15% | 22% | 28% | 36% | 42% | 54% | 64% | 81% | 97% |
| 30 mg | 7% | 14% | 23% | 31% | 39% | 46% | 56% | 66% | 82% | 99% |

The dissolution profile is shown in FIG. 11.

Characteristics of Orismilast

The orismilast used in the modified release tablet formulations was orismilast crystalline Form E. The powder X-ray diffraction pattern (XRPD) for Form E is shown in FIG. 9. The XRPD was obtained using an X'pert PRO MPD diffractometer from PANalytical configured with transmission geometry and equipped with a PIXcel detector. A continuous 2θ scan range of 3-45° was used with a CuKα radiation λ=1.5418 Å source and a generator power of 40 mA and 45 kV. A 2θ step size of 0.0070°/step with a step time of 148.92 s was used. Samples were gently flattened onto a well in a 96-well plate for transmission measurements. The well plate was moved forward and backward in the x direction and all experiments were performed at room temperature. The 2θ peak values of the XRPD for orismilast Form E is shown in Table C:

TABLE C

| Peak Position (2θ ± 0.2°) | Relative Intensity (%) |
|---|---|
| 5.9 | 4.1 |
| 8.0 | 18.0 |
| 8.6 | 8.6 |
| 8.7 | 5.0 |
| 9.8 | 3.2 |
| 11.8 | 11.4 |
| 12.1 | 3.5 |
| 14.1 | 11.9 |
| 14.4 | 5.8 |
| 15.0 | 24.1 |
| 15.2 | 3.3 |
| 16.0 | 73.5 |
| 16.4 | 22.5 |
| 16.6 | 13.0 |
| 16.8 | 28.5 |
| 17.0 | 8.1 |
| 17.3 | 15.4 |
| 17.7 | 8.1 |
| 18.1 | 100.0 |
| 18.5 | 31.6 |
| 19.3 | 5.1 |
| 19.7 | 25.1 |
| 19.9 | 16.8 |
| 20.0 | 28.1 |
| 20.2 | 25.0 |
| 20.3 | 16.1 |
| 21.4 | 34.2 |
| 21.5 | 32.6 |
| 21.6 | 11.2 |
| 21.9 | 6.6 |
| 22.0 | 8.0 |
| 22.3 | 18.9 |
| 22.9 | 11.9 |
| 23.1 | 9.6 |
| 23.4 | 39.5 |
| 23.6 | 19.3 |
| 23.9 | 12.2 |
| 24.1 | 11.8 |
| 24.4 | 16.5 |
| 24.7 | 9.4 |
| 25.6 | 19.6 |
| 25.8 | 19.4 |
| 26.2 | 11.0 |
| 26.3 | 11.5 |
| 26.6 | 9.0 |
| 27.3 | 17.7 |
| 27.8 | 12.8 |
| 28.1 | 13.7 |
| 28.3 | 12.2 |
| 28.6 | 9.8 |
| 29.2 | 9.4 |
| 29.5 | 19.2 |
| 29.7 | 27.8 |
| 30.0 | 14.1 |
| 30.5 | 14.3 |
| 31.5 | 5.8 |
| 31.7 | 5.2 |

The Form E was also characterised using DSC using a TA instrument Q20 systems. A few mg of sample was gently charged into and weighed in A1 pans. A lid with pre-made pin-hole was adapted and crimped onto the pan. Both modulated temperature profiles and traditional temperature profiles were used with varying heating rates of 2-10° C./min. The DSC traces for two batches (mean of two measurements) of orismilast is shown in FIG. 10. The Form E exhibited meting endotherms with onset temperatures of 211.6° C. and 211.7° C. and enthalpy changes of 83 J/g and 85 J/g. No glass transition was observed in the modulated DSC of the two samples, indicating the Form E was crystalline with no detectable amorphous material present.

Example 2: Dose Rational

The modified-release formulation was studied in a clinical trial (LP0058-1442) and administered in a total of 36 healthy volunteers: 18 in part 1, 9 in part 2, and 9 in part 3. Twenty-seven (27) healthy volunteers received a single administration of 30 mg orismilast, and 9 subjects received multiple administrations over a period of 17 days with an up-titration up to a maximum of 60 mg BID. Part 1 of this study was to evaluate the key PK parameters of the new modified-release formulation compared to the reference capsule formulation with immediate release. Orismilast was rapidly absorbed from both formulations with median tmax values of 3.00 hours post-dose for the immediate-release capsule and 2.52 hours post-dose for the modified-release tablet. The individual tmax ranges were approximately 1 to 6 hours post-dose for the immediate-release capsule and 1 to 4 hours post-dose for the modified-release tablet. Following tmax, the plasma concentrations of orismilast declined in a generally biphasic manner for both formulations with geometric mean terminal half-life (t1/2) values of 6.48 and 6.67 hours for the modified-release tablet and immediate-release capsule, respectively. With a geometric mean value of 507 ng·h/mL for $AUC_{0-\infty}$, systemic exposure to orismilast following administration of the modified-release tablet was comparable to the one of the immediate-release capsules (506 ng·h/mL). Statistical analyses comparing key PK parameters of orismilast for both formulations did not show any significant difference and it was concluded that the systemic exposure following administration of the modified-release formulation is not different from the one following the administration of the immediate-release formulation. It can therefore be reasonably assumed that the safety profile resulting from systemic effects can be extrapolated from studies having investigated the immediate-release formulation and in particular, study LP0058-1072, a Phase 2a study including 36 patients with moderate to severe psoriasis vulgaris.

In that study, patients received orismilast 30 mg BID immediate release or placebo for 16 weeks. The efficacy in psoriasis was confirmed on each predefined endpoint. No significant safety concerns were identified during the trial, and no adverse reaction not already seen with PDE4 inhibitors was reported. However, there was a high level of intolerance in the orismilast group. Most patients treated with orismilast had treatment-induced Aes related to GI functions, predominantly nausea and diarrhoea, throughout the treatment period. These tolerability issues resulted in half of the patients in the orismilast group being withdrawn from the trial. The hypothesis was that this high incidence of GI side effects was related to high local concentration of orismilast in the stomach, thus the formulation work to identify a slow-release formulation that would reduce local concentration of active compound in the stomach while preserving a similar systemic exposure for maintaining efficacy. Study LP0058-1442 in healthy volunteers has confirmed these characteristics by showing a similar PK profile and an improved safety profile. Following multiple dosing up to 60 mg BID, the orismilast modified-release tablet was safe and well-tolerated. There were no clinically relevant findings in the vital signs data, clinical laboratory evaluations, 12-lead ECG parameters, or physical examinations for any subject, and there were no deaths or SAEs during any part of the trial. A total of 113 Aes were reported: 12 Aes in 3 subjects randomized to placebo and 101 Aes in 9 subjects following administration of up to 60 mg orismilast BID modified-release tablet. Headache, nausea, dizziness, pain in extremity, and diarrheal were the most commonly reported Aes. Of the 14 adverse events of headache reported in subjects receiving orismilast, 6 occurred at the 40-mg dose level. Dizziness was only reported following dosing of 30 mg orismilast or above. Nausea was reported in 5 subjects receiving orismilast, with the majority of events occurring at the 60-mg dose level. Only 2 participants experienced nausea at a dose equal or lower to 40 mg, and these side effects lasted approximately 1 day before spontaneously disappearing, despite dosing and up-titration being maintained. It was thus concluded that 40 mg BID was the maximal tolerated dose with 30 mg BID being the target dose for further development.

Orismilast Modified Release Tablet Formulations Used in Clinical Trials

The following orismilast modified release tablet formulations were used in the clinical trials described in Examples 3, 4, 5, 8 and 13 herein

| Component | Amount | | |
|---|---|---|---|
| | 10 mg MR tablet | 20 mg MR tablet | 30 mg MR tablet |
| Orismilast[1] | 10 mg | 20 mg | 30 mg |
| Lactose monohydrate[2] | 233 mg | 223 mg | 213 mg |
| HPMC[3] | 52.5 mg | 52.5 mg | 52.5 mg |
| Anhydrous colloidal silica[4] | 1.5 mg | 1.5 mg | 1.5 mg |
| Magnesium stearate[5] | 3.0 mg | 3.0 mg | 3.0 mg |
| Core weight | 300 mg | 300 mg | 300 mg |
| Opadry® II [6] | 12 mg | 12 mg | 12 mg |
| Coated core weight | 312 mg | 312 mg | 312 mg |

[1] The orismilast was used as milled crystalline Form E with a D50 particle size distribution of <1 to 6 μm and a D(90) ≤ 10 μm
[2] Ph. Eur. 0187
[3] Hypromellose: Methocel™ K100 Premium LV DC2; 2% viscosity in water at 20° C. 80-120 mPa · s; methoxyl content 22-24%, and hydroxpropxyl content 7.5 to 9.5%
[4] Ph. Eur. 0434
[5] Ph. Eur. 0229
[6] Contain polyvinyl alcohol (Ph. Eur. 1961), macrogol (Ph. Eur. 1444), titanium dioxide (Ph. Eur. 0150), talc(Ph. Eur. 0438) and ferric oxide, yellow (NF).

Example 3: A Randomized, Double-Blind, Placebo-Controlled, Parallel-Group, Phase 2b Dose-Ranging Study to Evaluate the Efficacy and Safety of Orismilast in Adults with Moderate-to-Severe Plaque-Type Psoriasis The following phase 2b clinical trial was carried out:
Primary Objective:
To evaluate the efficacy and safety of a modified-release orismilast tablet versus placebo in adults with moderate-to-severe plaque-type psoriasis.
Primary Endpoint:
  Percentage change in Psoriasis Activity and Severity Index (PASI) score from Baseline at Week 16.
Key Secondary Endpoints
  Patients achieving 75% reduction in PASI (PASI75) response at Week 16.
  Patients achieving a score of Clear (0) or Almost Clear (1) and an at least 2-point improvement in Investigator Global Assessment (IGA) at Week 16.
Other Secondary Endpoints
  Patients achieving a score of Clear (0) or Almost Clear (1) and an at least 2-point improvement in IGA at Weeks 4, 8, 12, and 20.
  Patients achieving PASI75 response at Weeks 4, 8, 12, and 20.
  Patients achieving 50% reduction in PASI (PASI50) and 90% reduction in PASI (PASI90) response at Weeks 4, 8, 12, 16, and 20.
  Change from Baseline in PASI at Weeks 4, 8, 12, and 20.
  Change from Baseline in total Psoriasis Symptoms Scale (PSS) score at Weeks 4, 8, 12, 16, and 20.
  Change from Baseline in each individual item of the PSS at Weeks 4, 8, 12, 16, and 20.
  Change from Baseline in the affected body surface area (BSA) at Weeks 4, 8, 12, 16, and 20.
  Change from Baseline in Dermatology Life Quality Index (DLQI) score at Weeks 16 and 20.
  Patients experiencing psoriasis rebound by Week 20, defined as PASI≥125% of Baseline or new generalized pustular, erythrodermic, or more inflammatory psoriasis.
Safety Endpoints:
  The occurrence, severity, and seriousness of treatment-emergent adverse events (TEAEs) reported over the 16-week Treatment Period and the 4-week Follow-up Period.
  Changes from Baseline in physical examination; vital sign measurements (body temperature, respiration rate, heart rate, and systolic and diastolic blood pressure measurements); and body weight over the 16-week Treatment Period and the 4-week Follow-up Period.
  Changes from Baseline in electrocardiogram (ECG) findings over the 16-week Treatment Period and the 4-week Follow-up Period.
  Changes from Baseline in safety laboratory values (haematology, serum chemistry, and urinalysis) over the 16-week Treatment Period and the 4-week Follow-up Period.
  Hospital Anxiety and Depression Scale at each visit except Week 2.
  Columbia-Suicide Severity Rating Scale (C-SSRS) at each visit except Weeks 1 and 2.
Exploratory Endpoints:
  Change from Baseline in Physician's Global Assessment of Fingernails (PGA-F) at Week 16.
  Change in Scalp-Specific Investigator Global Assessment (ss-IGA) from Baseline at Week 16 in the subgroup of patients with Baseline score of at least 2 (mild scalp psoriasis).
  Change from Baseline of scalp itch Numeric Rating Scale (NRS) at Week 16 in the subgroup of patients with Baseline score of at least 4 on the 11-point NRS.
  Change from Baseline in joint pain NRS at Week 16 in patients with psoriatic arthritis (PsA) and a Baseline joint pain score of at least 4.
  Change in cardiovascular risk factors at Week 16. The following parameters will be collected: weight, body mass index, waist and hip circumferences, blood pressure, fasting serum glucose, triglycerides, cholesterol (total and high-density lipoprotein/low-density lipoprotein fractions), and C-reactive protein.

Change from Baseline in skin biomarkers at Week 16 collected via tape stripping and analysed using proteomic methods.

Plasma levels of the drug and its metabolites at scheduled visits.

Study Design

A multicentre, randomized, double-blind, placebo-controlled, parallel group, Phase 2b dose-ranging study designed to assess the efficacy and safety of modified-release orismilast compared with placebo in adult patients with moderate-to-severe plaque-type psoriasis. Efficacy and safety outcomes will be evaluated to select an appropriate orismilast dose for subsequent Phase 3 studies.

After a Screening visit up to 28 days before Baseline, 202 patients were assigned randomly in a 1:1:1:1 ratio to receive 1 of the 3 orismilast doses (20 mg, 30 mg, or 40 mg) or placebo twice daily (BID) for 16 weeks, with a 4-week Follow-up visit. Administration will begin at Baseline with a dose titration period. The maximum duration of study participation was approximately 24 weeks.

Patients were seen at the site on Screening, Baseline (Day 1), and Weeks 1, 2, 4, 8, 12, 16 (End-of-Treatment visit), and 20 (Follow-up visit, 4 weeks after treatment completion or discontinuation). Visits at Weeks 1 and 2 could be conducted via a telemedicine procedure at Investigator's discretion.

At Baseline and each visit from Week 4 onwards, PASI, BSA, IGA, and PSS were assessed. Quality of life was assessed by administration of DLQI at Baseline and at Weeks 16 and 20 visits. Additional efficacy parameters include: an ss-IGA, a Physician Global Assessment of fingernail psoriasis (PGA-F), and patient's joint pain NRS for those with a diagnosis of PsA. These parameters were assessed at Baseline and Weeks 16 and 20. Safety evaluations include adverse events (Aes), laboratory and vital sign assessments, physical examinations, as well as mood change evaluation by patient (Hospital Anxiety and Depression Scale) and suicidal ideation evaluation by Investigator (C-SSRS). A panel of cardiovascular risk factors were assessed at Baseline and Week 16.

Before administration of the study drug at Baseline and on Weeks 4, 8, and 16, blood was collected for orismilast concentration determination. In addition, non-invasive superficial skin sampling using tape stripping was conducted on a target lesion at Baseline and Week 16 in all patients proteomic analysis.

Inclusion Criteria

Patients are eligible to be included in the study only if all of the following criteria apply:
1. Capable of giving signed informed consent, which includes compliance with the requirements and restrictions listed in the Informed Consent Form (ICF) and in the protocol.
2. Male and female patients ≥18 years of age at the time of signing the ICF.
3. Body weight of >40 kg at the time of signing the ICF.
4. Diagnosis of chronic, stable plaque-type psoriasis at least 2 months before the Screening visit. If the patient is diagnosed with psoriasis arthritis, the arthritis should be stable.
5. Moderate-to-severe plaque-type psoriasis as defined by PASI≥12, BSA ≥10%, and IGA ≥3 at the screening and baseline visits.
6. Candidate for systemic antipsoriatic treatment or phototherapy.
7. Women of childbearing potential (WOCBP) must have a negative serum pregnancy test at the Screening visit and a negative urine pregnancy test at the Baseline visit. In addition, sexually active WOCBP must agree to use a highly effective method of contraception until at least 4 weeks after the end of study treatment.

Exclusion Criteria

Patients are excluded from the study if any of the following criteria apply:
1. Therapy-resistant psoriasis defined as ≥2 treatment failures due to inadequate efficacy within the past 5 years of any biologic therapies (including but not limited to etanercept adalimumab, infliximab, certolizumab pegol, guselkumab, secukinumab, risankizumab, ixekizumab, tildrakizumab, or ustekinumab) administered in adequate dose and duration according to the label or local/national guidelines (patients who stopped systemic treatment for reasons not related to lack of efficacy are not excluded).
2. Unstable psoriasis or PsA with acute deterioration within 4 weeks of the Screening visit.
3. History of allergy or hypersensitivity to any component of the study treatment.
4. Active infection (e.g., bacteria, viral, fungal) requiring treatment with systemic antibiotics within 4 weeks of the Screening visit.
5. Malignancy or history of malignancy except for treated (i.e., cured) basal cell skin carcinomas.
6. Current diagnosis of predominant guttate, erythrodermic, exfoliative, or pustular psoriasis, or of drug-induced psoriasis, or other skin conditions that might confound the evaluation of psoriasis vulgaris, as judged by the Investigator (e.g. AD, lupus).
7. Any recurrent medical condition associated with serious GI diseases, such as inflammatory bowel disease.
8. Any medical or psychiatric condition (e.g., current major depression with a score for depressive symptoms ≥15 of HADS at Baseline, schizophrenia, suicidal behaviour, psychiatric hospitalization within the prior year) which, in the Investigator's opinion, would preclude the patient from adhering to the protocol, completing the study per protocol, and/or would place the patient at unacceptable risk for receiving the investigational therapy.
9. Any therapies and systemic treatments which do not comply with the indicated washout interval.
10. Any previous treatment with orismilast or failure of treatment with apremilast or any other systemic PDE4 inhibitor.
11. Any condition, including laboratory or ECG abnormalities, that places the patient at unacceptable risk to participate in the study or confounds the ability to interpret data from the study.
12. Severe hepatic impairment based upon medical history and laboratory abnormalities (e.g., low albumin and abnormal bilirubin).
13. Any abnormalities in clinical laboratory tests at Screening, (low neutrophil count, low haemoglobin, low platelet count, low absolute lymphocyte count, high bilirubin, high alanine transferase or aspartate aminotransferase or high serum creatine.
14. History or evidence of hepatitis B virus (HBV) infection at Screening. Patients with positive hepatitis B surface antigen (HbsAg) are excluded. For patients with isolated positive antihepatitis B core antibody (HbcAb), hepatitis B surface antibody (HbsAb) result must also be positive to be considered for this study.
15. History or positive test result for hepatitis C virus (HCV) antibody, indicating ongoing infection, at Screening. Confirmatory testing for HCV RNA will be conducted for patients who have a positive test result. Patients who have a negative result for HCV RNA will be eligible to participate in the study.
16. History of positive HIV, or have congenital or acquired immunodeficiency (e.g., common variable immunodeficiency disease). Patients who are positive for HIV antibodies (HIV-1 or HIV-2) at Screening are excluded from the study.
17. Suicidal ideation or behaviour in the past 12 months as indicated by a positive response (yes) to questions 4 or 5 on the C-SSRS completed at the Screening visit or the C-SSRS completed at the Baseline visit.
18. Pregnant or breastfeeding.
19. History of alcohol or substance abuse within 6 months before Baseline that, in the opinion of the Investigator, will preclude participation in the study.
20. Institutionalized by court order or by local authority.

Treatments

Tablets were taken in the morning and in the evening approximately every 12 hours. The minimum time interval between 2 consecutive doses is 6 hours. The first dose of the study drug was taken in the evening of Day 1. The dosing schedule used is shown in Table 4:

TABLE 4

| ARM name: | Orismilast 20 mg BID | Orismilost 30 mg BID | Oriamilast 40 mg BID | Placebo |
|---|---|---|---|---|
| Name: | Orismilast | Orismilast | Orismilast | Placebo |
| Type: | | Drug | | |
| Dose formulation: | | 10 mg and 30 mg tablet or matching placebo tablet | | |
| Frequency: | | BID (approximately every 12 hours) | | |
| Administered | 2 × 10 mg orismilast tablets BID | 1 × 30 mg orismilast tablet and 1 × placebo tablet BID | 1 × 10 mg and 1 × 30 mg orismilast tablets BID | 1 × placebo tablets BID |
| Route: | | Oral | | |
| Use: | | Experimental | | Placebo |
| Sourcing: | | Provided centrally by the Sponsor | | |
| Packaging aad labeling: | | Investigational medicinal product will be provided in individually labeled wallet cards with blistered tablets. Each card will be labeled as required per country requirement | | |

Abbreviation: BID, twice daily.

Dose Titration

The orismilast modified release tablet doses were titrated over a period of a maximum of 2 weeks according to the schedule shown in Table 5:

TABLE 5

| | Day 1 (mg) | | Day 2 (mg) | | Day 3 (mg) | | Day 4 (mg) | | Day 5 (mg) | | Day 6 (mg) | | Day 7 (mg) | | Day 8 (mg) | |
|---|---|---|---|---|---|---|---|---|---|---|---|---|---|---|---|---|
| Arm | AM | | AM | PM | AM | PM | AM | PM | AM | PM | AM | PM | AM | PM | AM | PM |
| 20 mg BID | 10 | | 10 | 10 | 10 | 10 | 10 | 10 | 10 | 20 | 10 | 20 | 10 | 20 | 20 | 20 |
| 30 mg BID | 10 | | 10 | 10 | 10 | 20 | 20 | 20 | 20 | 20 | 20 | 30 | 20 | 30 | 20 | 30 |
| 40 mg BID | 10 | | 10 | 10 | 10 | 20 | 20 | 20 | 20 | 20 | 20 | 30 | 20 | 30 | 20 | 30 |
| Placebo | P | | P | P | P | P | P | P | P | P | P | P | P | P | P | P |

| | Day 9 (mg) | | Day 10 (mg) | | Day 11 (mg) | | Day 12 (mg) | | Day 13 (mg) | | Day 14 (mg) | | From Day 15 (mg) | |
|---|---|---|---|---|---|---|---|---|---|---|---|---|---|---|
| Arm | AM | PM | AM | PM | AM | PM | AM | PM | AM | PM | AM | PM | AM | PM |
| 20 mg BID | 20 | 20 | 20 | 20 | 20 | 20 | 20 | 20 | 20 | 20 | 20 | 20 | 20 | 20 |
| 30 mg BID | 30 | 30 | 30 | 30 | 30 | 30 | 30 | 30 | 30 | 30 | 30 | 30 | 30 | 30 |
| 40 mg BID | 30 | 30 | 30 | 30 | 30 | 30 | 30 | 40 | 30 | 40 | 30 | 40 | 40 | 40 |
| Placebo | P | P | P | P | P | P | P | P | P | P | P | P | P | P |

Efficacy Assessments

Psoriasis Area and Severity Index: The PASI is a measure of psoriatic disease severity, taking into account qualitative lesion characteristics (erythema, induration, and desquamation) and percentage of affected skin surface area on defined anatomical regions. The PASI is a validated instrument that is the most widely used tool for measurement of severity of psoriasis. Psoriasis Area Severity Index scores range from 0 to 72, with higher scores reflecting greater disease severity (Fredriksson et al., Dermatologica. 1978; 157(4):238-244). Erythema, induration/thickness, and scaling are scored on a scale of 0 (none) to 4 (very severe) on 4 anatomic regions of the body: head, trunk, upper limbs, and lower limbs. Degree of involvement on each of the 4 anatomic regions is scored on a scale of 0 (no involvement) to 6 (90% to 100% involvement). The total qualitative score (sum of erythema, thickness, and scaling scores) is multiplied by the degree of involvement for each anatomic region and then multiplied by a constant. The scores for each anatomic region are combined to yield the final PASI. Investigator Global Assessment: The IGA is a measure used by physicians to determine the patient's overall severity of disease. The static version (Langley et al., J Dermatolog Treat. 2015, February; 26(1):23-31) is used in this trial for measurement at a single point in time as indicated in the schedule of assessments. The Investigator will rate the severity of patient's psoriasis on a 5-point scale ranging from 0 (clear) to 4 (severe):

| Score | Definition |
| --- | --- |
| 0 = clear | No signs of psoriasis (postinflammatory hyperpigmentation may be present) |
| 1 = almost Clear | Normal to pink coloration of lesions<br>No thickening<br>No to mininal focal scaling |
| 2 = mild disease | Pink to light red coloration<br>Just detectable to mild thickening<br>Predominantly fine scaling |
| 3 = moderate disease | Dull to bright red. clearly distinguishable erythema<br>Clearly distinguishable to moderate thickening<br>Moderate scaling |
| 4 = severe disease | Bright to deep dask red coloration<br>Severe thickening with hard edges<br>Severe coarse scaling covering almost all of all lesions |

Scalp-specific Investigator Global Assessment: The ss-IGA assesses lesions on the scalp for degree of redness, thickness, and scaling on a 5—point scale, with 0 indicating absence of disease and 4 indicating severe disease.

Physician's Global Assessment of Fingernail Psoriasis: The PGA-F is used in this trial to evaluate abnormalities in the fingernails, and the severity of these, in patients with nail psoriasis. It is a simple and reliable clinician-rated scale, which is easy to use in clinical practice and research. The scale rates the overall condition of the fingernails and is based on a 5-point scale, with 0 indicating clear and 4 indicating severe.

Body Surface Area: The BSA assessment estimates the extent of disease or skin affected by psoriasis and is expressed as a percentage of total body surface. BSA will be determined by the Investigator or designee using the patient palm=1% BSA rule.

Patient-Reported Outcomes

Psoriasis Symptom Scale: The PSS is a 4-item patient-completed questionnaire (Rentz et al., J Patient Rep Outcomes. 2017; 1(1):4.). It is patient relevant, its domains are reliable and valid, and it takes few minutes to complete. The PSS assesses severity of pain, itching, redness, and burning during the past 24 hours using a 5-point severity scale from 0=none to 4=very severe.

Scalp Itch Numeric Rating Scale (NRS): itch will be assessed by requesting the patients to grade their worst scalp itch over the past 24 hours on a 11-point with an NRS with 0 corresponding to no itch and 10 to worst imaginable itch.

Arthritis Pain: Patients with a PsA diagnosis at Screening will assess their joint pain due to arthritis over the past 24 hours on a 11-point with an NRS with 0 corresponding to No pain and 10 to Worst imaginable pain.

Dermatology Life Quality Index: The DLQI is a 10-item validated questionnaire completed by the patient used to assess the impact of skin disease on the patient's QoL during the previous week. The 10 questions cover the following topics: symptoms, embarrassment, shopping and home care, clothes, social and leisure, sport, work or study, close relationships, sex, and treatment. Each question is scored from 0 to 3 ("not at all," "a little," "a lot," and "very much," respectively), giving a total score ranging from 0 to 30. A high score is indicative of a poor QoL.

Summary of Results 202 patients were randomized and treated for 16 weeks. In the phase 2b dose ranging study, a statistically significant treatment effect was observed for all doses of orismilast versus placebo for the percentage change in PASI from baseline to Week 16 (primary endpoint).

The mean percentage change in PASI from baseline to Week 16 was −52.6%, −61.2%, −63.7% and −17.3% on 20 mg twice-daily (BID), 30 mg BID, 40 mg BID and placebo, respectively.

The percentage of patients achieving PASI75, PASI90 and IGA 0/1 at Week 16 were higher in the two lowest dose groups of orismilast (20 mg and 30 mg) than in the 40 mg dose group when missing data at Week 16 was treated as non-response.

Figure 1B:
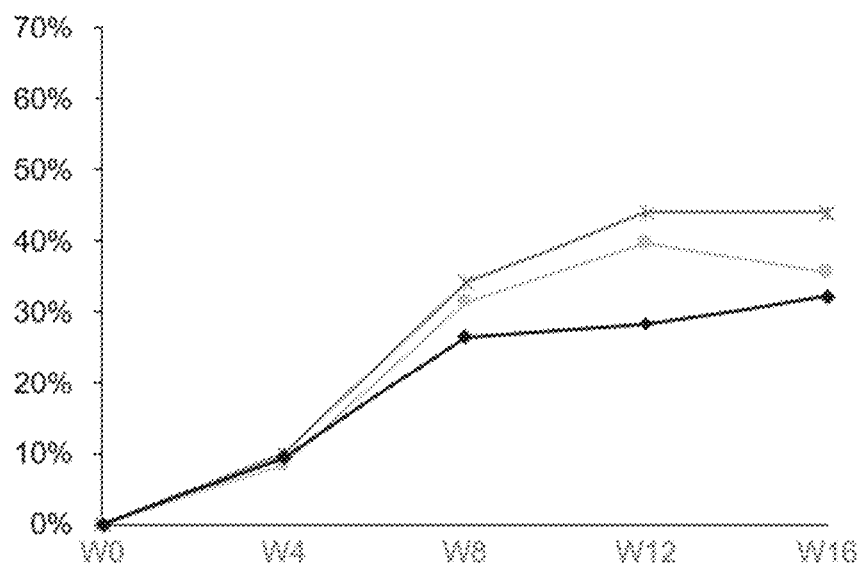

Analysis of the efficacy data shows that 20 mg and 30 mg BID treatment arms showed a similar efficacy in the first 8 weeks of treatment in both PASI-cl and PASI-75 groups (FIG. 1). This data also shows that the 30 mg BID dose provided a higher and more sustained response after week 8 in some patients.

Table 6 shows the most frequent treatment-emergent adverse events (occurring in ≥5% of subjects on orismilast) treated with 20 mg and 30 mg BID.

TABLE 6

| System-organ class | Adverse event | Placebo | Orismilast 20 mg | Orismilast 30 mg | Orismilast 40 mg |
| --- | --- | --- | --- | --- | --- |
| Gastro-intestinal | Diarrhea (incl. loose stool) | 3.9% | 37.5% | 48.0% | 45.3% |
| | Nausea | 3.9% | 22.9% | 38.0% | 41.5% |
| | Vomiting | 2.0% | 6.3% | 8.0% | 13.2% |
| | Abdominal pain upper | 0 | 2.1% | 6.0% | 11.3% |

TABLE 6-continued

| System-organ class | Adverse event | Placebo | Orismilast 20 mg | Orismilast 30 mg | Orismilast 40 mg |
|---|---|---|---|---|---|
| Nervous system | Headache | 5.9% | 12.5% | 26.6% | 20.8% |
| | Dizziness | 0 | 6.3% | 14.0% | 15.1% |

Table 7 shows the frequent treatment-emergent adverse events leading to treatment discontinuation in the 20 mg and 30 mg BID orismilast treatment arms.

TABLE 7

| System-organ class | Adverse event | Placebo | Orismilast 20 mg | Orismilast 30 mg | Orismilast 40 mg |
|---|---|---|---|---|---|
| Gastro-intestinal | Diarrhea (incl. loose stool) | 2.0% | 10.4% | 6.0% | 20.8% |
| | Nausea | 2.0% | 4.2% | 8.0% | 11.3% |
| | Vomiting | 0 | 0 | 2.0% | 5.7% |
| | Abdominal pain upper | 0 | 2.1% | 2.0% | 7.5% |
| Nervous system | Headache | 0 | 2.1% | 4.0% | 3.8% |
| | Dizziness | 0 | 2.1% | 2.0% | 1.9% |

Figure 2:
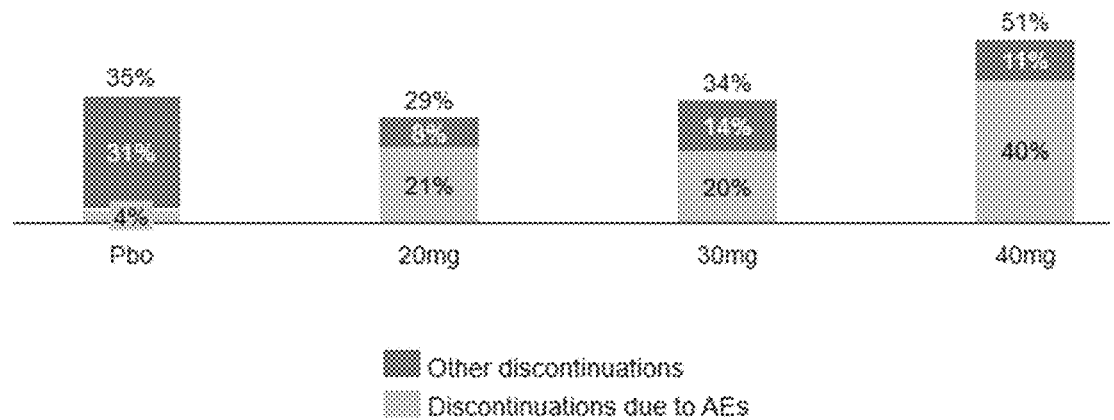
FIG. 2 shows the total % of patients discontinuing treatment and the split of discontinuations due to adverse events and other reasons for the placebo (Pbo), 20 mg BID, 30 mg BID and 40 mg BID orismilast treatment arms in the phase 2b clinical trial described in Example 3

The adverse events observed in the clinical trial were considered to be mild or moderate. The total % of patients discontinuing treatment and the split of discontinuations due to adverse events is shown in FIG. 2 for the placebo, 20 mg BID, 30 mg BID and 40 mg BID treatment arms. The discontinuations due to adverse events is similar in the patients treated with 20 and 30 mg orismilast BID (21% and 20% respectively). Only in the high 40 mg BID treatment group was the % of discontinuations higher than that observed in the placebo group.

Figure 3:
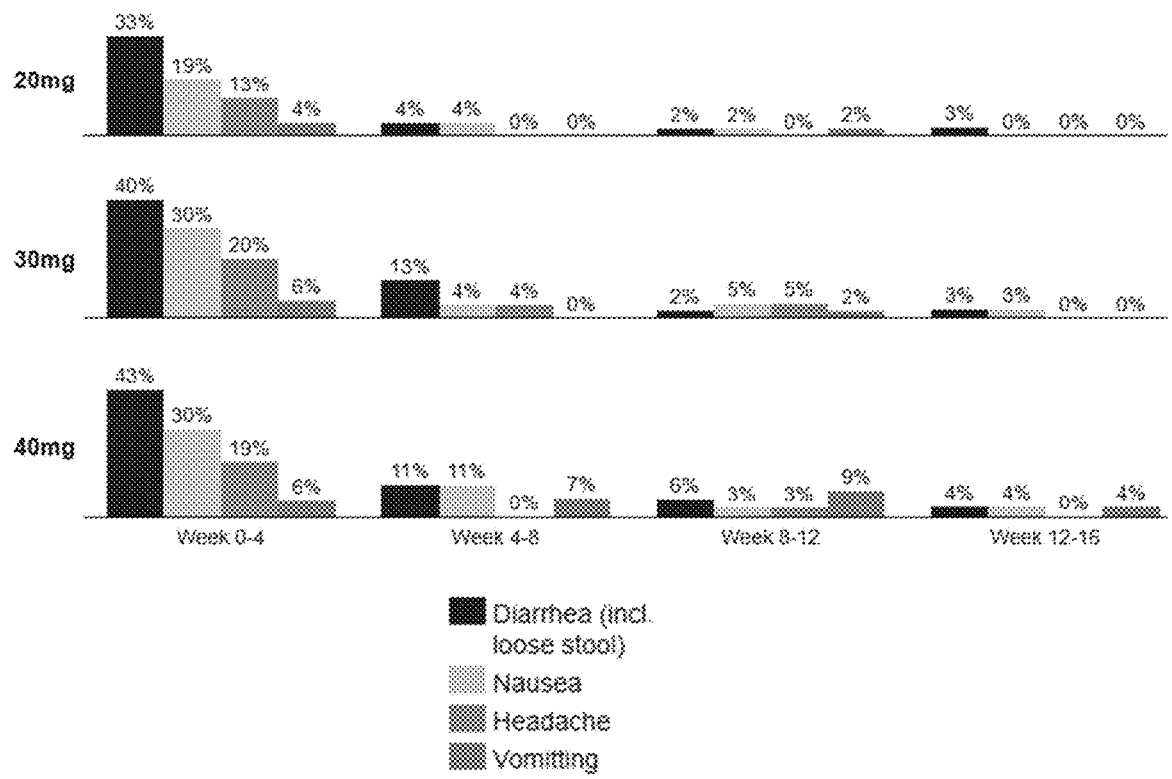
FIG. 3 shows the share of patients experiencing an adverse event with an onset in the treatment periods of 0-4 weeks, 4-8 weeks, 8-12 weeks and 12-16 weeks, for patients treated with 20 mg, 30 mg or 40 mg orismilast BID. The bars in each treatment period show patients that experienced diarrhoea, nausea, headache or vomiting.

Most of the observed gastrointestinal adverse events were transient and occurred before week 8 of treatment (FIG. 3), with the majority occurring during the first 4 weeks of treatment. As discussed above FIG. 1 shows that shows that 20 mg and 30 mg BID treatment arms showed a similar efficacy in the first 8 weeks. Accordingly, dose titration to a final maintenance dose during an initial treatment period (e.g. 2 to 8 weeks) may provide treatment efficacy, whilst also reducing undesirable side-effects and discontinuation of treatment.

Table 7a shows additional effects of orismilast treatment on a range of other parameters.

TABLE 7a

| Mean change from baseline Week 16 | Placebo (n-51) | 20 mg BID (n-48) | 30 mg BID (n-50) | 40 mg BID (n-53) |
|---|---|---|---|---|
| Weight (kg) | −0.2 | −2.6 | −2.8 | −3.1 |
| BMI (kg/m$^2$) | −0.1 | −0.9 | −0.9 | −1.0 |
| Waist circumference (cm) | −1.5 | −3.1 | −1.0 | −1.9 |
| Hip circumference (cm) | −1.0 | −0.9 | −2.8 | −3.4 |
| Systolic blood pressure (mmHg) | −2.4 | −1.1 | 2.1 | 1.5 |
| Diastolic blood pressure (mmHg) | −1.6 | −1.6 | 1.3 | 1.0 |
| Fasting serum glucose (mmol/L) | −0.3 | −0.2 | −0.2 | −0.1 |
| Triglycerides (mmol/L) | −0.1 | −0.2 | −0.1 | 0.2 |
| Cholesterol (mmol/L) | −0.1 | −0.2 | 0.0 | −0.1 |
| LDL cholesterol (mmol/L) | 0.2 | −0.1 | 0.0 | −0.2 |
| HDL cholesterol (mmol/L) | −0.1 | 0.0 | 0.0 | 0.0 |
| C Reactive Protein (mmol/L) | 3.0 | 3.4 | −33.1 | −27.2 |

Effects of Patient Weight on Response and Tolerability

Figure 4A:
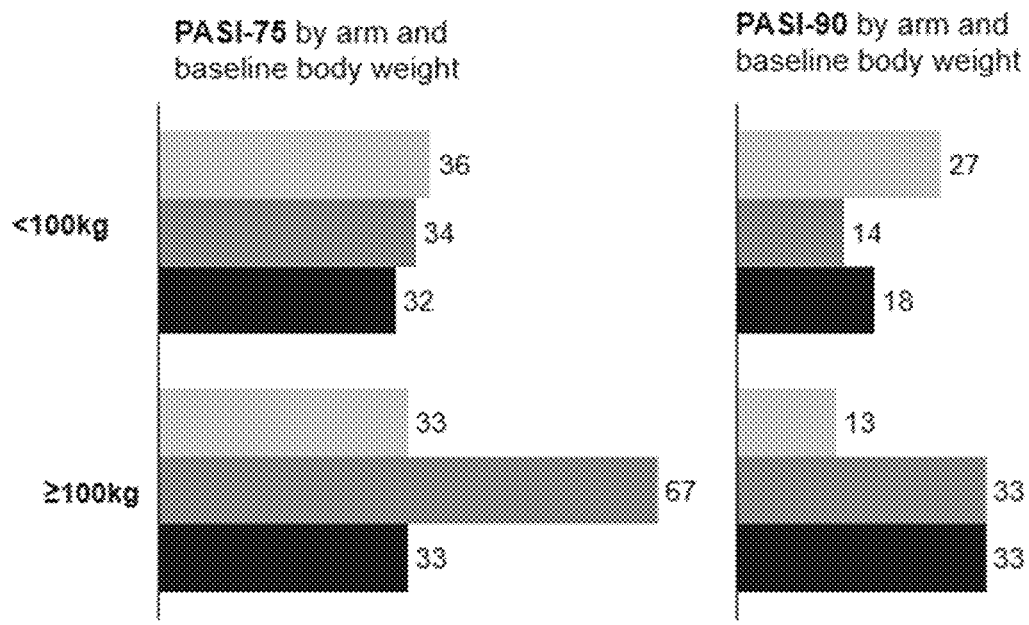
FIG. 4A shows the PASI-75 and PASI-90 values for patients with a body mass of less than 100 kg and greater than 100 kg treated with 20 mg, 30 mg or 40 mg orismilast BID.
Figure 4B:
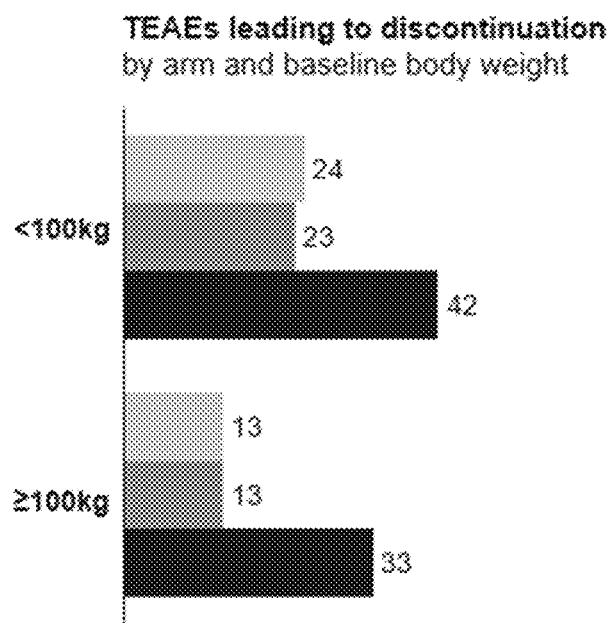
FIG. 4B shows the number of treatment related adverse events that led to patient discontinuation in each treatment arm for patients with a body mass of less than 100 kg and more than 100 kg.

Sub-group analysis of key responder endpoints indicated that patients with high body weight at baseline (≥100 kg) could benefit from 30 mg BID while 20 mg BID is a sufficient dose for lower body weight (<100 kg) patients (FIG. 4, panel 4A). However, patients with a body weight greater than or equal to 100 kg treated with 30 mg orismilast BID had a lower incidence of adverse events leading to discontinuation (FIG. 4, Panel 4B). These data suggest that patients with a body weight that is greater than or equal to 100 kg treated with 30 mg orismilast BID showed an improved treatment response, but without showing an increase in treatment discontinuations compared to treatment with 20 mg orismilast BID. These data also suggest that lighter patients (<100 kg) achieve a full treatment effect with 20 mg orismilast BID and do not benefit from treatment with the higher 30 mg orismilast BID dose.

Post-Hoc Analysis

A new treatment group was defined post-hoc consisting of all patients with baseline weight <100 kg in the orismilast 20 mg BID arm and all patients with baseline weight ≥100 kg in the orismilast 30 mg BID arm.

Figure 5A:
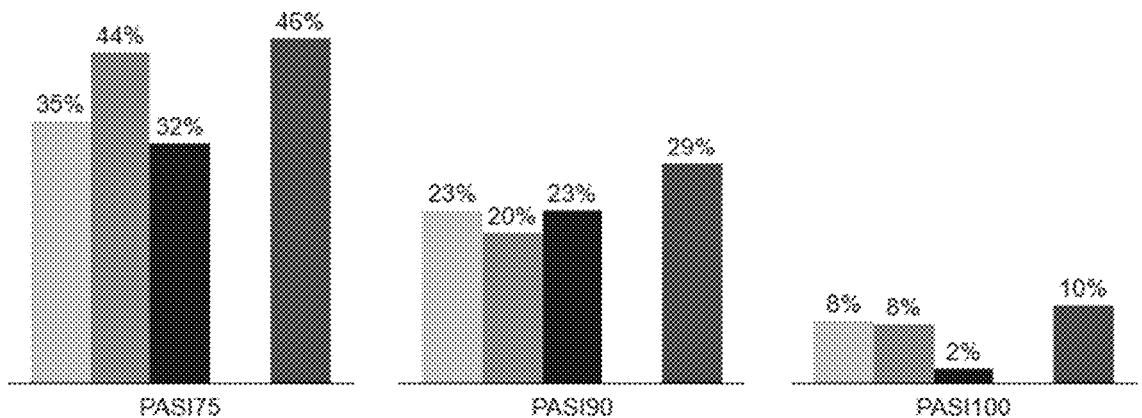
FIG. 5A shows a post-hoc analysis showing patients treated with 20 mg orismilast BID if they are less than 100 kg and 30 mg orismilast if they are greater than or equal to 100 kg ("20/30 mg BID"). These results are compared to the pre-specified treatment arms in the clinical trial (20 mg BID, 30 mg BID and 40 mg BID).
Figure 5B:
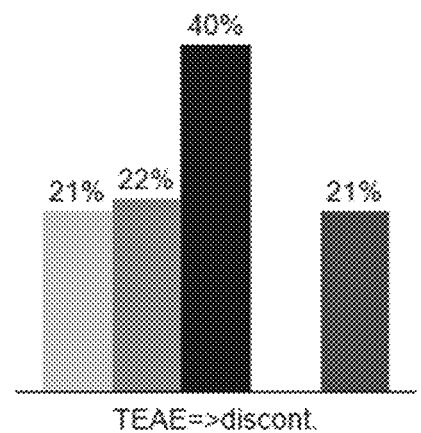
FIG. 5B shows the % of treatment-related adverse events leading to discontinuation for the post-hoc 20/30 mg BID treated patients and the pre-specified 20 mg BID, 30 mg BID and 40 mg BID treatment arms.

This new treatment group consisting of lighter patients (<100 kg) treated with 20 mg BID and heavier patients treated with 30 mg BID was analyzed similarly to the predefined treatment arms (of placebo, 20, 30, and 40 mg BID respectively) using non-responder imputation (NRI) for missing data. For this group as a whole, efficacy was improved relative to all pre-specified treatment arms (FIG. 5, panel 5A), while the rate of discontinuation remained similar to that observed in the 20 mg and 30 mg BID arms (FIG. 5, panel 5B) showing improved tolerability in heavier subjects treated with 30 mg orismilast BID. The improved responses were observed in each of the PASI-75, PAS-90 and PASI-100 responders. The results of the post-hoc analysis are shown in Table 8.

TABLE 8

| PASI-75 | | | PASI-90 | | | PASI-100 | | |
|---|---|---|---|---|---|---|---|---|
| 20 mg BID | 30 mg BID | 20 mg BID (<100 kg)/ 30 mg BID (≥100 kg) | 20 mg BID | 30 mg BID | 20 mg BID (<100 kg)/ 30 mg BID (≥100 kg) | 20 mg BID | 30 mg BID | 20 mg BID (<100 kg)/ 30 mg BID (≥100 kg) |
| 35% | 44% | 46% | 23% | 20% | 29% | 8% | 8% | 10% |

The findings discussed above indicate that:
(i) When assessing the total patient population subjects treated with 20 mg orismilast BID exhibit similar efficacy to subjects treated with 30 mg orismilast in the first 8 weeks of treatment,
(ii) the majority of side effects occurred in the first 8 weeks of treatment, the highest number occurring in the first 4 weeks of treatment;
(iii) heavier patients (100 kg) benefited from a higher 30 mg orismilast BID dosing without an increase in treatment discontinuations; and
(iv) patients less than 100 kg were adequately treated with 20 mg orismilast BID.

Figure 6:
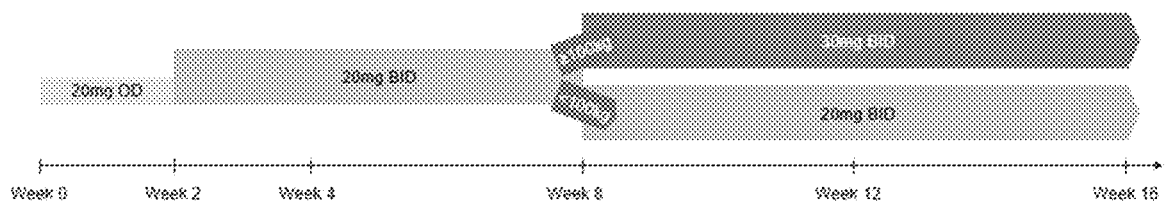
FIG. 6 shows a representative dosage regimen according to the present invention wherein 20 mg orismilast is administered once per day ("OD") for 2 weeks, followed by 20 mg orismilast twice per day for 6 weeks. The orismilast dose is increased to 30 mg twice per day for subjects with a body mass≥100 kg at week 8 of treatment, subjects with a body mass<100 kg are maintained on 20 mg orismilast twice per day.

Taken together these data support an orismilast dosage regimen wherein the initial orismilast dose is titrated up over an initial period (e.g. 2-8 weeks or more) followed by an increased maintenance dose for subjects with a body mass of ≥100 kg will maximise response to orismilast treatment and improve tolerability to the treatment. A representative dosage regimen is shown in FIG. 6.

Figure 7:
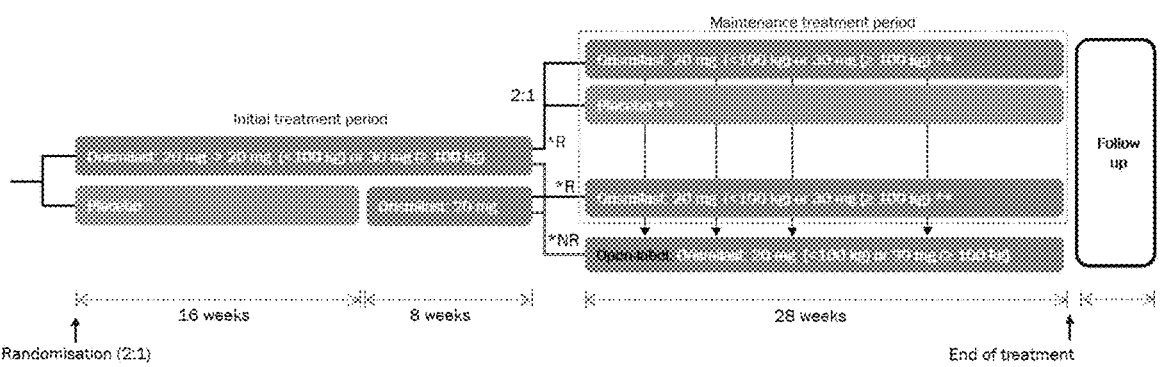
FIG. 7 shows the design of the phase 3 clinical study described in Example 4.

Example 4: A Randomised, Double-Blind, Placebo-Controlled, Phase 3 Study to Evaluate the Efficacy and Safety of Orismilast in Adult Patients with Moderate-to-Severe Plaque-Type Psoriasis The following phase 3 clinical trial can be carried out.
Primary Endpoints:
  Achieving sPGA of 0 (clear) or 1 (almost clear) at Week 16[1]
  Achieving PASI75 at Week 16
Secondary Endpoints:
  Achieving PASI90 at Week 16
  Achieving Scalp Specific Physician Global Assessment (ScPGA) of 0 (clear) or 1 (almost clear) at Week 16[2]
Secondary Endpoints:
[1] With at least 2-point improvement from baseline
[2] With at least 2-point improvement from baseline among patients with baseline score ≥3
  Achieving reduction of Dermatology Life Quality Index (DLQI) score of ≥4 points at Week 16[4]
  Achieving PASI100 at Week 16
  Achieving sPGA of 0 (clear) or 1 (almost clear) at Week 4, 8 and 12
  Achieving PASI75 at Week 4, 8 and 12
  Achieving PASI90 at Week 4, 8 and 12
Tertiary Endpoints:
  Percentage change in PASI from baseline to Week 4, 8, 12 and 16
  Change in PASI from baseline to Week 4, 8, 12 and 16
  Achieving PASI50 at Week 4, 8, 12 and 16
  Achieving PASI100 at Week 4, 8 and 12
  Achieving ScPGA of 0 (clear) or 1 (almost clear) at Week 4, 8 and 12[2]
  Change in the affected body surface area (BSA) from baseline to Week 4, 8, 12 and 16
  Achieving Static Physician Global Assessment of Genitalia (sPGA-G) of 0 (clear) or 1 (minimal) at Week 16
  Achieving Palmoplantar Psoriasis Physician Global Assessment (PPPGA) of 0 (clear) or 1 (almost clear) at Week 16
  Change in Itch Numerical Rating Scale (NRS)[3] from baseline to Week 2, 4, 8 and 16
  Achieving reduction of Itch NRS[3] of ≥4 points at Week 2, 4, 8 and 16[4]
  Change in scalp Itch NRS[3] from baseline to Week 2, 4, 8 and 16
  Achieving reduction of scalp Itch NRS[3] of ≥4 points at Week 2, 4, 8 and 16[4]
  Change in pain NRS[3] from baseline to Week 2, 4, 8 and 16
  Achieving reduction of pain NRS[3] of ≥4 points at Week 2, 4, 8 and 16[4]
  Change in WHO-5 total score from baseline to Week 16
  Achieving DLQI score of ≥4 points at Week 8[4]
  Achieving DLQI score of 0 or 1 at Week 8 and 16
  Change in DLQI from baseline to Week 8 and 16
  Change in EQ-5D-5L from baseline to Week 16
  Percentage change in body weight from baseline to Week 16
  Achievement of weight loss equal to or above 5% (yes/no) from baseline to Week 16 among patients with baseline BMI ≥30
  Achievement of weight loss equal to or above 10% (yes/no) from baseline to Week 16 among patients with baseline BMI ≥30
  Percentage change in $HbA_{1c}$ from baseline to Week 16
  Change to normoglycemia (yes/no) (Normoglycemia is defined as having $HbA_{1c}$ below 5.7% (below 39 mmol/mol)) from baseline to Week 16 among patients with baseline $HbA_{1c}$ 5.7-6.4% (39-47 mmol/mol)
  Achievement of $HbA_{1c}$ equal to or below 6.5% (yes/no) from baseline to Week 16 among patients with baseline $HbA_{1c}$ 6.5-7% (48-53 mmol/mol)
  Achievement of $HbA_{1e}$ equal to or below 7% (yes/no) from baseline to Week 16 among patients with baseline $HbA_{1c}$>7% (>53 mmol/mol)
  Change in waist circumference from baseline to Week 16
[3] Weekly average
[4] From baseline among patients with a baseline score ≥4
Safety Assessments:
  Number of TEAEs from Week 16 to Week 56
  Number of AESIs from Week 16 to Week 56
  Change from baseline in body weight, vital signs, laboratory tests and ECG during Week 24 to Week 52
  C-SSRS at Weeks 20, 24, 28, 34, 40, 46, 52, 56
  PHQ-8 at Weeks 20, 24, 28, 34, 40, 46, 52, 56.
Study Design This is a randomised (2:1), double-blind, placebo-controlled study to evaluate the efficacy and safety of orismilast monotherapy in adults with moderate-to-severe plaque-type psoriasis. The study will consist of a 52-weeks treatment period: an initial double-blind treatment period of 24 weeks and a double-blind maintenance/open-label treatment period of 28 weeks. The primary endpoints are assessed at Week 16. An off-treatment follow-up period for the assessment of safety and rebound effects is also included (Weeks 52 to 56). Patients not achieving a clinical response at Week 24 as well as those who meet certain criteria during maintenance treatment will be transferred to open-label orismilast treatment. A schematic of the trial design is provided in FIG. 7.
Screening Period (Day—28 to Day 0)

The screening period has a maximum duration of 4 weeks. The exact duration of the screening period for the individual patient depends on the length of any washout period needed, as specified in the exclusion criteria.
Initial Treatment Period (Week 0 to Week 24)

Following the screening period, approximately 540 patients will be randomised 2:1 to one of the following groups stratified by region (Europe, North America, and China), baseline disease severity (sPGA 3/4) and body weight (<100 kg, ≥100 kg):

Orismilast

Placebo

The orismilast dose regimen is described in detail below.

At Week 16, patients in the placebo arm will be switched to orismilast

Maintenance treatment period (Week 24 to Week 52)

Patients achieving a clinical response at Week 24 will continue into maintenance treatment that will continue until Week 52. Clinical response is defined as at least 75% reduction in PASI score from baseline (PASI75) or sPGA of 0 or 1.

Patients randomised to orismilast in the initial treatment period will be re-randomised 2:1 to one of the following groups stratified by region and sPGA response at Week 24 (sPGA 0/1 or sPGA >1):

Orismilast

Placebo

Patients randomised to placebo in the initial treatment period (and switched to orismilast at Week 16) who achieve a clinical response at Week 24 will continue on orismilast.

Transfer to Open-Label Treatment

Patients will be transferred from blinded maintenance treatment to open-label orismilast treatment if they meet the loss of effect criteria listed below. Transfer to open-label may occur at any visit while the patients is in the maintenance treatment period.

Patients with sPGA=0 at Week 24:
  PASI Week 24 improvement from baseline is reduced by >50% and sPGA 2 at two consecutive visits.

Patients with sPGA≥1 at Week 24:
  PASI Week 24 improvement from baseline is reduced by >50% and sPGA 3 at one visit.

Open-Label Treatment Period (Week 24 to Week 52)

Any patient that does not achieve clinical response at Week 24 will be treated with open-label orismilast.

Follow-Up Period (Week 52 to 56)

Patients will complete a 4-week off-treatment follow-up period for the assessment of safety and rebound.

Psoriasis Area and Severity Index (PASI)

The PASI is a measure of psoriatic disease severity taking into account qualitative lesion characteristics (erythema, thickness, and scaling) and degree of skin surface area involvement on defined anatomical regions. The PASI is a validated instrument that has become standard in clinical trials for psoriasis.

Psoriasis Area Severity Index scores range from 0 to 72, with higher scores reflecting greater disease severity (Fredriksson, 1978, supra). Erythema, thickness, and scaling are scored on a scale of 0 (none) to 4 (very severe) on 4 anatomic regions of the body: head, trunk, upper limbs, and lower limbs. Degree of involvement on each of the 4 anatomic regions is scored on a scale of 0 (no involvement) to 6 (90% to 100% involvement).

PASI score is the most extensively studied psoriasis clinical severity score and the most thoroughly validated according to methodological validation criteria (Puzenat 2010). While a PASI50 is already recognized as a meaningful improvement of the disease, PASI75 is considered the benchmark of primary endpoints for most clinical trials of psoriasis (Carlin et al. J Eur Acad Dermatol Venereol. 2010 April; 24 Suppl 2:10-6 2004 and Mrowitz Arch Dermatol Res. 2011 January; 303(1):1-10). However, in the new era of biologics, an improvement of 90% or better (PASI90 response) with respect to baseline Psoriasis Area and Severity Index (PASI) is considered as treatment success (Kirsten et al., Life (Basel). 2021 Oct. 28; 11(11):1151).

Static Physician Global Assessment (sPGA)

The sPGA is a measure used by physicians to determine the patient's overall severity of disease (Feldman et al. Ann Rheum Dis. 2005 March; 64 Suppl 2(Suppl 2):ii65-8; discussion ii69-73). The static version used in this, sPGA, determines psoriasis severity at a single point in time on a 5-point scale as clear (0), almost clear (1), mild (2), moderate (3), or severe (4). The sPGA is an average assessment of all psoriatic lesions based on characteristics for erythema I, induration (1) and scaling (S), as shown below (the average of the 3 characteristic scales i.e. (E+I+S)/3=total average, which is rounded to the nearest whole number, is the final sPGA score).

| Characteristics | Score and definition |
| --- | --- |
| Erythema (E) (averaged over the whole body) | 0 = No evidence of erythema, but post inflammatory hyper/hypopigmentation changes may be present<br>1 = Faint erythema<br>2 = Light red coloration<br>3 = Moderate red coloration<br>4 = Bright red coloration |
| Induration (I) (averaged over the whole body) | 0 = No evidence of plaque elevation<br>1 = Minimal plaque elevation, barely palpable, =0.25 mm<br>2 = Mild plaque elevation, slight but definite elevation, indistinct edge, =0.5 mm<br>3 = Moderate plaque elevation, elevated with distinct edges, =0.75 mm<br>4 = Severe plaque elevation, hard/sharp borders, ≥1 mm |
| Scaling (S) (averaged over the whole body) | 0 = No evidence of scaling<br>1 = Minimal; occasional fine scaling<br>2 = Mild; fine scale dominates<br>3 = Moderate; coarse scale predominates<br>4 = Severe; thick scale predominates |

Main Assessments

Investigator Assessments of Efficacy

Investigator Assessments of Efficacy are to be performed at protocol-specified visits, as specified in the Schedule of Study Procedures, Section 9.

Body Surface Area (BSA)

The BSA assessment estimates the extent of disease or skin involvement with respect to psoriasis and is expressed as a percentage of total body surface. The total BSA affected by plaque-type psoriasis will be estimated using the patient's palm=1% BSA rule.

The patient's palm is measured from the wrist to the proximal interphalangeal and thumb. The surface area of the whole body is made up of approximately 100 palms or "handprints".

The investigator will estimate the number of palms it takes to cover the psoriasis affected area. Adding up the number of palms will give a total estimate of the area covered by psoriasis.

Scalp Specific Physician Global Assessment (ScPGA)

The ScPGA is a measurement of overall scalp involvement by the Investigator at the time of evaluation. The ScPGA is a 5-point scale ranging from 0 (clear) to 4 (severe), incorporating an assessment of the severity of the three primary signs of the disease: erythema, scaling and plaque elevation (Van Voorhees et al., J Am Acad Dermatol. 2020 July; 83(1):96-103) as shown below. When making the assessment of overall scalp severity, the Investigator should factor in areas that have already been cleared (i.e., have scores of 0) and not just evaluate remaining lesions for severity, i.e., the severity of each sign is averaged across all areas of involvement, including cleared lesions. In the event of different severities across signs of psoriasis, the sign that is the predominant feature of psoriasis should be used to help determine the ScPGA score.

| Score | Category | Description |
|---|---|---|
| 0 | Clear | Scalp Plaque Elevation = 0 (no elevation over normal skin) |
|   |   | Scalp Scaling = 0 (no evidence of scaling) |
|   |   | Scalp Erythema = 0 (except for residual hyperpigmentation/hypopigmentation) |
| 1 | Almost Clear | Scalp Plaque Elevation = ±(possible but difficult to ascertain whether there is a slight elevation above normal skin) |
|   |   | Scalp Scaling = ±(surface vith some de anation) |
|   |   | Scalp Erythema = ±(faint,diffuse pink or slight red coloration) |
| 2 | Mild | Scalp Plaque Elevation = slight (slight but definite elevation, typically edges are indistinct or sloped) |
|   |   | Scalp Scaling = fine (fine scale partially or mostly covering lesions) |
|   |   | Scalp Erythema = mild (light red coloration) |
| 3 | Moderate | Scalp Plaque Elevation = marked (marked definite elevation with rough or sloped edges) |
|   |   | Scalp Scaling = coarser (coarser scale covering most or all of the lesions) |
|   |   | Scalp Erythema = moderate (definite red coloration) |
| 4 | Severe | Scalp Plaque Elevation = marked (marked elevation typically with hard of sharp edges) |
|   |   | Scalp Scaling = coarser (coarse, non tenacious scale predominates covering most of all of the lesions) |
|   |   | Scalp Erythema = severe (very bright red coloration) |

Static Physician Global Assessment of Genitalia (sPGA-G™)

The sPGA-G is a measure used by physicians to determine the degree of erythema, plaque elevation and scale in the genital area. Severity is determined by a combination of the three plaque characteristics (erythema, elevation, and scale) based on descriptions of each characteristic. Erythema is the primary characteristic that should influence the rating, with plaque elevation and scaling considered secondarily (Merola et al.). Assessment does not require all three characteristics to be present. The Investigator rates the severity of lesions at a given time point over in the genital area using a 6-point numeric rating scale ranging from 0 (clear) to 5 (very severe), as shown below.

| Score | Category | Description |
|---|---|---|
| 0 | Clear | Erythema: residual or no erythema |
|   |   | Plaque elevation: no elevation |
|   |   | Scaling: no scale |
| 1 | Minimal | Erythema: faint, light pink erythema |
|   |   | Plaque elevation: elevation is very slight and difficult to confirm |
|   |   | Scaling: some fine, white surface dryness |
| 2 | Mild | Erythema: mild, pink erythema |
|   |   | Plaque elevation: slight elevation with sloped edges |
|   |   | Scaling: fine scale on some or most lesions |
| 3 | Moderate | Erythema: moderate, red erythema |
|   |   | Plaque elevation: moderate elevation with definite edges that are either sloped or rough |
|   |   | Scaling: coarse scale on most lesions |
| 4 | Severe | Erythema: severe, bright red erythema |
|   |   | Plaque elevation: substantial elevation, hard or sharp edges |
|   |   | Scaling: coarse, non-adherent scale on most to all lesions |
| 5 | Very severe | Erythema: very severe, deep red erythema |
|   |   | Plaque elevation: very significant elevation with hard and sharp edges |
|   |   | Scaling: very coarse, thick, and adherent scale completely or nearly completely covering most to all lesions |

Palmoplantar Psoriasis Physician Global Assessment (PPPGA)

The PPPGA is a measure used by physicians to determine the patient's overall severity of palmoplantar psoriasis. The Investigator will rate the severity of patient's palmoplantar psoriasis on a 5-point scale ranging from clear (0) to severe (4), as shown below (Bissonnette et al., J Am Acad Dermatol. 2016 July; 75(1):99-105).

| Score | Category | Definition |
|---|---|---|
| 0 | Clear | No signs of plaque psoriasis on hands and/or feet |
| 1 | Almost clear | Just perceptible erythema and just perceptible scaling on the hands and/or feet |
| 2 | Mild | Light-pink erythema with minimal scaling with or without pustules on hands and/or feet |
| 3 | Moderate | Dull-red, clearly distinguishable erythema with diffuse scaling and thickening of the skin, with or without fissures, and with or without pustule formation on the hands and/or feet |
| 4 | Severe | Deep-/dark-red erythema with clearly obvious and diffuse scaling and thickening, and numerous |

| Score | Category | Definition |
|---|---|---|
| | | fissures with or without pustule formation on the hands and/or feet |

Patient-Reported Outcomes

Whole body itch and pain numeric rating scales (NRS)

A self-administered, 11-point numeric rating scale (NRS, 0-10) will be used daily to evaluate the patient's assessment of their current pain and itching.

Respondents will answer the following questions for the assessment of:

Pain: Overall, how severe was your psoriasis-related pain over the past 24 hours?

Itching: Overall, how severe was your psoriasis-related itch over the past 24 hours?

Scalp itch numeric rating scale (NRS)

A self-administered, 11-point numeric rating scale (NRS, 0-10) will be used to evaluate the patient's assessment of their current scalp itch.

Respondents will answer the following questions for the assessment of:

Please rate the itching severity of your scalp due to your psoriasis by circling the number that best describes your worst level of itching in the past 24 hours.

Dermatology Life Quality Index (DLQI)

The DLQI© is a validated 10-item general dermatology disability index designed to assess Health-related quality of life (HRQoL) in adult patients with skin diseases such as eczema, psoriasis, acne, and viral warts (Finlay and Khan Clin Exp Dermatol. 1994; 19(3):210-216).

The measure is self-administered and includes domains of daily activities, leisure, personal relationships, symptoms and feelings, treatment, and work/school. The measure is widely used: it has been tested across 33 different skin conditions and is available in 85 languages.

The DLQI© is the most frequently used instrument in randomized controlled studies in dermatology.

The recall period is the previous week, and the instrument takes 1 to 2 minutes to complete.

Each item has 4 response categories ranging from 0 (not at all) to 3 (very much). "Not relevant" is also a valid response and is scored as 0. The DLQI© total score is a sum of the 10 questions. Scores range from 0 to 30, with higher scores indicating greater HRQoL impairment. Each subscale of the DLQI© may also be analysed separately.

EuroQol Quality of Life 5-Dimension-5 five-level (EQ-5D-5L)

The EQ-5D-5L© is a generic instrument developed by the EuroQoL group to assess patients' health status for clinical and economic appraisal, which was introduced in 1990 (The EuroQol Group 1990). Available in over 100 official language versions, it provides a simple descriptive profile and a single index value for health status. The recall period is "today", and the instrument takes 1 to 2 minutes to complete. The instrument essentially consists of 2 pages—the EQ-5D-5L© descriptive system and the EQ visual analogue scale. The EQ-5D-5L© descriptive system comprises the following 5 dimensions: mobility, self-care, usual activities, pain/discomfort and anxiety/depression. Each dimension has 5 response levels: no problems, slight problems, moderate problems, severe problems and unable. The patient is asked to indicate the patient's health state by ticking (or placing a cross) in the box against the most appropriate statement in each of the 5 dimensions. A unique health state is defined by combining one level from each of the 5 dimensions. Health states may be converted into a single number, called weighted index, by applying values (also called weights) to each of the levels in each dimension (Dolan et al 1997). The weighted index constitutes a measure of utility.

The VAS records the respondent's self-rated health on a vertical 20-cm VAS where the endpoints are labelled "best imaginable health state" and "worst imaginable health state." This information can be used as a quantitative measure of health outcome as judged by the individual respondents.

WHO-5

The 5-item World Health Organization Well-Being Index (WHO-5) is a short and generic global rating scale measuring subjective well-being. Because the WHO considers positive well-being to be another term for mental health, the WHO-5 only contains positively phrased items.

The WHO-5 items are: (1) 'I have felt cheerful and in good spirits', (2) 'I have felt calm and relaxed', (3) 'I have felt active and vigorous', (4) 'I woke up feeling fresh and rested' and (5) 'My daily life has been filled with things that interest me'.

The respondent is asked to rate how well each of the 5 statements applies to him or her when considering the last 14 days. Each of the 5 items is scored from 5 (all of the time) to 0 (none of the time). The raw score therefore theoretically ranges from 0 (absence of well-being) to 25 (maximal well-being). Because scales measuring health-related quality of life are conventionally translated to a percentage scale from 0 (absent) to 100 (maximal), it is recommended to multiply the raw score by 4.

Safety Assessments

Safety assessments are to be performed at protocol-specified visits.

AEs will be collected throughout the study. AESI will be defined as below:

Any TEAE assessed as ≥Grade 3 (_Grade 2 for the SOC of Cardiac Disorders) according to CTCAE v. 5

Any AE of occurrence of suicidal ideation or behaviour, including a positive response to question 1 to 5 of C-SSRS A depression assessed as moderately severe or worse by the Investigator or a PHQ-8 score ≥15

Any grade 3 or higher psychiatric condition

Any weight loss >5% compared to Baseline

Any transaminase level (ALT or AST) at Grade 3 (level >5 times ULN)

Vital signs will include body temperature, respiration rate, heart rate, and systolic and diastolic blood pressure measurements. All vital signs will be measured after the patient has been resting in a sitting position for at least 5 minutes. Blood pressure measurements are to be taken in the same arm for the duration of the study.

Body weight must be measured with one decimal (with an empty bladder, without shoes and only wearing light clothing). The body weight should be assessed on the same calibrated weighing scale equipment throughout the study, if possible. Height (without shoes) will be recorded at Baseline with one decimal.

The waist circumference is defined as the minimal abdominal circumference located midway between the lower rib margin and the iliac crest. Waist circumference is measured in the horizontal plane and rounded up or down to the nearest 1% cm or ⅛ inch using a non-stretchable measuring tape. The same measuring tape should be used throughout the study. The circumference should be measured when the patient is in a standing position, with an empty bladder and wearing light clothing.

A complete physical examination will include a check of the head, eyes, ears, nose and throat; heart; lungs; abdomen; skin; cervical and axillary lymph nodes; and neurological and musculoskeletal systems. A limited physical examination is performed to verify continued patient eligibility and to follow up regarding any change in medical condition.

ECG will be performed as a single-measurement 12-lead, resting ECG.

Laboratory assessment samples are to be obtained at designated visits as detailed in the Schedule of Study Procedures, Section 9. Patients should be in fasting condition (no food or fluids other than water for 6 hours) before sample collection at Baseline, Week 16, Week 24 and Week 52.

Samples will be analysed at a central laboratory facility which will define normal ranges and alert levels. Urine samples will be analysed by dipstick at site; if the results of the dipstick indicate abnormalities a urine sample will be collected for microscopic analysis to be performed at a central laboratory for further investigation.

Screening or Baseline there are "yes" answers on items 4 or 5 in the past year, the patient will not be included in the study.

Any patient with a positive response on the C-SSRS (answers "yes" to questions 1-5) should be referred to a mental health specialist (psychiatrist or clinical psychologist) for further evaluation, and the study medication should be paused. After a mental health specialist evaluation, the final decision on restarting or permanently discontinuing study treatment will be at the discretion of the Investigator in consultation with the mental health specialist. These cases should be reported as an Adverse Events of Special Interest (AESI).

Patient Health Questionnaire-8 (PHQ-8)

The Patient Health Questionnaire-8 (PHQ-8) is an eight-item questionnaire established as a valid diagnostic and severity measure for depressive disorders in large clinical studies (Kroenke et al., J Affect Disord. 2009; 114(1-3):163-173). Each of the 8 questions is based on a 2-week recall and scored on a scale of 0 to 3 by a tick box as: Not at All, Several Days, More than Half the Days, and Nearly Every Day. A score of ≥10 is suggestive of moderate depressive

| Haematology | Serum Chemistry | Urinalysis (Dipstick) |
|---|---|---|
| Full and differential blood count | Albumin | Appearance |
| Hct | ALT | pH |
| Hb | ALP | Protein |
| MCH | AST | Glucose |
| MCHC | BUN or urea | Ketone bodies |
| MCV | Creatinine | Indicators of blood and |
| Platelet count | Electrolytes (sodium, | WBCs |
| RBC count | potassium, chloride, | Specific gravity |
| WBC count with differential | calcium, phosphorus) | Urine hCG (premenopausal |
| (neutrophils, lymphocytes, | GGT | females only) |
| monocytes, eosinophils, | LDH | Urobilinogen |
| and basophils) | Total bilirubin | |
| | Direct bilirubin | |

| Cardiovascular Risk Factors (fasting condition) | Other Screening Tests |
|---|---|
| CRP | HIV antibody |
| Glucose | HBV |
| $HbA_{1c}$ | HCV |
| Total cholesterol | HbsAg |
| HDL | HbcAb |
| LDL | HBsAb |
| Triglycerides | FSH (confirmatory test for female patients in a postmenopausal status defined as cessation of menses for at least 12 months without an alternative medical cause) |

Pregnancy test: A serum pregnancy test will be performed on all women of childbearing potential at Screening, and a urine pregnancy test will be performed at all other visits.
Abbreviations: ALP, alkaline phosphatase; ALT, alanine aminotransferase; AST, aspartate aminotransferase; BUN, blood urea nitrogen; GGT, gamma-glutamyl transpeptidase; CRP, c-reactive protein; hCG, human chorionic gonadotropin; Hb, haemoglobin; $HbA_{1c}$, haemoglobin $A_{1c}$; Hct, haematocrit; HBcAb, hepatitis B core antibody; HBsAb, hepatitis B surface antibody; HBsAg, hepatitis B surface antigen; HBV, hepatitis B virus; HCV, hepatitis C virus; HDL, high-density lipoprotein; HIV, human immunodeficiency virus; LDL, low-density lipoprotein; LDH, lactate dehydrogenase; MCH, mean corpuscular haemoglobin; MCHC, mean corpuscular haemoglobin concentration; MCV, mean corpuscular volume; RBC, red blood cell; WBC, white blood cell.

Columbia-Suicide Severity Rating Scale (C-SSRS)

The C-SSRS, Investigator administered version, was designed to provide a prospective, standardized measure of suicidality. The scale allows clinicians and researchers alike to assess the severity and lethality of suicidal behaviours and ideations and can be used to monitor treatment outcomes and establish suicide risk in a variety of research and clinical settings. Requiring approximately 5 min for completion, the C-SSRS is administered in the form of a clinical interview. This C-SSRS is available in 2 versions: 1 for use at Screening referring to the past year and 1 for use throughout the rest of the study referring to the time since the prior visit. If, at symptoms (Dhingra et al. Population Health Metrics. 2011; 9:11. doi:10.1186/1478-7954-9-11), see tables below.

| Over the last 2 weeks, how often have you been bothered by any of the following problems? | Not at all | Several days | More than half the days | Nearly every day |
|---|---|---|---|---|
| 1. Little interest or pleasure in doing things | 0 | 1 | 2 | 3 |
| 2. Feeling down, depressed, or hopeless | 0 | 1 | 2 | 3 |

| Over the last 2 weeks, how often have you been bothered by any of the following problems? | Not at all | Several days | More than half the days | Nearly every day |
|---|---|---|---|---|
| 3. Trouble falling or staying asleep, or sleeping too much | 0 | 1 | 2 | 3 |
| 4. Feeling tired or having little energy | 0 | 1 | 2 | 3 |
| 5. Poor appetite or overeating | 0 | 1 | 2 | 3 |
| 6. Feeling bad about yourself, or that you are a failure, or have let yourself or your family down | 0 | 1 | 2 | 3 |
| 7. Trouble concentrating on things, such as reading the newspaper, or watching television | 0 | 1 | 2 | 3 |
| 8. Moving or speaking so slowly that other people could have noticed? Or the opposite, being so fidgety or restless that you have been moving around a lot more than usual | 0 | 1 | 2 | 3 |

| Total Score | Depression Severity |
|---|---|
| 0-4 | no significant depressive symptoms |
| 5-9 | mild depressive symptoms |
| 10-14 | moderate depressive symptoms |
| 15-19 | moderately severe depressive |
| 20-24 | severe depressive symptoms |

Study Population
Inclusion Criteria
1. Capable of giving signed informed consent, which includes compliance with the requirements and restrictions listed in the Informed Consent Form (ICF) and in the protocol.
2. Male and female patients ≥18 years of age at the time of signing the ICF.
3. Body weight of >40 kg at the time of signing the ICF.
4. Diagnosis of chronic, stable plaque-type psoriasis at least 2 months before the Screening visit. If the patient is diagnosed with psoriatic arthritis, the arthritis should be stable.
5. Moderate-to-severe plaque-type psoriasis as defined by PASI >12, BSA 10%, and sPGA ≥3 at the screening and baseline visits.
6. Candidate for systemic antipsoriatic treatment or phototherapy.
7. Women of childbearing potential (WOCBP) must have a negative serum pregnancy test at the Screening visit and a negative urine pregnancy test at the Baseline visit. In addition, sexually active WOCBP must agree to use an effective method of contraception until at least 4 weeks after the end of study treatment.

Exclusion Criteria
1. Non-plaque forms of psoriasis (including guttate, erythrodermic, or pustular) or drug-induced psoriasis.
2. Psoriatic arthritis with acute deterioration during the Screening phase.
3. History of allergy or hypersensitivity to any component of the study treatment.
4. Active infection (e.g., bacteria, viral, fungal) requiring treatment with systemic antibiotics within 4 weeks of the Screening visit.
5. Malignancy or history of malignancy except for treated (i.e., cured) basal cell skin carcinomas and successfully treated malignancies with no recurrence within five years from enrolment.
6. Active ongoing inflammatory diseases or skin conditions other than psoriasis that might confound the evaluation of orismilast or likely to require systemic anti-inflammatory drugs during the study.
7. Any medical or psychiatric condition (e.g., at least moderately severe depression (PHQ-8 ≥15), schizophrenia, suicidal behaviour, psychiatric hospitalization within the prior year) which, in the Investigator's opinion, would preclude the patient from adhering to the protocol, completing the study per protocol, and/or would place the patient at unacceptable risk for receiving the investigational therapy.
8. Patient has current or planned concurrent use of the following therapies that may have a possible effect on psoriasis during the course of the treatment phase of the trial:
   a. Topical therapy within 2 weeks of randomization (including but not limited to topical corticosteroids, topical retinoid or vitamin D analog preparations, tacrolimus, pimecrolimus, or anthralin/dithranol).
   b. Conventional systemic therapy for psoriasis within 4 weeks prior to randomization (including but not limited to deucravacitinib, cyclosporine, corticosteroids, methotrexate, oral retinoids, mycophenolate, thioguanine, hydroxyurea, sirolimus, sulfasalazine, azathioprine, or fumaric acid esters).
   c. Biologics (including cell depleting therapies but excluding TNF inhibitors) for psoriasis within 6 months prior to randomization (including but not limited to guselkumab, tildrakizumab, bimekizumab, risankizumab, secukinumab, ustekinumab, brodalumab, ixekizumab).
   d. TNF inhibitor(s) for psoriasis within 3 months prior to randomization (including but not limited to etanercept, adalimumab, infliximab, certolizumab).
   e. Phototherapy treatment of body within 4 weeks prior to randomization (i.e., ultraviolet B [UVB], psoralen and ultraviolet A [PUVA] radiation).
   f. Use of any investigational drug beginning 4 weeks prior to randomization, or 5 pharmacokinetic/pharmacodynamic half-lives, if known (whichever is longer).
   g. Use of any Chinese herbal medicine beginning 4 weeks prior to randomization.
9. Patient had prior treatment with orismilast.
10. Patient had previous experience with other systemic PDE4 inhibitors having led to premature treatment discontinuation because of tolerability issues.
11. Any condition, including laboratory or ECG abnormalities, that places the patient at unacceptable risk to participate in the study or confounds the ability to interpret data from the study.
12. Moderate to severe hepatic impairment based upon Child-Pugh system (score ≥7).
13. Any of the following abnormalities in clinical laboratory tests at Screening, as assessed by the study-specific laboratory and confirmed by a single repeat, if deemed necessary:
   a. Absolute neutrophil count of $<1.5 \times 10^9$/L ($<1500$/mm$^3$)
   b. Haemoglobin of <10.0 g/dL or haematocrit <30%
   c. Platelet count of $<100 \times 10^3$ cells/mm$^3$ (SI: $<100 \times 10^9$ cells/L).
   d. Absolute lymphocyte count of $<0.8 \times 10^9$/L ($<800$/mm$^3$)

e. Total bilirubin >1.5×the upper limit of normal (ULN); except patient with a known history of Gilbert's syndrome.
f. Alanine aminotransferase or aspartate aminotransferase >2.5× the ULN.
g. Creatinine clearance of <30 mL/min (calculated using the CKD-EPI Creatinine Equation).
14. Active hepatitis B or C virus infection at Screening. Patients with isolated hepatitis B antibody resulting from vaccination can be included.
15. History of positive HIV. Patients who are positive for HIV antibodies (HIV-1 or HIV-2) at Screening are excluded from the study.
16. Suicidal ideation or behaviour in the past 12 months as indicated by a positive response (yes) to questions 4 or 5 on the C-SSRS completed at the Screening visit or the C-SSRS completed at the Baseline visit.
17. Pregnant or breastfeeding.
18. History of alcohol or substance abuse within 6 months before Baseline that, in the opinion of the Investigator, will preclude participation in the study.
19. Institutionalized by court order or by local authority.

Rationale for Study Population

The study population will consist of a representative group of male and female patients (≥18 years old) with moderate-to-severe chronic plaque-type psoriasis and candidates for systemic treatment. Moderate-to-severe chronic plaque-type psoriasis is defined by a total PASI score of 12 and a body surface area (BSA) of ≥10% and an sPGA ≥3 in line with expectation from FDA.

Study Intervention(s) and Concomitant Therapy
Study Intervention(s) Administered All investigational products will be provided in blister cards throughout the entire study. Orismilast will be provided as 20 mg and 30 mg modified release tablets. Placebo will be provided as identically appearing tablets.

All investigational products will be taken orally BID, approximately 12 hours apart, without restriction of food or drink, though it is advised that the patient eat smaller, less fatty and more frequent meals to prevent gastrointestinal side effects. To mitigate potential gastrointestinal (GI) side effects, dose titration will be implemented.

All patients assigned to orismilast will receive 20 mg QD for the first 2 weeks (placebo in the morning and orismilast in the evening), then 20 mg BID for 6 weeks and thereafter patients with a body weight of less than 100 kg at randomisation will continue on 20 mg BID while patients with a body weight of 100 kg or more at randomisation will receive 30 mg BID. Patients assigned to placebo will receive placebo BID. Thus, the dosing regimen will be as shown below:

| Arm | Subject Weight | Day 1 | | Day 2-14 (Week 0-2) | Day 15-56 (Week 2 to 8) | | From Day 57 (Week 8 and onwards) | |
|---|---|---|---|---|---|---|---|---|
| Orismilast | <100 kg | 20 mg | P | 20 mg | 20 mg | 20 mg | 20 mg | 20 mg |
| Orismilast | ≥100 kg | 20 mg | P | 20 mg | 20 mg | 20 mg | 30 mg | 30 mg |
| Placebo | All | P | P | P | P | P | P | P |

Alternative Dosage Regimen

Also contemplated is the dosage regimen wherein subjects are dosed according to the weight-based dosage regimen below:

| Arm | Subject Weight | Day 1 | | Day 2-14 (Week 0-2) | Day 15-56 (Week 2 to 8) | | From Day 57 (Week 8 and onwards) | |
|---|---|---|---|---|---|---|---|---|
| Orismilast | <lower limit body mass | 10 mg | P | 10 mg | 10 mg | 10 mg | 10 mg | 10 mg |
| Orismilast | ≥lower limit body mass to <100 kg | 20 mg | P | 20 mg | 20 mg | 20 mg | 20 mg | 20 mg |
| Orismilast | ≥100 kg | 20 mg | P | 20 mg | 20 mg | 20 mg | 30 mg | 30 mg |
| Placebo | All | P | P | P | P | P | P | P |

"P" refers to placebo dose
"lower limit body mass" refers to a subject body mass of from 50 kg to 75 kg. In some embodiments the lower limit body mass is 50 kg. In some embodiments the lower limit body mass is 60 kg. In some embodiments the lower limit body mass is 75 kg.

Patients randomised to placebo for the first 16 weeks will be switched to orismilast at Week 16 and dose titrated as illustrated above. Patients achieving clinical response on orismilast at Week 24 and who are re-randomised to placebo will not initiate a new dose titration with orismilast if transferred from the maintenance treatment period to the open-label treatment period. To keep the blind, all patients will receive identically appearing titration/treatment cards.

Compliance will be assessed by direct questioning and counting returned tablets during the site visits and documented in the source documents and relevant form. Deviation from the prescribed dosage regimen should be recorded.

Concomitant Therapy

Any concomitant medication, supplement, or procedure within 6 months prior to Baseline or received during the study must be recorded along with:

Reason for use

Dates of administration including start and end dates

Dosage information including dose and frequency

Allowed Medication

Patients may take any medication that is not restricted by the protocol and would not be expected to interfere with the conduct of the study or affect assessments. Chronic medication should be dosed on a stable regimen.

Over the course of this study, additional medications may be required to manage side effects from trial treatments or non-psoriasis disease progression. Supportive care, including but not limited to antiemetic (e.g. metoclopramide) or anti-diarrheic medications (e.g. loperamide) or paracetamol/acetaminophen for headaches, may be administered at the discretion of the Investigator. Non sedative antihistamines, inhaled corticosteroids or corticosteroid drops in the eye or ear are allowed during the study.

Unmedicated skin moisturizers and non-medicated shampoos will be permitted for body lesions and scalp lesions. The definition of unmedicated excludes all topical products that contain pharmacologically active ingredients such as (but not limited to) lactic acid, salicylic acid, urea, α-hydroxy acids, fruit acids or Chinese herbal medicine.

Low potency topical corticosteroids (Class 6 and 7) are allowed in the face, axilla and genitoanal area when affected by psoriasis. However, patients should not use these topical treatments within 24 hours prior to the clinic visit.

The use of non-steroidal anti-inflammatory drugs (NSAIDs), analgesic treatments or any other treatment given to treat psoriatic arthritis will be permitted only if already prescribed at Screening. Dose adjustments of these medications should be avoided during the study.

Use of any other topical therapy is not permitted during the first 24 weeks of treatment or during the maintenance treatment period. During the open label period, topical therapy including potent corticosteroids, retinoids, vitamin D analog preparations, tacrolimus, pimecrolimus, or anthralin/dithranol, coal tar, salicylic acid preparations, or medicated shampoos for scalp lesions are allowed for disease control if needed.

Use of all these products must be recorded in the eCRF.

Disallowed/Prohibited Medication

The following psoriasis medications cannot be administered for the duration of the study:

Topical therapies: Higher than moderate topical corticosteroids and Intralesional corticosteroid injections for psoriasis lesions Conventional systemic therapies including but not limited to cyclosporine, corticosteroids, methotrexate, retinoids, mycophenolate, thioguanine, hydroxyurea, sirolimus, sulfasalazine, azathioprine, or fumaric acid esters Phototherapy including UVB or PUVA Biologic agents, including TNF or IL-17 blockers, anti-IL-12, anti-IL-23 or IL-12/23 monoclonal antibodies or biosimilars for each Use of Janus kinase (JAK), Tyrosine Kinase 2 (TYK2) or PDE4 inhibitors Use of any investigational drug or device Prolonged sun exposure or any use of tanning booths or other ultraviolet light sources In case a patient has used any disallowed medication, the duration and rationale of the use must be discussed and evaluated by the Investigator. It is the responsibility of the Investigator to judge if the investigational treatment and participation in the study should be continued, according to the patient's benefit and wellbeing, in agreement with Sponsor. However, in this study, the Sponsor proposes to maintain the patient in the study in case of topical therapy and to discontinue the patient in case of systemic therapy. The AE decision must be documented in the patient's medical records.

Abbreviations

AE Adverse Events
AESI Adverse Events of Special Interest
ALP alkaline phosphatase
ALT alanine aminotransferase
AST aspartate aminotransferase
BID twice daily
BMI Body Mass Index
BSA Body Surface Area
BUN blood urea nitrogen
cAMP cyclic Adenosine Monophosphate
CRP c-reactive protein
C-SSRS Columbia-Suicide Severity Rating Scale
CMH Cochran Mantel-Haenzel
CTCAE Common Terminology Criteria for Adverse Events
DLQI Dermatology Life Quality Index
ECG electrocardiogram
EOT End of Trial
EQ-5D-5L EuroQol Quality of Life 5-Dimension-5 five-level
GCP Good Clinical Practice
GGT gamma-glutamyl transpeptidase
Hb haemoglobin
$HbA_{1c}$ haemoglobin $A_{1c}$/glycosylated haemoglobin
HBcAb hepatitis B core antibody
HBsAb hepatitis B surface antibody
HBsAg hepatitis B surface antigen
HBV hepatitis B virus
hCG human chorionic gonadotropin
HCV hepatitis C virus
Hct haematocrit
HDL high-density lipoprotein
HIV human immunodeficiency virus
HRQoL Health-Related Quality of Life
ICF Informed Consent Form
ICH International Conference on Harmonisation
IEC Independent Ethics Committee
IMP Investigational Medicinal Product
IRB Institutional Review Board
ITT intent-to-treat
LDL low-density lipoprotein
LDH lactate dehydrogenase
MCH mean corpuscular haemoglobin
MCHC mean corpuscular haemoglobin concentration
MCV mean corpuscular volume
MedDRA Medical Dictionary for Regulatory Activities
NRS Numerical Rating Scale
PASI Psoriasis Area Severity Index
PDE phosphodiesterase
PGA Physician Global Assessment
PHQ-8 Patient Health Questionnaire-8-item
PK pharmacokinetic PPPGA Palmoplantar Psoriasis Physician Global Assessment
PUVA psoralen and ultraviolet A
QD once-daily
RBC red blood cell
ScPGA Scalp Specific Physician Global Assessment
sPGA static Physician Global Assessment
sPGA-G static Physician Global Assessment of Genitalia
TEAE Treatment Emergent Adverse Event
ULN upper limit of normal
UVB ultraviolet B
W Week
WBC white blood cell
WHO World Health Organisation
WHO-5 The 5-item World Health Organization Well-Being Index
WOCBP women of childbearing potential Example 5: A Randomised, Double-Blind, Placebo- and Active-Controlled, Phase 3 Study to Evaluate the Efficacy and Safety of Orismilast in Adult Patients with Moderate-to-Severe Plaque-Type Psoriasis The following phase 3 clinical trial may be carried out.
A randomised (4:3:2), double-blind, placebo- and active controlled study to evaluate the efficacy and safety of orismilast monotherapy in adults with moderate-to-severe plaq3ue-type psoriasis. The study will compare the response to orismilast with subjects treated with apremilast (30 mg BID) and placebo.

Primary Endpoints:
  Achieving sPGA of 0 (clear) or 1 (almost clear) at Week 16[1]
  Achieving PASI75 at Week 16
Main Secondary Endpoints:
  Achieving PASI90 at Week 16
  Achieving Scalp Specific Physician Global Assessment (ScPGA) of 0 (clear) or 1 (almost clear) at Week 16[2]
Main Secondary Endpoints (Only for Comparison to Apremilast):
  Achieving sPGA of 0 (clear) or 1 (almost clear) at Week 16[1]
  Achieving PASI75 at Week 16
  Achieving PASI90 at Week 16
Further Secondary Endpoints:
  Achieving sPGA of 0 (clear) or 1 (almost clear) at Week 24[1]
  Achieving PASI75 at Week 24
  Achieving PASI90 at Week 24
  Achieving reduction of Dermatology Life Quality Index (DLQI) score of 24 points at Week 16[4]
  Achieving PASI100 at Week 16
  Achieving sPGA of 0 (clear) or 1 (almost clear) at Week 4, 8 and 12
  Achieving PASI75 at Week 4, 8 and 12
  Achieving PASI90 at Week 4, 8 and 12
  Achieving sPGA 0/1 at Week 8, 12 and 20
  Achieving PASI75 at Week 8, 12 and 20
  Achieving PASI90 at Week 12 and 20
  Achieving sPGA of 0 (clear) or 1 (almost clear) at Weeks 28, 34, 40, 46, 52, 56
  Achieving PASI75 at Weeks 28, 34, 40, 46, 52, 56
  Achieving PASI90 at Weeks 28, 34, 40, 46, 52, 56
Tertiary Endpoints:
  Percentage change in PASI from baseline to Week 4, 8, 12 and 16
  Change in PASI from baseline to Week 4, 8, 12 and 16
  Achieving PASI50 at Week 4, 8, 12 and 16
  Achieving PASI100 at Week 4, 8 and 12
  Achieving ScPGA of 0 (clear) or 1 (almost clear) at Week 4, 8 and 12[2]
  Change in the affected body surface area (BSA) from baseline to Week 4, 8, 12 and 16
  Achieving Static Physician Global Assessment of Genitalia (sPGA-G) of 0 (clear) or 1 (minimal) at Week 16
  Achieving Palmoplantar Psoriasis Physician Global Assessment (PPPGA) of 0 (clear) or 1 (almost clear) at Week 16
  Change in Itch Numerical Rating Scale (NRS)[3] from baseline to Week 2, 4, 8 and 16
  Achieving reduction of Itch NRS[3] of ≥4 points at Week 2, 4, 8 and 16[4]
  Change in pain NRS[3] from baseline to Week 2, 4, 8 and 16
  Achieving reduction of pain NRS[3] of ≥4 points at Week 2, 4, 8 and 16[4]
  Change in scalp Itch NRS[3] from baseline to Week 2, 4, 8 and 16
  Achieving reduction of scalp Itch NRS[3] of 24 points at Week 2, 4, 8 and 16[4]
  Change in WHO-5 total score from baseline to Week 16
  Achieving DLQI score of 24 points at Week 8[4]
  Achieving DLQI score of 0 or 1 at Week 8 and 16
  Change in DLQI from baseline to Week 8 and 16
  Change in EQ-5D-5L from baseline to Week 16
  Percentage change in PASI from baseline to Week 8, 12, 16 and 24
  Change in PASI from baseline to Week 8, 12, 16 and 24
  Achieving PASI100 at Week 16 and 24
  Achieving ScPGA of 0 (clear) or 1 (almost clear) at Week 16 and 24[2]
  Change in BSA from baseline to Week 16 and 24
  Achieving sPGA-G of 0 (clear) or 1 (minimal) at Week 16 and 24
  Achieving PPPGA of 0 (clear) or 1 (almost clear) at Week 16 and 24
  Achieving PASI50 at Week 8, 12, 16 and 24
  Change in Itch NRS[3] from baseline to Week 16 and 24
  Achieving reduction of Itch NRS[3] of ≥4 points at Week 16 and 24[4]
  Change in scalp Itch NRS[3] from baseline to Week 16 and 24
  Achieving reduction of scalp Itch NRS[3] of 24 points at Week 16 and 24[4]
  Change in pain NRS[3] from baseline to Week 16 and 24
  Achieving reduction of pain NRS[3] of 24 points at Week 16[4]
  Change in WHO-5 total score from baseline to Week 16 and 24
  Achieving DLQI score of 4 points at Week 16 and 24[4]
  Achieving DLQI score of 9 or 1 at Week 16 and 24
  Change in DLQI from baseline to Week 16 and 24
  Change in EQ-5D-5L from baseline to Week 16 and 24
  Percentage change in body weight from baseline to Week 16
  Achievement of weight loss equal to or above 5% (yes/no) from baseline to Week 16 among patients with baseline BMI ≥30
  Achievement of weight loss equal to or above 10% (yes/no) from baseline to Week 16 among patients with baseline BMI ≥30
  Percentage change in $HbA_{1c}$ from baseline to Week 16

Change to normoglycemia (yes/no) (Normoglycemia is defined as having $HbA_{1c}$ below 5.7% (below 39 mmol/mol)) from baseline to Week 16 among patients with baseline $HbA_{1c}$ 5.7-6.4% (39-47 mmol/mol)

Achievement of $HbA_{1c}$ equal to or below 6.5% (yes/no) from baseline to Week 16 among patients with baseline $HbA_{1c}$ 6.5-7% (48-53 mmol/mol)

Achievement of $HbA_{1c}$ equal to or below 7% (yes/no) from baseline to Week 16 among patients with baseline $HbA_{1c}$>7% (>53 mmol/mol)

Change in waist circumference from baseline to Week 16

Safety Assessments:
Number of treatment emergent adverse events (TEAE) from baseline to Week 16
Number of Adverse Event of Special Interest (AESI) from baseline to Week 16
Change from baseline in body weight, vital signs, laboratory tests and electrocardiogram (ECG) during initial 16-week treatment period
Columbia-Suicide Severity Rating Scale (C-SSRS) at Week 4, 8, 12 and 16
Patient Health Questionnaire-8 (PHQ-8) at Week 4, 8, 12 and 16

Footnotes
1) With at least 2-point improvement from baseline, 2) With at least 2-point improvement from baseline among patients with baseline score 23, 3) Weekly average, 4) From baseline among patients with a baseline score 4, 5) In patients with a baseline score >0.

Study Design

Figure 8:
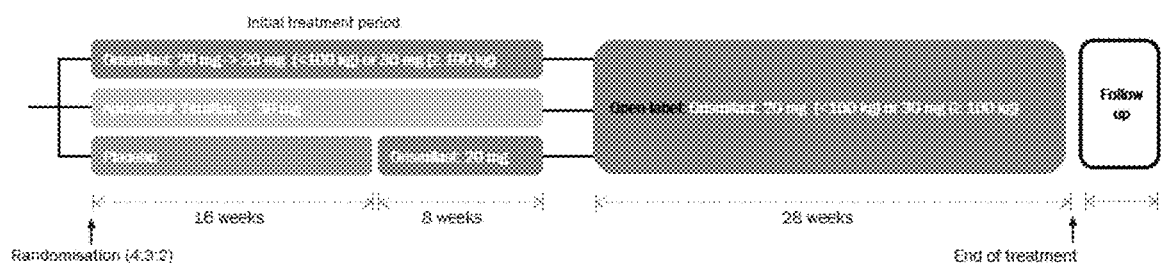
FIG. 8 shows the design of the phase 3 clinical study described in Example 5.

This is a randomised (4:3:2), double-blind, placebo- and active-controlled study to evaluate the efficacy and safety of orismilast monotherapy in adults with moderate-to-severe plaque-type psoriasis. The study will consist of a 52-weeks treatment period: initial double-blind treatment period of 24 weeks and an open-label extension treatment period of 28 weeks. The primary endpoints are assessed at Week 16. An off-treatment follow-up period for the assessment of safety and rebound effects is also included (weeks 52 to 56). A schematic of the trial design is provided in FIG. 8.

Main Assessments

Investigator Assessments of Efficacy

Investigator Assessments of Efficacy are to be performed at protocol-specified visits. The following assessments will be made:
Psoriasis Area and Severity Index (PASI)
Static Physician Global Assessment (sPGA)
Body Surface Area (BSA)
Scalp Specific Physician Global Assessment (ScPGA)
Static Physician Global Assessment of Genitalia (sPGA-G™)
Palmoplantar Psoriasis Physician Global Assessment (PPPGA)

The details of each investigator assessment are as described in Example 4.

Patient-Reported Outcomes
Whole body itch and pain numeric rating scales (NRS)
Scalp itch numeric rating scale (NRS)
Dermatology Life Quality Index (DLQI)
EuroQol Quality of Life 5-Dimension-5 five-level (EQ-5D-5L)
WHO-5

The details of each patient-reported outcome are as described in Example 4.

Safety Assessments

Safety assessments will be performed, which are the same as those described in Example 4.

Inclusion and Exclusion Criteria

These are the same as those set out in Example 4.

Rationale for Study Population

The study population will consist of a representative group of male and female patients (≥18 years old) with moderate-to-severe chronic plaque-type psoriasis and candidates for systemic treatment. Moderate-to-severe chronic plaque-type psoriasis is defined by a total PASI score of 12 and a body surface area (BSA) of ≥10% and an sPGA ≥3 in line with expectation from FDA.

Study Intervention(s) Administered

All investigational products will be provided in blister cards throughout the entire study. Orismilast (20 mg and 30 mg modified release tablet formulations), apremilast (10 mg, 20 mg and 30 mg) and placebo will be provided as over encapsulated tablets from Week 0 to Week 23. All capsules will be identical in appearance. From Week 24 orismilast 20 mg and 30 mg will be provided as tablets to all patients.

All investigational products will be taken orally BID, approximately 12 hours apart, without restriction of food or drink, though it is advised that the patient eat smaller, less fatty and more frequent meals to prevent gastrointestinal side effects. To mitigate potential gastrointestinal (GI) side effects, dose titration will be implemented.

All patients assigned to orismilast will receive 20 mg QD for the first 2 weeks (placebo in the morning and orismilast in the evening), then 20 mg BID for 6 weeks and thereafter patients with a body weight of less than 100 kg at randomisation will continue on 20 mg BID while patients with a body weight of 100 kg or more at randomisation will receive 30 mg BID. Patients assigned to placebo (PBO) will receive placebo BID. Thus, the orismilast dosing regimen will be as shown below:

| Arm | Subject Weight | Day 1 | Day 2-14 (Week 0-2) | | Day 15-56 (Week 2 to 8) | | From Day 57 (Week 8 and onwards) | |
|---|---|---|---|---|---|---|---|---|
| Orismilast | <100 kg | 20 mg | P | 20 mg | 20 mg | 20 mg | 20 mg | 20 mg |
| Orismilast | ≥100 kg | 20 mg | P | 20 mg | 20 mg | 20 mg | 30 mg | 30 mg |
| Placebo | All | P | P | P | P | P | P | P |

Alternative Weight-Based Dosage Regimen for Orismilast

Also contemplated is the dosage regimen wherein subjects are dosed according to the weight-based dosage regimen below:

| Arm | Subject Weight | Day 1 | | Day 2-14 (Week 0-2) | Day 15-56 (Week 2 to 8) | From Day 57 (Week 8 and onwards) |
|---|---|---|---|---|---|---|
| Orismilast | <lower limit body mass | 10 mg | P | 10 mg | 10 mg | 10 mg | 10 mg | 10 mg |
| Orismilast | ≥lower limit body mass to <100 kg | 20 mg | P | 20 mg | 20 mg | 20 mg | 20 mg | 20 mg |
| Orismilast | ≥100 kg | 20 mg | P | 20 mg | 20 mg | 20 mg | 30 mg | 30 mg |
| Placebo | All | P | P | P | P | P | P | P |

"P" refers to placebo dose
"lower limit body mass" refers to a subject body mass of from 50 kg to 75 kg. In some embodiments the lower limit body mass is 50 kg. In some embodiments the lower limit body mass is 60 kg. In some embodiments the lower limit body mass is 75 kg.

| | Day 1 (mg) | | Day 2 (mg) | | Day 3 (mg) | | Day 4 (mg) | | Day 5 (mg) | | Day 6 (mg) | |
|---|---|---|---|---|---|---|---|---|---|---|---|---|
| Arm | AM | PM | AM | PM | AM | PM | AM | PM | AM | PM | AM | PM |
| | 10 | P | 10 | 10 | 10 | 20 | 20 | 20 | 20 | 30 | 30 | 30 |

Patients randomised to placebo for the first 16 weeks will be switched to orismilast at Week 16 and dose titrated as illustrated above for the orismilast dose regimen. Patients randomised to apremilast for the first 24 weeks will be switched directly to orismilast dose of either 20 mg or 30 mg BID (depending of baseline weight of <100 kg or 100 kg, respectively) from Week 24 with no titration. To keep the blind all patients will receive identically appearing titration/treatment cards.

Concomitant Therapy

The allowed and disallowed/prohibited medications are as described in Example 4.

Example 6: Simulation of Dosage Regimen in Patient Populations Using a Population Pharmacokinetics (popPK) Model The inventors have developed a population pharmacokinetics (popPK) model for orismilast based on data from orismilast Phase I and Phase II studies. The model has been used to perform model-based simulations of dosage regimens in patient populations as described herein.

6.1 Development of a Population Pharmacokinetics (popPK) Model for Orismilast 6.1.1 Dataset The popPK model was built on 6 healthy volunteer (HV) studies (LP0058-S01, LP0058-1005, LP0058-1114, LP0058-1362, LP0058-1324, and LP0058-1442), one additional Chinese healthy volunteer study (CIB1353A101) and two psoriasis Phase II studies (LP0058-1072 (Phase IIa) and UN150001-203 (Phase IIb)).

All subjects were treated with orismilast as IR capsule, IR solution, IR tablet or MR tablet with available PK samples. Although the modified release tablet was the formulation selected for further studies, the popPK model was also built using the immediate release formulations (IR solution, IR tablet and IR capsule), especially to obtain stable estimates of elimination parameters (clearances) across formulations and obtain a robust model to support the simulation.

Overall, a total of 372 subjects were included in the analysis (207 healthy volunteers with rich data (191 healthy non-Chinese subjects and 16 healthy Chinese subjects) and 165 psoriasis patients with sparse data).

Orismilast dose and mode of administration: from 0.5 to 60 mg, per os, q.d, b.i.d. or t.i.d.

The analysis dataset was created and formatted according to MONOLIX requirement using SAS®.

6.1.2 Strategy for Development of the Model

PopPK parameters were estimated by non-linear mixed effect modelling using MONOLIX. Mixed effects models describe the influence of both fixed effects and random effects. The random effects are typically used to capture the variability which can be split in residual variability (error) and between-subject variability.

The population model was defined by 4 components:
1. The structural popPK model components, which defines the PK parameters and describe the plasma concentration-time profiles of orismilast.
2. The inter-individual random effect model component, which describes the inter-individual variation (IIV) and inter-occasion variation (IOV) in PK parameters after correction for fixed effects.
3. The residual error (or random effect) model component, which describes the underlying distribution of the error in the measured concentrations.
4. The covariate model component, which describes the influence of fixed effects (i.e., demographic factors) on PK parameters.

The search for the final model followed the following stepwise strategy:
1. Selection of the simplest structural model, which predicts the plasma concentration as a function of time and dose, based on smallest objective function (OF) and by the pattern in the residual plots. The best structural model, the most appropriate.IIV and IOV models, and the residual error model, were identified. The structural model was determined using the rich Phase I data from healthy volunteers (LP0058-S01, LP0058-1005, LP0058-1114, LP0058-1362, LP0058-1324 and LP0058-1442).

2. Preliminary visual check using predictive check approach was applied to sparse data from psoriasis patients (study LP0058-1072) to assess the predictability capacities of the structural model for patient data.
3. Psoriasis patient data were included in the model and the model was refined or adjusted if necessary.
4. Graphical exploration of the covariates: between individual covariates and EBE of parameter or random effects.
5. Determination of the covariate model.
6. Selection of significant covariates to obtain the FINAL model.
7. Inclusion of new studies in the model (e.g. UN1500001-203 and CIB1353A101) was performed by repeating steps 2 to 6.

Due to the preliminary and exploratory purpose of the modelling at this stage, the covariates investigated were limited to:

Influence of gender, health status and ethnicity/race on all parameters

The pre-specified covariates that were suspected a priori of having an influence on PK parameters, were included in the full model and the selection of the final model with relevant covariates were based on the statistical Wald test (keep covariates with p-value <0.05). The influence of body weight on PK parameters was included using fixed standard allometric scales.

The model was evaluated using diagnostic and goodness of fit plots and validated using Visual Predictive Checks. SAS® software V9.4 and Monolix Suite version 2021R1 release were used.

6.1.3 Results of Model Development and Final Model for Orismilast

Following administration of modified release tablet as a single oral dose and after multiple doses up to 60 mg, orismilast reached a $C_{max}$ around 3 h under fasting state. There was a significant increase of systemic exposure with high-fat meals but no statistical difference on $C_{max}$ and $t_{max}$ by food conditions was shown.

A biphasic decline for orismilast can be observed in particular for MR formulation after QD administration but with large between-subject variability on the terminal phase which could not be observed in all subjects.

Figure 12:
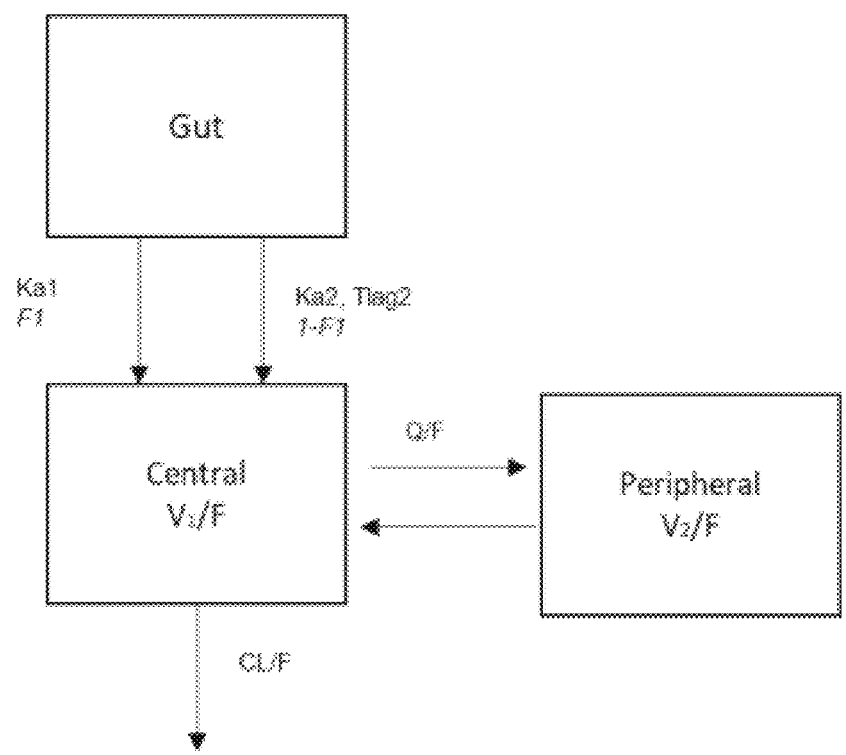
FIG. 12 shows a 2 compartment model for orismilast as described in Example 6.

A 2-compartment model with 2 rate constants of absorption and a linear elimination was considered as suitable to describe the kinetic of orismilast. The structural model for the fit or orismilast including all data is presented in FIG. 12.

The structural model was parameterised in terms of apparent clearance (CL/F), volume of distribution of central compartment ($V_1$/F), inter-compartmental clearance (Q/F) and volume of distribution for peripheral compartment ($V_2$/F). The absorption was described by a 1st—order rate constant ($k_{a1}$) for first absorption process, 1st—order rate constant ($k_{a2}$) for second absorption process, fraction of dose absorbed through the first process (F1) and lag time ($t_{lag2}$) for the start of the second phase. The relative bioavailability was also added to characterize the difference between the formulations, it was set to 1 for the IR solution, so, the other formulations were expressed relatively to the IR solution.

Clearance and volume of distribution were scaled to body weight using standard allometric rules. These scales were specifically evaluated and found adequate for both normal weight and overweight subjects.

For the orismilast modified release formulation:
$k_{a1}$ was of 0.21 h−1 and $k_{a2}$ was 0.65 h−1 (~0.01 min-1), 98% of the dose was absorbed by the second absorption phase. Thus, the first process was limited, and the second phase was major and lead the absorption of orismilast. Drug absorption after oral administration is a complex process depending on solubility, permeability of the drug and gastrointestinal location. All these processes interplay and results in drug absorption, the rate of absorption is the reflects of the interactions between the different processes.

the typical clearance (CL/F) was 53.8 L/h,
the volume of distribution for the central compartment ($V_1$/F) was 108.9 L,
the apparent intercompartmental clearance (Q/F) was 3.54 L/h,
the volume of distribution of the peripheral compartment ($V_2$/F) was 130 L.
F1 was 0.02.
All parameters but kas were expressed for a typical subject of 70 kg.

The PK parameters were correctly estimated and were common for all formulations. The variability of the central PK parameters was moderate (27 and 34%), and very high for the peripheral compartment (383 and 495% for Q/F and $V_2$/F, respectively). This high variability for the peripheral compartment parameters resulted from the fact that the terminal elimination phase was not observed in all subject or regimen and because of the lack of data in the terminal phase of the kinetic. Indeed, the second decline of the terminal phase was observed to start around 12 h after dosing, when orismilast was mainly administered for the second time in b.i.d regimen, and few samples were available after the 12th hour.

Exposure in Chinese HV ($AUC_{0-12}$ and $C_{max}$) was found to be higher than in Caucasian HV. This difference can be almost entirely erased for AUC by normalizing by body-weight, but a small difference persisted for $C_{max}$ that could not be captured statistically, possibly due of the small sample size and the variability.

Formulation and food effects were used as structural covariates in the popPK model, as food (high-fat meals) increase the relative bioavailability and delayed the absorption ($k_{a2}$).

Once accounting for body weight through the allometric scales on all clearances and volumes of distributions, sex was still found to have a statistical effect on CL/F. However, according to forest plots, this covariate did not have a sufficiently large effect to be included in the model. Moreover, at this step with the current data, the health status covariate was not formally tested but according to the diagnostic plots and VPC, no difference in exposure can be evidenced between healthy volunteers and psoriasis patients.

Figure 13:
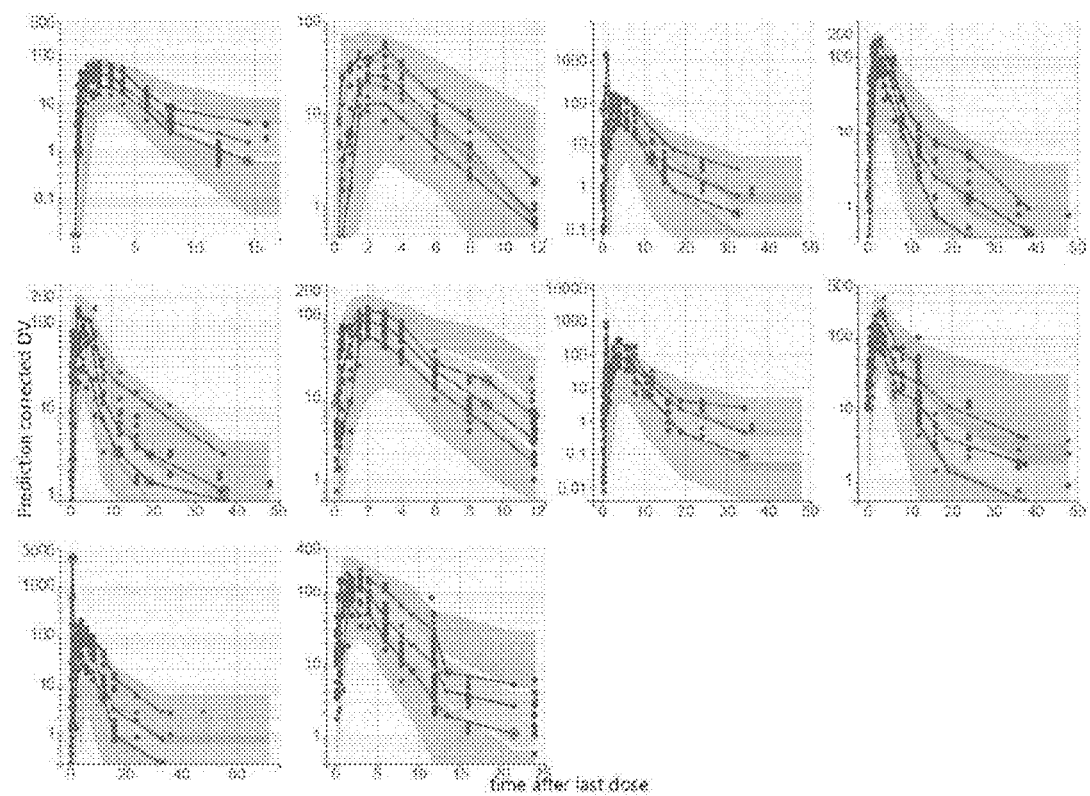
FIG. 13 shows pcVPC results for healthy volunteer (HV) modified release (MR) studies as described in Example 6.
Figure 14:
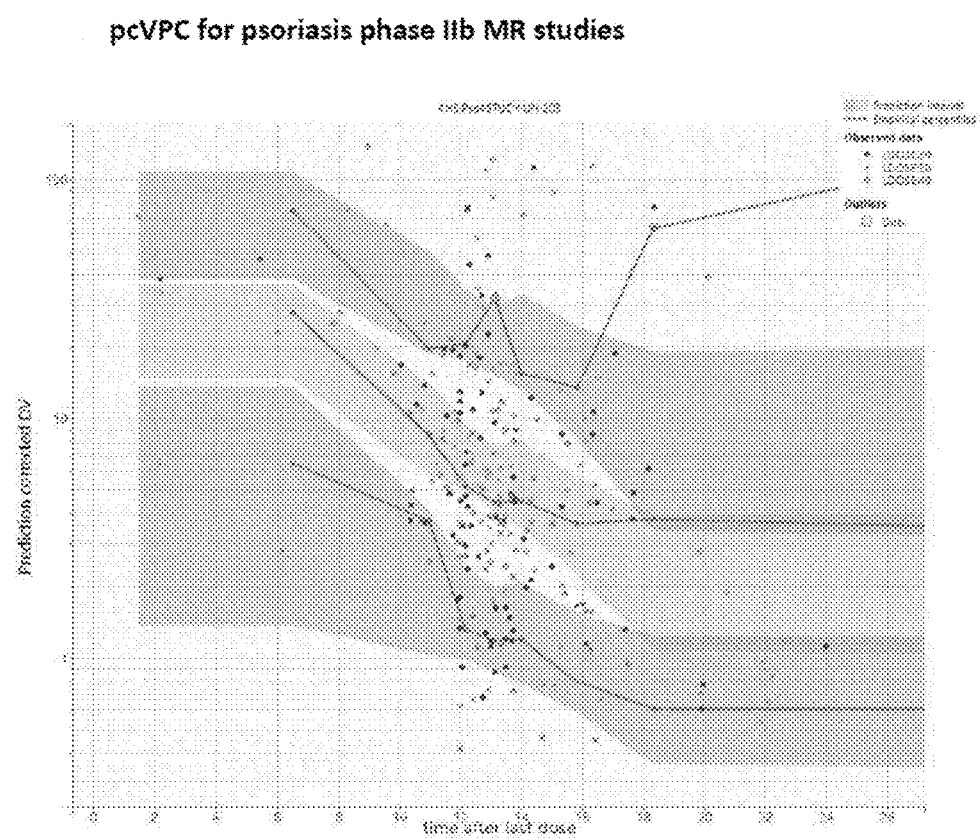
FIG. 14 shows pcVPC results for psoriasis Phase IIb MR studies as described in Example 6.
Figure 15:
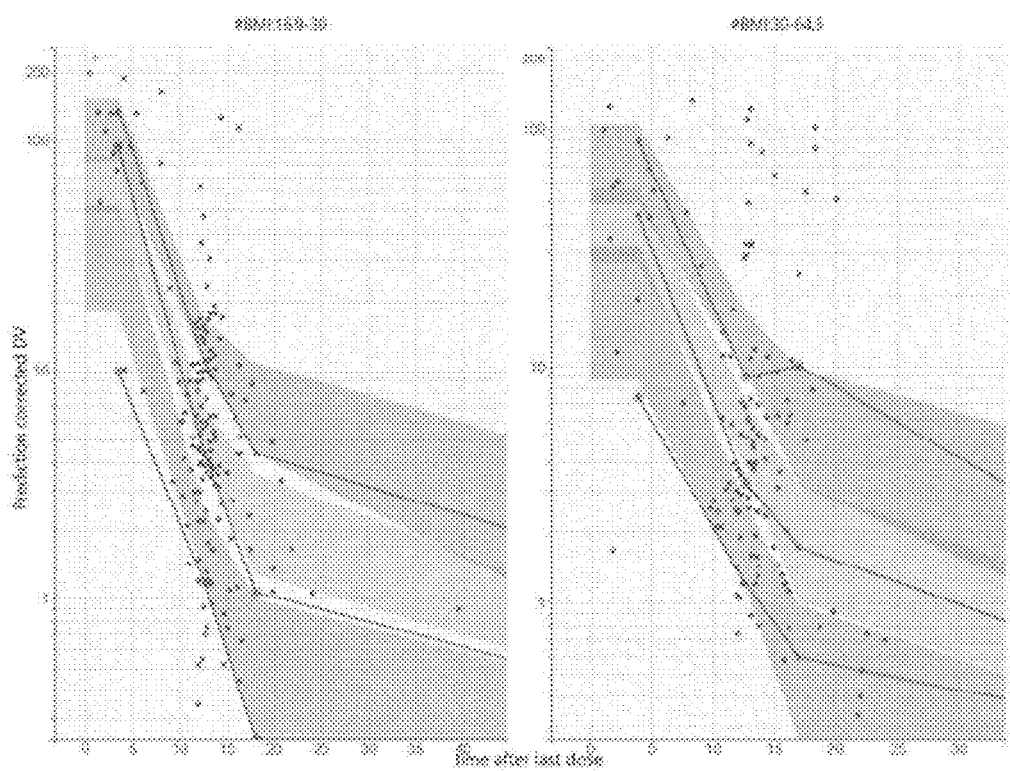
FIG. 15 shows pcVPC results for HV MR studies for normal weight and obese patients (psoriasis patients) as described in Example 6. The plot on the left is for subjects with a BMI from 16.9 to 30 kg/m². The plot on the left is for obese subjects with a BMI from 30 to 64.5 kg/m²

6.1.4 Evaluation and Validation of Final Model pcVPC for the final model were presented by study and occasion for HV MR formulation (see FIG. 13) and for psoriasis Phase IIb (see FIG. 14). The pcVPC confirmed that both the general pattern and the variability of orismilast concentrations for the MR formulation were well captured by the model. Indeed, the 5th, median and 95th percentiles were fully within the 90% prediction band obtained from the simulations, there was however a gap with study P1442—Part 1 (30 mg) which appeared to be slightly under predicted at the terminal phase, in a minimal extent closed to the lower limit of quantification. In addition, for the psoriasis Phase IIb data, the observed values coloured by dose level were added to observe any dose related bias, and the only gap was at the latest time point due to outlier patients (quantifiable concentration long time after the last dose), otherwise the pcVPC confirmed that the model correctly fitted the data for psoriasis patients. Moreover, pcVPC were similar between subjects with BMI higher or lower than 30 kg/m² (FIG. 15). Additionally, diagnostics and goodness of fit plots, support that the model was considered suitable for use in simulations of MR tablets.

Overall, population parameters were derived with good precision (RSE <21%) and the model was able to reproduce orismilast concentrations in terms of central tendency and variability with very good adequacy (percentiles of observed data were overall included in the simulated band using the model). Indeed, to go further, the AUClast derived by the popPK model were compared with those obtained from the NCA after different dosing regimens and following single and repeated dosing (see Table below). These checks confirmed that the exposure was well predicted by the popPK model, and that the model is suitable for predicting or simulating exposure at steady state.

Exposure parameters were simulated for this virtual population using the final model for various dosage regimen. The exposure parameters obtained from these simulations were compared graphically to the same exposure parameters determined in patients from Phase 11 studies at the dosage regimen considered the most appropriate (in term of safety and efficacy) for adults (defined as reference regimen).

For the simulation of overweight patients, exposure parameters for at least 100 subjects with body weight varying from 100 kg to 150 kg by steps of 10 kg were simulated from the final model. The same kind of graphical display as proposed for adolescents was provided to compare the regimens simulated for high weight subjects with prediction of the same exposure parameters for the reference regimen (adult with body weight less than 100 kg).

Results of the simulations consisted of box plot for the comparison of distribution for each exposure parameter, summary of the exposure parameters by dosage regimen and % of simulated exposure parameters falling outside reference regimen 5-95% percentile interval as well as below or above the reference median.

SAS® software V9.4 and Monolix Suite version 2021R1 release were used.

| PK parameters | Studies | N | NCA GM (CV %) | popPK GM (CV %) | GM ratio (popPK/NCA) |
|---|---|---|---|---|---|
| $AUC_{last}$ (h*ng/mL) | 1442 - Part 1 (MR, 30 mg) | 18 | 482 (22%) | 495 (20%) | 1.03 |
| | 1442 - Part 2 (Fast, 30 mg) | 9 | 480 (31%) | 547 (32%) | 1.14 |
| | 1442 - Part 3 (D1 = 10 mg) | 9 | 112 (46%) | 110 (33%) | 0.98 |
| | 1442 - Part 3 (D17 = 60 mg) | 9 | 763 (36%) | 738 (41%) | 0.97 |
| | CIBI3S3A101 (D1 = 10 mg) | 18 | 167 (23%) | 162 (21%) | 0.98 |

The specific investigation performed on obese patients indicated that the model was also able to fit them adequately (e.g. Figure E) and therefore could be an informative tool for the simulation in a high weight population, even if some limitations may appear due to the use of bodyweight allometric scaling as the only predictive covariate.

6.2 Simulation of Patient Populations

The final model was used to perform simulations of the exposure ($AUC\tau$-ss, $C_{trough}$-SS and $C_{max-ss}$) in special patient populations (adolescent and overweight subjects) and support dosage selection. Three sets of simulations were performed: two for adolescents and overweight subjects respectively, and an additional one to mimic the proposed dose regimen for Phase 3 in psoriasis.

6.2.1 Methods

For the simulation of adolescents, 1000 virtual children aged between 12 and 17 years were sampled from the National Health and Nutrition Examination Survey (NHANES) database. The sampling procedure ensured the balance between male and female.

6.2.2 Simulations in adolescents

The simulation population included 1000 virtual subjects aged from 12 to 17 years, for whom demographics characteristics (age, gender and weight) were taken from National Health and Nutrition Examination Survey (NHANES) database. Paediatric simulated population characteristics are described in the Table below:

| Age category | Gender | Age | | | Bodyweight | | |
|---|---|---|---|---|---|---|---|
| | | N | P5/Median/P95 | Mean (SD) | N | P5/Median/P95 | Mean (SD) |
| 12-17 years | Female | 523 | 12.0/14.00/17.0 | 14.48 (1.52) | 523 | 39.2/49.20/65.9 | 52.42 (10.70) |
| | Male | 477 | 12.0/14.00/17.0 | 14.42 (1.51) | 477 | 330.8/61.20/85.7 | 59.46 (17.71) |

The population was gender balanced and body weight varied from 30 kg to 86 kg.

The regimens considered for simulations were 10 b.i.d, 20 b.i.d, 30 b.i.d and 40 b.i.d. The following PK parameters were calculated: $AUC_{\tau-ss}$, $C_{max-ss}$ and $C_{trough-ss}$, and the same regimens were simulated in adults. The target exposure was the median values at steady state for the 20 b.i.d regimen in adults (the simulated adult population was resampled from the original database).

Figures 16A, 16B:
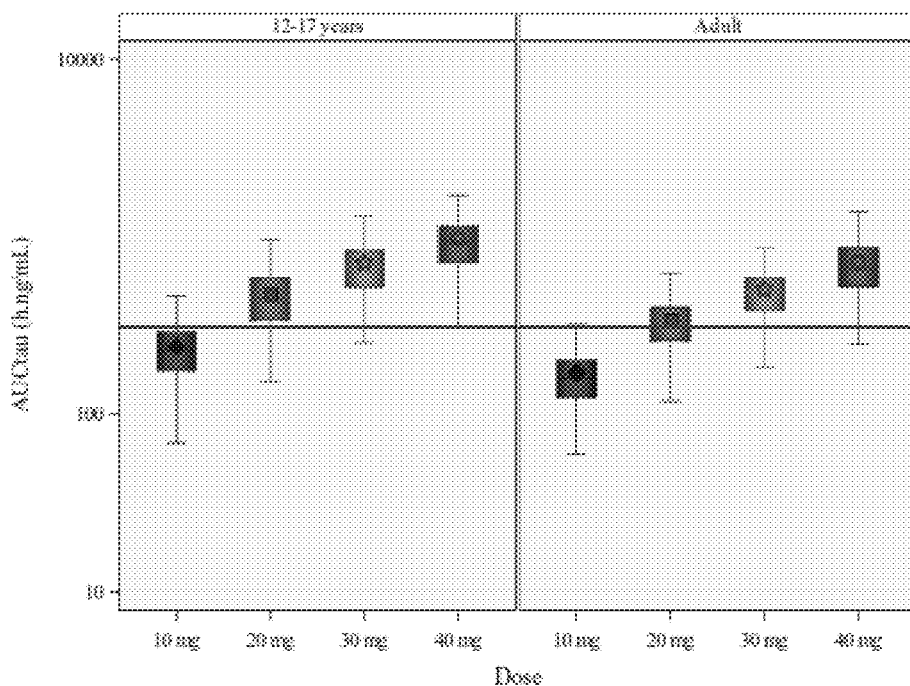
FIG. 16A shows orismilast $AUC_{\tau\text{-}ss}$ at steady-state in adolescents after repeated administration of MR formulation with dose 10, 20, 30 and 40 mg b.i.d compared to adults as described in the simulation in Example 6. AUCtau in this and other figures refers to the AUC for a dosing interval.
FIG. 16B Table providing descriptive statistics of orismilast $AUC_{\tau\text{-}ss}$ at steady-state in adolescents after repeated administration of MR formulation with dose 10, 20, 30 and 40 mg b.i.d as described in the simulation in Example 6.

Boxplots of simulated $AUC_{\tau SS}$ were plotted for the overall adolescent population (see FIG. 16(*a*)), and descriptive statistics are presented in FIG. 16(*b*).

Figure 17:
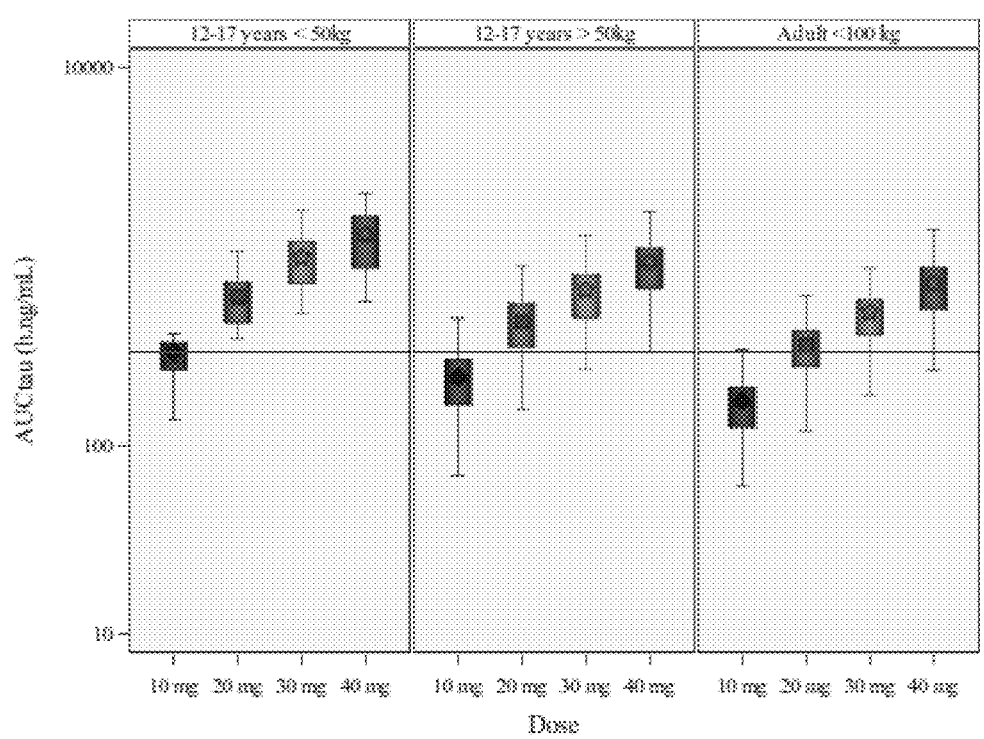
FIG. 17 shows orismilast $AUC_{\tau\text{-}ss}$ at steady-state in adolescents stratified by bodyweight after repeated BID administration of MR formulation with dose 10, 20, 30 and 40 mg b.i.d as described in the simulation in Example 6.
Figures 18A, 18B:
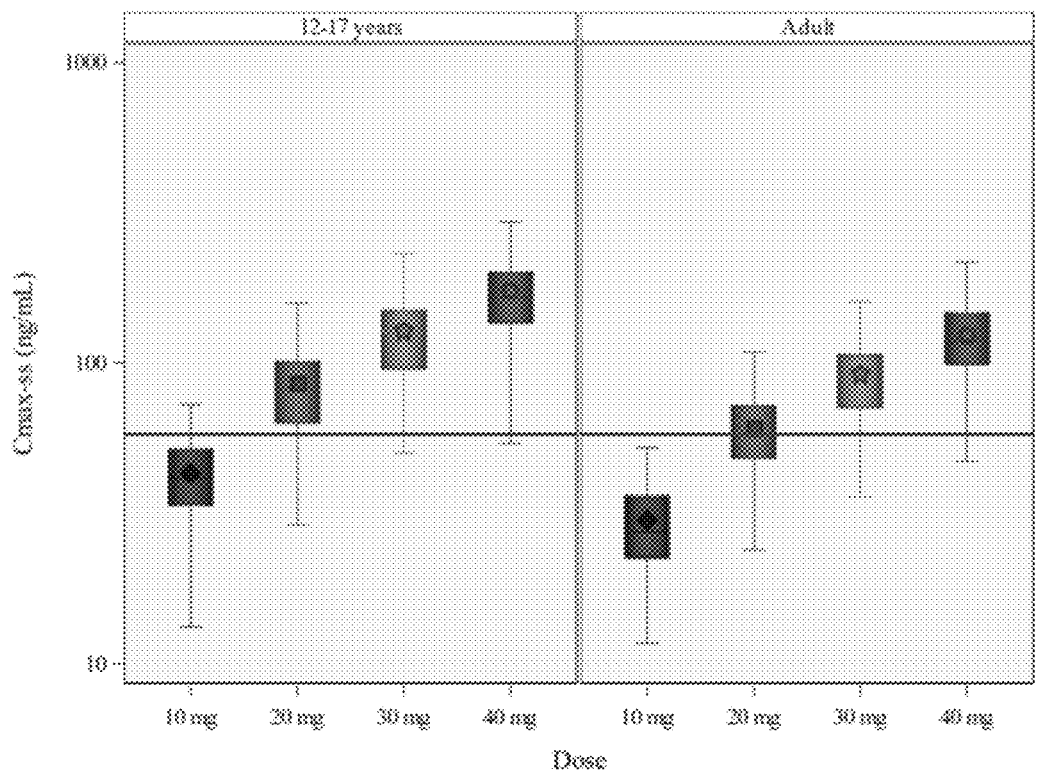
FIG. 18A shows orismilast $C_{max\text{-}ss}$ at steady-state in adolescent population overall after repeated b.i.d administration of MR formulation with dose 10, 20, 30 and 40 mg b.i.d as described in the simulation in Example 6.
FIG. 18B Table providing descriptive statistics of orismilast $C_{max\text{-}ss}$ at steady-state in adolescent population overall after repeated b.i.d administration of MR formulation with dose 10, 20, 30 and 40 mg b.i.d as described in the simulation in Example 6.
Figures 19A, 19B:
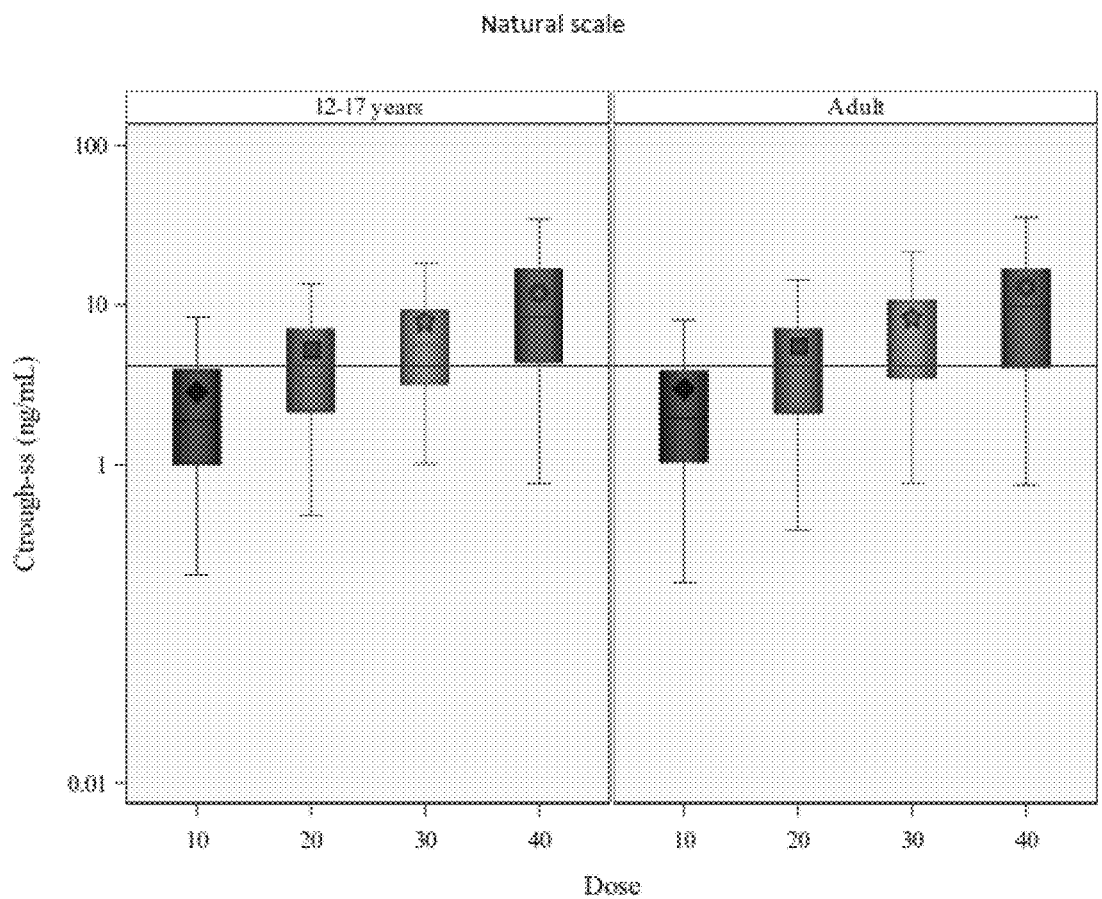
FIG. 19A shows orismilast $C_{trough\text{-}ss}$ at steady-state in adolescent population overall after repeated b.i.d administration of MR formulation with dose 10, 20, 30 and 40 mg b.i.d as described in the simulation in Example 6.
FIG. 19B Table providing descriptive statistics of orismilast $C_{trough\text{-}ss}$ at steady-state in adolescent population overall after repeated b.i.d administration of MR formulation with dose 10, 20, 30 and 40 mg b.i.d as described in the simulation in Example 6.
Figures 20A, 20B:
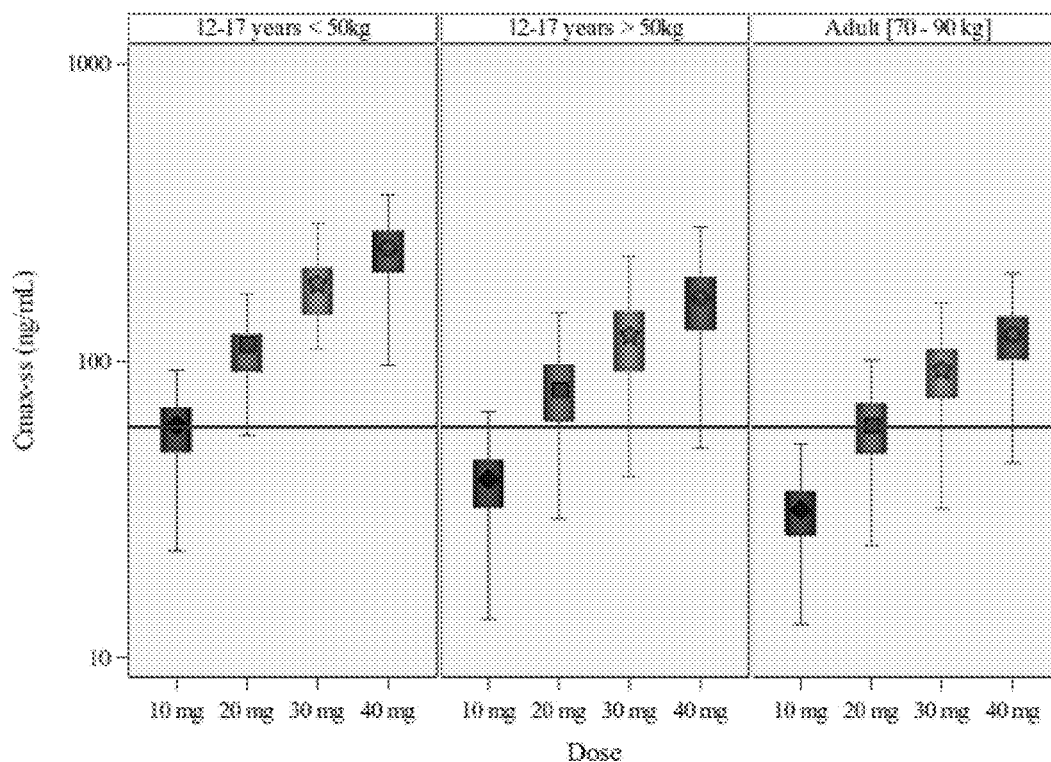
FIG. 20A shows orismilast $C_{max\text{-}ss}$ at steady-state in adolescents after repeated b.i.d administration of MR formulation with dose 10, 20, 30 and 40 mg b.i.d—by weight category as described in the simulation in Example 6.
FIG. 20B Table providing descriptive statistics of $C_{max\text{-}ss}$ (ng/mL)steady-state in adolescents after repeated b.i.d administration of MR formulation with dose 10, 20, 30 and 40 mg b.i.d—by weight category as described in the simulation in Example 6.
Figures 21A, 21B:
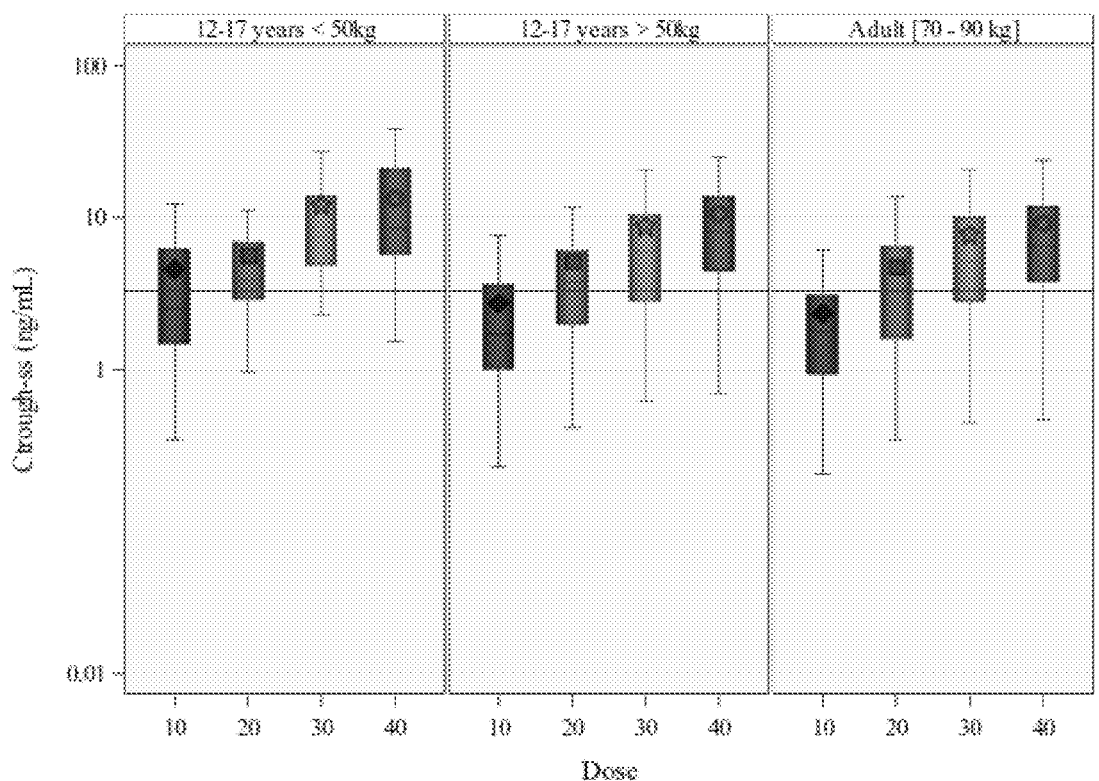
FIG. 21A shows orismilast $C_{trough\text{-}ss}$ at steady-state in adolescents after repeated b.i.d administration of MR formulation with dose 10, 20, 30 and 40 mg b.i.d—by weight category as described in the simulation in Example 6.
FIG. 21B Table providing descriptive statistics of $C_{trough\text{-}ss}$ (ng/mL) at steady-state in adolescents after repeated b.i.d administration of MR formulation with dose 10, 20, 30 and 40 mg b.i.d—by weight category as described in the simulation in Example 6.

According to the simulations, simulated exposure with 20 mg b.i.d in adolescents was higher than with 20 mg b.i.d in adults and it was therefore decided to perform simulations stratified by weight group: simulated subjects with a body weight below 50 kg and above 50 kg and results are presented in FIG. 17.

According to Figure G, adolescents with age between 12 and 17 years old and bodyweight greater than 50 kg will have a slightly higher exposure level than adults with body weight less than 100 kg receiving the same dose. However, for lighter adolescents (bodyweight less than 50 kg), the target adult $AUC_{ss}$ with 20 b.i.d should be reached with a lower dose of 10 b.i.d.

These results were consistent with $C_{max}$ level at steady-state and less marked for $C_{trough}$ as shown in FIGS. 18-21.

In summary, based on $AUC_{\tau\text{-}ss}$ ($\tau=12h$), adolescents with bodyweight greater than 50 kg could receive the same dose as adults, i.e., 20 mg b.i.d. However, for adolescents with bodyweight less than 50 kg the simulations indicated that a dose of 10 mg b.i.d would better match the adults 20 mg b.i.d.

6.2.3 Simulations in Overweight Subjects

The overweight population was determined directly in Monolix, considering a uniform distribution of body weight between 100 and 150 kg, then the population was stratified in groups of 10 kg as follows:

Group 1: Subjects with bodyweight between 100 and 109 kg
Group 2: Subjects with bodyweight between 110 and 119 kg
Group 3: Subjects with bodyweight between 120 and 129 kg
Group 4 Subjects with bodyweight between 130 and 139 kg
Group 5: Subjects with bodyweight between 140 and 150 kg The reference group was the same adult group used for adolescents' simulation. Overweight simulated population characteristics (bodyweight) are described in the Table below.

| Age category | N | Bodyweight PS/Median/P95 | Mean (SD) |
| --- | --- | --- | --- |
| Group 1 (100-109 kg) | 80 | 100.3/103.99/109.7 | 104.42 (3.10) |
| Group 2 (110-119 kg) | 72 | 110.8/114.89/119.3 | 114.86 (2.86) |
| Group 3 (120-129 kg) | 78 | 120.8/125.02/129.8 | 125.03 (2.72) |
| Group 4 (130-139 kg) | 86 | 130.5/134.61/139.4 | 134.67 (3.00) |
| Group 5 (140-150 kg) | 84 | 140.8/144.94/148.7 | 144.80 (2.70) |

The regimens considered for simulations were 10 mg b.i.d, 20 mg b.i.d, 30 mg b.i.d and 40 mg b.i.d. As for adolescents' simulations, PK parameters calculated were $AUC_{\tau\text{-}ss}$, $C_{max\text{-}ss}$ and $C_{trough\text{-}ss}$. The target exposure was the median value of the 20 b.i.d regimen in the reference population.

Figure 22A:
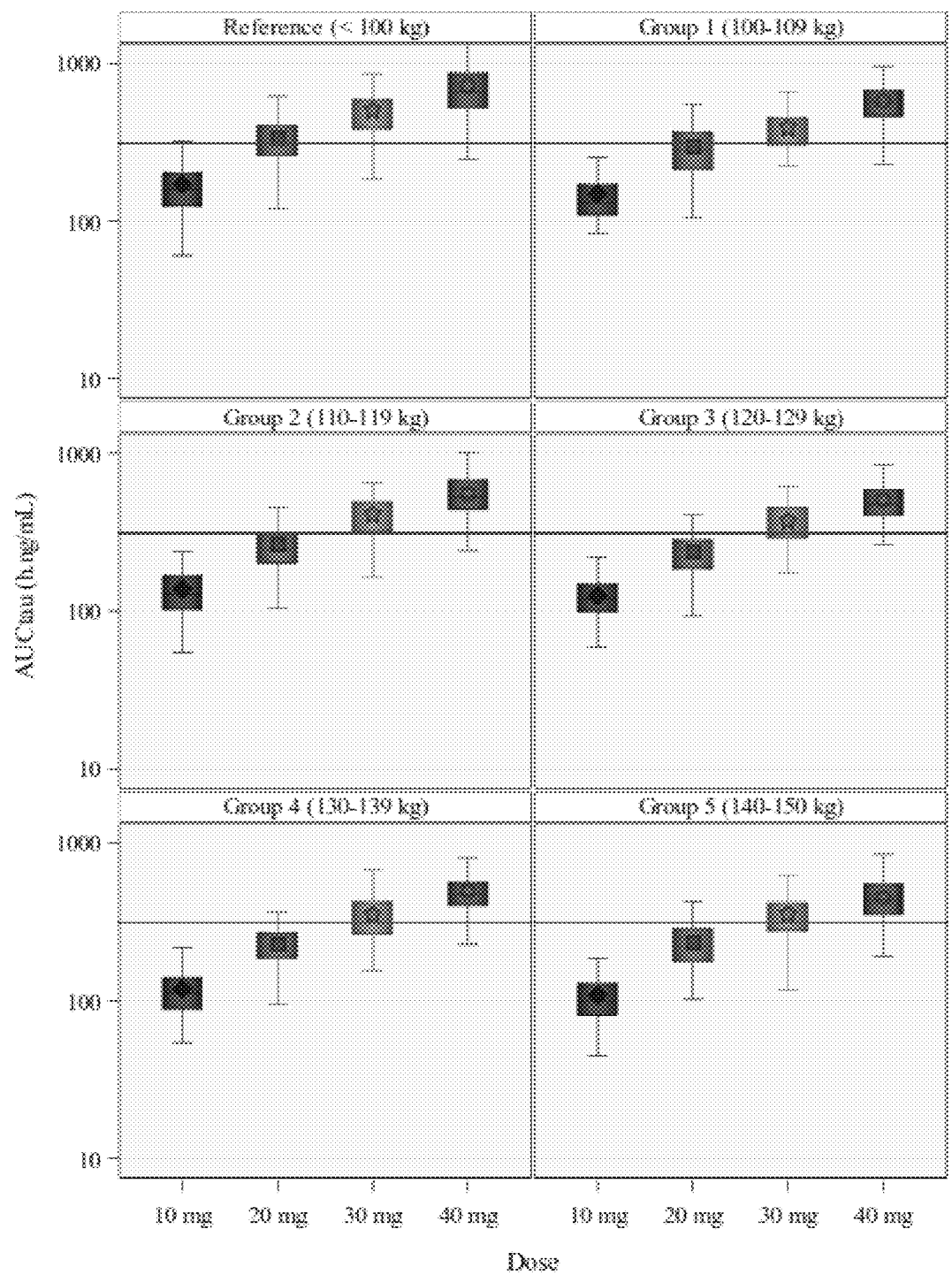
FIG. 22A shows orismilast $AUC_{\tau\text{-}ss}$ at steady-state in overweight subjects after repeated administration of MR formulation with dose 10, 20, 30 and 40 mg b.i.d as described in the simulation in Example 6.

Boxplots of simulated $AUC_{\tau\text{-}ss}$ were plotted against weight groups in FIG. 22(a) and descriptive statistics are presented in the Table in FIG. 22(b).

According to the simulations, it seems reasonable to increase the dose to 30 mg b.i.d from 100 kg and above to maintain exposure in the subjects with high weight close to the target $AUC_{\tau\text{-}ss}$ for adults weighing less than 100 kg at the dose 20 mg b.i.d.

Figure 23A:
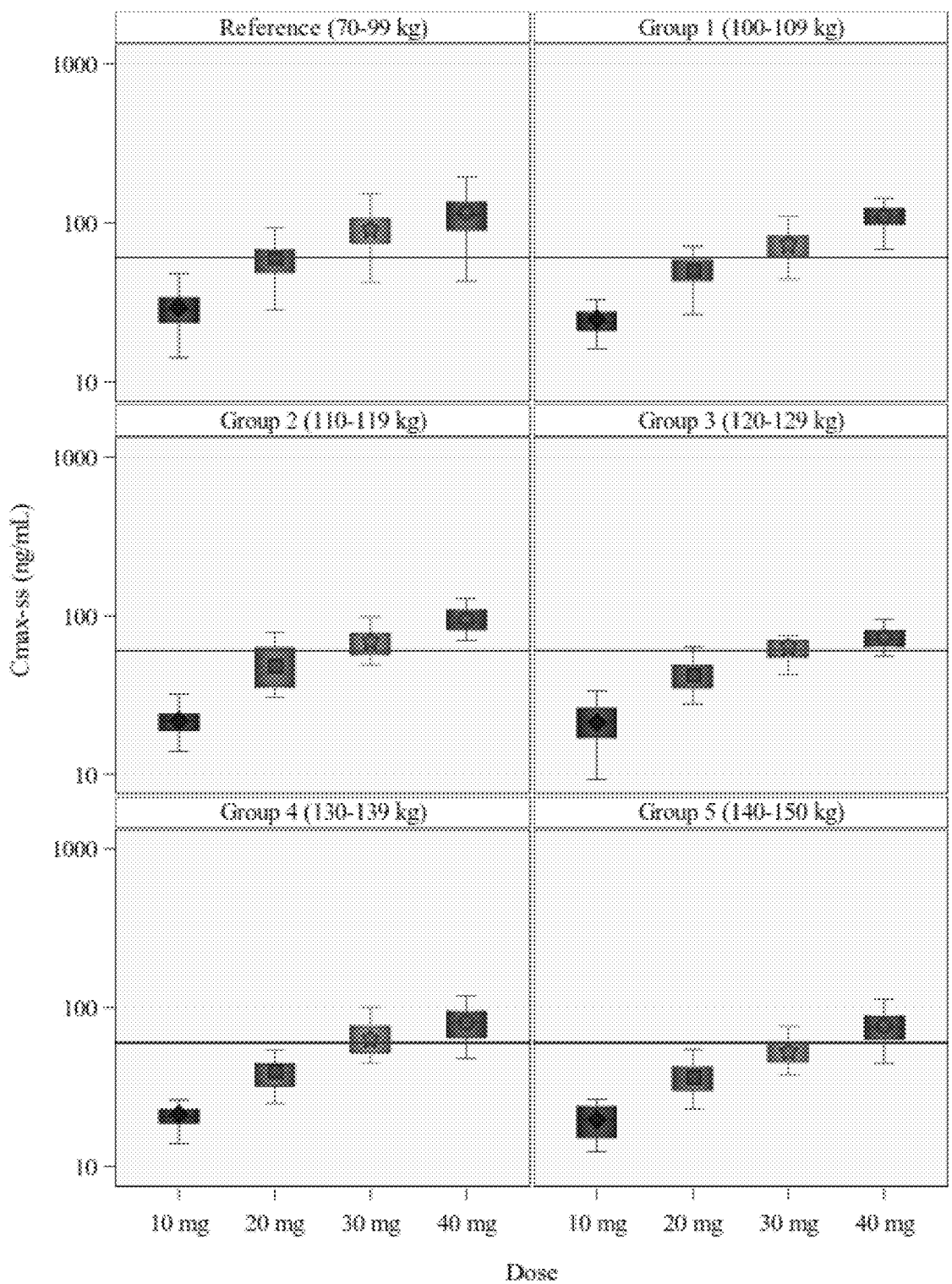
FIG. 23A shows orismilast $C_{max\text{-}ss}$ at steady-state in obese subjects after repeated b.i.d administration of MR formulation with dose 10, 20, 30 and 40 mg b.i.d as described in the simulation in Example 6.
Figure 24A:
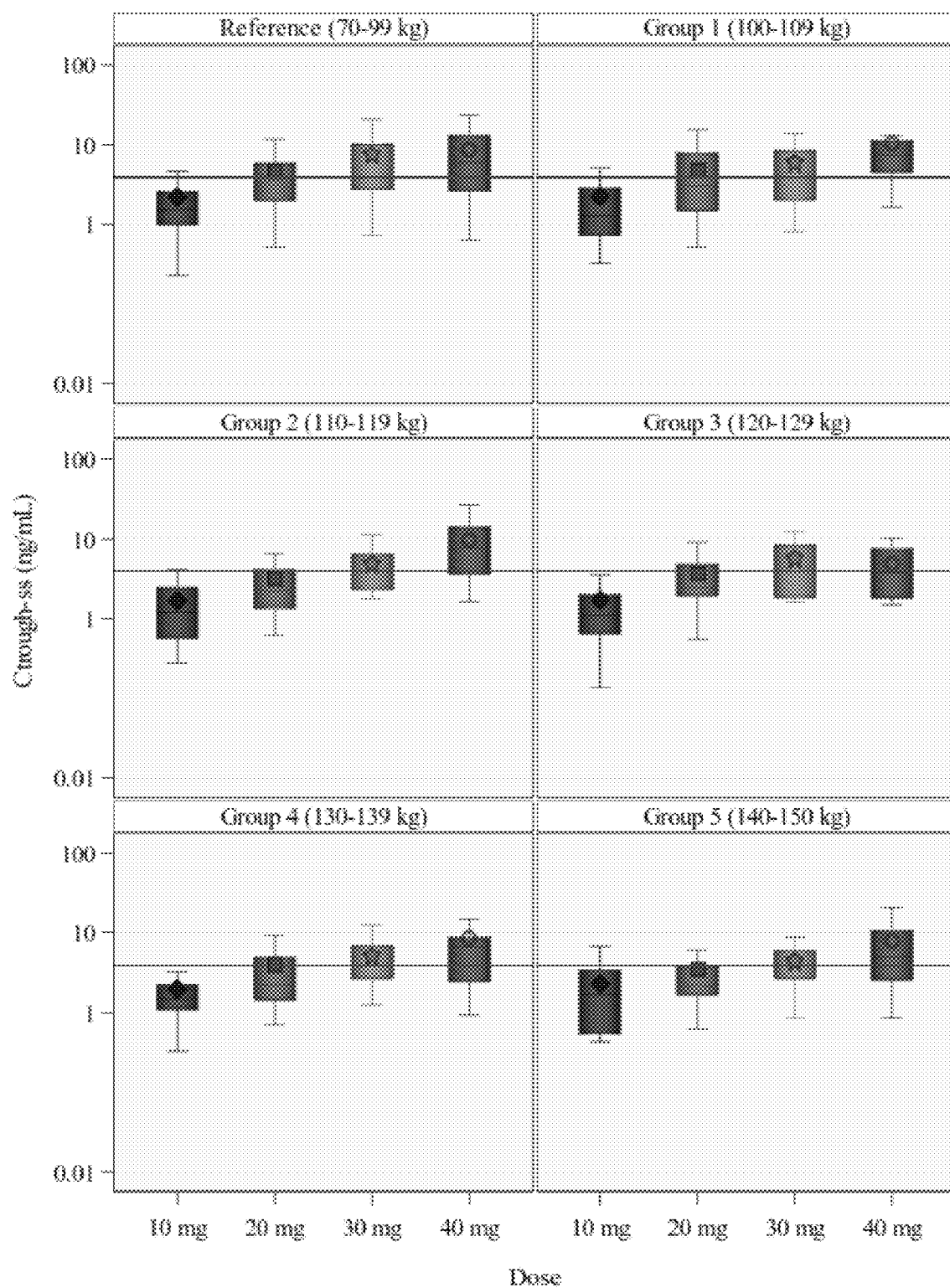
FIG. 24A shows orismilast $C_{trough\text{-}ss}$ at steady-state in obese subjects after repeated b.i.d administration of MR formulation with dose 10, 20, 30 and 40 mg b.i.d as described in the simulation in Example 6.

These results were consistent with $C_{max}$ level at steady-state and less marked for $C_{trough}$ both presented in FIGS. 23-24.

In summary, based on $AUC_{\tau s}$s, from 100 kg and above, a dose of 30 mg b.i.d. might be required to achieve the reference exposure with 20 mg b.i.d. for subjects of less than 100 kg.

6.2.4 Simulations for Phase III Design

According to the previous simulations and to support the design of the Phase III study, orismilast simulations were performed as presented in the Table below.

| Arm | Weight | Day 1 Single dose | Day 2-14 (Week 0-2) Morning dose | Day 2-14 (Week 0-2) Evening dose | Day 15-56 (Week 2 to 8) Morning dose | Day 15-56 (Week 2 to 8) Evening dose | From Day 57 [Week 8 and onwards) Morning dose | From Day 57 [Week 8 and onwards) Evening do |
| --- | --- | --- | --- | --- | --- | --- | --- | --- |
| Orismilast | <1.00 kg | 20 mg | P | 20 mg | 20 mg | 20 mg | 20 mg | 20 mg |
| Orismilast | ≥100 kg | 20 mg | P | 20 mg | 20 mg | 20 mg | 30 mg | 30 mg |
| Placebo | All | P | P | P | P | P | P | P |

P = Placebo

Healthy volunteers with bodyweight less than 100 kg were resampled from the original database used in the popPK model and considered as a reference for the simulations. For subjects with bodyweight greater than 100 kg, the population was directly determined in Monolix, considering a uniform distribution of body weight between 100 and 150 kg.

The following PK parameters were calculated: $AUC_{\tau\text{-}ss}$, $C_{max\text{-}ss}$ and $C_{trough\text{-}ss}$ on day 14 (steady-state with 20 mg QD), day 55 (steady-state with 20 mg b.i.d as in both populations) and day 79 (steady-state comparing the two dosing regimens according to bodyweight).

Figures 25A, 25B:
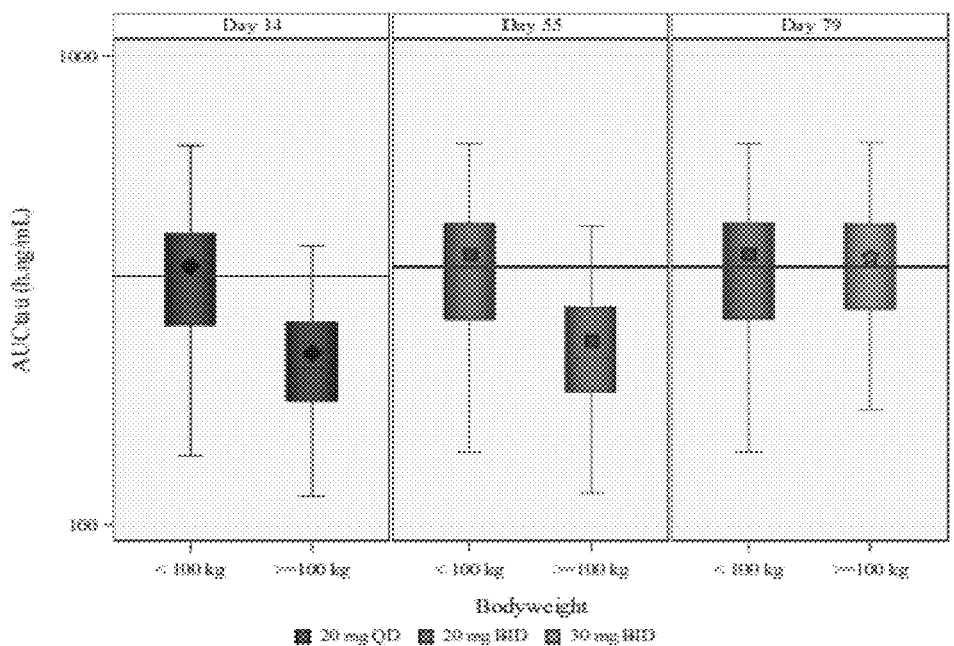
FIG. 25A shows orismilast $AUC_{\tau\text{-}ss}$ at steady-state in subjects according to Phase III design as described in the simulation in Example 6.
FIG. 25B Table providing descriptive statistics of orismilast $AUC_{\tau\text{-}ss}$ at steady-state in subjects according to Phase III design as described in the simulation in Example 6.

Boxplots of simulated $AUC_{\tau\text{-}ss}$ were plotted against weight groups in FIG. 25(a) and descriptive statistics are presented in the Table in FIG. 25(b).

At day 14 and day 55, when both populations will receive the same simulated doses, it appears that subjects with bodyweight greater than 100 kg will have lower AUC with 20 mg b.i.d compared to the reference population and at day 79 when dose will be increased to 30 mg b.i.d for subjects with bodyweight greater than 100 kg their concentrations should be comparable to the reference population at 20 mg b.i.d.

Figures 26A, 26B:
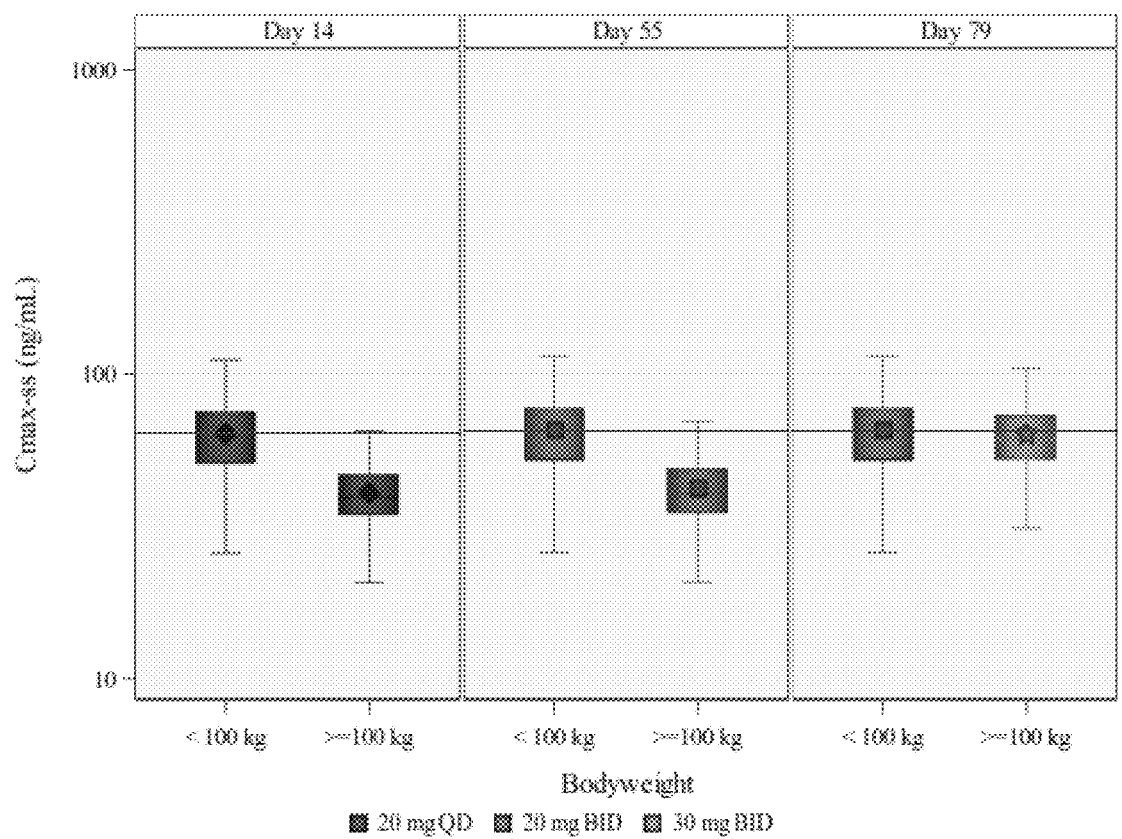
FIG. 26A shows orismilast $C_m$ax-ss at steady-state in subjects according to Phase III design as described in the simulation in Example 6.
FIG. 26B Table providing descriptive statistics of orismilast $C_{max\text{-}ss}$ at steady-state in subjects according to Phase III design) as described in the simulation in Example 6.
Figures 27A, 27B:
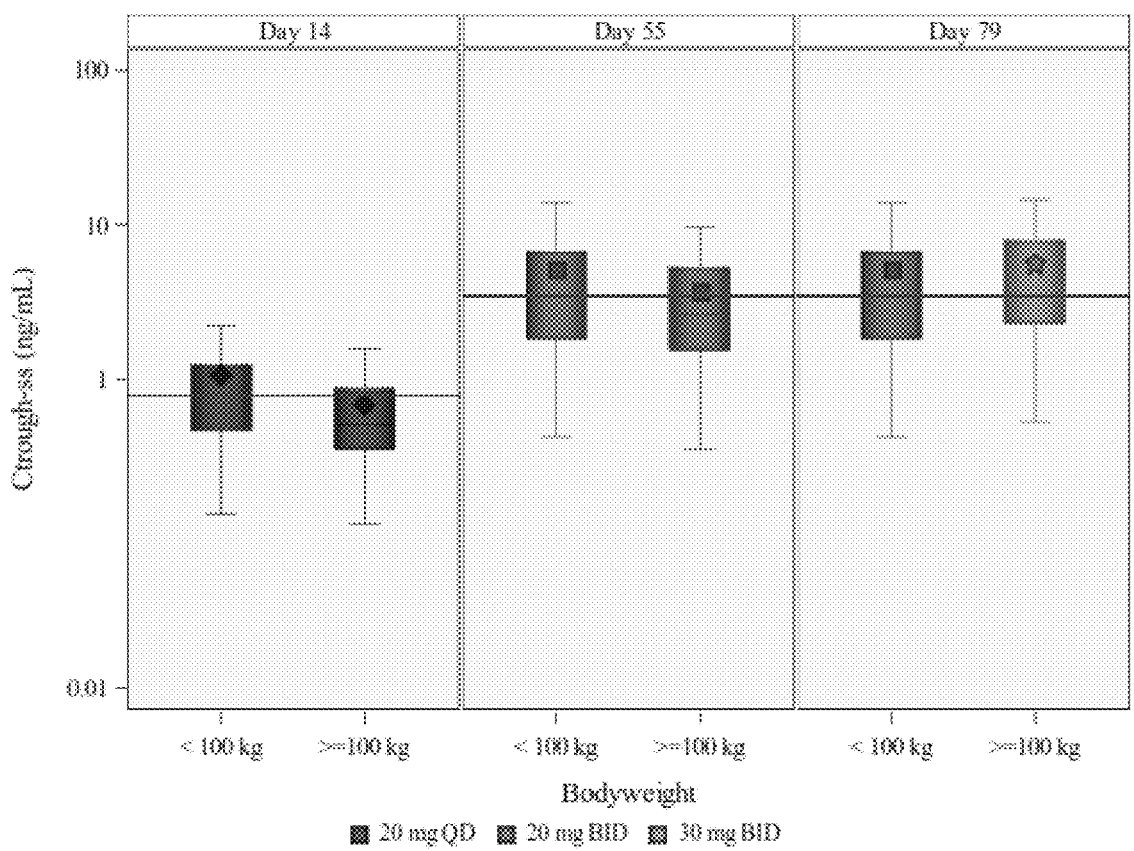
FIG. 27A shows orismilast $C_{trough\text{-}ss}$ at steady-state in subjects according to Phase III design as described in the simulation in Example 6.
FIG. 27B Table providing descriptive statistics of orismilast $C_{trough\text{-}ss}$ at steady-state in subjects according to Phase III design as described in the simulation in Example 6.

These results were consistent with $C_{max}$ level at steady-state and less marked for $C_{trough}$ both presented in FIGS. 26-27.

With 20 mg b.i.d, subjects weighing more than 100 kg had a lower AUC compared to subjects weighing less than 100 kg at Day 14 and 55 (ratio: 0.66 for both days), but after dose adjustment to 30 mg b.i.d. the steady-state exposure was similar at Day 79 between the two groups, meaning that the dose adjustment based on weight could be appropriate for this population. Indeed, simulations in high weight patients (body weight between 100 and 150 kg) indicates that a dose of 30 mg b.i.d. would be required to achieve the reference exposure with 20 mg b.i.d. for subjects of less than 100 kg. Thus, it seems reasonable to consider a cut-off of 100 kg in agreement with the conclusion based on the evaluation of tolerability, safety and efficacy in Phase 2b trial and also supported by the simulations of Phase III design.

6.3 List of Abbreviations and Definition of Terms

| | |
|---|---|
| $\varepsilon$ | Random effect for residual variability/error, assumed to be distributed according to N(0, $\sigma^2$) |
| $\eta$ | Random effect for Inter-individual variability, assumed to be distributed according to N(0, $\omega^2$) |
| $\theta$ | Fixed effect parameter (of structural model or covariate) |
| $\tau$ | dosing interval |
| $\omega^2$ | Variance for Inter-individual variability |
| AD | Atopic dermatitis |
| AUC | Area under the curve |
| $AUC_{\tau\text{-}ss}$ | Area under the curve between two consecutive doses at steady state |
| b.i.d./BID | bis in die (twice a day) |
| BLQ | Below limit of quantification |
| BMI | Body mass index |
| CI | Confidence interval |
| CL, CL/F | Clearance, apparent clearance |
| $C_{max\text{-}ss}$ | Maximal concentration at steady state |
| $C_{trough\text{-}ss}$ | Trough concentration at steady state |
| CV | Coefficient of variation |
| DTA | Data transfer agreement |
| DTS | Data transfer specification |
| DDI | Drug-drug interaction |
| DV | Dependent variable |
| EBE | Empirical bayes estimate |
| EVID | Event identification |
| GM | Geometric mean |
| GOF | Goodness of fit |
| GI | Gastro-intestinal |
| ICF | Informed consent form |
| IIV | Inter individual variability |
| IOV I | inter-occasion variability |
| IMP | Investigational medicinal product |
| IPRED | Individual prediction |
| IR | Immediate release |
| IWRES | Individual Weighted Residuals |
| $k_a$ | Absorption rate constant |
| Max | Maximum |
| MC | Monte Carlo |
| MDV | Missing dependent variable |
| MR | Modified release |
| Min | Minimum |
| min | Minutes |
| MTD | Maximal tolerated dose |
| NPDE | Normalized predicted distribution error |
| OFV | Objective function value |
| pcVPC | prediction-corrected visual predictive checks |
| PD | Pharmacodynamic |
| PK | Pharmacokinetic |
| popPK | Population pharmacokinetics |
| PPRED | Population prediction |
| PWRES | Population weighted residuals |
| q.d./QD | Quoque die (Once a day) |
| RSE | Relative standard error |
| SAEM | Stochastic Approximation Expectation Maximization |
| SD | Standard deviation |
| SE | Standard error |
| $t_{1/2}$ | Elimination half-life |
| t.i.d./TID | Three times a day |
| V, V/F | Volume of distribution, apparent volume of distribution |
| VPC | Visual predictive check |

Example 7: Further analysis of the results of the Phase2b study in Example 3

7.1 Methods

An analysis of the results of the Phase 2b study in Example 3 testing oral modified release orismilast in moderate-to-severe psoriasis patients (IASOS) was conducted for various efficacy parameters (PASI50, PASI75, PASI90) for the two active arms of 20 mg BID and 30 mg BID. The results were further analyzed for two sub-groups of patients based on their body weight at baseline, namely <100 kg and ≥100 kg. AUC values shown in FIG. 32 were taken from the simulations in Example 6 as follows:

>100 kg, 20 mg—FIG. 25(b) ≥100 kg, 20 mg BID, day 55;
>100 kg, 30 mg—FIG. 25(b) 100 kg, 30 mg BID, day 79;
<100 kg 20 mg—FIG. 25(b)<100 kg, 20 mg BID, day 79; and
<100 kg 30 mg—FIG. 22(b)<100 kg, 30 mg.

7.2 Results

Figure 28A:
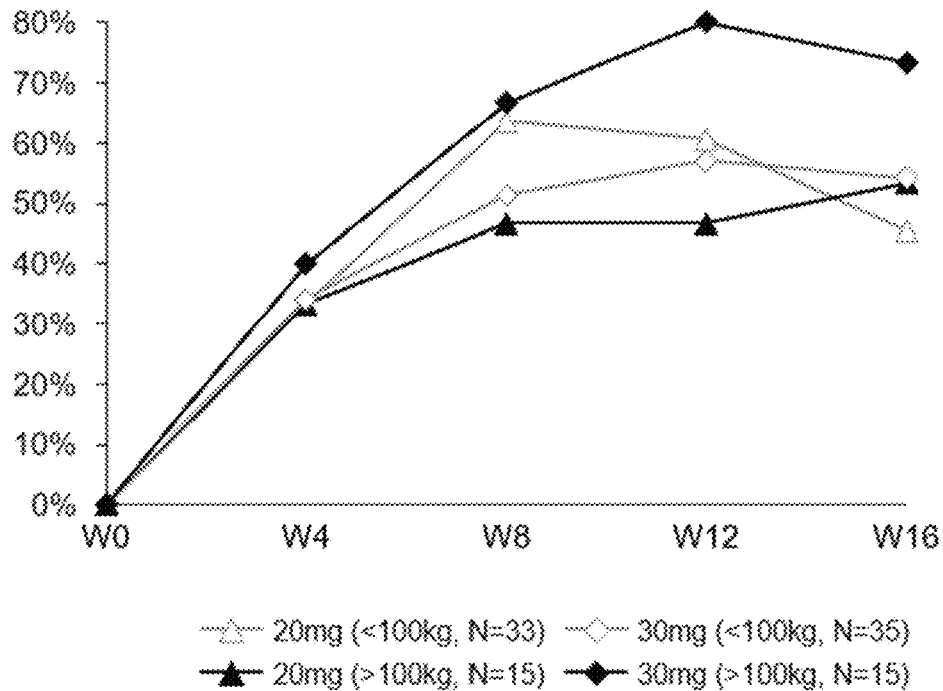
FIG. 28A and FIG. 28B shows the percentage of patients that achieved a 50% reduction in PASI score (PASI-50) at weeks 0, 4, 8, 12 and 16 for two sub-groups of patients based on their body weight at baseline (<100 kg and >100 kg) and for the two active arms in the Phase 2b study in Example 3 (20 mg BID and 30 mg BID)
Figure 28B:
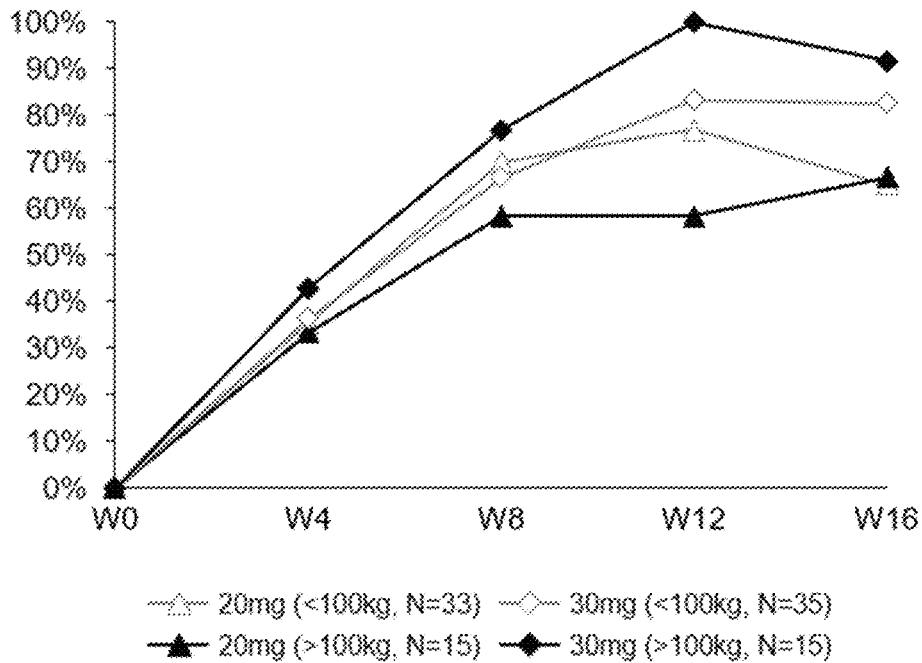
Figure 29A:
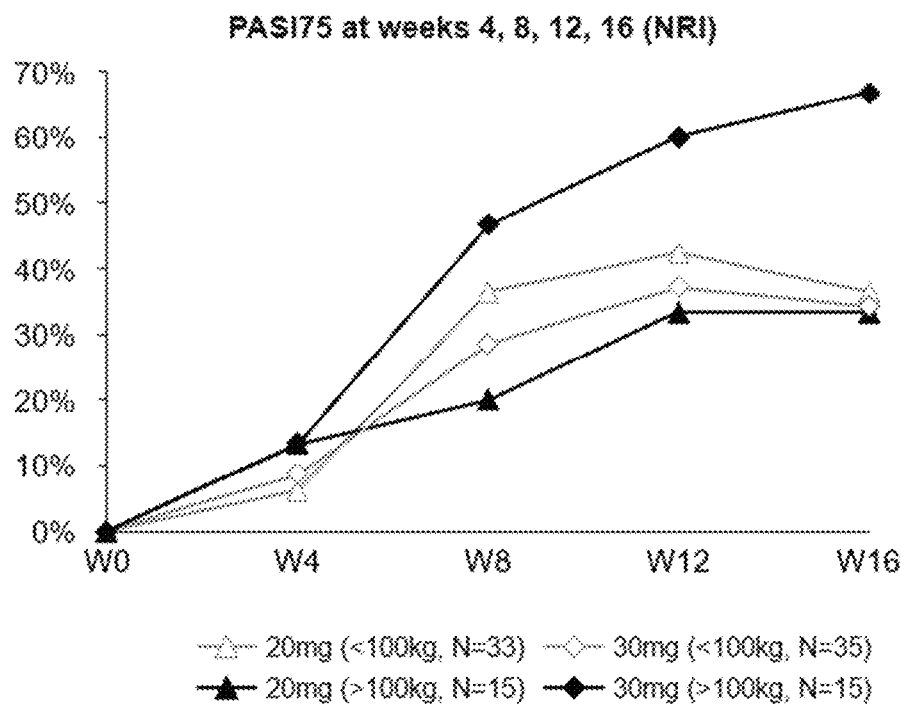
FIG. 29A and FIG. 29B shows the percentage of patients that achieved a 75% reduction in PASI score (PASI-75) at weeks 0, 4, 8, 12 and 16 for two sub-groups of patients based on their body weight at baseline (<100 kg and >100 kg) and for the two active arms in the Phase 2b study in Example 3 (20 mg BID and 30 mg BID).
Figure 29B:
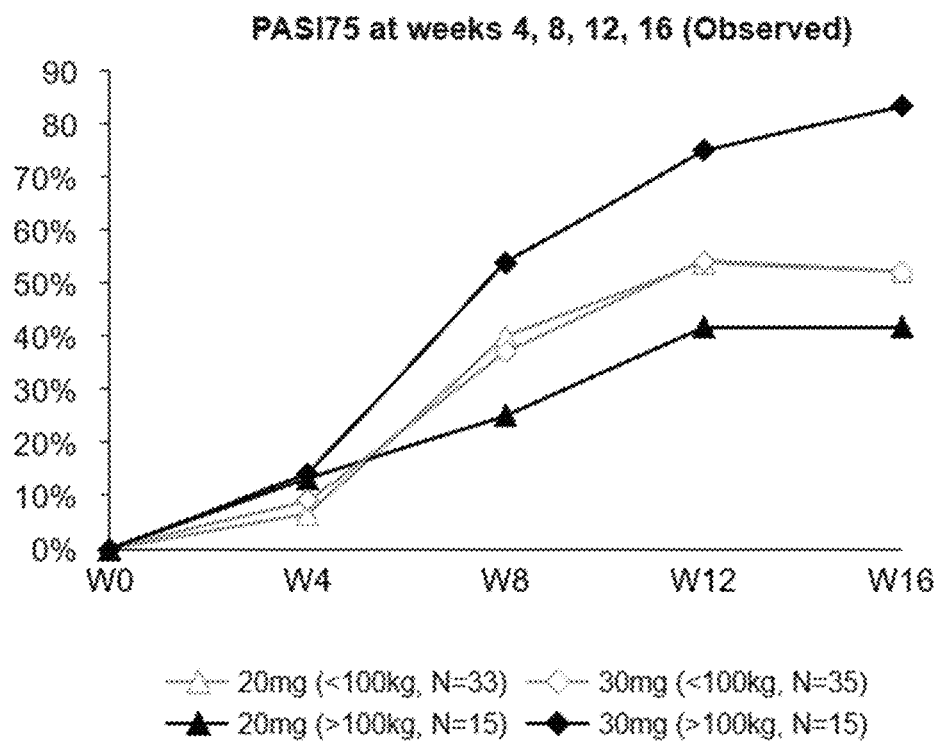
Figure 30A:
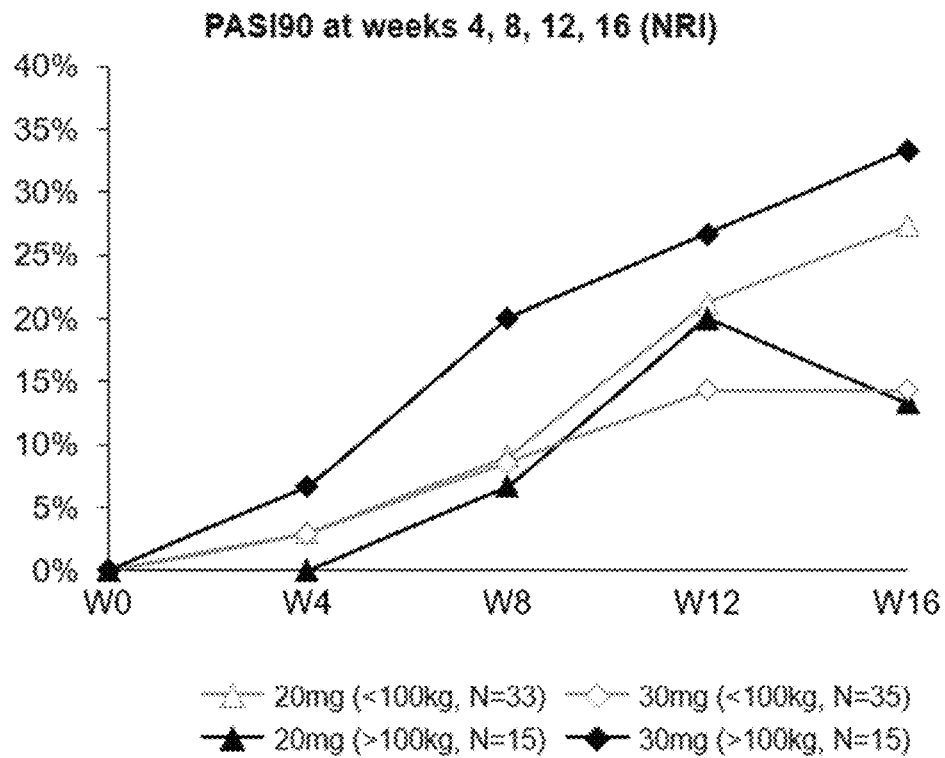
FIG. 30A and FIG. 30B shows the percentage of patients that achieved a 90% reduction in PASI score (PASI-90) at weeks 0, 4, 8, 12 and 16 for two sub-groups of patients based on their body weight at baseline (<100 kg and >100 kg) and for the two active arms in the Phase 2b study in Example 3 (20 mg BID and 30 mg BID).
Figure 30B:
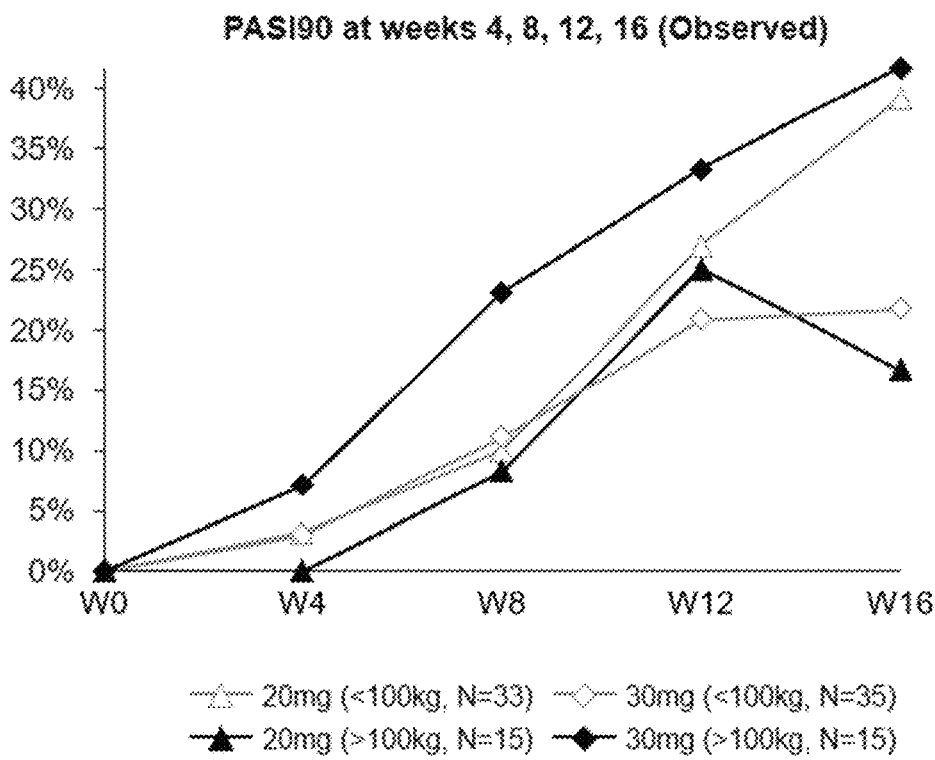

7.2.1 the Efficacy of the 30 mg BID Dose was Consistently Higher in Those Patients Weighing ≥100 kg at Baseline Compared to Those Patients Weighing <100 kg at Baseline Interestingly, the inventors observed that the efficacy of the 30 mg BID dose was consistently higher in those patients weighing ≥100 kg at baseline compared to those patients weighing <100 kg at baseline (for all 3 endpoints and at all time points during treatment, namely at weeks 4, 8, 12 and 16, see FIGS. 28-30).

This observation is counterintuitive and therefore unexpected, as efficacy is usually driven by higher systemic exposure with active drug. Pharmacokinetic (PK) measurements and modeling with the data from the Phase 2b study show, as expected, that patients weighing <100 kg achieve on average a higher exposure (as measured by AUC PK data) with orismilast than those with a weight 100 kg (see FIG. 32), which would normally indicate that those patients weighing <100 kg should achieve at least the same or better efficacy than those patients weighing 100 kg. The opposite was the case in the Phase 2b study in Example 3.

Figure 31:
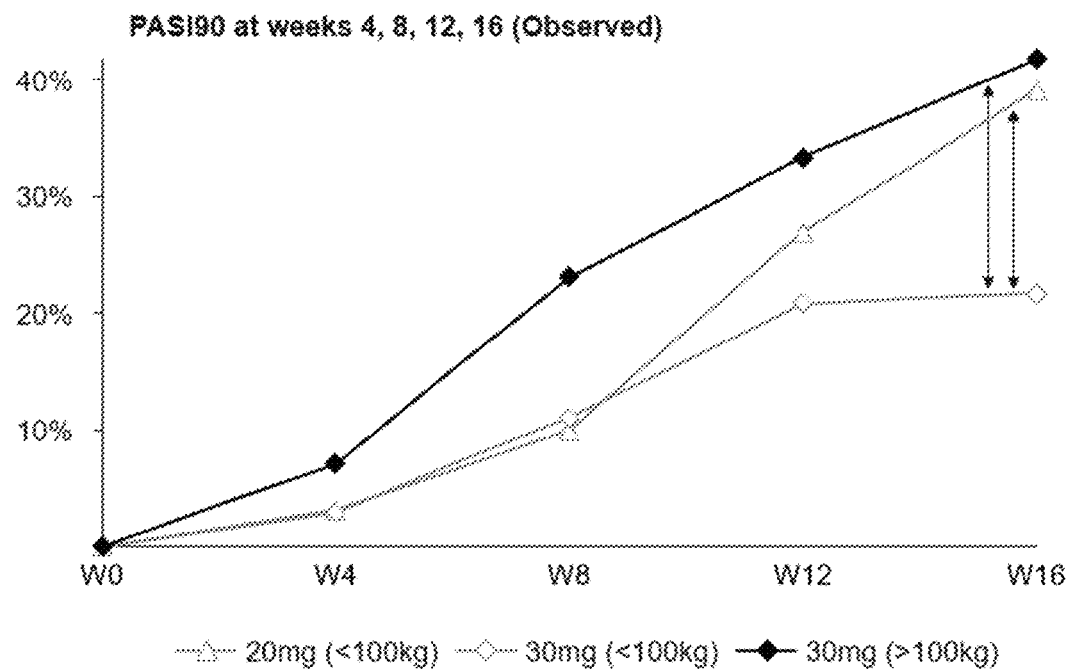
FIG. 31 shows the percentage of patients that achieved a 90% reduction in PASI score (PASI-90) at weeks 0, 4, 8, 12 and 16 for: patients having a body weight at baseline of <100 kg for the 20 mg BID and 30 mg BID arms; and for patients having a body weight at baseline of >100 kg for the 30 mg BID arm in the Phase 2b study in Example 3.

7.2.2 in Patients Weighing <100 kg at Baseline, the 20 mg BID Dose Seems to be (Similar or) More Efficacious than the 30 mg BID Dose The inventors also observed that in those patients weighing <100 kg at baseline, the 20 mg BID dose appeared to be (similar or) more efficacious than the 30 mg BID dose, in PASI75 (see FIG. 29) and in particular in the "hardest-to-achieve" endpoint of PASI90 (see FIGS. 30 and 31).

Figure 32:
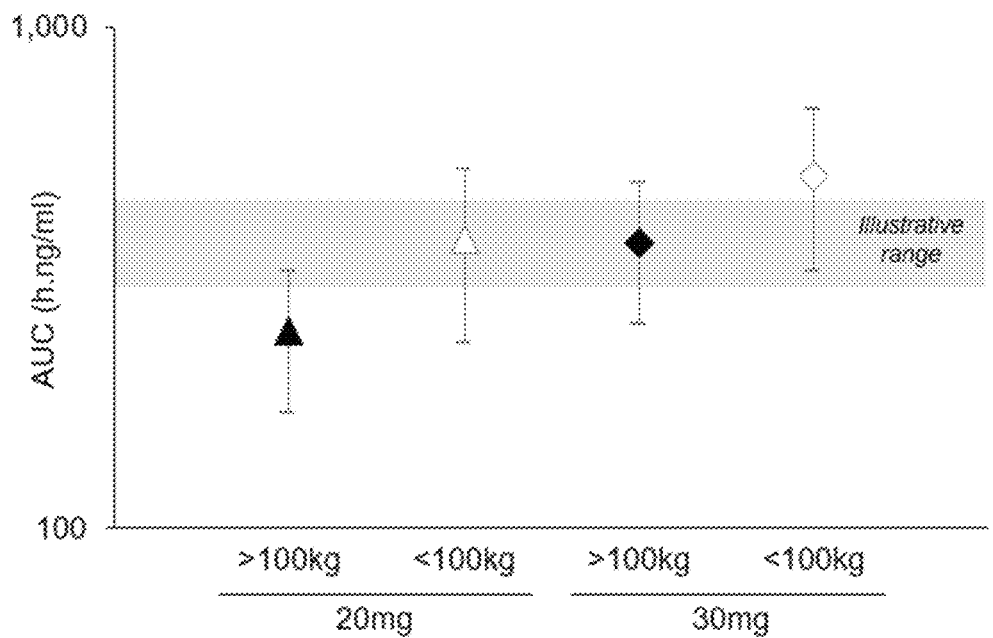
FIG. 32 shows orismilast exposure (AUC) at steady state for different body weights (<100 kg and >100 kg) and doses (20 mg and 30 mg) AUC values are taken from data obtained in simulations in Example 6. The Figure shows mean AUC and standard deviation (SD) and includes an illustrative optimal exposure range to maximise efficacy.

Again this is counterintuitive and therefore surprising, considering that the systemic exposure (as measured by AUC PK data) to orismilast of patients weighing <100 kg was, as expected, higher when dosed with 30 mg BID compared to 20 mg BID (see FIG. 32).

7.2.3 the 20 mg BID Dose is Less Efficacious than the 30 mg BID Dose in Patients Weighing ≥100 kg The inventors further observed that the 20 mg BID dose is less efficacious than the 30 mg BID dose in patients weighing ≥100 kg (for all 3 endpoints and at all time points during treatment, namely at weeks 4, 8, 12 and 16, see FIGS. 28-30).

The 20 mg BID dose results in significantly lower exposure in those heavier patients than the 30 mg dose (see FIG. 32), indicating that one needs a minimal exposure to maximize efficacy.

The systemic exposure analysis is supported by detailed Population PK modeling, which incorporated all clinical studies conducted with orismilast to-date, clearly showing that exposure correlates with both dose administered as well as body weight (see Example 6 and FIG. 32).

7.3 CONCLUSIONS

The results of the analysis suggest that there may be an optimal range of systemic exposure to orismilast that maximizes its efficacy (see FIG. 32):
  if exposure is lower than that "optimal range" (e.g. the 20 mg BID dose in patients weighing ≥100 kg), efficacy will not be optimal, but also (and unexpectedly);
  if exposure is higher than the "optimal range" (e.g. the 30 mg BID dose in patients weighing <100 kg), efficacy will also not be maximized, indicating a (potentially) "bell-shaped" dose-efficacy relationship of PDE4 inhibition by orismilast.

Example 8: A Randomized, Double-Blind, Placebo-Controlled, Parallel-Group, Phase 2b Dose-Ranging Study to Evaluate the Efficacy and Safety of Orismilast in Adults with Moderate to Severe Atopic Dermatitis (Protocol No. UNI50001-202)

A 16-week, phase 2b, double-blinded, placebo-controlled, dose-finding study assessing efficacy and safety of orismilast modified-release (MR) tablets in adults with moderate-to-severe atopic dermatitis was carried out (NCT05469464). Patients were randomized (1:1:1:1) to orismilast 20, 30, 40 mg or placebo, twice daily. Randomized and dosed patients were included in the Intent-to-Treat Population (used for efficacy and safety). Missing data was handled using Multiple Imputation (MI) for the analysis of primary and secondary efficacy endpoints.

8.1 Trial Protocol

Primary Objective
  The primary objective is to evaluate the efficacy and safety of a modified-release orismilast tablet versus placebo in adults with moderate to severe atopic dermatitis (AD).
Secondary Objectives
  The secondary objectives are to evaluate the dose response of orismilast and identify the dose to be further evaluated in a Phase 3 program.
  Exploratory Objectives
  The exploratory objectives are to:
  Evaluate pharmacokinetic (PK) and pharmacodynamic parameters relevant to AD
  Evaluate the effect of orismilast on the pulmonary status and course of the disease in patients with asthma
Primary Endpoint
  Percentage change in Eczema Area and Severity Index (EASI) score from Baseline at Week 16.
Key Secondary Endpoints
  Patients achieving 75% reduction in EASI (EASI75) response at Week 16
  Patients achieving a score of clear (0) or almost clear (1) and at least a 2-point improvement in Investigator Global Assessment for AD (IGA-AD) at Week 16
Other Secondary Endpoints
  Patients achieving a score of clear (0) or almost clear (1) and at least a 2-point improvement in IGA-AD at Weeks 2, 4, 8, 12, and 20
  Patients achieving EASI75 at Weeks 2, 4, 8, 12, and 20
  Patients achieving 50% reduction in EASI (EASI50) and 90% reduction in EASI (EASI90) response at Weeks 2, 4, 8, 12, 16, and 20
  Percent change from Baseline in EASI at Weeks 2, 4, 8, 12, and 20
  Change from Baseline in the peak pruritus numerical rating scale (PPNRS) score at Weeks 1, 2, 4, 8, 12, 16, and 20
  Patients achieving at least a 4-point improvement in the peak pruritus NRS from baseline at Weeks 1, 2, 4, 8, 12, 16, and 20
  Change from Baseline in affected body surface area (BSA) at Weeks 2, 4, 8, 12, 16, and 20
  Change from Baseline in Dermatology Life Quality Index (DLQI) score at Weeks 8, 16, and 20
  Change from Baseline in Patient Oriented Eczema Measure (POEM) score at Weeks 2, 4, 8, 12, 16, and 20
  Change from Baseline in Patient Global Impression of Severity (PGIS) score at Weeks 2, 4, 8, 12, 16, and 20
  Change from Baseline in Patient Global Impression of Change (PGIC) score at Weeks 2, 4, 8, 12, 16, and 20
  Change from Baseline in sleep disturbance NRS score at Weeks 1, 2, 4, 8, 12, 16, and 20
  Change from Baseline in skin pain NRS score at Weeks 1, 2, 4, 8, 12, 16, and 20
Safety Endpoints
  The occurrence, severity, and seriousness of treatment-emergent adverse events reported over the 16-week Treatment Period and the 4-week Follow-up Period
  Changes from Baseline in physical examination findings; vital signs measurements (body temperature, respiration rate, heart rate, and systolic and diastolic blood pressure measurements); and body weight over the 16-week Treatment Period and the 4-week Follow-up Period
  Clinically significant abnormal changes in electrocardiogram (ECG) findings over the 16-week Treatment Period
  Changes from Baseline in safety laboratory values (hematology, serum chemistry, and urinalysis) over the 16-week Treatment Period
  Change from Baseline in Hospital Anxiety and Depression Scale score at each visit except Week 1
  Columbia-Suicide Severity Rating Scale (C-SSRS) score at each visit except Week 1
Exploratory Endpoints
  Change from Baseline in skin biomarkers at Week 16 collected via tape stripping and analysed using proteomic methods
  Patients achieving at least a 2-point improvement in the peak pruritus NRS from baseline at Weeks 1, 2, 4, 8, 12, 16, and 20
  Plasma levels of the drug and its metabolites at Weeks 4, 8, and 16
  Change from Baseline in pulmonary status NRS in patients with asthma at Weeks 4, 8, 12, 16, and 20
Study Design
  A multicenter, randomized, double-blind, placebo-controlled, parallel-group, Phase 2b dose-ranging study designed to assess the efficacy and safety of modified-release orismilast compared with placebo in patients aged at least 18 years with moderate to severe AD. Efficacy and safety outcomes will be evaluated to select an appropriate orismilast dose for subsequent Phase 3 studies. The study was conducted at approximately 48 centers in Europe and United States.

After a Screening visit up to 28 days before Baseline, 210 patients were assigned randomly in a 1:1:1:1 ratio to receive 1 of the 3 orismilast doses (20 mg, 30 mg, or 40 mg) or placebo twice daily (BID) for 16 weeks, with a 4-week follow-up visit. Administration began at Baseline with a dose titration period of up to 2 weeks' duration depending on the dose level. The maximum duration of study participation for each patient was approximately 24 weeks.

Patients were seen at the site at Screening, Baseline (Day 1), and Weeks 1, 2, 4, 8, 12, 16 (End-of-Treatment visit), and 20 (Follow-up visit, 4 weeks after treatment completion or discontinuation). The visit at Week 1 could be conducted via a telemedicine procedure at the Investigator's discretion.

Patients who have been diagnosed with moderate to severe AD for a minimum of 1 year (before the Screening visit) using the Hanifin and Rajka criteria with affected BSA of at least 10%, EASI score of at least 16, and IGA-AD grade of at least 3 at the screening and baseline visits were included in the study. Patients must also have a documented history of inadequate response to treatment with topical medications given for at least 4 weeks (at least 2 weeks for high potency topical corticosteroids), or as labelled, or for whom topical treatments are otherwise medically inadvisable.

At Baseline and at each visit from Week 2 onwards, EASI, affected BSA, and IGAAD were assessed. BSA is defined as all areas with eczematous lesional skin and does not include xerosis (dryness), ichthyosis, keratosis pilaris, urticaria, infection (unless there is underlying eczema), or post inflammatory pigmentation changes. If patients need to manage areas with dry skin and/or pruritus, they were allowed to continue using their current emollient (however, emollients that contain pharmacologically active ingredients such as lactic acid, salicylic acid, urea, alphahydroxy acids, or fruit acids were not allowed from the Screening visit). The severity of itch was assessed by peak pruritus NRS at each visit from baseline to end of the treatment. Disease symptoms were assessed by Patient Oriented Eczema Measure scores at Baseline and at the Weeks 2, 4, 8, 12, 16, and 20 visits. Quality of life related to the disease was assessed by Dermatology Life Quality Index scores at Baseline and at the Weeks 8, 16, and 20 visits. Pulmonary disease status was assessed in patients with asthma by pulmonary status NRS at Baseline and at the Weeks 4, 8, 12, 16, and 20 visits. The severity of disease was assessed by Patient Global Impression of Severity and Patient Global Impression of Change scores at Baseline and at the Weeks 2, 4, 8, 12, 16, and 20 visits. In addition, the sleep disturbance NRS and skin pain NRS was administered at Baseline and at the Weeks 1, 2, 4, 8, 12, 16, and 20 visits.

Safety evaluations include medical history, adverse events (AEs), laboratory and vital sign assessments, physical examination including body weight and height, 12-lead ECG, and mood change evaluations by the patient (Hospital Anxiety and Depression Scale score) and suicidal behaviour and ideation evaluation by the Investigator (C-SSRS).

Before administration of the study drug at Baseline and Weeks 4, 8, and 16, blood was collected for orismilast and the major human metabolite LEO 40815 PK concentration determination. In addition, non-invasive superficial skin sampling using tape stripping was conducted on a target lesion (lesional and no lesional skin sample) at Baseline and Week 16 (only lesional skin sample) in all patients for proteomic analysis.

Selection of Patients

Main Inclusion Criteria

Patients are eligible to be included in the study only if all of the following criteria apply at both the screening and baseline visits:

1. Capable of giving signed informed consent, which includes compliance with the requirements and restrictions listed in the Informed Consent Form (ICF) and in the protocol.
2. Male and female patients at least 18 years of age at the time of signing the ICF.
3. Body weight of greater than 40 kg at the time of signing the ICF.
4. Diagnosis of AD for a minimum of 1 year (before the Screening visit) using the Hanifin and Rajka criteria.
5. Moderate to severe AD (affected BSA at least 10%, IGA-AD grade of at least 3, and EASI score of at least 16) at the Screening and Baseline visits.
6. Candidate for systemic treatment or phototherapy for AD.
7. Patients having a documented history of inadequate response to treatment with topical medications given for at least 4 weeks (at least 2 weeks for high potency topical corticosteroids), or as labelled, or for whom topical treatments are otherwise medically inadvisable.
8. Women of childbearing potential (WOCBP) must have a negative serum pregnancy test result at the Screening visit and a negative urine pregnancy test result at the Baseline visit. In addition, sexually active WOCBP must agree to use a highly effective method of contraception throughout the study and until at least 4 weeks after the end of study treatment.

Main Exclusion Criteria

Individuals meeting any of the following criteria at screening or baseline are ineligible to participate in this study:

1. Therapy-resistant AD, defined as ≥2 treatment failures due to inadequate efficacy within the past 2 years of any biologic therapy, JAK inhibitor treatment or phototherapy administered at an adequate dose and duration according to the label or local/national guidelines. (Patients who stopped systemic treatment for reasons not related to lack of efficacy are not excluded.)
2. Unstable AD with acute deterioration, requiring rescue therapy for AD within 4 weeks of the Screening visit or expected to require rescue therapy within 2 weeks after randomization.
3. History of allergy or hypersensitivity to any component of the study treatment.
4. Currently have active forms of other inflammatory skin disease or have evidence of skin conditions (e.g., psoriasis, seborrheic dermatitis, lupus) at the Baseline visit that would interfere with evaluation of AD or response to Treatment.
5. Active infection (ego, bacterial, viral, fungal) requiring treatment with systemic antibiotics within 4 weeks of the Screening visit.
6. Malignancy or history of malignancy except for treated (i.e., cured) basal cell skin carcinoma.
7. Any chronic or recurrent medical condition associated with serious gastrointestinal diseases, such as inflammatory bowel disease.

8. Any medical or psychiatric condition (e.g., current major depression with a score for depressive symptoms ≥15 of Hospital Anxiety and Depression Scale [HADS] at baseline, schizophrenia, suicidal behaviour, psychiatric hospitalization within the prior year) that, in the Investigator's opinion, would preclude the patient from adhering to the protocol, completing the study per protocol, and/or would place the patient at unacceptable risk while receiving the investigational therapy.
9. Individuals with severe or uncontrolled asthma or any other concomitant condition that is likely to require systemic corticosteroid bursts during the study.
10. Any therapies and systemic treatments as described in the Table listing Restricted Medications that do not comply with the indicated washout interval.
11. Any previous treatment with orismilast or failure of treatment for AD with apremilast or any other systemic phosphodiesterase-4 inhibitor.
12. Any condition, including laboratory or ECG abnormalities, that places the patient at unacceptable risk to participate in the study or confounds the ability to interpret data from the study.
13. Severe hepatic impairment based upon medical history and laboratory abnormalities (e.g., low albumin and abnormal bilirubin levels).
14. Any of the following abnormalities in clinical laboratory test results at Screening, as assessed by the study-specific laboratory and confirmed by a single repeat test, if deemed necessary:
Absolute neutrophil count of less than the lower normal range of the Central Laboratory (LNR) i.e. $1.7 \times 10^9$/L ($1700/mm^3$)
Hemoglobin of less than 10.0 g/dL or hematocrit less than 30%
Platelet count of less than 100,000 $mm^3$
Absolute lymphocyte count of less than the lower normal range of the Central Laboratory (LNR) i.e. $0,9 \times 10^9$/L ($900/mm^3$)
Total bilirubin greater than 1.5× the upper limit of normal (ULN); patients with a history of Gilbert's syndrome may have direct bilirubin measured and would be eligible for this study provided the direct bilirubin result is less than or equal to the ULN
Alanine aminotransferase or aspartate aminotransferase greater than 2.5 xthe ULN
Serum creatinine greater than or equal to 1.5 mg/dL. For patients with a value of greater than or equal to 1.5 mg/dL, if their creatinine clearance is at least 60 mL/min (calculated using the Chronic Kidney Disease Epidemiology Collaboration creatinine equation) enrollment may be allowed.
15. History or evidence of hepatitis B virus infection at Screening. Patients with a positive hepatitis B surface antigen result are excluded. For patients with an isolated positive antihepatitis B core antibody result, the hepatitis B surface antibody result must also be positive to be eligible for this study.
16. History or positive test result for hepatitis C virus (HCV) antibody, indicating ongoing infection, at Screening. Confirmatory testing for HCV RNA will be conducted for patients who have a positive test result. Patients who have a negative result for HCV RNA will be eligible to participate in the study.
17. History of positive HIV test result or congenital or acquired immunodeficiency (e.g., common variable immunodeficiency disease). Patients who are positive for HIV antibodies (HIV-1 or HIV 2) at Screening are excluded from the study.
18. Suicidal ideation or behaviour in the past 12 months as indicated by a positive response (yes) to questions 4 or 5 on the C-SSRS completed at the Screening visit or at Baseline.
19. Pregnant or breastfeeding.
20. History of alcohol or substance abuse within 6 months before Baseline that, in the opinion of the Investigator, will preclude participation in the study.
21. Institutionalized by court order or by local authority.
22. Regular use (more than 2 visits per week) of a tanning booth/parlor.

Pharmacokinetics

Blood samples for PK analysis of orismilast and its major metabolite levels were collected at the designated time points). The actual date and time of each blood sample collection was recorded. Patients were offered optional participation in specific blood sampling for calculation of PK profiles.

The concentration of study drug and main metabolite were determined from the plasma samples using a validated analytical method.

Pharmacodynamics

Stratum corneum skin samples were collected at the designated time points using the tape stripping method to evaluate biomarker expression levels. Tape stripping is a minimally invasive, nonscarring approach using serial adhesive films to capture the stratum corneum and the upper part of the granular layer.

At Baseline, before administration of study drug, 1 lesional and 1 non-lesional area were identified, and 20 consecutive skin samples were collected from each area. At Week 16, the same procedure was repeated only from the same lesional areas sampled at Baseline.

Treatments

The following applied to the study.

Details of Study Treatments and Dosage Schedule

The study treatment was formulated as modified-release tablets (10 mg and 30 mg) or placebo tablets for oral administration. Tablets were taken in the morning and in the evening, approximately every 12 hours. The minimum time interval between 2 consecutive doses is 6 hours. The first dose of the study drug was taken in the evening of Day 1 (Baseline visit). PK studies have shown no difference in PK properties whether the product is taken under fasted condition or with a low-fat meal. Intake with a high-fat meal leads to a higher incidence of GI side effects and should therefore be avoided. The Table below provides details about study treatment and dosage schedule.

TABLE

Study Treatment and Dosage Schedule

| Arm name | Orismilast 20 mg BID | Orismilast 30 mg BID | Orismilast 40 mg BID | Placebo |
|---|---|---|---|---|
| Drug name | Orismilast | Orismilast | Orismilast | Placebo |
| Type | | Drug | | |
| Dose formulation | | 10 mg and 30 mg tablet or matching placebo tablet | | |

TABLE-continued

Study Treatment and Dosage Schedule

| Arm name | Orismilast 20 mg BID | Orismilast 30 mg BID | Orismilast 40 mg BID | Placebo |
|---|---|---|---|---|
| Frequency | | BID (approximately every 12 hours) | | |
| Administered tablets | 2 × 10-mg orismilast tablets BID | 1 × 30-mg orismilast tablet and 1 placebo tablet BID | 1 × 10-mg and 1 × 30-mg orismilast tablets BID | 2 × placebo tablets BID |
| Route | | Oral | | |
| Use | | Experimental | | Placebo |
| Sourcing | | Provided centrally by the Sponsor | | |
| Packaging and labeling | Investigational medicinal product will be provided in individually labeled wallet cards with blistered tablets. Each card will be labeled as required per country requirement. | | | |

Abbreviation: BID, twice daily.

Dosing Schedule

The study treatment dose was titrated over a maximum period of 2 weeks (see Table below).

TABLE

Dose Titration Schedule

| Arm | Day 1 (mg) AM | Day 2 (mg) AM | Day 2 (mg) PM | Day 3 (mg) AM | Day 3 (mg) PM | Day 4 (mg) AM | Day 4 (mg) PM | Day 5 (mg) AM | Day 5 (mg) PM | Day 6 (mg) AM | Day 6 (mg) PM | Day 7 (mg) AM | Day 7 (mg) PM | Day 8 (mg) AM | Day 8 (mg) PM |
|---|---|---|---|---|---|---|---|---|---|---|---|---|---|---|---|
| 20 mg BID | 10 | 10 | 10 | 10 | 10 | 10 | 10 | 10 | 20 | 10 | 20 | 10 | 20 | 20 | 20 |
| 30 mg BID | 10 | 10 | 10 | 10 | 20 | 20 | 20 | 20 | 20 | 20 | 30 | 20 | 30 | 20 | 30 |
| 40 mg BID | 10 | 10 | 10 | 10 | 20 | 20 | 20 | 20 | 20 | 20 | 30 | 20 | 30 | 20 | 30 |
| Placebo | P | P | P | P | P | P | P | P | P | P | P | P | P | P | P |

| Arm | Day 9 (mg) AM | Day 9 (mg) PM | Day 10 (mg) AM | Day 10 (mg) PM | Day 11 (mg) AM | Day 11 (mg) PM | Day 12 (mg) AM | Day 12 (mg) PM | Day 13 (mg) AM | Day 13 (mg) PM | Day 14 (mg) AM | Day 14 (mg) PM | From Day 15 (mg) AM | From Day 15 (mg) PM |
|---|---|---|---|---|---|---|---|---|---|---|---|---|---|---|
| 20 mg BID | 20 | 20 | 20 | 20 | 20 | 20 | 20 | 20 | 20 | 20 | 20 | 20 | 20 | 20 |
| 30 mg BID | 30 | 30 | 30 | 30 | 30 | 30 | 30 | 30 | 30 | 30 | 30 | 30 | 30 | 30 |
| 40 mg BID | 30 | 30 | 30 | 30 | 30 | 30 | 30 | 40 | 30 | 40 | 30 | 40 | 40 | 40 |
| Placebo | P | P | P | P | P | P | P | P | P | P | P | P | P | P |

Treatment Accountability and Compliance

The patients will receive the study drug at the site directly from the Investigator or designee. The date of the first dose should be recorded in the source documents and recorded in the eCRF. At all site visits beginning with the Week 2 visit, patients will return all study drug, including packaging, dispensed at the previous visit, and it will be documented using the IWRS.

The patients will self-administer the study drug at home, and compliance with the protocol will be assessed at each visit beginning with the Week 2 visit. Compliance will be assessed by direct questioning and counting returned tablets during the site visits and documented in the source documents and relevant form. Deviation from the prescribed dosage regimen should be recorded.

A record of the quantity of study drug dispensed to and administered by each patient must be maintained and reconciled with study drug and compliance records. Study drug administration dates, including dates for administration delays and/or dose reductions, will also be recorded.

Discontinuation for noncompliance is at the investigator's discretion and is to be noted on the eCRF.

Prior and Concomitant Therapy

Any concomitant medication, supplement, or procedure within 6 months before Baseline or received during the study must be recorded, along with:

Reason for use
Dates of administration, including start and end dates
Dosage information, including dose and frequency Patients may take any medication that is not restricted by the protocol and would not be expected to interfere with the conduct of the study or affect assessments. Chronic medication should be dosed on a stable regimen.

Emollients can be used at patient discretion for managing dry skin on non-eczematous areas or for reducing pruritus on eczematous areas. The use of emollients is to be recorded as concomitant treatment. In order not to generate local tolerance issues, patients should only use emollients that they have already used (and that they tolerated well) and refrain from initiating treatment with a new emollient. Emollients that contain pharmacologically active ingredients such as lactic acid, salicylic acid, urea, alpha-hydroxy acids, or fruit acids are not allowed from the Screening visit.

Over the course of this trial, additional medications may be required to manage adverse events from trial treatment. At the discretion of the Investigator antiemetic medications (e.g. metoclopramide) or anti-diarrheic medications (e.g. loperamide), or mild analgesics for headaches, (e.g. acetyl-salicylic acid/aspirin or paracetamol/acetaminophen and NSAIDs) may be administered. This approach is well established for other PDE4-inhibitors, and described by Tello E D et al. 2021 (Tello E D, Dauden, et al. Multidisciplinary management of the adverse effects of apremilast. Actas Dermo-Sifiliográficas (English Edition), 2021, 112.2:134-141.)

Restricted Medications

Restricted prior therapies are provided in the Table below. In addition, patients with any prior treatment with orismilast or failure of treatment for AD with apremilast or any other systemic PDE4 inhibitor are ineligible.

TABLE

Restricted medications

| Compound | Washout and Prohibition During the Study |
|---|---|
| Topical medications/treatments that could affect AD or study evaluations (eg, antihistamines, corticosteroids, tazarotene, pimecrolimus, tacrolimus, or PDE4 inhibitor) | ≥2 weeks before Baseline and throughout the study |
| Systemic treatment with medications other than biologics with a possible effect on AD, like apremilast, corticosteroids, retinoids, and systemic immunosuppressants (eg, methotrexate, azathioprine, cyclosporine, Janus kinase inhibitors) | ≥4 weeks before Baseline or 5 half-lives (whichever is longer) and throughout the study |
| Investigational drugs other than the study drug | ≥4 weeks before Baseline, or 5 half-lives, if known (whichever is longer) and throughout the study |
| Use of phototherapy or prolonged sun exposure or use of tanning booths or other ultraviolet light sources (ie, ultraviolet B, psoralens, and long-wave ultraviolet radiation) | ≥4 weeks before Baseline and throughout the study |
| Dupilumab or any biologic targeting the immune system | ≥12 weeks before Baseline and throughout the study |
| Concomitant medication mainly metabolized via the cytochrome 2D6 isozyme and with a narrow therapeutic window, such as tricyclic antidepressants (eg, nortriptyline, amitriptyline, imipramine, and desipramine) or type IC antiarrhythmics (propafenone, flecainide, and encainide) | ≥4 weeks before Baseline and throughout the study |
| Systemic antibiotics | ≥4 weeks before Screening visit |
| Initiation of new emollient or emollients containing pharmacologically active ingredients (such as lactic acid, salicylic acid, urea, alpha-hydroxy acids, or fruit acids) and regular use (more than 2 visits per week) of a tanning booth/parlor | From the Screening and throughout the study |

Abbreviations: AD, atopic dermatitis; PDE, phosphodiesterase.

Concomitant medication mainly metabolized via cytochrome 3A4 and with a narrow therapeutic window (such as anticoagulant or digoxine) are not to be excluded but require close medical monitoring. The Medical Monitor should be contacted for questions regarding concomitant or prior therapy.

Drug-Drug Interactions

From clinical studies, orismilast can be considered a weak inhibitor of CYP3A4, and concomitant use of orismilast with CYP3A4 substrates may increase the systemic exposure to these medicinal products. Patients receiving orismilast concurrently with these medicinal products should be monitored for related AEs, especially if they have a narrow therapeutic window.

In vitro orismilast is a competitive direct inhibitor of CYP2D6. Concomitant use of orismilast with other drugs mainly metabolized by the cytochrome CYP2D6 has not been studied clinically.

Because of a potential increase of systemic exposure to medicinal products metabolized by CYP2D6 when concomitantly administered with orismilast, patients should be monitored for AEs related to these medicinal products. Coadministration of drugs with a narrow therapeutic index, such as tricyclic antidepressants (e.g., nortriptyline, amitriptyline, imipramine, and desipramine) or type 1C antiarrhythmics (propafenone, flecainide, and encainide) is prohibited (see Table above).

Efficacy Assessments—Investigator Assessments

The following applied to the study.

Eczema Area and Severity Index

The EASI is an investigator-assessed instrument measuring the severity of clinical signs and the percentage of affected BSA in patients with AD. The EASI is a composite scoring system used by the AD clinical evaluator to evaluate the degree of erythema, induration/papulation, excoriation, and lichenification (each scored separately) for each of 4 body regions, with adjustment for the percentage of BSA involved for each body region and for the proportion of the body region to the whole body (Hanifin JM, Thurston M, Omoto M, Cherill R, Tofte S J, Graeber M. The eczema area and severity index (EASI): assessment of reliability in atopic dermatitis. EASI Evaluator Group. Exp Dermatol. 2001; 10(1):11-18. doi:10.1034/j.1600-0625.2001.100102.x).

EASI scores range from 0 to 72, with higher scores reflecting greater disease severity. Erythema, induration/papulation, excoriation, and lichenification are scored on a scale of 0 (absent) to 3 (severe) for each body region: head and neck, upper limbs (including the external axillae and hands), trunk (including the internal axillae and groin), and lower limbs (including the buttocks and feet). The extent of affected skin in each body region is scored on a scale of 0 (no involvement) to 6 (90% to 100% involvement). The EASI assessment will exclude the scalp, palms, and soles from scoring.

The Investigator Global Assessment for Atopic Dermatitis

The IGA-AD is a measure used by physicians to determine a patient's overall severity of disease.

The static version is used in this trial for measurement at a single point in time. The Investigator will rate the severity of the patient's AD on a 5-point scale ranging from 0 (clear) to 4 (severe) (Simpson E, Bissonnette R, Eichenfield L F, et al. The Validated Investigator Global Assessment for Atopic Dermatitis (vIGA-AD): the development and reliability testing of a novel clinical outcome measurement instrument for the severity of atopic dermatitis. J Am Acad Dermatol. 2020; 83(3):839-846. doi:10.1016/j.jaad.2020.04.104).

Body Surface Area

The BSA assessment estimates the extent of disease or skin affected by AD and is expressed as a percentage of total BSA. BSA will be determined by the Investigator or designee using the patient's hand (palm+fingers)=1% BSA rule.

Efficacy Assessments—Patient-Reported Outcomes

The following applied to the study.

Peak Pruritus Numerical Rating Scale (PPNRS)

The severity of itch (pruritus) due to AD will be assessed using a horizontal 11-point NRS. Patients will be asked to assess their "worst itching due to AD over the past 24 hours" on an NRS anchored by the terms "no itching" (0) and "worst possible itching" (10). The item will be completed at each visit via an application on an electronic device in the clinic or the patient's own electronic device from baseline through Week 20.

Skin Pain Numerical Rating Scale

The skin pain NRS is a patient-administered, 11-point horizontal scale anchored at 0 and 10, with 0 representing "no pain" and 10 representing "worst pain imaginable." Overall severity of a participant's skin pain is indicated by selecting the number that best describes the worst level of skin pain in the past 24 hours. The item will be completed at each visit via an application on an electronic device in the clinic or the patient's own electronic device from baseline through Week 20.

Sleep Disturbance Numerical Rating Scale

The sleep disturbance NRS is a scale used by the patients to report their degree of sleep loss related to AD. Patients will be asked the following question in their local language: how would you rate your sleep last night≥On a scale of 0 to 10, with 0 being "no sleep loss related to signs/symptoms of AD" and 10 being "I cannot sleep at all because of the signs/symptoms of AD". Higher scores indicate worse outcomes. The item will be completed at each visit via an application on an electronic device in the clinic or the patient's own electronic device from baseline through Week 20.

Patient Oriented Eczema Measure

The POEM is a 7-item, validated questionnaire completed by the patient to assess disease symptoms. Patients are asked to respond to questions on frequency of sleep loss and skin dryness, itching, flaking, cracking, bleeding, and weeping over the past week. All answers carry equal weight, with a total possible score ranging from 0 to 28. A high score is indicative of a poor quality of life. The item will be completed at each visit via an application on an electronic device in the clinic or at the patient's own electronic device from baseline through Week 20 except Week 1.

Patient Global Impression of Severity Scale

The PGIS scale is a single question asking the patient how he or she would rate his or her overall AD symptoms over the past 24 hours. The 5 categories of responses are (0) "no symptoms", (1) "very mild", (2) "mild", (3) "moderate", and (4) "severe." The item will be completed at each visit via an application on an electronic device in the clinic or the patient's own electronic device from baseline through Week 20 except Week 1.

Patient Global Impression of Change Scale

The PGIC scale measures change in clinical status of AD. The PGIC is based on a 7-point scale, and the patient will rate the change from the start of treatment as 1 "very much improved," 2 "much improved," 3 "minimally improved," 4 "no change," 5 "minimally worse," 6 "much worse," and 7 "very much worse." The item will be completed at each visit via an application on an electronic device in the clinic or the patient's own electronic device from baseline through Week 20 except Week 1.

Dermatology Life Quality Index

The DLQI is a 10-item validated questionnaire completed by the patient and used to assess the effect of skin disease on the patient's quality of life during the previous week. The 10 questions cover the following topics: symptoms; embarrassment; interference with shopping and home care, clothing choices, social and leisure activities, sports participation, work or study, close relationships, and sex; and treatment. Each question is scored from 0 to 3 ("not at all," "a little", "a lot," and "very much" respectively), giving a total score ranging from 0 to 30. A high score is indicative of a poor quality of life. The item will be completed at each visit via an application on an electronic device in the clinic or the patient's own electronic device at baseline and Weeks 8, 16, and 20.

Pulmonary Status Numerical Rating Scale in Patients with Asthma

Pulmonary disease status will be assessed in patients with asthma using a horizontal NRS. Patients will be asked to assess their "symptoms due to asthma over the past 7 days" on an NRS anchored by the terms (0) "no symptoms" and (10) "very bad symptoms". The item will be completed at each visit via an application on an electronic device in the clinic or the patient's own electronic device at baseline and Weeks 4, 8, 12, 16, and 20.

Safety Assessments

The following applied to the study.

Safety assessments (medical history, vital signs and body weight, physical examinations, Electrocardiograms (ECGs), clinical laboratory results [routine hematology, urinalysis and biochemistry], The Hospital Anxiety and Depression Scale (HADS), The Columbia-Suicide Severity Rating Scale (C-SSRS), and Adverse Events (AEs)) are to be performed at protocol-specified visits.

The HADS is a patient-reported outcome, comprising 7 questions for anxiety and 7 questions for depression, with each answer being graded from 0 to 3 with a higher score indicating a worse condition. For each group of questions, scores of 7 or less indicate cases without anxiety or depression, whereas scores of 8 to 10, 11 to 14, and 15 to 21 indicate mild, moderate, and severe cases, respectively. The HADS is one of the tools recommended by the National Institute for Health and Care Excellence for diagnosis of depression and anxiety.

Any patient with a score for depressive symptoms ≥15 at baseline will not be eligible for enrolment in the study. Patients with a clinically significant worsening of depressive symptoms or new occurrence of clinically significant depression during the study may be referred to a mental health specialist (psychiatrist or clinical psychologist) for further evaluation. After a mental health specialist evaluation, the final decision on restarting or permanently discontinuing study treatment will be at the discretion of the Investigator in consultation with the mental health specialist.

The C-SSRS, Investigator-administered version, was designed to provide a prospective, standardized measure of suicidality. The scale allows clinicians and researchers alike to assess the severity and lethality of suicidal behaviours and ideations and can be used to monitor treatment outcomes and establish suicide risk in a variety of research and clinical settings. Requiring approximately 5 minutes for completion, the C-SSRS is administered in the form of a clinical interview. This C-SSRS is available in 2 versions: 1 for use at screening referring to the past year and 1 for use throughout the rest of the study referring to the time since the prior visit. If at screening or baseline there are "yes" answers on item 4 or 5, the patient will not be included in the study. Any patient with a positive response at subsequent visits (answers "yes" to questions 1-5) should be referred to a mental health specialist (psychiatrist or clinical psychologist) for further evaluation, and the study medication should be paused. After a mental health specialist evaluation, the final decision on restarting or permanently discontinuing study treatment will be at the discretion of the Investigator in consultation with the mental health specialist.

AEs will be collected throughout the study.

8.2 Results

Baseline demographics and disease characteristics were generally balanced across groups for the 233 dosed patients. Mean EASI at baseline was the least severe reported in Phase 2b/3 studies in moderate-to-severe AD (Silverberg J I, Ho S, Collazo R. Dermatol Ther (Heidelb). 2023 December; 13(12):3019-3029). The mean bodyweight in each dose group was 80.9 kg (Placebo), 80.5 kg (20 mg BID), 80.7 kg (30 mg BID) and 86.6 kg (40 mg).

Significantly more patients achieved IGA0/1 responses at week 16 in orismilast 20 mg BID (n=58), 30 mg BID (n=61), and 40 mg BID (n=59) groups, compared to placebo (n=55) (26.3%, 24.3%, 30.9%, and 9.5%, respectively. All p-values <0.05, MI). All active arms demonstrated a significant 24-point reduction in itch NRS at week 2 (MI p<0.05 compared to placebo. Similarly, Patient Global Impression of Change of "much improved" or "very much improved" improved significantly in active arms compared to placebo at week 16. The mean percentage change in EASI at week 16, was−55.1%, −52.2%,−61.4% and−50.4%, in orismilast 20 mg BID, 30 mg BID, 40 mg BID and placebo groups, respectively (p>0,05). In a subgroup analysis of patients with a baseline EASI >21, separation from placebo was increased (20 mg BID and 40 mg BID arms) as EASI75 and EASI90 placebo responses reduced by 50% and 67%, respectively (all patients 54% and 21%; EASI >21:27% and 7%).

Given the small number of patients weighing >=100 kg in the relevant dose groups (N=4 in 20 mg BID, N=5 in 30 mg BID), a weight-based split on efficacy parameters was not performed.

Through Week 16, percentages of patients experiencing any Treatment Emergent Adverse Event (TEAE) were; orismilast 20 mg BID: 76%; 30 mg BID: 79%; 40 mg BID: 86%; placebo: 64%. Infection rates were numerically lower in active compared to placebo. The most common adverse events were diarrhea, nausea, and headache, mainly seen within the first month, mostly mild in severity and few lead to treatment discontinuation.

8.4 Conclusions

Orismilast demonstrated early itch reduction NRS≥4 and statistically significant efficacy versus placebo at week 16 as measured by IGA0/1. The study was impacted by a high EASI placebo rate; however, in severe patients the 20 mg and 40 mg doses separated from placebo on EASI75 and EASI90, consistent with the overall findings by IGA 0/1, patient reported efficacy and objective biomarkers.

No new safety signals were identified, and the profile was aligned with the well-established experience from the PDE4 class. The most frequent TEAEs were gastrointestinal-related and headache.

These data confirmed the clinical relevance of high potency PDE4B/D selective inhibition with orismilast.

8.3 Abbreviations

| Abbreviation | Definition |
| --- | --- |
| AD | atopic dermatitis |
| AE | adverse event |
| AESI | adverse event of special interest |
| AUC | area under the curve |
| BID | twice daily |
| BSA | body surface area |
| cAMP | cyclic adenosine monophosphate |
| $C_{max}$ | maximum (or peak) serum concentration |
| C-SSRS | Columbia-Suicide Severity Rating Scale |
| CTCAE | National Cancer Institute Common Terminology Criteria for Adverse Events |
| DLQI | Dermatology Life Quality Index |
| EASI | Eczema Area and Severity Index |
| EASI50 | 50% reduction in Eczema Area and Severity Index |
| EASI75 | 75% reduction in Eczema Area and Severity Index |
| EASI90 | 90% reduction in Eczema Area and Severity Index |
| ECG | electrocardiogram |
| eCRF | electronic case report form |
| GCP | Good Clinical Practice |
| GI | gastrointestinal |
| HADS | Hospital Anxiety and Depression Scale |
| HCV | hepatitis C virus |
| HIPAA | Health Insurance Portability and Accountability Act |
| ICF | Informed Consent Form |
| ICH | International Council for Harmonisation |
| IEC | independent ethics committee |
| IFN | interferon |
| IGA-AD | Investigator Global Assessment for Atopic Dermatitis |
| IL | interleukin |
| IRB | institutional review board |
| ITT | intent-to-treat |
| IWRS | Interactive Web Response System |
| IFN | interferon |
| IGA-AD | Investigator Global Assessment for Atopic Dermatitis |
| IL | interleukin |
| IRB | institutional review board |
| ITT | intent-to-treat |
| IWRS | Interactive Web Response System |
| JAK | Janus kinase inhibitors |
| LS | least squares |
| MH | Mantel-Haenszel |
| NRS | numerical rating scale |
| PASI | Psoriasis Area and Severity Index |
| PD | pharmacodynamic |
| PDE | phosphodiesterase |
| PGIC | Patient Global Impression of Change |
| PGIS | Patient Global Impression of Severity |
| PK | pharmacokinetic |
| POEM | Patient Oriented Eczema Measure |
| PRO | patient-reported outcomes |
| PT | preferred term |
| SAE | serious adverse event |
| SOC | system organ class |
| SUSAR | suspected unexpected serious adverse reactions |
| TEAE | treatment-emergent adverse event |
| Th | T helper |
| $t_{max}$ | time drug was present at the maximum concentration in serum |
| TNF | tumor necrosis factor |
| TSS | total sign score |

| Abbreviation | Definition |
| --- | --- |
| WOCBP | women of childbearing potential |
| ULN | upper limit of normal |

Example 9: Analysis of the Results of the Trial in Example 8 to Assess the Effect of Orismilast on Pruritus (Itch) Associated with AD An analysis of the results of the Phase 2b study in Example 8 testing oral modified release orismilast in moderate-to-severe atopic dermatitis patients was conducted to assess the effect of orismilast on pruritus (itch). All statistical analyses were conducted using SAS® for Windows® Version 9.4 or higher.

9.1 Methods

The binary secondary efficacy endpoint, 4-point improvement in the peak pruritus numerical rating scale ("responders"), was analysed using the Mantel-Haenszel (MH) test and Fisher's exact tests, comparing the proportions of PPNRS responders in each active treatment group with placebo (intent-to-treat (ITT) population). Every subject that was part of the ITT Population and had a baseline PPNRS score of ≥4 was included in the analysis.

The ITT population included all randomized subjects who received at least 1 dose of orismilast. The treatment group assignment was designated according to initial randomization. The ITT population served as the basis for the analysis of efficacy.

PPNRS assesses the severity of itch (pruritus) due to atopic dermatitis using a horizontal 11-point NRS. Patients were asked to assess their "worst itching due to AD over the past 24 hours" on an NRS anchored by the terms "no itching" (0) and "worst possible itching" (10).

Missing data was handled using Multiple Imputation (MI) or Non-Response Imputation (NRI).

Figure 34:
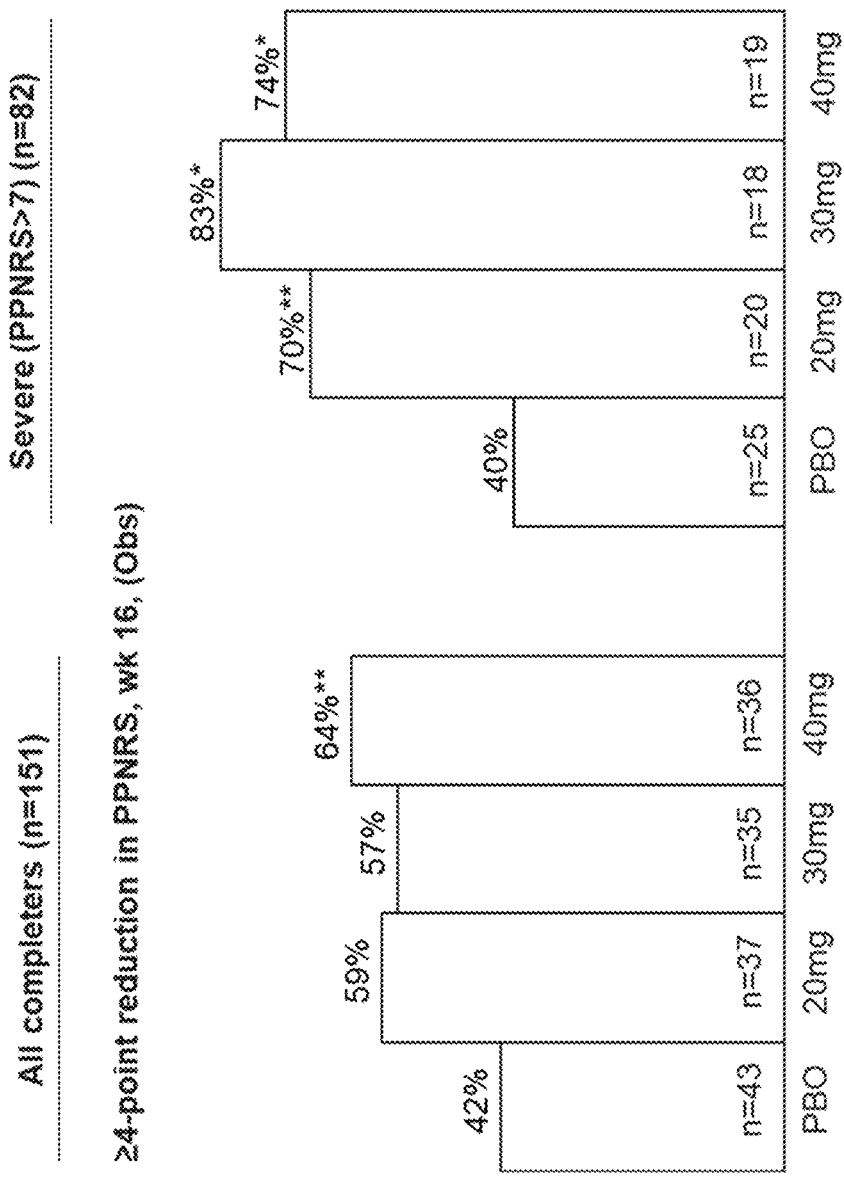
FIG. 34 shows the percentage of subjects with 4 point reduction in peak pruritus NRS at week 16 (observed) for each of the active arms (20 mg BID, 30 mg BID and 40 mg BID) and for placebo in all completers and subjects with severe itch (PPNRS>7) at baseline. PPNRS=peak pruritus numerical rating scale, *p<0.05, ** p<0.1; 7 is the PPNRS median at baseline, Obs=observed values.

In FIG. 34, "Observed" or "Obs" refers to all subjects in the ITT Population with a recorded PPNRS score, i.e. if the PPNRS score is missing the value was not imputed. In the NRI analysis, if a PPNRS score is missing or 'treated as missing', the value will be handled as non-response. In the MI analysis, if a PPNRS score is missing or 'treated as missing', the value will be imputed by multiple imputation.

9.2 Results

The analysis showed a rapid and statistically significant itch improvement observed with orismilast. The effect was particularly clear in AD patients having more severe itch (PPNRS >7) at baseline.

Figure 33:
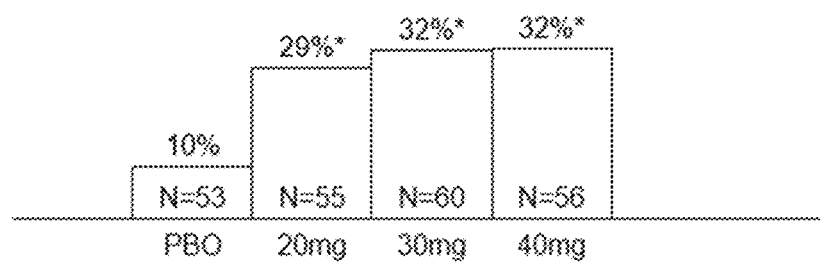
FIG. 33 shows the percentage of subjects with 24 point reduction in peak pruritus NRS at week 2 MI and NRI data) for each of the active arms: 20 mg BID, 30 mg BID and 40 mg BID long with placebo. * p<0.05; ** p<0.1; MI=multiple imputation (primary analysis); NRI=Non-responder imputation.
Figure 33:
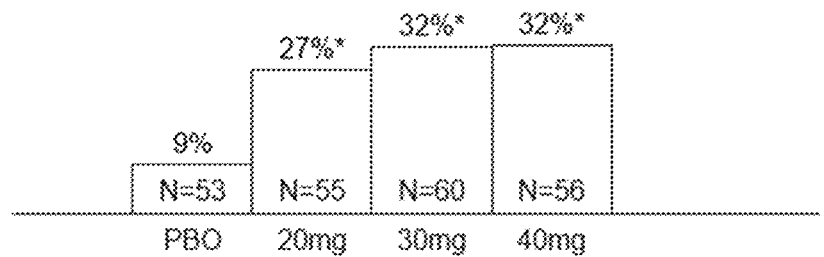

At week 2, all active arms (20 mg BID, 30 mg BID and 40 mg BID orismilast) demonstrated a significant 24-point reduction in PPNRS (MI $p<0.05$ compared to placebo, see FIG. 33.

At week 16, all active arms showed a statistically significant improvement compared to placebo for ≥4 point reduction in PPNRS, in subjects having severe itch (PPNRS>7) at baseline (Observed $p<0.05$ or $p<0.1$ compared to placebo, see FIG. 34.

Example 10: Analysis of the Results of the Phase2b Moderate to Severe Psoriasis Study in Example 3 to Assess Changes from Baseline in Skin Biomarkers

10.1 Methods

Skin tape strip samples were taken from lesional and non-lesional skin at baseline and lesional skin at week 16 of patients participating in the phase 2b, dose-ranging study assessing oral modified release orismilast in adults with moderate-to-severe plaque psoriasis (NCT05190419) described in Example 3. Approximately twenty consecutive stratum corneum samples were collected from the same skin site by tape stripping (D-squames; Monaderm DS100) of both lesional and non-lesional skin at baseline and lesional skin at week 16. To extract the proteins from the tapes the first ten tapes were pooled together and used for subsequent protein extraction by incubation in 800 µL of PBS containing 0.2% Triton X-100 together with a mixture of protease inhibitors and incubated overnight at 4° C. under stirring at 1400 rpm in a thermo mixer (Eppendorf). The insoluble material was removed by filtration on 0.22 µm filters by centrifugation. The protein extracts were analyzed using the Olink® technology (Target 96 Inflammation panel). Protein extracts from patients treated with placebo, 20 mg orismilast BID, and 30 mg orismilast BID as described in Example 3 were analyzed.

OLINK data was analyzed in R 2023.09.0+463 using a linear mixed effect model (OlinkAnalyse and lme4) to estimate log 2 fold changes between Week 16 lesional skin versus baseline lesional skin and baseline lesional versus baseline non-lesional skin levels. P-values were corrected for multiple testing using the Benjamini-Hochberg method. The data was further modeled according to a weight-based dosing regimen in which data of the 20 mg Orismilast BID arm was used for patients with a bodyweight at baseline of <100 kg and combined with using data of the 30 mg Orismilast BID arm for patients ≥100 kg, respectively (named "P3DR").

10.2 Results

Expression of key disease driving cytokines were significantly reduced in psoriatic lesions after treatment with oral orismilast for 16 weeks with 20 mg BID and 30 mg BID (see Table below).

TABLE

Log2 foldchanges of selected cytokines with related immune pathway at Week 16.

| Pathway | Protein | 20 mg BID log2FCH (FDR); | 30 mg BID W16_L - BL_L | P3DR |
| --- | --- | --- | --- | --- |
| General Chemokine Cytokine | CXCL6 | −2.34 *** | −3.15 *** | −3.02 *** |
| | IL18R1 | −1.25 ** | −1.99 *** | −1.83 *** |
| | CXCL5 | −1.67 ** | −2.26 *** | −2.25 *** |
| | IL18 | −2.10 ** | −3.46 *** | −2.96 *** |
| Innate Immunity | IL8 | −1.82 * | −2.76 *** | −2.42 *** |
| | IL. 17C | −2.49 *** | −3.39 *** | −3.20 *** |
| Macrophage | CSF1 | −1.35 ** | −1.97 *** | −1.86 *** |
| MMPs | CCL4 | −2.46 *** | −2.83 *** | −3.14 *** |
| | MMP1 | −2.41 ** | −3.30 *** | −3.31 *** |
| $T_H$1-pathway | CXCL10 | −2.20 *** | −2.89 *** | −2.94 *** |
| | CXCL9 | −2.40 *** | −3.32 *** | −3.24 *** |
| | IFNγ | −1.21 * | −2.02 *** | −1.91 *** |
| | TNFα | −1.92 *** | −2.48 *** | −2.50 *** |
| | CCL3 | −2.68 *** | −3.42 *** | −3.60 *** |

TABLE-continued

Log2 foldchanges of selected cytokines
with related immune pathway at Week 16.

| Pathway | Protein | 20 mg BID | 30 mg BID | P3DR |
|---|---|---|---|---|
| | | log2FCH (FDR); W16_L - BL_L | | |
| T$_H$17-pathway | CXCL1 | −1.83 * | −2.84 *** | −2.34 *** |
| | CCL20 | −2.53 *** | −3.36 *** | −3.22 *** |
| | IL17A | −2.19 *** | −2.66 *** | −2.66 *** |
| | IL12B | −2.21 ** | −3.38 *** | −3.09 *** |
| TNF/TNFR family | TNFSF14 | −1.38 * | −2.23 *** | −2.08 *** |
| | TRAIL | −1.40 ** | −2.04 *** | −1.91 *** |
| | TNFRSF9 | −1.45 *** | −2.03 *** | −1.98 *** |
| Number of Differentially expressed proteins (log2FCH <− 1.2 and FDR < 0.05) | | 41 | 48 | 48 |

* FDR < 0.05,
** FDR p < 0.01,
*** FDR < 0.001; W16_L = Week 16 lesional, BL_L = Baseline lesional, log2FCH = log2 fold change, BID = twice daily. P3DR = combined group of 20 mg < 100 kg and 30 mg for >= 100 kg patients. $N_{W16\_L}$ = 28 (20 mg BID), $N_{W16\_L}$ = 30 (30 mg BID).

A broad immunomodulatory effect was observed as demonstrated by a statistical significant reduction in key proteins related to immune axes relevant for psoriasis:
 TH17 (e.g. IL-17A, CCL20 and IL-12B)
 TH1 (e.g. TNFα, IFNγ, CXCL9 and CXCL10)
 Innate immunity (e.g. IL-6 and IL-17C).

Figure 35:
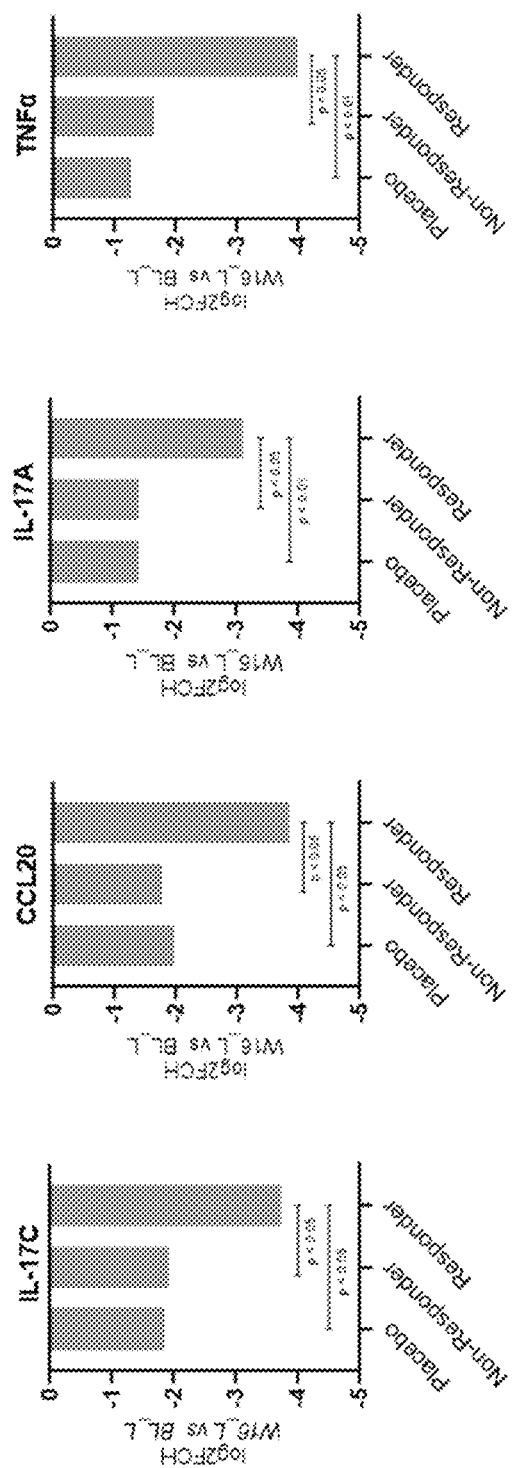
FIG. 35 shows Log2fold changes of selected cytokines in PASI75 responder and non-responders (treatment arms merged) versus placebo in the phase 2b, dose-ranging study assessing oral orismilast in adults with moderate-to-severe plaque psoriasis described in Example 3. W16_L=Week 16 lesional, BL_L=Baseline lesional, log2FCH=log 2 fold change, BID=twice daily. $N_{w16\_L}=33$ (PASI75 Responder), $N_{w16\_L}=25$ (PASI75 Non-responder), $N_{w16\_L}=27$ (Placebo).

Stratifying the biomarker response into PASI75 responders and non-responders (PASI75 responder defined as percent change in PASI Score at Week 16 from Baseline greater or smaller than 75%), key disease driving markers (e.g. IL17C, IL17A, CCL20) are statistically significant at Week 16 in PASI75 responders versus non-responders and placebo (FIG. 35), highlighting that the change in these markers is aligned with the clinical response.

In a posthoc analysis, a combined weight-based group was created in which patients <100 kg where allocated to 20 mg orismilast BID and patients ≥100 kg to 30 mg orismilast BID (called P3DR). In the weight-based dosing regimen group ("P3DR"), the reduction in key biomarkers and overall in the skin proteome (number of downregulated differential expressed proteins) is comparable to the 30 mg BID arm (Table above), demonstrating that the depth and degree in biomarker response is maintained with a weight-based dosing regimen.

Example 11: Analysis of the Results of the Phase2b Moderate to Severe Atopic Dermatitis Study in Example 8 to Assess Changes from Baseline in Skin Biomarkers 11.1 Methods Skin tape strip samples were taken from lesional and non-lesional skin at baseline and lesional skin at week 16 of patients participating in the phase 2b, double-blinded, placebo-controlled, dose-finding study (20 mg, 30 mg and 40 mg orismilast modified release tablets BID) in patients with moderate-to-severe atopic dermatitis (NCT05469464) described in Example 8. 134/152 subjects that completed the treatment had a tape strip collected at week 16. The primary objective of the biomarker study was to evaluate the effect of orismilast on a broad spectrum of inflammatory markers in atopic dermatitis skin lesions using tape strips as a non-invasive sampling technology combined with the Olink® technology (OLINK® FLEX panel) using analogous methods to those described in Example 10.

A linear mixed effect model was used on all patients to estimate lsmeans with standard error and adjusted p value.

11.2 Results

The analysis compared changes in biomarker levels in lesions of patients with atopic dermatitis (baseline vs. week 16) after treatment with different oral doses of orismilast (20 mg, 30 mg or 40 mg BID). A broad immunomodulatory effect was observed for patients treated with orismilast as demonstrated by a significant reduction in key proteins related to:
 Th2 (e.g. thymus and activation-regulated chemokine (TARC) and IL4R)
 Th17 (e.g. IL-17A and CCL20) and innate immunity (e.g. IL-6 and IL-17C)

Figure 36:
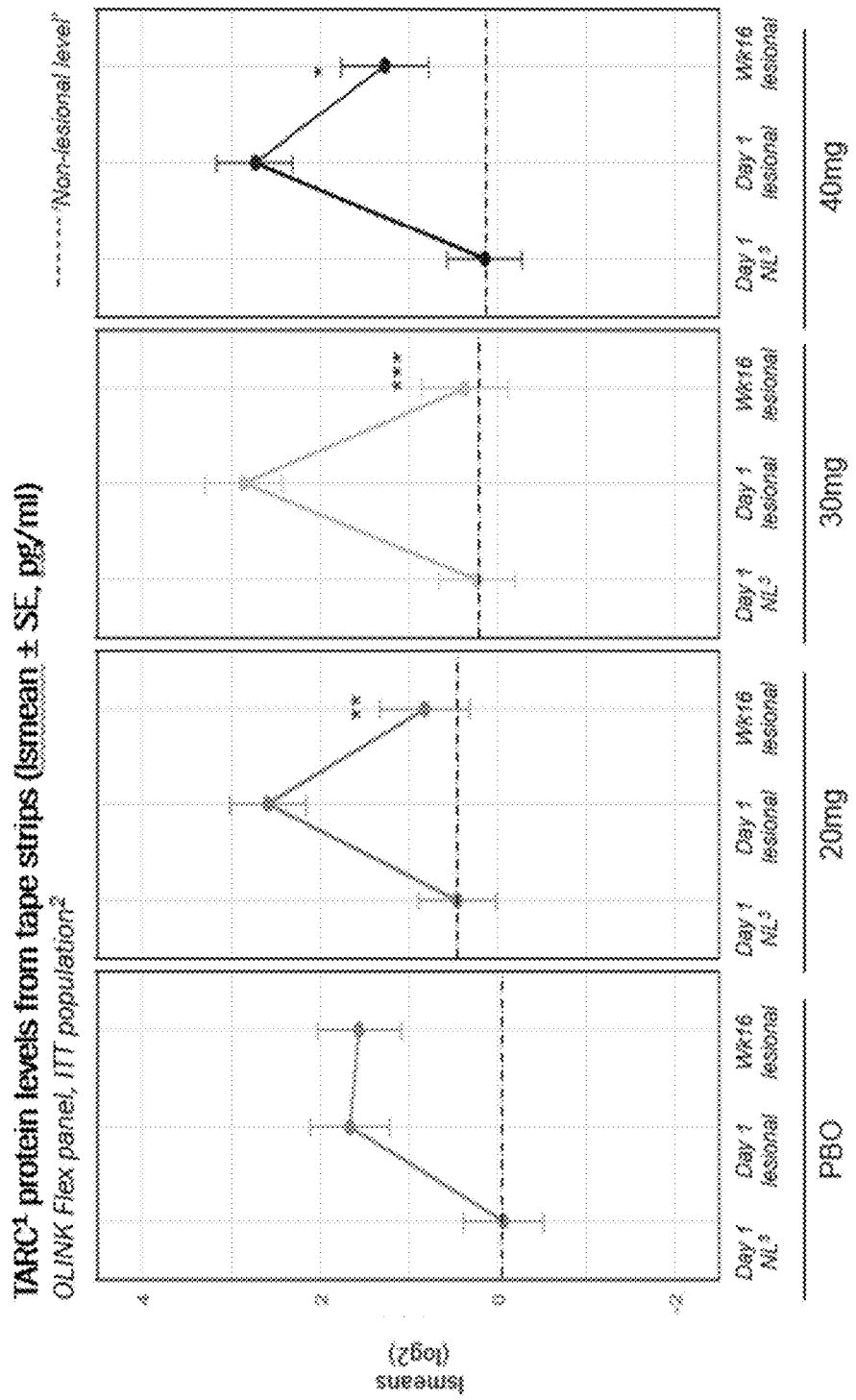
FIG. 36 shows skin levels of TARC (log 2) in the IIT population in the phase 2b, dose-ranging study assessing oral orismilast in adults with moderate-to-severe atopic dermatitis described in Example 8 after 16 weeks of treatment. P value indicates comparison of lesional skin levels at Week 16 compared to baseline lesional skin levels (day 1). * FDR<0.001,  FDR<0.01, * FDR<0.05 for week 16 lesional skin vs. day 1 lesional skin. TARC=thymus and activation-regulated chemokine, also known as CCL17=chemokine C—C motif ligand 17.

A significant reduction in TARC were observed for all treatment arms at week 16 of treatment (FIG. 36). The reduction in TARC is supportive of the clinical efficacy observed for orismilast because serum TARC level has been described as the most reliable disease severity biomarker in atopic dermatitis (Renert-Yuval et al. Biomarkers in atopic dermatitis-a review on behalf of the International Eczema Council. J Allergy Clin Immunol. 2021; 147(4):1174-1190.e1).

Figure 37:
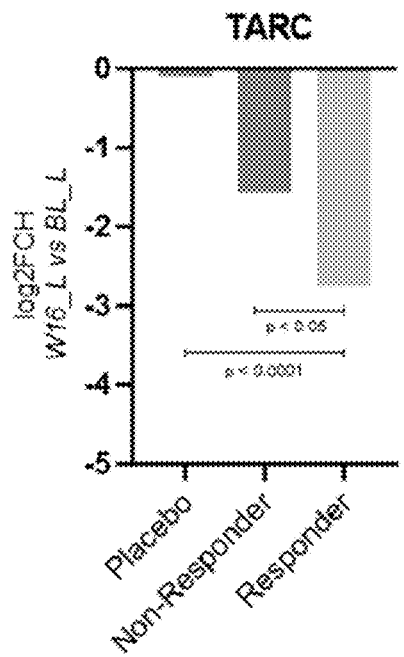
FIG. 37 shows Log2fold changes of TARC in IGA0/1 responder and non-responder (treatment arms merged) versus placebo adults with moderate-to-severe atopic dermatitis described in Example 8. W16_L=Week 16 lesional, BL_L=Baseline lesional, $N_{w16\_L}=40$ (Placebo), $N_{w16\_L}=66$ (Non-responder), $N_{w16\_L}=28$ (Responder). TARC=thymus and activation-regulated chemokine, also known as CCL17=chemokine C—C motif.

TARC levels at Week 16 were significantly reduced in IGA 0/1 responders (defined as subjects reaching IGA0/1 at Week 16 and a ≥2-point IGA improvement from baseline) compared to non-responders and placebo (FIG. 37). This analysis indicates that the reduction in TARC levels in lesional skin from baseline is correlated with clinical response (in FIG. 37 all treatment arms were combined to enrich the dataset).

Example 12: Evaluation of Clinical Data from the Phase 2b Moderate to Severe Atopic Dermatitis Study in Example 8 Using the Population Pharmacokinetics (PopPK) Model Described in Example 6

During the phase 2b moderate to severe atopic dermatitis study described in Example 8 blood samples were taken from subjects at 12 hours after the dosing on day 1 (baseline), week 4, week 8 and week16 and the plasma concentration of orismilast determined.

An external visual predictive check (external VPC) was performed using the PopPK model described in Example 6 with the orismilast plasma concentration clinical data. No adjustments were made to the PopPK model described in Example 6 prior to the external VPC.

Figure 38:
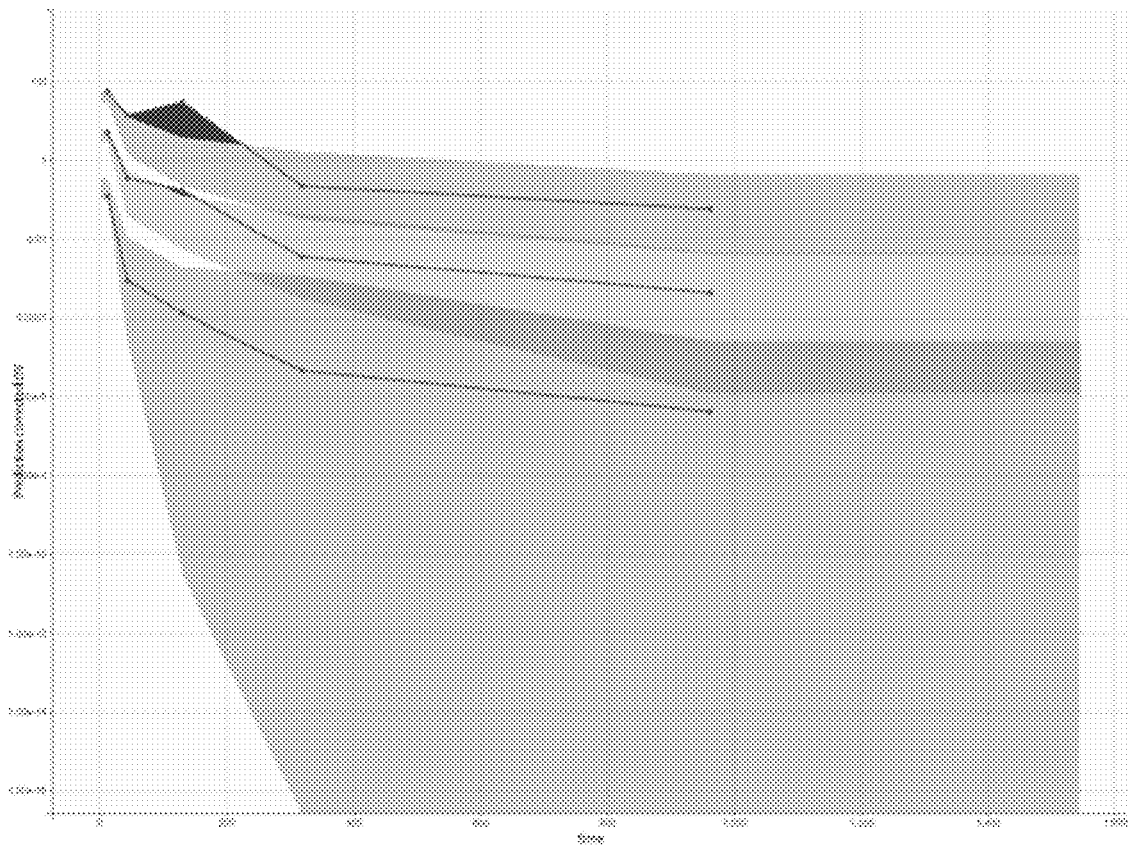
FIG. 38 shows an external visual predictive check using the PopPK model described in Example 6 using the orismilast plasma concentration data obtained from the phase 2b atopic dermatitis trial described in Example 8. The dots and lines correspond to the 5th percentile (bottom), the median (middle) and the 95th percentile (top) of the orismilast clinical data. The central shaded area represents the predicted median values from the PopPK model. The shading either side represents the predicted 95th percentile (top shading) and the 5th percentile (lower shading).
Figure 39:
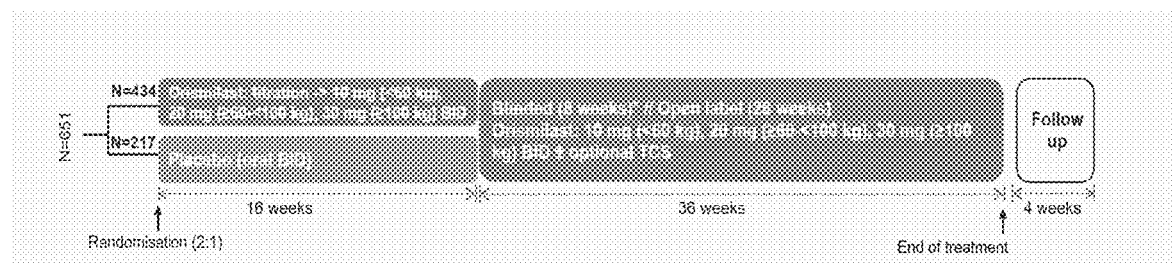
FIG. 39 shows the design of the phase 3 clinical study described in Example 13.

The observed orismilast concentrations were captured well by the PopPK model predicted median values (FIG. 38). The external VPC confirms that the PopPK model is suitable for modelling pharmacokinetics in both psoriasis and atopic dermatitis patient populations.

Example 13: A Randomised, Double-Blind, Placebo-Controlled Trial to Evaluate the Efficacy and Safety of Orismilast Monotherapy in Adults and Adolescents with Moderate-to-Severe Atopic Dermatitis The following phase 3 trial may be carried out. A total of 651 participants will be randomised, of which 141 will be adolescents and 510 adults. The proportion severe atopic dermatitis (vIGA 4) in the adult population will be at least 30% in order to represent a population who are candidates for systemic treatment in atopic dermatitis (AD). The trial will consist of a 52-weeks treatment period: initial double-blind treatment period of 16 weeks, an 8-week double-blind period (titration of participants coming from placebo) and an open-label extension treatment period of 28 weeks. The primary endpoints are assessed at Week 16. An off-treatment follow-up period for the assessment of safety and rebound effects is also included (Weeks 52 to 56). A schematic of the trial design is provided in FIG. 1.

Primary Objective

To assess superiority of twice-daily oral modified release orismilast compared to placebo at Week 16 in the treatment of adults and adolescents with moderate-to-severe atopic dermatitis.

Secondary Objective
1. To evaluate the health-related quality of life and efficacy of twice-daily oral modified release orismilast compared to placebo in the treatment of adults and adolescents with moderate-to-severe atopic dermatitis.
2. To evaluate the safety and tolerability of twice-daily oral modified release orismilast compared to placebo in the treatment of adults and adolescents with moderate-to-severe atopic dermatitis.
3. To evaluate long-term efficacy and safety of twice-daily oral modified release orismilast up to Week 56 in the treatment of adults and adolescents with moderate-to-severe atopic dermatitis.

Primary Endpoints
  Achieving vIGA-AD of 0 (clear) or 1 (almost clear) at Week 16 with at least a 2-point improvement from baseline.

Key Secondary Endpoints
  Achieving EASI75 at Week 16.
  Achieving reduction of Worst Pruritus $NRS^2 \geq 4$ at Week 16[3].

Other Secondary Endpoints
  Achieving EASI90 at Week 16.
  Achieving reduction of Skin Pain NRS2 ≥4 at Week 16[3].
  Percentage change in Worst Pruritus $NRS^2$ from baseline to Week 4 and 16.
  Percentage change in Worst Pruritus $NRS^2$ from baseline to Week 4 and 16.
  Achieving reduction of POEM≥4 at Week 16[3].
  Achieving reduction of DLQI ≥4 in participants age ≥16 years at Week 16[3].
  Achieving vGA-AD of 0 or 1 at Week 2, 4, 8 and 12[1].
  Achieving EASI75 at Week 2, 4, 8 and 12.
  Achieving EASI90 at Week 2, 4, 8 and 12.
  Achieving vIGA-AD of 0 or 1 at Weeks 20, 24, 32, 40, 52, 56[1].
  Achieving EASI75 at Weeks 20, 24, 32, 40, 52, 56.
  Achieving EASI90 at Weeks 20, 24, 32, 40, 52, 56.

Tertiary Endpoints
  Percentage change in EASI from baseline to Week 2, 4, 8, 12 and 16.
  Change in EASI from baseline to Week 2, 4, 8, 12 and 16.
  Achieving EASI50 at Week 2, 4, 8, 12 and 16.
  Achieving EASI100 at Week 4, 8, 12 and 16.
  Change in the affected body surface area (BSA) from baseline to Week 2, 4, 8, 12 and 16.
  Percentage change in Worst Pruritus $NRS^2$ from baseline to Week 1, 2, 4, 8, 12.
  Achieving reduction of Worst Pruritus $NRS^2 \geq 4$ at Week 1, 2, 4, 8, 123.
  Percentage change in Skin Pain $NRS^2$ from baseline to Week 1, 2, 4, 8, 12, 16.
  Achieving reduction of Skin Pain $NRS^2 \geq 4$ at Week 1, 2, 4, 8, 12[3'].
  Change in POEM from baseline to Week 8 and 16.
  Achieving reduction of POEM 4 at Week 83.
  Change in DLQI in participants age 16 years from baseline to Week 8 and 16.
  Achieving reduction of DLQI 4 in participants age 16 years at Week 83.
  Change in CDLQI in participants aged 12-15 years from baseline to Week 8 and 16.
  Change in Sleep Disturbance NRS (SD-NRS) from baseline to Week 4 and 16.
  Change in PGIS from baseline to Week 4, 12 and 16.
  Change in EQ-5D-5L from baseline to Week 8 and 16.
  Change in ACQ-5 score from baseline to Week 16.
  Change in WPAI:AD from baseline to Week 16.
  Achieving vIGA-AD of 0 or 1 at Weeks 20, 24, 32, 40, 52, 56 among participants with vIGA-AD 0 or 1 at Week 16.
  Time to loss of vIGA-AD 0 or 1 (defined as two consecutive assessments without vIGA-AD 0 or 1) among participants with vIGA-AD 0 or 1 at Week 16.
  Achieving EASI75 at Weeks 20, 24, 32, 40, 52, 56 among participants with EASI75 at Week 16.
  Time to loss of EASI75 (defined as two consecutive assessments without EASI75) among participants with EASI75 at Week 16.
  Percentage change in EASI from baseline to Weeks 20, 24, 32, 40, 52, 56.
  Change in EASI from baseline to Weeks 20, 24, 32, 40, 52, 56.
  Achieving EASI100 at Weeks 20, 24, 32, 40, 52, 56.
  Change in BSA from baseline to Week 20, 24, 32, 40, 52 and 56.
  Percentage change in Worst Pruritus $NRS^2$ from baseline to Week 20, 24, 32, 40, 52.
  Achieving reduction of Worst Pruritus $NRS^2 \geq 4$ at Week 20, 24, 32, 40, 523.
  Percentage change in Skin Pain $NRS^2$ from baseline to Week 20, 24, 32, 40, 52.
  Achieving reduction of Skin Pain $NRS^2 \geq 4$ at Week 20, 24, 32, 40, 523.
  Change in POEM from baseline to Week 24 and 52.
  Achieving reduction of POEM ≥4 at Week 24 and 523.
  Change in DLQI in participants age ≥16 years from baseline to Week 24 and 52.
  Achieving reduction of DLQI 4 in participants age 16 years at Week 24 and 523.
  Change in CDLQI in participants age 12-15 years from baseline to Week 24 and 52.
  Change in EQ-5D-5L from baseline to Week 24 and 52.
  Change in ACQ-5 score from baseline to Week 24 and 52.
  Change in WPAI:AD from baseline to Week 52.

Safety Assessments
  Number of treatment emergent adverse events (TEAE) from baseline to Week 16.
  Number of Adverse Event of Special Interest (AESI) from baseline to Week 16.
  Change from baseline in body weight, vital signs, laboratory tests and electrocardiogram (ECG) during initial 16-week treatment period.
  Columbia-Suicide Severity Rating Scale (C-SSRS) at Week 4, 8, 12 and 16.
  Hospital Anxiety and Depression Scale (HADS) at Week 4, 8, 12 and 16.

Foot Notes for Endpoints

[1] With at least 2-point improvement from baseline. 2 Weekly average. [3] From baseline among participants with a baseline score 24. a From baseline among participants with a baseline score ≥2.

Rationale for Trial Population

The trial population will consist of a representative group of adult (z 18 years old) and adolescent (212 years to <18 years) male and female participants with moderate-to-severe AD and candidates for systemic treatment. Moderate-to-severe AD is defined by a diagnosis of AD according to the Hanifin and Rajka criteria, a total EASI score of 2:16, a body surface area (BSA) of ≥10% and an vIGA-AD ≥3.

Selection of Patients

Inclusion Criteria

To be eligible to participate in this trial, an individual must meet all the following criteria:

1. Male and female participants 12 years of age at the time of signing the Informed Consent Form (ICF). Adolescent participants below the age of 18 years old will be enrolled if approved by the country or regulatory/health authority. If these approvals have not been granted, only participants ≥18 years old at the time of signing ICF will be enrolled.
2. Participants ≥18 years of age at the time of signing the ICF must be capable of giving signed informed consent, which includes compliance with the requirements and restrictions listed in the ICF and in the protocol.
3. For participants ≥12 years old and <18 years old at the time of signing the ICF: Parent or legal guardian must be capable of giving signed informed consent and participants must be capable of giving verbal and/or written assent. Parent/legal guardian and participant must comply with the requirements of this trial protocol. If a participant becomes of legal age during the course of the trial, the participant will need to be consented using the approved ICF.
4. Body weight of >40 kg at the time of signing the ICF.
5. Diagnosis of AD for a minimum of 1 year (before the Screening visit) using the Hanifin and Rajka criteria.
6. Participants to consent to photographic documentation of their AD over the course of the trial.
7. Moderate-to-severe AD (affected BSA of at least 10%, vIGA-AD grade of at least 3 (minimum 30% grade 4), and EASI score of at least 16) at the Screening and Baseline visits.
8. Baseline Worst Pruritus NRS (weekly average)≥4. The baseline weekly average will be calculated from the 7 consecutive days immediately preceding the Baseline Visit. A minimum of 4 daily scores out of the 7 days is needed.
9. Participant must have applied topical emollient (moisturizer) at least once daily for at least 14 days preceding the Baseline Visit.
10. Candidate for systemic treatment or phototherapy for AD.
11. Participants having a documented history of inadequate response to treatment with topical medications given for at least 4 weeks (at least 2 weeks for high potency topical corticosteroids), or as labelled, or for whom topical treatments are otherwise medically inadvisable.
12. Women of childbearing potential (WOCBP) must have a negative serum pregnancy test at the Screening visit and a negative urine pregnancy test at the Baseline visit.

EXCLUSION CRITERIA

An individual who meets any of the following criteria will be excluded from participation in this trial:

AD Related Exclusion Criteria:

1. Unstable AD with acute deterioration, requiring rescue therapy for AD within 4 weeks of the Screening visit or expected to require rescue therapy within 2 weeks after randomisation.
2. History of allergy or hypersensitivity to any component of the trial intervention.
3. Currently have active forms of other inflammatory skin disease or have evidence of skin conditions (e.g., psoriasis, seborrheic dermatitis, lupus) at the Baseline visit that would interfere with evaluation of AD or response to treatment Use of treatment that may impact the safety or efficacy data of orismilast:
4. Participants who have been treated with the following therapies:
   a. Topical corticosteroid (TCS), topical calcineurin inhibitors (TCI) (for example, tacrolimus and pimecrolimus), topical PDE4 inhibitor (crisaborole) or bleach baths, 1 week before randomisation
   b. Sedating, systemic antihistamines including but not limited to alimemazine, chlorphenamine, clemastine, cyproheptadine, diphenhydramine, hydroxyzine, ketotifen, and promethazine, 4 weeks before randomisation
   c. Leukotriene inhibitors (for example, montelukast [Singulair®], zafirlukast [Accolate], and zileuton [Zyflo®]), 4 weeks before randomisation
   d. Systemic corticosteroids and Intra-articular or soft tissue (bursa, tendons, and ligaments) corticosteroid injection, 4 weeks before randomisation
   e. Systemic therapy for AD, including but not limited to corticosteroids, methotrexate, cyclosporine, azathioprine, interferon-γ, and mycophenolate mofetil within 4 weeksbefore randomization
   f. Biologic treatments for AD within 5 half-lives or 12 weeks, whichever is longer, before randomisation
   g. Allergen immunotherapy, 4 weeks before randomisation
   h. Phototherapy, including PUVA (psoralen and ultraviolet A), ultraviolet B, tanning booth, and excimer laser, 4 weeks before randomisation
   i. Any oral systemic therapy, investigational or commercial (approved or off-label use), used for the treatment of AD or symptoms of AD, 4 weeks or 5 half-lives (if known), whichever longer before randomisation
5. Participant had prior treatment with orismilast or previous experience with other systemic PDE4 inhibitors having led to premature treatment discontinuation because of tolerability issues Other conditions that may impact the safety of the participant or Investigator:
6. Active infection (e.g., bacterial, viral, fungal) requiring treatment with systemic therapy within 4 weeks of the Baseline visit
7. Any documented active or suspected malignancy or history of malignancy within 5 years prior to the screening visit, except appropriately treated basal cell carcinoma of the skin, squamous cell carcinoma of the skin or in situ carcinoma of uterine cervix
8. Active ongoing inflammatory diseases other than Atopic Dermatitis that might confound the evaluation of the trial intervention (i.e., recurrent medical condition associated with serious GI diseases, such as inflammatory bowel disease).

9. Any medical or psychiatric condition (e.g. depression, schizophrenia, suicidal behaviour, psychiatric hospitalization within the prior year) which, in the Investigator's opinion, would preclude the participant from adhering to the protocol, completing the trial per protocol, and/or would place the participant at unacceptable risk for receiving the trial intervention
10. Individuals with severe or uncontrolled asthma or any other concomitant condition that is likely to require systemic corticosteroid bursts during the trial
11. Any current liver disease (with or without liver enzymes or bilirubin increases) that would place the participant at unacceptable risk for receiving the trial intervention
12. Participant with a transplanted organ (with exception of a corneal transplant >12 weeks prior to screening) or who have ever received stem cell therapy (e.g., Remestemcel-L)
13. Any condition, including laboratory or ECG abnormalities, that places the participant at unacceptable risk to participate in the trial or confounds the ability to interpret data from the trial
14. Any of the following abnormalities in clinical laboratory test results at Screening, as assessed by the trial-specific laboratory and confirmed by a single repeat test, if deemed necessary:
Absolute neutrophil count of less than the lower normal range of the Central Laboratory (LNR) i.e. $1.7 \times 10^9$/L ($1700//mm^3$)
Haemoglobin of less than 10.0 g/dL or haematocrit less than 30%
Platelet count of less than 100,000 $mm^3$ (SI: $<100 \times 10^1$ cells/L)
Absolute lymphocyte count of less than the LNR i.e. $0.9 \times 10^9$/L ($900/mm^3$)Total bilirubin greater than $1.5 \times$ the upper limit of normal (ULN); participants with a history of Gilbert's syndrome may have direct bilirubin measured and would be eligible for this trial provided the direct bilirubin result is less than or equal to the ULN
Alanine aminotransferase (ALT) or aspartate aminotransferase (AST) greater than $2.5 \times$ the ULN
Serum creatinine greater than or equal to 1.5 mg/dL. For participants with a value of greater than or equal to 1.5 mg/dL, if their creatinine clearance is at least 60 mL/min (calculated using the Chronic Kidney Disease Epidemiology Collaboration creatinine equation), enrolment may be allowed.
15. History or evidence of hepatitis B virus infection at Screening. Participants with a positive hepatitis B surface antigen result are excluded. For participants with an isolated positive antihepatitis B core antibody result, the hepatitis B surface antibody result must also be positive to be eligible for this trial
16. Positive test result for hepatitis C virus (HCV) antibody, indicating ongoing infection, at Screening. Confirmatory testing for HCV RNA will be conducted for participants who have a positive test result. Participants who have a negative result for HCV RNA will be eligible to participate in the trial
17. History of positive HIV test result or congenital or acquired immunodeficiency (e.g., common variable immunodeficiency disease). Participants who are positive for HIV antibodies (HIV-1 or HIV-2) at Screening are excluded from the trial
18. Suicidal ideation in the past 12 months as indicated by a positive response (yes) to question 4 (Active suicidal ideation with some intent to act, without specific plan) or 5 (Active suicidal ideation with specific plan and intent) or answering "yes" to suicidal behaviour on the C-SSRS completed at the Screening visit or at Baseline.
19. Pregnant, breastfeeding or considering becoming pregnant.
20. History of alcohol or substance abuse within 6 months before Baseline that, in the opinion of the Investigator, will preclude participation in the trial
21. Institutionalized by court order or by local authority Trial Periods Screening Period (Day—28 to Day 0)

The screening period has a maximum duration of 4 weeks. The exact duration of the screening period for the individual participant depends on the length of any washout period needed, as specified in the exclusion criteria. Participants will be required to use emollients at least once daily during the 14 days preceding randomisation and throughout the study.

Blinded Treatment Period (Week 0 to Week 16)

Following the screening period, approximately 651 participants will be randomised 2:1 to one of the following groups stratified by region (Europe, North America), baseline disease severity (vIGA-AD 3/4) and age (adolescent vs. adult):

Orismilast

Placebo BID

Open Label Treatment Period (Week 16 to Week 52)

At Week 16, all participants will be assigned to treatment with orismilast. The first 8 weeks (Week 16 to Week 24) will be double-blind as participants coming from placebo will have a titration phase of up to 8 weeks before reaching their maintenance dose of orismilast, while participants assigned to treatment with orismilast continue with their maintenance dose unchanged from week 16 and onwards.

Follow-Up Period (Week 52 to 56)

Participants will complete a 4-week off-treatment follow-up period for the assessment of safety and rebound.

Trial Interventions (Dosing with Orismilast Modified Release Tablet)

All trial interventions will be taken orally BID, approximately 12 hours apart, without restriction of food or drink, though it is advised that the participant eats smaller, less energy dense meals to prevent gastrointestinal side effects, and stay well hydrated. To mitigate potential gastrointestinal side effects, dose titration will be implemented.

The dosing regimen in the active arm will be weight-based and have a target of 10 mg BID for participants with a baseline body weight <60 kg, 20 mg for participants with a baseline body weight between ≥60 kg to <100 kg, and 30 mg BID for participants with a baseline body weight 100 kg versus placebo BID, all administered orally.

In order to ensure tolerable treatment initiation and similar systemic exposure across body weights, participants will follow a weight-based fixed titration schedule, please see Table 3 for the orismilast dosing regimen.

Participants with a baseline body weight <60 kg will receive 10 mg once daily for the initial 14 days, dose escalation to 10 mg BID is planned at Day 15, and the participants will remain on 10 mg BID.

Participants with a baseline body weight ≥60 kg to <100 kg will receive 20 mg once daily for the initial 14 days, dose escalation to 20 mg BID is planned at day 15, and the participants will remain at 20 mg BID.

Participants with a baseline body weight 2100 kg, will receive 20 mg once daily for the initial 14 days, dose escalation to 20 mg BID is planned at day 15. Further dose escalation to 30 mg BID is planned at Day 57, and the participants will remain at 30 mg BID. Participants assigned to placebo will receive placebo BID. Thus, the dosing regimen will be as shown in the table below:

Dosing Regimen

| Arm | Weight | Day 1-14 (Week 0-2) morning | Day 1-14 (Week 0-2) evening | Day 15-56 (Week 2 to 8) morning | Day 15-56 (Week 2 to 8) evening | From Day 56 (Week 8 and onwards) morning | From Day 56 (Week 8 and onwards) evening |
|---|---|---|---|---|---|---|---|
| Active (orismilast) | <60 kg | PBO | 10 mg | 10 mg | 10 mg | 10 mg | 10 mg |
| Active (orismilast) | ≥60 kg to <100 kg | PBO | 20 mg | 20 mg | 20 mg | 20 mg | 20 mg |
| Active (orismilast) | ≥100 kg | PBO | 20 mg | 20 mg | 20 mg | 30 mg | 30 mg |
| Placebo | All | PBO | PBO | PBO | PBO | PBO | PBO |

Alternative Dosage Regimen

Also contemplated is the dosage regimen wherein subjects are dosed with the orismilast modified release tablet according to the weight-based dosage regimen below:

| Arm | Subject Weight | Day 1 | Day 2-14 (Week 0-2) | Day 15-56 (Week 2 to 8) | | From Day 57 (Week 8 and onwards) | |
|---|---|---|---|---|---|---|---|
| Orismilast | <lower limit body mass | 10 mg | P | 10 mg | 10 mg | 10 mg | 10 mg |
| Orismilast | ≥lower limit body mass to <100 kg | 20 mg | P | 20 mg | 20 mg | 20 mg | 20 mg |
| Orismilast | ≥100 kg | 20 mg | P | 20 mg | 20 mg | 30 mg | 30 mg |
| Placebo | All | P | P | P | P | P | P |

"P" refers to placebo dose
"lower limit body mass" refers to a subject body mass of from 50 kg to 75 kg. In some embodiments the lower limit body mass is 50 kg. In some embodiments the lower limit body mass is 75 kg.

Pharmacokinetics

Blood samples for pharmacokinetic (PK) analysis of orismilast and its major metabolite levels will be collected at the time points indicated in the Schedule of Study Procedures.

Biomarkers

Blood samples for biomarker research will be collected from all participants as specified in the Schedule of Trial Procedures and will be analysed for exploratory purposes, and include TARC and C6A6.

Investigator Assessments

Eczema Area and Severity Index (EASI)

The EASI scoring system is described in Example 8.

Validated Investigator Global Assessment for Atopic Dermatitis (vIGA-AD)

The vIGA-AD is a measure used by physicians to determine a patient's overall severity of disease. The static version is used in this trial for measurement at a single point in time. The Investigator will rate the severity of the participant's AD on a 5-point scale ranging from 0 (clear) to 4 (severe) (Simpson E,2020).

| Score | Morphological Description |
|---|---|
| 0 - Clear | No inflammatory signs of atopic dermatitis: no erythema, no induration/papulation, no lichenification, no oozing/crusting. Post-inflammatory hyperpigmentation and/or hypopigmentation may be present |
| 1 - Almost clear | Barely perceptible erythema, barely perceptible induration/papulation and/or minimal lichenification. No oozing/crusting. |
| 2 - Mild | Slight but definite erythema (pink), slight but definite induration/papulation and/or slight but definite lichenification. No oozing/crusting. |
| 3 - Moderate | Clearly perceptible erythema (dull red), clearly perceptible induration/papulation, and/or clearly perceptible lichenification. Oozing and crusting may be present. |
| 4 - Severe | Marked erythema (deep or bright red), marked induration/papulation and/or marked lichenification. Disease is widespread in extent*. Oozing/crusting may be present. |

*Patient with marked deep or bright red erythema with marked induration/papulation and/or marked lichenification that is limited in extent will be considered as 3-Moderate The Body Surface Area (BSA), skin pain NRS, Sleep disturbance Numerical Rating Scale (SD-NRS), Patient-Oriented Eczema Measure (POEM), Dermatology Life Quality Index (DLQI), Patient Global Impression of Severity Scale (PGIS), The Hospital Anxiety and Depression Scale (HADS), The Columbia-Suicide Severity Rating Scale (C-SSRS) are as described in Example 8. The EuroQol Quality of Life 5-Dimension-5 five-level (EQ-5D-5L) is described in Example 4.

Children's Dermatology Life Quality Index (CDLQI)

The CDLQI is a 10-item, validated questionnaire used in clinical practice and clinical trials to assess the impact of AD disease symptoms and treatment on QoL. The CDLQI has been validated for use in participants 4-16 years old (Lewis-Jones M S, 1995). In this trial, participants ≤15 years of age at the time of signing ICF will complete the CDLQI throughout the trial. The CDLQI will be completed by the participant with the help of the child's parent or guardian, as necessary. It consists of 10 questions assessing impact of skin diseases on different aspects of participant's QoL over the prior week. The CDLQI items include symptoms and feelings, daily activities, leisure, school, relationships, sleep, and treatment. Each item is scored on a 4-point scale: 0=not at all; 1=only a little; 2=quite a lot; and 3=very much. Item scores (0 to 3) are added to provide a total score range of 0 to 30; higher scores indicate greater impairment of QoL.

The invention claimed is:

1. A method of treating a disease selected from psoriasis and atopic dermatitis in a subject, the method comprising orally administering orismilast to the subject, wherein:
   (Ai) (i) an initial orismilast dose of 10 mg is administered to the subject once per day for two weeks if the subject has body mass of less than 60 kg, or
   (ii) an initial orismilast dose of 20 mg is administered to the subject once per day for two weeks if the subject has body mass of greater than or equal to 60 kg;
   followed by
   (Aii) (i) an interim orismilast dose of 10 mg administered to the subject twice per day for an interim time period if the subject has body mass of less than 60 kg; or
   (ii) an interim orismilast dose of 20 mg administered to the subject twice per day for an interim time period if the subject has body mass of greater than or equal to 60 kg;
   followed by;
   (Aiii) (i) a maintenance orismilast dose of 10 mg administered to the subject twice per day if the subject has a body mass of less than 60 kg, or
   (ii) a maintenance orismilast dose of 20 mg administered to the subject twice per day if the subject has body mass of greater than or equal to 60 kg to less than 100 kg, or
   (iii) a maintenance orismilast dose of 30 mg administered to the subject twice per day if the subject has a body mass of greater than or equal to 100 kg;
   wherein the interim time period is one to eight weeks.

2. The method according to claim 1, wherein the interim time period is two weeks.

3. The method according to claim 1, wherein the interim time period is four weeks.

4. The method according to claim 1, wherein the interim time period is six weeks.

5. The method according to claim 1, wherein the interim time period is eight weeks.

6. The method according to claim 1, wherein the disease is psoriasis.

7. The method according to claim 1, wherein the disease is moderate to severe plaque-type psoriasis.

8. The method according to claim 7, wherein:
   (i) the subject has a 75% reduction in PASI (PASI75) from baseline after 16 weeks of treatment; or
   (ii) the subject has a 90% reduction in PASI (PASI90) from baseline after 16 weeks of treatment; or
   (iii) the subject has a 100% reduction in PASI (PASI100) from baseline after 16 weeks of treatment; or
   (iii) the subject achieves a Investigator Global Assessment (IGA) of clear (0) or almost clear (1) after 16 weeks of treatment.

9. The method according to claim 1, wherein the disease is atopic dermatitis.

10. The method according to claim 1, wherein the disease is moderate to severe atopic dermatitis.

11. The method of claim 10, wherein:
    (i) the subject has a 75% reduction in EASI (EASI75) from baseline after 16 weeks of treatment; or
    (ii) the subject has a 90% reduction in EASI (EASI90) from baseline after 16 weeks of treatment; or
    (iii) the subject has a 100% reduction in EASI (EASI100) from baseline after 16 weeks of treatment; or
    (iv) the subject achieves an Investigator Global Assessment for AD (IGA-AD) score of clear (0) or almost clear (1) and at least a 2-point improvement in IGA-AD from baseline after 16 weeks of treatment; or
    (v) the subject achieves an Investigator Global Assessment for AD (IGA-AD) score of clear (0) after 16 weeks of treatment.

12. The method according to claim 1, wherein the orismilast is orally administered to the subject in the form of a modified release formulation comprising the orismilast.

13. The method according to claim 12, wherein the modified release formulation releases a mean amount of about 10% to about 70% of the orismilast after 45 minutes and more than about 70% after 180 minutes, when measured in-vitro using Ph. Eur. 2.9.3 Apparatus II, with a dissolution medium of 900 ml 0.5% sodium dodecyl sulfate in 0.1N HCl, a paddle speed of 75 rpm, and the dissolution medium at 37±0.5° C.

14. The method according to claim 12, wherein the modified release formulation comprises orismilast and a polymeric matrix.

15. The method according to claim 14, wherein the polymer matrix comprises a hydrophilic or hydrophobic matrix.

16. The method according to claim 14, wherein the polymer matrix is selected from one or more polymers selected from hydroxypropyl methylcellulose, methyl cellulose, hydroxypropyl cellulose, hydroxyethyl cellulose, sodium carboxymethyl cellulose a polyethylene oxide, a polyethylene glycol, a polyethyleneoxide-polypropyleneoxide block-co-polymer, cellulose acetate phthalate, hydroxypropylmethyl cellulose phthalate, polyvinylpyrrolidone (PVP), a copolymers of PVP and vinyl acetate, a poly(ethylene-vinyl acetate), polyvinyl alcohol, a sugar alcohol and a biodegradable polymer.

17. The method of claim 14, wherein the polymeric matrix comprises hydroxypropyl methylcellulose.

18. The method of claim 12, wherein the modified release formulation comprises of from about 15% w/w to about 20% w/w hydroxypropyl methylcellulose, wherein a 2% solution of the hydroxypropyl methylcellulose in water at 20° C. has a viscosity of from 80 to 120 mPa·s.

19. The method of claim 12, wherein the modified release formulation comprises a core comprising:
    (i) orismilast;
    (ii) a hydrophilic matrix former, wherein the hydrophilic matrix former is present in a concentration of from about 15% w/w to about 20% w/w hydroxypropyl methylcellulose based on the weight of the core;

(iii) from about 30% w/w to about 78% w/w lactose monohydrate based on the weight of the core; and (iv) optionally one or more pharmaceutically acceptable excipients selected from the group consisting of glidants and lubricants;

wherein the composition further comprises a pharmaceutically acceptable coating system on the core.

20. The method of claim 19, wherein a 2% solution of the hydroxypropyl methylcellulose in water at 20° C. has a viscosity of from 80 to 120 mPa·s; and the pharmaceutically acceptable coating system is a PVA-based coating system.

21. The method of claim 12, wherein the modified release formulation comprises Core 1, Core 2 or Core 3 selected from Table A or Core 4, Core 5 or Core 6 selected from Table B:

TABLE A

| Component | % w/w of the core | | |
|---|---|---|---|
| | Core 1 | Core 2 | Core 3 |
| orismilast | 2.5-4.5% | 5.5-7.7% | 9-11% |
| Lactose monohydrate | 70-85% | 69-80% | 66-76% |
| Hydroxypropyl methylcellulose | 12-23% | 12-23% | 12-23% |
| Anhydrous colloidal silica | 0.01-1.5% | 0.01-1.5% | 0.01-1.5% |
| Magnesium stearate | 0.01-2.0% | 0.01-2.0% | 0.01-2.0% | wherein the core in Table A is coated with a water-soluble film coating in an amount to provide about 3% to 5% weight gain of the core;

TABLE B

| Component | Amount | | |
|---|---|---|---|
| | Core 4 | Core 5 | Core 6 |
| orismilast | 10 mg | 20 mg | 30 mg |
| Lactose monohydrate | 233 mg | 223 mg | 213 mg |
| Hydroxypropyl methylcellulose | 52.5 mg | 52.5 mg | 52.5 mg |
| Anhydrous colloidal silica | 1.5 mg | 1.5 mg | 1.5 mg |
| Magnesium stearate | 3.0 mg | 3.0 mg | 3.0 mg |
| Core weight | 300 mg | 300 mg | 300 mg |
| Water-soluble film coating | 12 mg | 12 mg | 12 mg |
| Coated core weight | 312 mg | 312 mg | 312 mg. |

22. The method of claim 21, wherein a 2% solution of the hydroxypropyl methylcellulose in water at 20° C. has a viscosity of from 80 to 120 mPa·s; and the water-soluble film coating is a PVA-based pharmaceutically acceptable coating system is a polyvinyl alcohol-based coating.

23. The method of claim 22, wherein the hydroxypropyl methylcellulose in Core 1, Core 2 and Core 3 is present in an amount of about 17.5% w/w of the core.

\* \* \* \* \*